United States Patent
Mortazavi et al.

(10) Patent No.: US 12,338,438 B2
(45) Date of Patent: Jun. 24, 2025

(54) CONJUGATED OLIGONUCLEOTIDE COMPOUNDS, METHODS OF MAKING AND USES THEREOF

(71) Applicant: E-Therapeutics PLC, London (GB)

(72) Inventors: Ahmad Ali Mortazavi, London (GB);
Viviana Mannella, London (GB);
Muthusamy Jayaraman, London (GB)

(73) Assignee: E-Therapeutics PLC, London (GB)

( * ) Notice: Subject to any disclaimer, the term of this patent is extended or adjusted under 35 U.S.C. 154(b) by 0 days.

(21) Appl. No.: 18/106,149

(22) Filed: Feb. 6, 2023

(65) Prior Publication Data

US 2024/0102008 A1   Mar. 28, 2024

Related U.S. Application Data

(63) Continuation of application No. PCT/EP2022/052067, filed on Jan. 28, 2022.

(60) Provisional application No. 63/271,686, filed on Oct. 25, 2021, provisional application No. 63/262,311, filed on Oct. 8, 2021, provisional application No. 63/143,805, filed on Jan. 30, 2021.

(51) Int. Cl.
*C12N 15/113* (2010.01)

(52) U.S. Cl.
CPC ........ *C12N 15/113* (2013.01); *C12N 2310/14* (2013.01); *C12N 2310/313* (2013.01); *C12N 2310/315* (2013.01); *C12N 2310/317* (2013.01); *C12N 2310/351* (2013.01); *C12N 2320/32* (2013.01); *C12N 2330/30* (2013.01)

(58) Field of Classification Search
CPC .............. A61K 47/549; C07D 207/404; C07H 15/04; C07H 15/08; C07H 21/00; C07H 21/02; C07H 21/04
See application file for complete search history.

(56) References Cited

U.S. PATENT DOCUMENTS

| | | |
|---|---|---|
| 7,452,987 B2 | 11/2008 | Giese et al. |
| 7,528,188 B2 | 5/2009 | Park et al. |
| 8,273,866 B2 | 9/2012 | Mcswiggen |
| 9,150,606 B2 | 10/2015 | Allerson et al. |
| 10,119,136 B2 | 11/2018 | Manoharan et al. |
| 10,266,825 B2 | 4/2019 | Allerson et al. |
| 10,995,336 B2 | 5/2021 | Schlegel |
| 11,504,391 B1 | 11/2022 | Schlegel |
| 11,725,207 B2 | 8/2023 | Schlegel |
| 2019/0350962 A1 | 11/2019 | Chan et al. |
| 2020/0270611 A1 | 8/2020 | Gryaznov et al. |
| 2023/0256001 A1 | 8/2023 | Schlegel |
| 2023/0310486 A1 | 10/2023 | Mortazavi et al. |
| 2023/0407311 A1 | 12/2023 | Mortazavi |
| 2024/0336922 A1 | 10/2024 | Whitmore |

FOREIGN PATENT DOCUMENTS

| | | |
|---|---|---|
| WO | 2014179620 A1 | 11/2014 |
| WO | 2014179626 A2 | 11/2014 |
| WO | 2014205451 A2 | 12/2014 |
| WO | 2015042447 A1 | 3/2015 |
| WO | 2018132432 A1 | 7/2018 |
| WO | 2018140920 A1 | 8/2018 |
| WO | 2020097342 A1 | 5/2020 |
| WO | 2020172755 A1 | 9/2020 |
| WO | 2020237391 A1 | 12/2020 |
| WO | 2021261992 A1 | 12/2021 |
| WO | 2022162153 A1 | 8/2022 |
| WO | 2022162154 A1 | 8/2022 |

OTHER PUBLICATIONS

Li (Bioconjugate Chem., 2017, 28, 1649-1657).*
Dongen (Mol Pharmaceutics, 2014, 11, 4049-4058).*
International Search Report and Written Opinion of the International Searching Authority mailed on May 12, 2022, for PCT Application No. PCT/EP2022/052069, filed on Jan. 28, 2022, 22 pages.
International Search Report and Written Opinion of the International Searching Authority mailed on May 13, 2022, for PCT Application No. PCT/EP2022/052067, filed on Jan. 28, 2022, 20 pages.
Li, M-H. et al. (Jun. 21, 2017, e-pub. May 12, 2017). "Ligand Characteristics Important to Avidity Interactions of Multivalent Nanoparticles," Bioconjugate Chemistry 28(6):1649-1657.
Park, H-K. et al. (Jun. 2016, e-pub. Jun. 24, 2016). "Reference Values of Clinical Pathology Parameters In Cynomolgus Monkeys (Macaca Fascicularis) Used In Preclinical Studies," Lab Anim Res. 32(2):79-86.
Wenska, M. et al. (Nov. 1, 2011, e-pub. Jul. 27, 2011). "An Activated Triple Bond Linker Enables 'Click' Attachment of Peptides to Oligonucleotides on Solid Support," Nucleic Acids Res. 39(20):9047-9059.
Sharma, V.K. et al. (Jun. 13, 2018). "Novel Cluster And Monomer-Based GalNAc Structures Induce Effective Uptake of siRNAs In Vitro and In Vivo," Bioconjugate Chemistry 29(7):2478-2488.
Prakash, T.P. et al. (Feb. 25, 2016). "Comprehensive Structure-Activity Relationship of Triantennary N-Acetylgalactosamine Conjugated Antisense Oligonucleotides for Targeted Delivery to Hepatocytes," Journal of Medicinal Chemistry 59(6):2718-2733.
U.S. Appl. No. 18/624,912, McCarthy et al., filed Apr. 2, 2024. (Copy not submitted herewith pursuant to the waiver of 37 C.F.R. § 1.98(a)(2)(iii) issued by the Office on Sep. 21, 2004).

* cited by examiner

*Primary Examiner* — Pancham Bakshi
(74) *Attorney, Agent, or Firm* — MORRISON & FOERSTER LLP

(57) ABSTRACT

The present invention relates to novel conjugated oligonucleotide compounds, which are suitable for therapeutic use. Additionally, the present invention provides methods of making these compounds, as well as methods of using such compounds for the treatment of various diseases and conditions.

19 Claims, 50 Drawing Sheets

Specification includes a Sequence Listing.

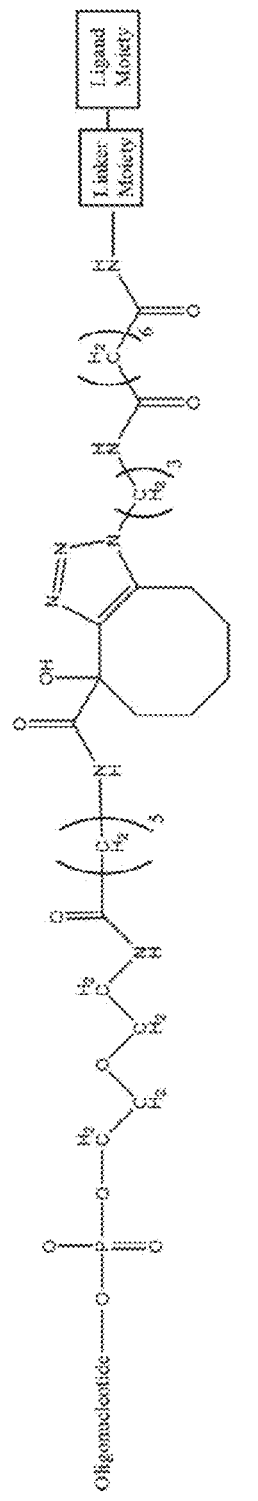
Formula (III)
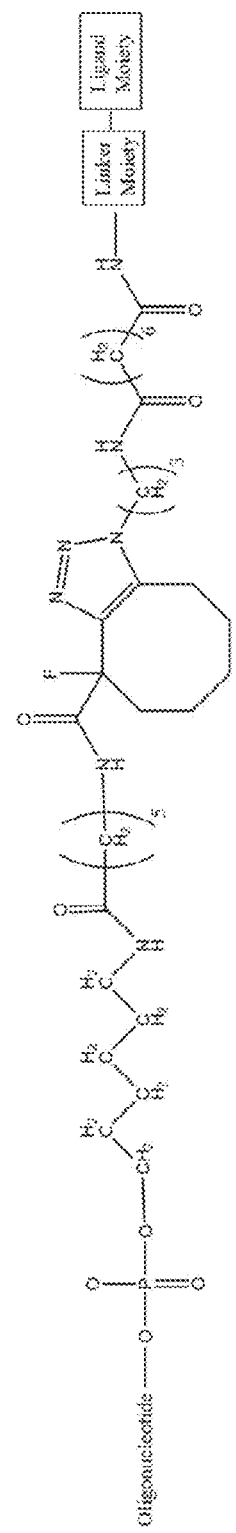
Formula (IV)
FIG. 28 (cont.)

FIG. 28 (cont.)
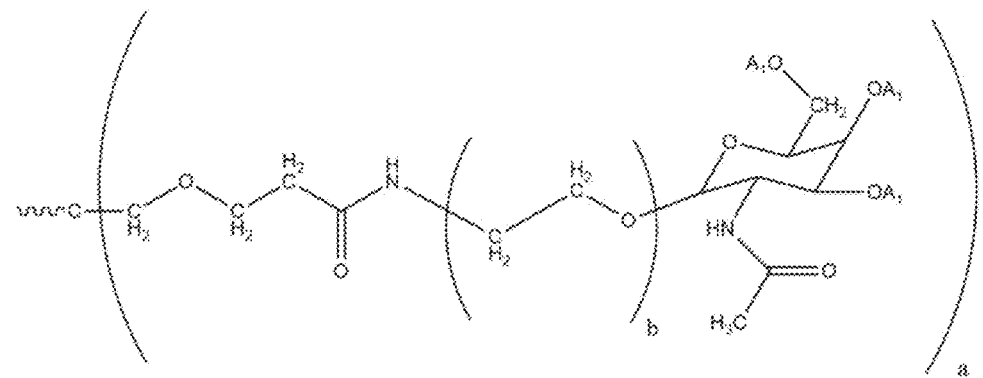
Formula (VIa)
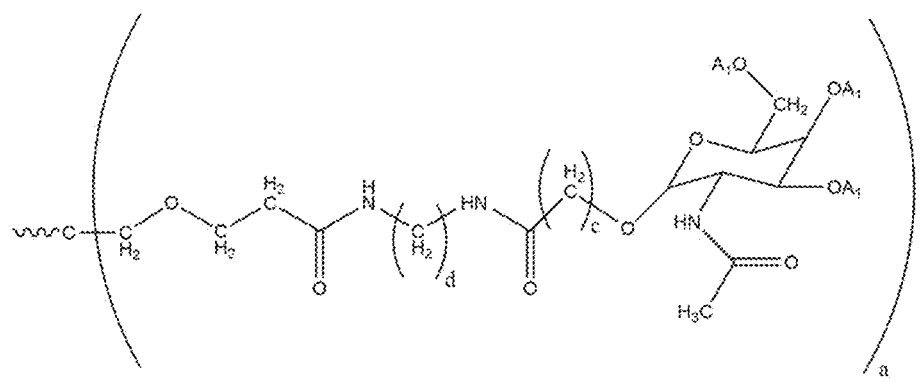
Formula (VIb)
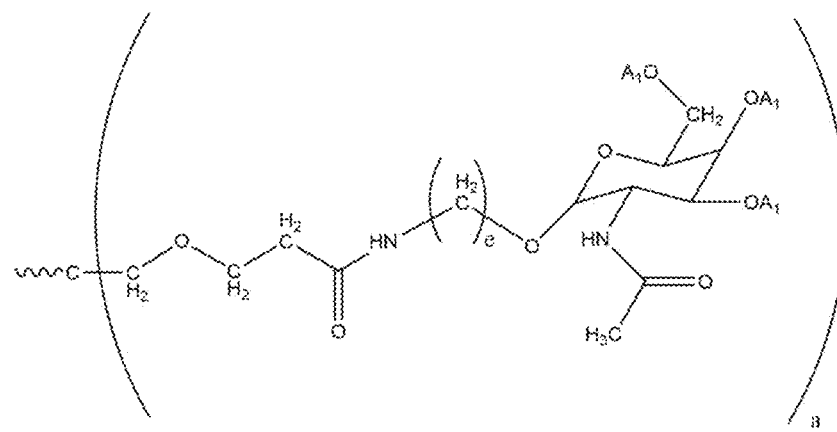
Formula (VIc)

Formula (VII)

Formula (IX)

FIG. 28 (cont.)
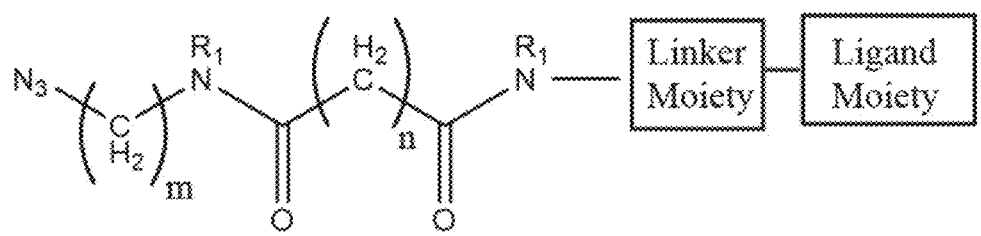
Formula (XIII)
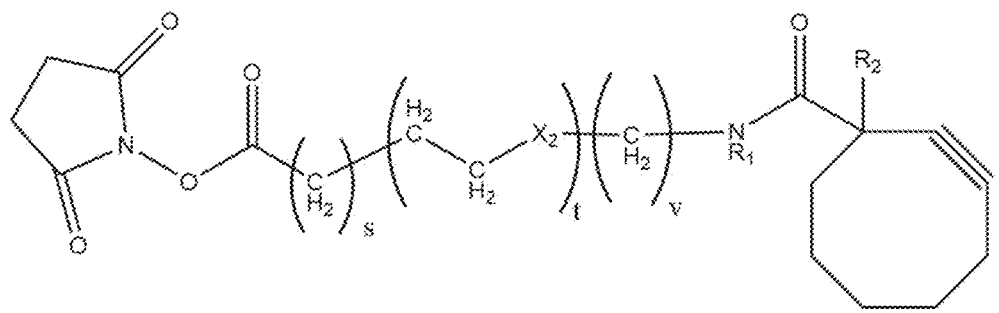
Formula (XIV)
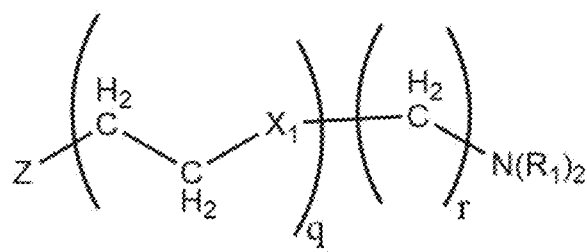
Formula (XV)
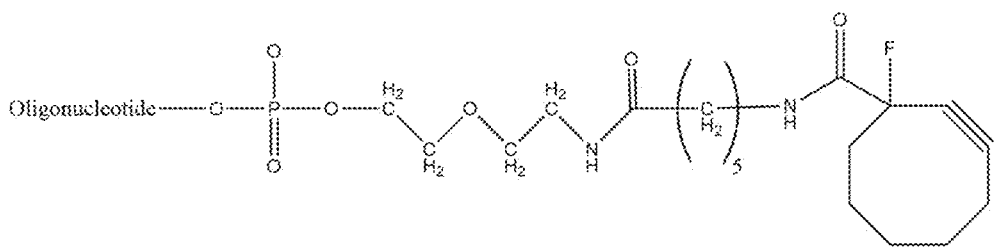
Formula (XIIa)

FIG. 28 (cont.)
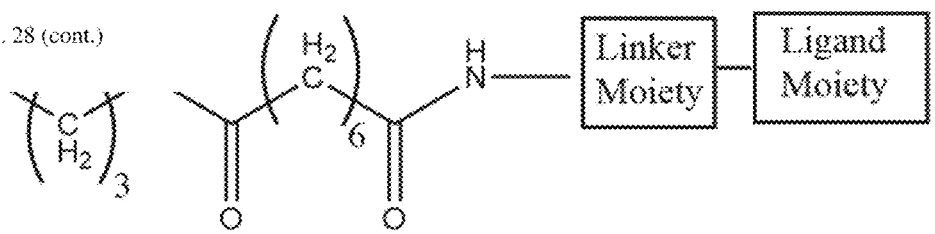
Formula (XIIIa)
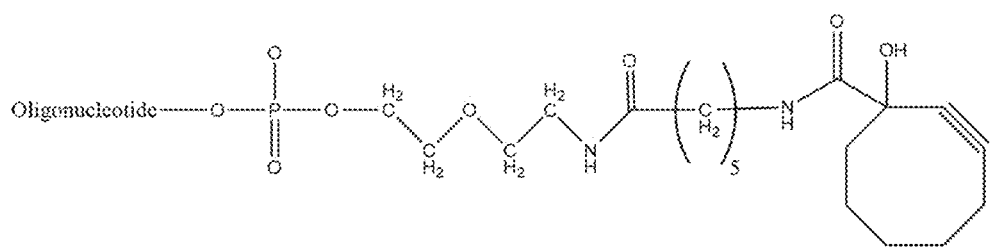
Formula (XIIb)
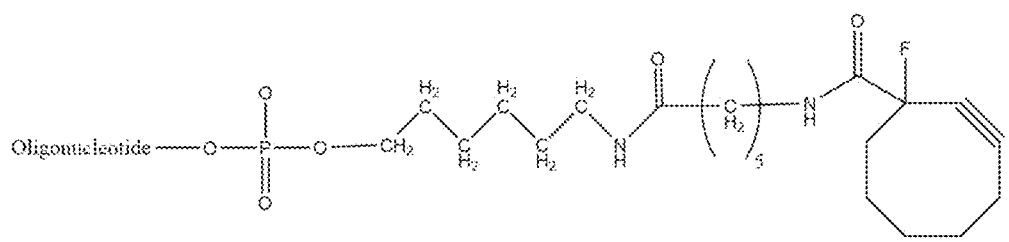
Formula (XIIc)
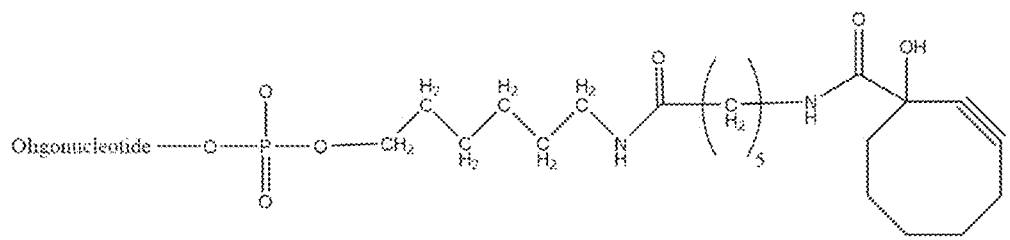
Formula (XIId)

FIG. 28 (cont.)
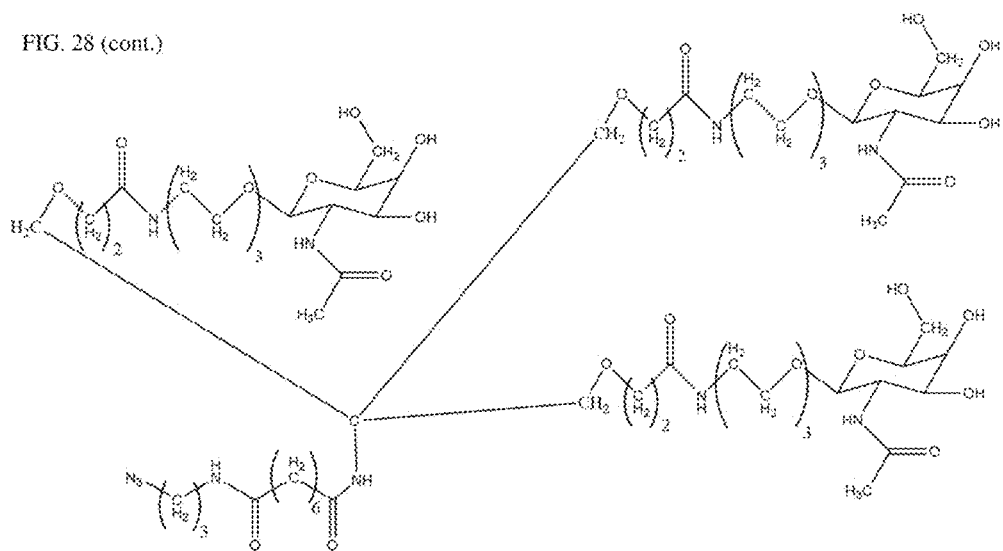
Formula (XIIIb)
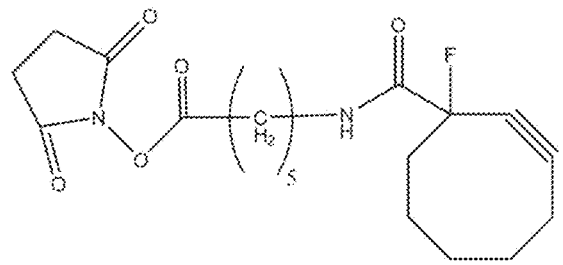
Formula (XIVa)
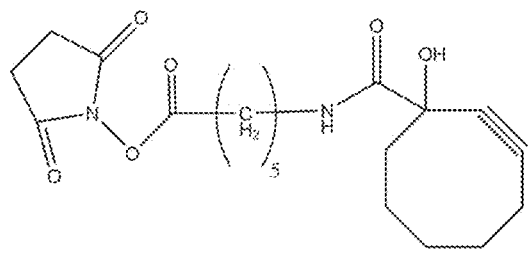
Formula (XIVb)

FIG. 28 (cont.)
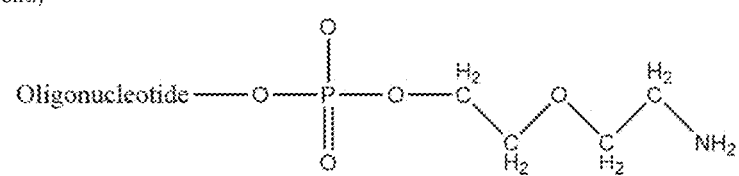
Formula (XVa)
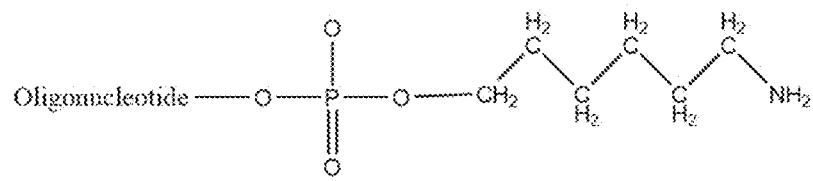
Formula (XVb)

FIG. 29A (HOA targeting constructs)

SS 5' GACUUCAUCCUGGAAAUAUA 3'
AS 3' ACGUGAAAGUAGGACCUUUAUAU 5'

FIG. 29B (HOA targeting constructs)

SS 5' GACUUCAUCCUGGAAAUAUA 3'
AS 3' ACGUGAAAGUAGGACCUUUAUAU 5'

FIG. 30A (C5 targeting constructs)

SS 5' AAGCAAGAUAUUUUAUAAUA 3'
AS 3' TTUUUCGUUCUAUAAAAUAUUAU 5'

FIG. 30B (C5 targeting constructs)

SS 5' AAGCAAGAUAUUUUAUAAUA 3'
AS 3' TTUUUCGUUCUAUAAAAUAUUAU 5'

FIG. 31A (TTR targeting constructs)

SS 5' UGGAUUUCAUGUAACCAAGA 3'
AS 3' CUACCUAAAGUACAUUGGUUCU 5'

FIG. 31B (TTR targeting constructs)

SS 5' UGGAUUUCAUGUAACCAAGA 3'
AS 3' CUACCUAAAGUACAUUGGUUCU 5'

CONJUGATED OLIGONUCLEOTIDE COMPOUNDS, METHODS OF MAKING AND USES THEREOF

CROSS REFERENCE TO RELATED APPLICATIONS

This application is Continuation of International Application No. PCT/EP2022/052067, filed internationally on Jan. 28, 2022, which claims priority to U.S. Provisional Application No. 63/143,805, filed Jan. 30, 2021, U.S. Provisional Application No. 63/262,311, filed on Oct. 8, 2021, and U.S. Provisional Application No. 63/271,686, filed on Oct. 25, 2021, the contents of each of which are incorporated herein by reference in their entireties.

REFERENCE TO AN ELECTRONIC SEQUENCE LISTING

The contents of the electronic sequence listing (228792000101substituteseglist.xml; Size: 230,685 bytes; and Date of Creation: Feb. 26, 2024) is herein incorporated by reference in its entirety.

FIELD

The present invention provides novel conjugated oligonucleotide compounds, which are suitable for therapeutic and therapeutic purposes, including SiRNA/RNAi therapeutic agents for the treatment of various diseases including central-nervous-system diseases, inflammatory diseases, metabolic disorders, oncology, infectious diseases, and ocular diseases.

Efficient delivery of oligonucleotides to cells in vivo requires specific targeting and substantial protection from the extracellular environment, particularly serum proteins. One method of achieving specific targeting is to conjugate a ligand targeting moiety to the oligonucleotide agent. The ligand targeting moiety helps delivering the oligonucleotide to the required target site. For example, attaching a ligand targeting moiety comprising a terminal galactose or derivative thereof to an oligonucleotide aids targeting to hepatocytes via binding to the asialoglycoprotein receptor (ASGPR).

There exists a need for novel, ligand-conjugated oligonucleotides, and methods for their preparation.

SUMMARY

The present invention provides novel, ligand-conjugated oligonucleotide compounds, methods of making these compounds and uses thereof.

Provided herein is a compound comprising the following structure:

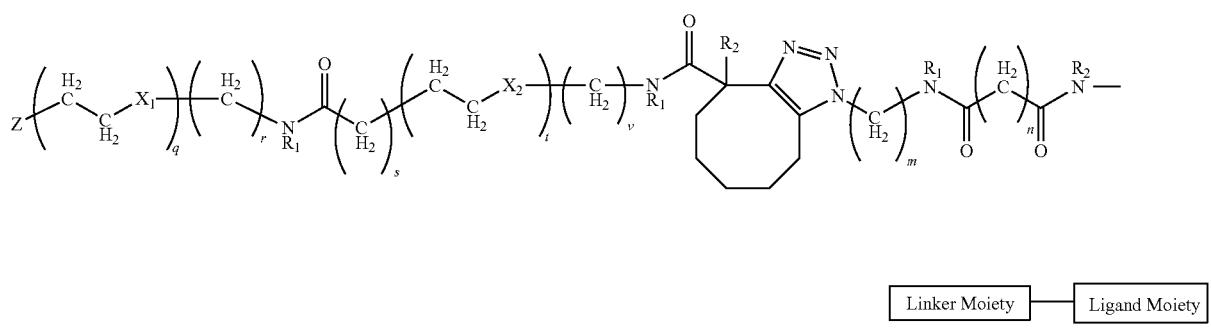

Formula (I)

wherein:

$R_1$ at each occurrence is independently selected from the group consisting of hydrogen, methyl and ethyl;

$R_2$ is selected from the group consisting of hydrogen, hydroxy, $-OC_{1-3}$alkyl, $-C(=O)OC_{1-3}$alkyl, halo and nitro;

$X_1$ and $X_2$ at each occurrence are independently selected from the group consisting of methylene, oxygen and sulfur;

m is an integer of from 1 to 6;

n is an integer of from 1 to 10;

q, r, s, t, v are independently integers from 0 to 4, with the proviso that:

(i) q and r cannot both be 0 at the same time; and (ii) s, t and v cannot all be 0 at the same time;

Z is an oligonucleotide moiety.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

A number of modified siRNA compounds in particular have been developed in the last two decades for diagnostic Provided herein is a compound of Formula (II):

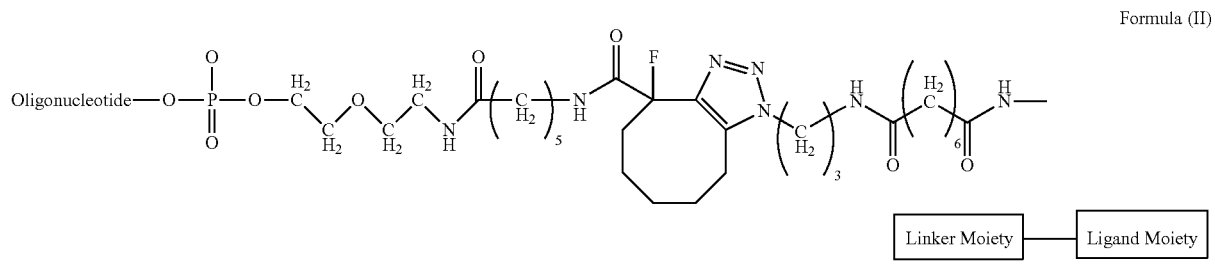

Formula (II)

Provided herein is a compound of Formula (III):

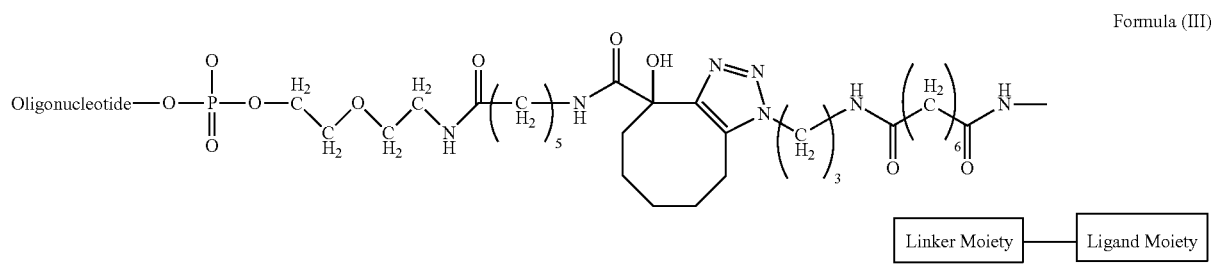

Formula (III)

Provided herein is a composition comprising a compound of Formula (II) as described anywhere herein, and a compound of Formula (III) as described anywhere herein.

Provided herein is a compound of Formula (IV):

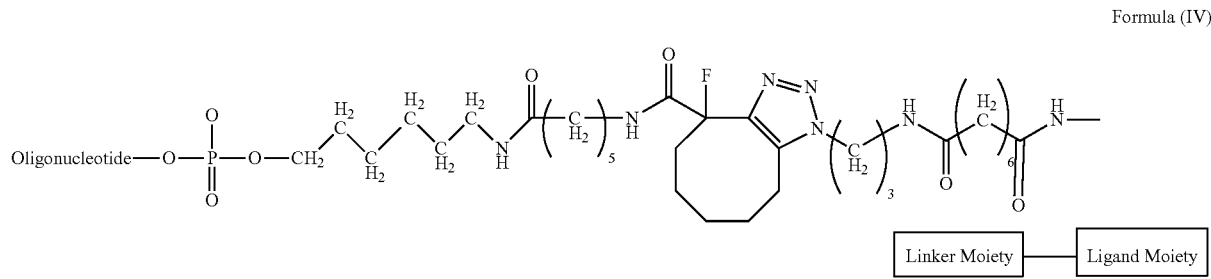

Formula (IV)

Provided herein is a compound of Formula (V):

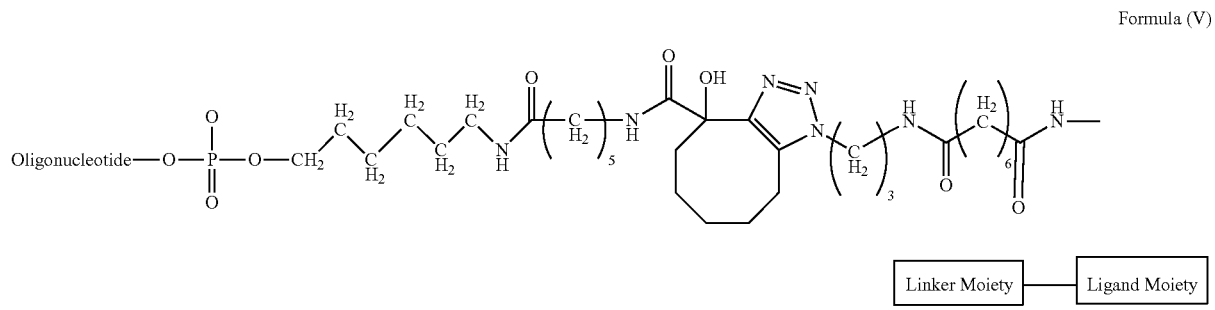

Formula (V)

Provided herein is a composition comprising a compound of Formula (IV) as described anywhere herein, and a compound of Formula (V) as described anywhere herein.

Provided herein is a compound of Formula (VIII):
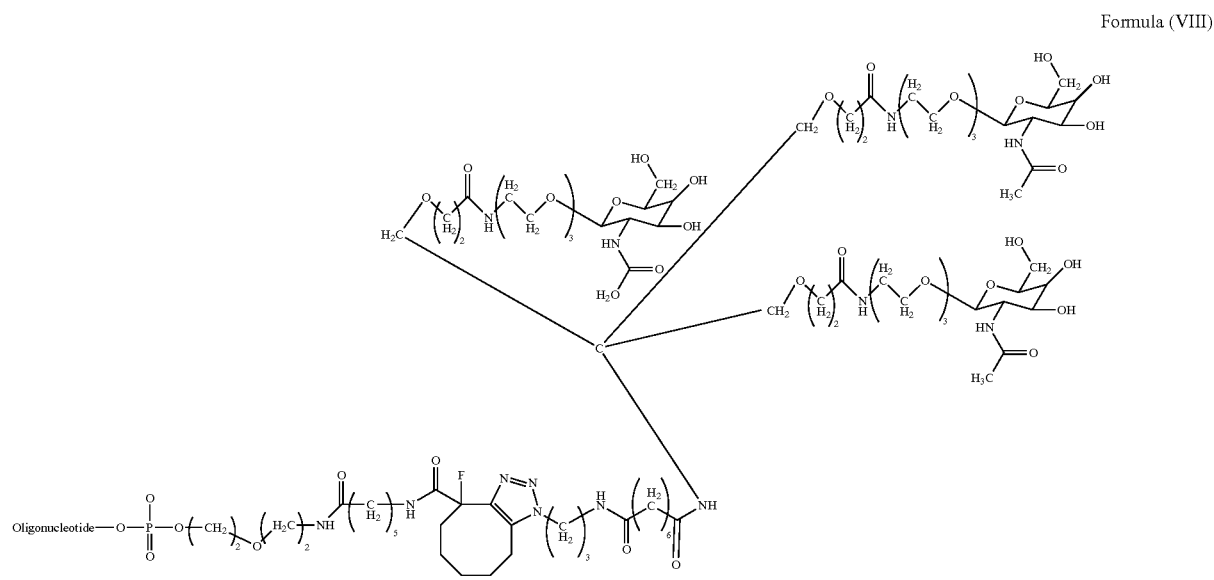
Formula (VIII)
Provided herein is a compound of Formula (IX):
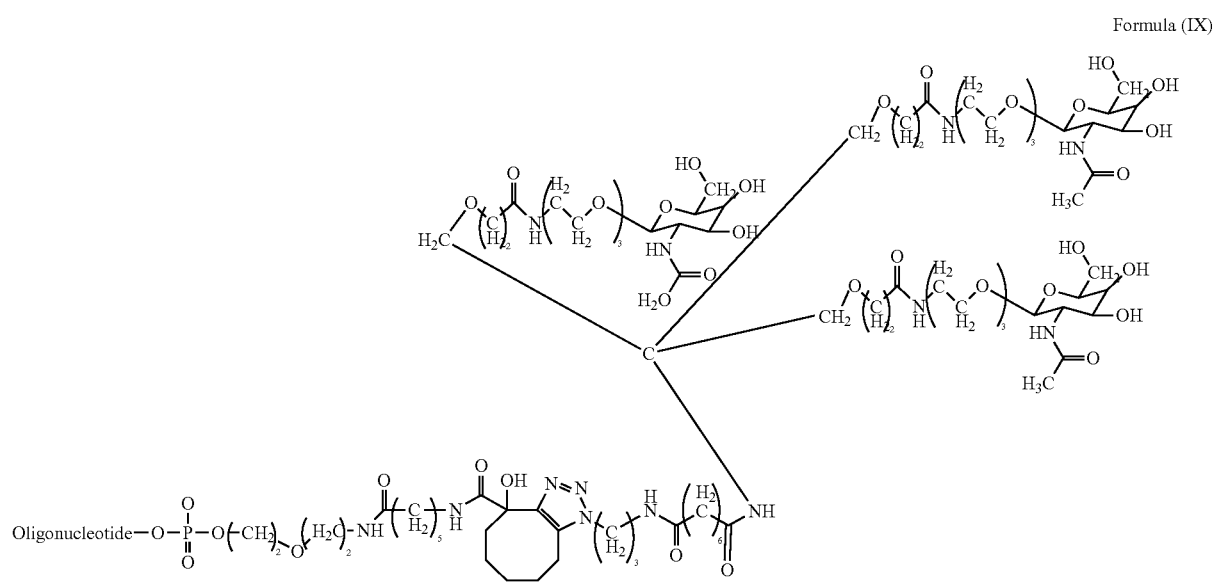
Formula (IX)

Provided herein is a compound of Formula (X):

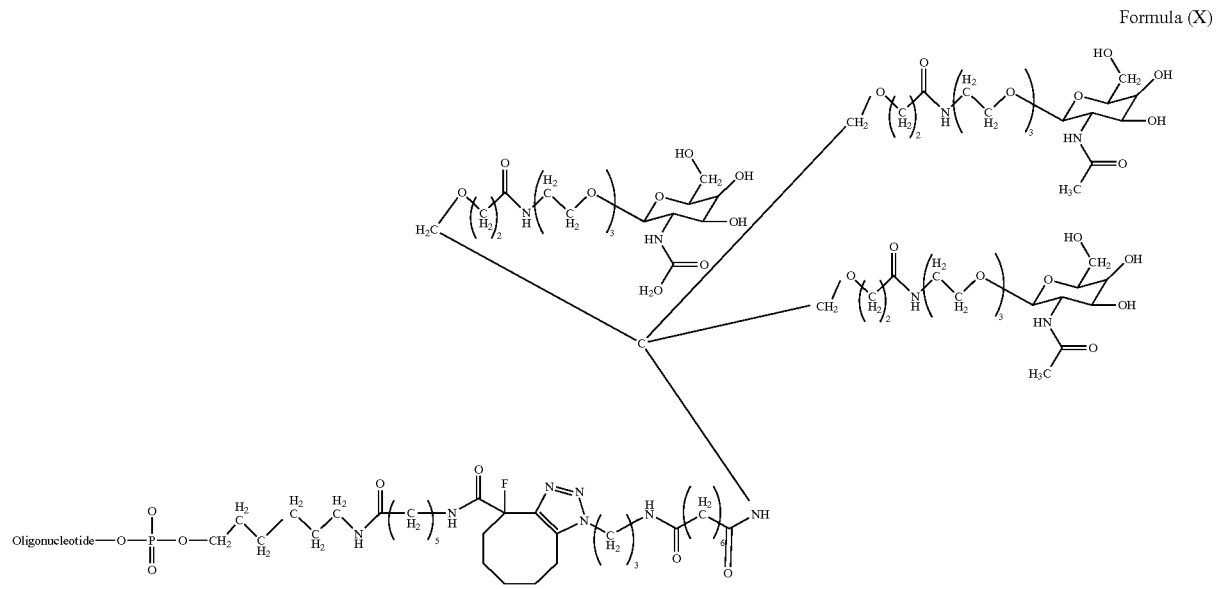

Formula (X)

Provided herein is a compound of Formula (XI):

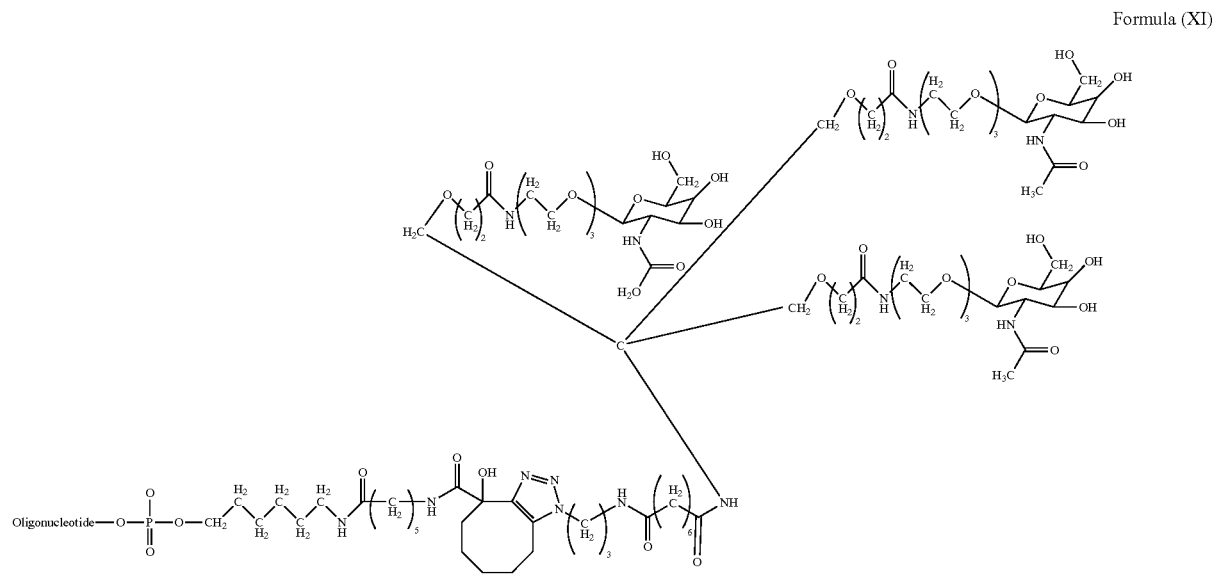

Formula (XI)

Provided herein is a composition comprising a compound of Formula (VIII) as described anywhere herein, and a compound of Formula (IX) as described anywhere herein.

Provided herein is a composition comprising a compound of Formula (X) as described anywhere herein, and a compound of Formula (XI) as described anywhere herein.

Provided herein is a process of preparing a compound as described anywhere herein, and/or a composition as described anywhere herein, which comprises reacting compounds of Formulae (XII) and (XIII):

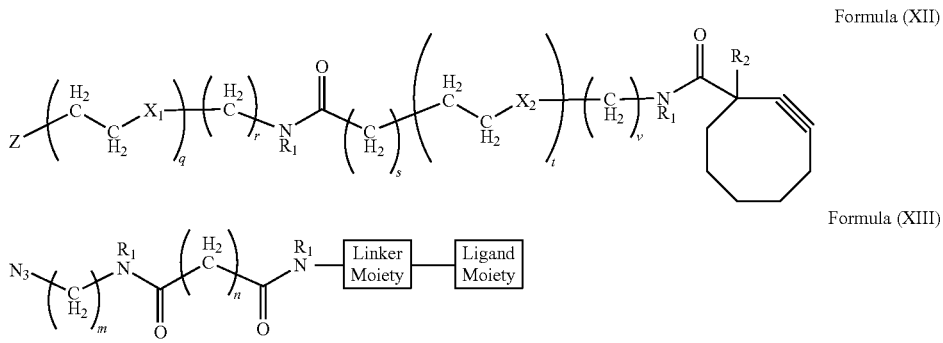

Formula (XII)

Formula (XIII)

wherein:
$R_1$ at each occurrence is independently selected from the group consisting of hydrogen, methyl and ethyl;
$R_2$ is selected from the group consisting of hydrogen, hydroxy, —$OC_{1-3}$alkyl, —$C(=O)OC_{1-3}$alkyl, halo and nitro;
$X_1$ and $X_2$ at each occurrence are independently selected from the group consisting of methylene, oxygen and sulfur;
m is an integer of from 1 to 6;
n is an integer of from 1 to 10;
q, r, s, t, v are independently integers from 0 to 4, with the proviso that:
(i) q and r cannot both be 0 at the same time; and
(ii) s, t and v cannot all be 0 at the same time; is an oligonucleotide moiety;
and where appropriate carrying out deprotection of the ligand and/or annealing of a second strand for the oligonucleotide moiety.

Provided herein is a compound of Formula (XII):

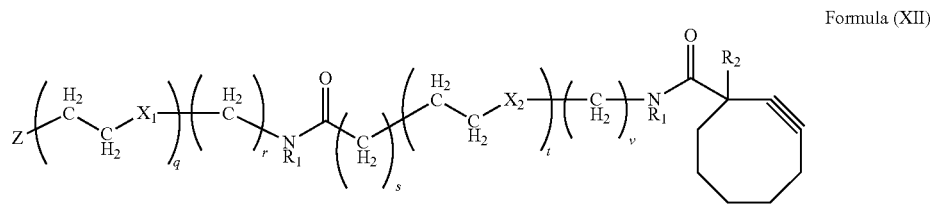

Formula (XII)

wherein:
$R_1$ at each occurrence is independently selected from the group consisting of hydrogen, methyl and ethyl;
$R_2$ is selected from the group consisting of hydrogen, hydroxy, —$OC_{1-3}$alkyl, —$C(=O)OC_{1-3}$alkyl, halo and nitro;
$X_1$ and $X_2$ at each occurrence are independently selected from the group consisting of methylene, oxygen and sulfur;
q, r, s, t, v are independently integers from 0 to 4, with the proviso that:
(i) q and r cannot both be 0 at the same time; and
(ii) s, t and v cannot all be 0 at the same time;
Z is an oligonucleotide moiety.

Provided herein is a compound of Formula (XIIa):

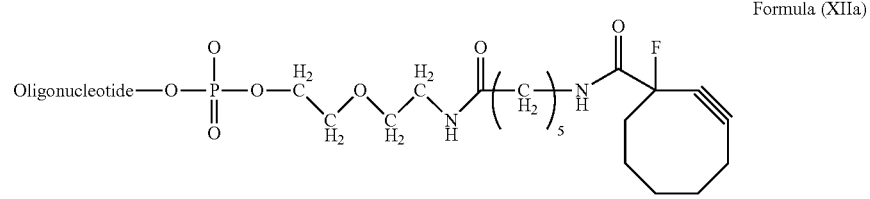

Formula (XIIa)

Provided herein is a compound of Formula (XIIb):

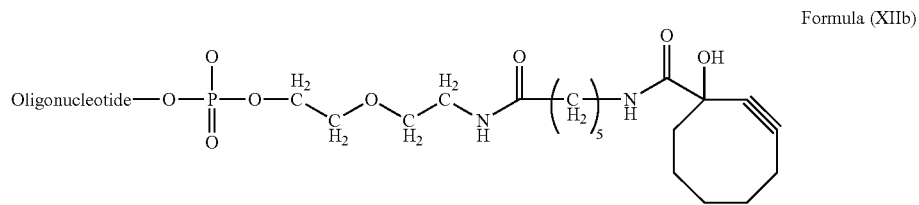

Formula (XIIb)

Provided herein is a compound of Formula (XIIc):

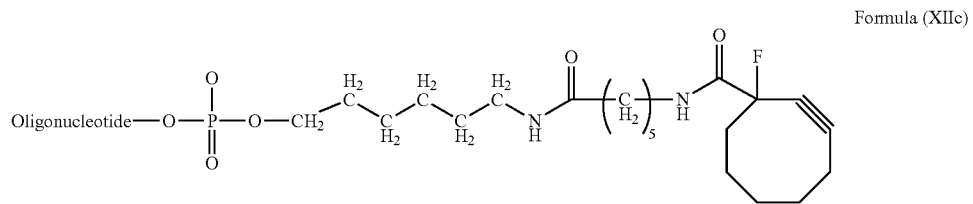

Formula (XIIc)

Provided herein is a compound of Formula (XIId):

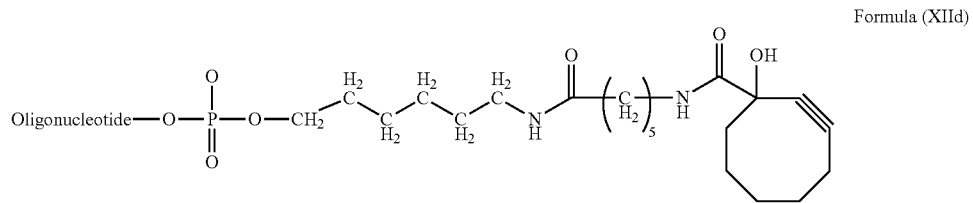

Formula (XIId)

Provided herein is a compound of Formula (XIII):

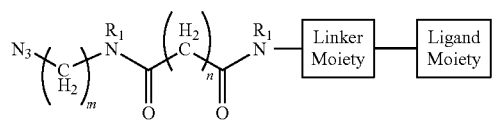

Formula (XIII)

wherein:
$R_1$ at each occurrence is independently selected from the group consisting of hydrogen, methyl and ethyl;

m is an integer of from 1 to 6;
n is an integer of from 1 to 10.

Provided herein is a compound of Formula (XIIIa):

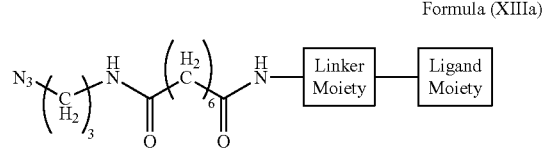

Formula (XIIIa)

Provided herein is a compound of Formula (XIIIb):

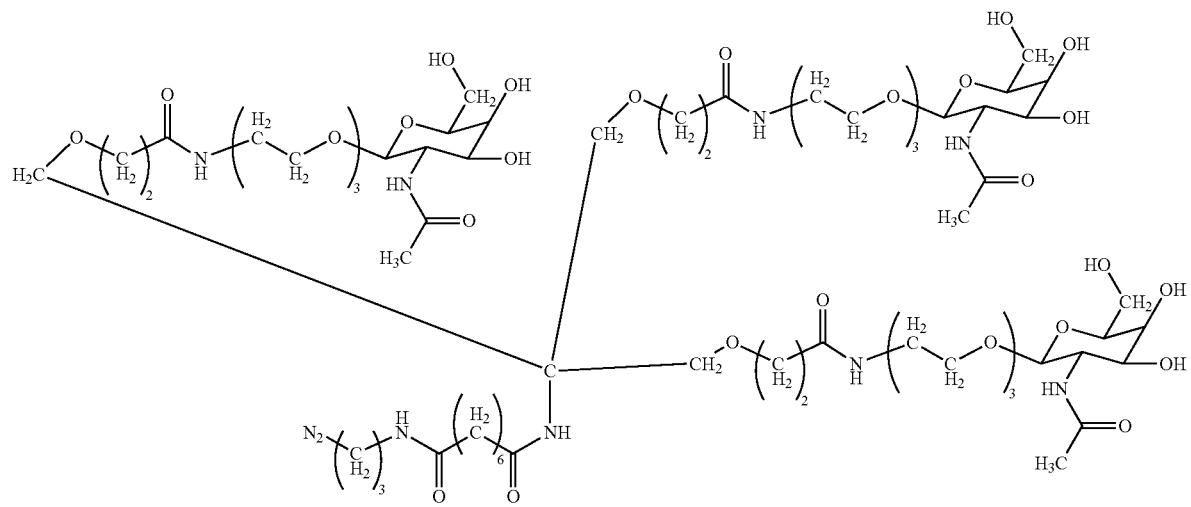

Formula (XIIIb)

Provided herein is a compound of Formula (XIV):

Formula (XIV)

wherein:

$R_1$ is selected from the group consisting of hydrogen, methyl and ethyl;

$R_2$ is selected from the group consisting of hydrogen, hydroxy, —$OC_{1-3}$alkyl, —$C(=O)OC_{1-3}$alkyl, halo and nitro;

$X_2$ is selected from the group consisting of methylene, oxygen and sulfur;

s, t, v are independently integers from 0 to 4, with the proviso that s, t and v cannot all be 0 at the same time.

Provided herein is a compound of Formula (XIVa):

Formula (XIVa)

Provided herein is a compound of Formula (XIVb):

Formula (XIVb)

Provided herein is a compound of Formula (XV):

Formula (XV)

wherein:

$R_1$ at each occurrence is independently selected from the group consisting of hydrogen, methyl and ethyl;

$X_1$ is selected from the group consisting of methylene, oxygen and sulfur;

q and r are independently integers from 0 to 4, with the proviso that q and r cannot both be 0 at the same time;

Z is an oligonucleotide moiety.

Provided herein is a compound of Formula (XVa):

Formula (XVa)

Provided herein is a compound of Formula (XVb):

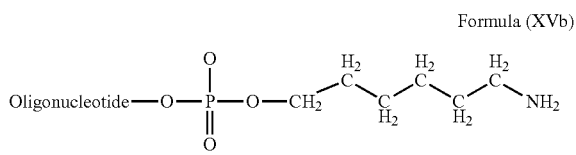

Formula (XVb)

Provided herein is use of a compound as described anywhere herein, for the preparation of a compound as described anywhere herein, and/or a composition as described anywhere herein.

Provided herein is use of a compound of Formula (XII) as described anywhere herein, for the preparation of a compound as described anywhere herein, and/or a composition as described anywhere herein.

Provided herein is use of a compound of Formula (XIII) as described anywhere herein, for the preparation of a compound as described anywhere herein, and/or a composition as described anywhere herein.

Provided herein is use of a compound of Formula (XIV) as described anywhere herein, for the preparation of a compound as described anywhere herein, and/or a composition as described anywhere herein.

Provided herein is use of a compound of Formula (XV) as described anywhere herein, for the preparation of a compound as described anywhere herein, and/or a composition as described anywhere herein.

Provided herein is use of a compound of Formula (XIIa) as described anywhere herein, for the preparation of a compound as described anywhere herein, and/or a composition as described anywhere herein.

Provided herein is use of a compound of Formula (XIIb) as described anywhere herein, for the preparation of a compound as described anywhere herein, and/or a composition as described anywhere herein.

Provided herein is use of a compound of Formula (XIIc) as described anywhere herein, for the preparation of a compound as described anywhere herein, and/or a composition as described anywhere herein.

Provided herein is use of a compound of Formula (XIId) as described anywhere herein, for the preparation of a compound as described anywhere herein, and/or a composition as described anywhere herein.

Provided herein is use of a compound of Formula (XIIIa) as described anywhere herein, for the preparation of a compound as described anywhere herein, and/or a composition as described anywhere herein.

Provided herein is use of a compound of Formula (XIIIb) as described anywhere herein, for the preparation of a compound as described anywhere herein, and/or a composition as described anywhere herein.

Provided herein is use of a compound of Formula (XIVa) as described anywhere herein, for the preparation of a compound as described anywhere herein, and/or a composition as described anywhere herein.

Provided herein is use of a compound of Formula (XIVb) as described anywhere herein, for the preparation of a compound as described anywhere herein, and/or a composition as described anywhere herein.

Provided herein is use of a compound of Formula (XVa) as described anywhere herein, for the preparation of a compound as described anywhere herein, and/or a composition as described anywhere herein.

Provided herein is use of a compound of Formula (XVb) as described anywhere herein, for the preparation of a compound as described anywhere herein, and/or a composition as described anywhere herein.

Provided herein is a compound or composition obtained, or obtainable by a process as described anywhere herein.

Provided herein is a pharmaceutical composition comprising of a compound as described anywhere herein, and/or a composition as described anywhere herein, together with a pharmaceutically acceptable carrier, diluent or excipient.

Provided herein is a compound as described anywhere herein, and/or a composition as described anywhere herein, for use in therapy.

Figure 20:
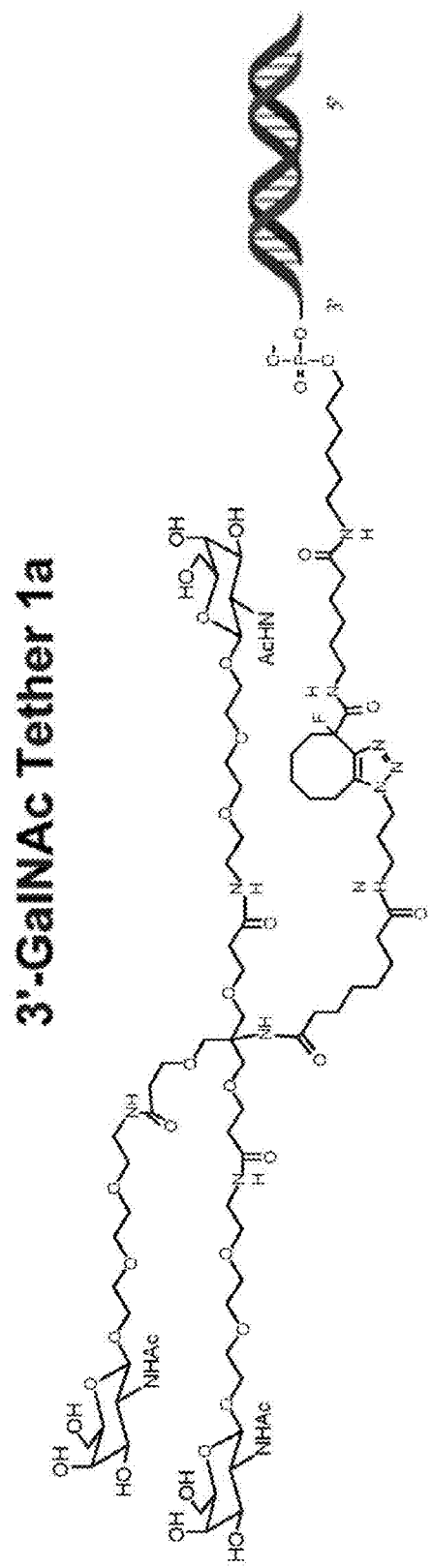
FIG. 20. Linker and ligand moiety for ETX005, 007, 0014, 0016, 0023 and 0025.

It should also be understood that where appropriate while ETX005 as a product includes molecules based on the linker and ligand portions as specifically depicted in FIG. 20 attached to an oligonucleotide moiety as also depicted herein, this ETX005 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX005 can consist essentially of molecules having linker and ligand portions specifically as depicted in FIG. 20, with a F substituent on the cyclo-octyl ring; or (b) ETX005 can consist essentially of molecules having linker and ligand portions essentially as depicted in FIG. 20 but having the F substituent as shown in FIG. 20 on the cyclo-octyl ring replaced by a substituent occurring as a result of hydrolytic displacement, such as an OH substituent, or (c) ETX005 can comprise a mixture of molecules as defined in (a) and/or (b).

It should also be understood that where appropriate while ETX007 as a product includes molecules based on the linker and ligand portions as specifically depicted in FIG. 20 attached to an oligonucleotide moiety as also depicted herein, this ETX007 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX007 can consist essentially of molecules having linker and ligand portions specifically as depicted in FIG. 20, with a F substituent on the cyclo-octyl ring; or (b) ETX007 can consist essentially of molecules having linker and ligand portions essentially as depicted in FIG. 20 but having the F substituent as shown in FIG. 20 on the cyclo-octyl ring replaced by a substituent occurring as a result of hydrolytic displacement, such as an OH substituent, or (c) ETX007 can comprise a mixture of molecules as defined in (a) and/or (b).

It should also be understood that where appropriate while ETX014 as a product includes molecules based on the linker and ligand portions as specifically depicted in FIG. 20 attached to an oligonucleotide moiety as also depicted herein, this ETX014 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX014 can consist essentially of molecules having linker and ligand portions specifically as depicted in FIG. 20, with a F substituent on the cyclo-octyl ring; or (b) ETX014 can consist essentially of molecules having linker and ligand portions essentially as depicted in FIG. 20 but having the F substituent as shown in FIG. 20 on the cyclo-octyl ring replaced by a substituent occurring as a result of hydrolytic displacement, such as an OH substituent, or (c) ETX014 can comprise a mixture of molecules as defined in (a) and/or (b).

It should also be understood that where appropriate while ETX016 as a product includes molecules based on the linker and ligand portions as specifically depicted in FIG. 20 attached to an oligonucleotide moiety as also depicted herein, this ETX016 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX016 can consist essentially of molecules having linker and ligand portions specifically as depicted in FIG. 20, with a F substituent on the cyclo-octyl ring; or (b) ETX016 can consist essentially of molecules having linker and ligand portions essentially as depicted in FIG. 20 but having the F substituent as shown in FIG. 20 on the cyclo-octyl ring replaced by a substituent occurring as a result of hydrolytic displacement, such as an OH substituent, or (c) ETX016 can comprise a mixture of molecules as defined in (a) and/or (b).

It should also be understood that where appropriate while ETX023 as a product includes molecules based on the linker and ligand portions as specifically depicted in FIG. 20 attached to an oligonucleotide moiety as also depicted herein, this ETX023 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX023 can consist essentially of molecules having linker and ligand portions specifically as depicted in FIG. 20, with a F substituent on the cyclo-octyl ring; or (b) ETX023 can consist essentially of molecules having linker and ligand portions essentially as depicted in FIG. 20 but having the F substituent as shown in FIG. 20 on the cyclo-octyl ring replaced by a substituent occurring as a result of hydrolytic displacement, such as an OH substituent, or (c) ETX023 can comprise a mixture of molecules as defined in (a) and/or (b).

It should also be understood that where appropriate while ETX025 as a product includes molecules based on the linker and ligand portions as specifically depicted in FIG. 20 attached to an oligonucleotide moiety as also depicted herein, this ETX025 product may alternatively further comprise, or consist essentially of, molecules wherein the linker and ligand portions are essentially as depicted in FIG. 20 attached to an oligonucleotide moiety but having the F substituent as shown in FIG. 20 on the cyclo-octyl ring replaced by a substituent occurring as a result of hydrolytic displacement, such as an OH substituent. In this way, (a) ETX025 can consist essentially of molecules having linker and ligand portions specifically as depicted in FIG. 20, with a F substituent on the cyclo-octyl ring; or (b) ETX025 can consist essentially of molecules having linker and ligand portions essentially as depicted in FIGS. 30A-30B but having the F substituent as shown in FIG. 20 on the cyclo-octyl ring replaced by a substituent occurring as a result of hydrolytic displacement, such as an OH substituent, or (c) ETX025 can comprise a mixture of molecules as defined in (a) and/or (b).

Figure 21:
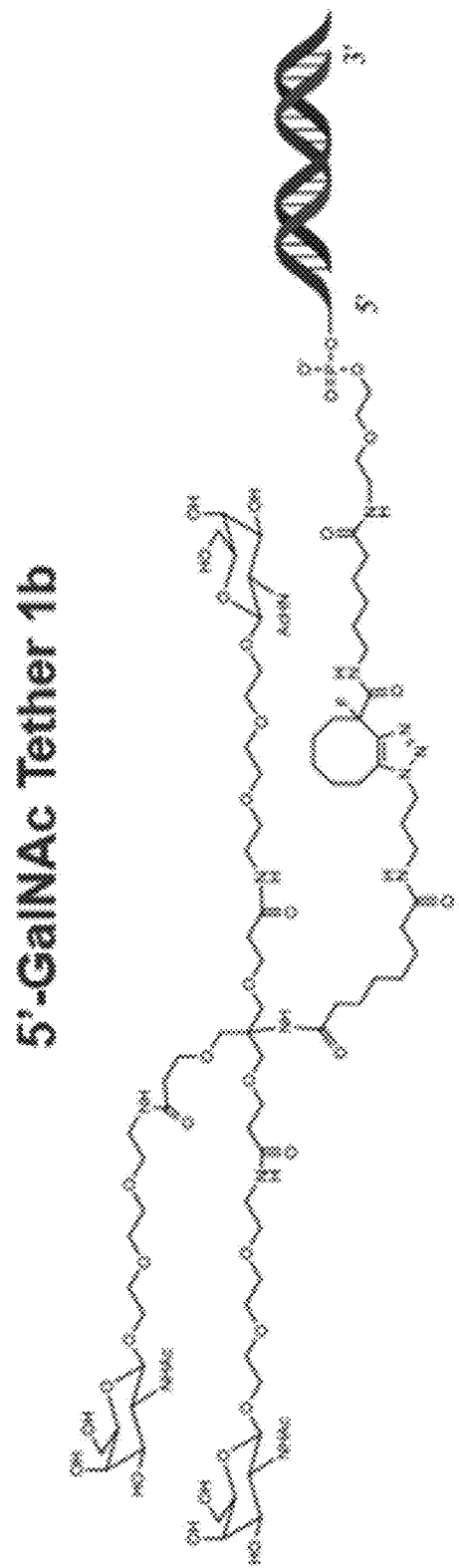

FIG. 21. Linker and ligand moiety for ETX003, 001, 0010, 0012, 0019 and 0021.

It should also be understood that where appropriate while ETX001 as a product includes molecules based on the linker and ligand portions as specifically depicted in FIG. 21 attached to an oligonucleotide moiety as also depicted herein, this ETX001 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX001 can consist essentially of molecules having linker and ligand portions specifically as depicted in FIG. 21, with a F substituent on the cyclo-octyl ring; or (b) ETX001 can consist essentially of molecules having linker and ligand portions essentially as depicted in FIG. 21 but having the F substituent as shown in FIG. 21 on the cyclo-octyl ring replaced by a substituent occurring as a result of hydrolytic displacement, such as an OH substituent, or (c) ETX001 can comprise a mixture of molecules as defined in (a) and/or (b).

It should also be understood that where appropriate while ETX003 as a product includes molecules based on the linker and ligand portions as specifically depicted in FIG. 21 attached to an oligonucleotide moiety as also depicted herein, this ETX003 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX003 can consist essentially of molecules having linker and ligand portions specifically as depicted in FIG. 21, with a F substituent on the cyclo-octyl ring; or (b) ETX003 can consist essentially of molecules having linker and ligand portions essentially as depicted in FIG. 21 but having the F substituent as shown in FIG. 21 on the cyclo-octyl ring replaced by a substituent occurring as a result of hydrolytic displacement, such as an OH substituent, or (c) ETX003 can comprise a mixture of molecules as defined in (a) and/or (b).

It should also be understood that where appropriate while ETX010 as a product includes molecules based on the linker and ligand portions as specifically depicted in FIG. 21 attached to an oligonucleotide moiety as also depicted herein, this ETX010 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX010 can consist essentially of molecules having linker and ligand portions specifically as depicted in FIG. 21, with a F substituent on the cyclo-octyl ring; or (b) ETX010 can consist essentially of molecules having linker and ligand portions essentially as depicted in FIG. 21 but having the F substituent as shown in FIG. 21 on the cyclo-octyl ring replaced by a substituent occurring as a result of hydrolytic displacement, such as an OH substituent, or (c) ETX010 can comprise a mixture of molecules as defined in (a) and/or (b).

It should also be understood that where appropriate while ETX012 as a product includes molecules based on the linker and ligand portions as specifically depicted in FIG. 21 attached to an oligonucleotide moiety as also depicted herein, this ETX012 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX012 can consist essentially of molecules having linker and ligand portions specifically as depicted in FIG. 21, with a F substituent on the cyclo-octyl ring; or (b) ETX012 can consist essentially of molecules having linker and ligand portions essentially as depicted in FIG. 21 but having the F substituent as shown in FIG. 21 on the cyclo-octyl ring replaced by a substituent occurring as a result of hydrolytic displacement, such as an OH substituent, or (c) ETX012 can comprise a mixture of molecules as defined in (a) and/or (b).

It should also be understood that where appropriate while ETX019 as a product includes molecules based on the linker and ligand portions as specifically depicted in FIG. 21 attached to an oligonucleotide moiety as also depicted herein, this ETX019 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX019 can consist essentially of molecules having linker and ligand portions specifically as depicted in FIG. 21, with a F substituent on the cyclo-octyl ring; or (b) ETX019 can consist essentially of molecules having linker and ligand portions essentially as depicted in FIGS. 30A-30B but having the F substituent as shown in FIG. 21 on the cyclo-octyl ring replaced by a substituent occurring as a result of hydrolytic displacement, such as an OH substituent, or (c) ETX019 can comprise a mixture of molecules as defined in (a) and/or (b).

It should also be understood that where appropriate while ETX021 as a product includes molecules based on the linker and ligand portions as specifically depicted in FIG. 21 attached to an oligonucleotide moiety as also depicted herein, this ETX021 product may alternatively further comprise, or consist essentially of, molecules wherein the linker and ligand portions are essentially as depicted in FIG. 21 attached to an oligonucleotide moiety but having the F substituent as shown in FIG. 21 on the cyclo-octyl ring replaced by a substituent occurring as a result of hydrolytic displacement, such as an OH substituent. In this way, (a) ETX021 can consist essentially of molecules having linker and ligand portions specifically as depicted in FIG. 21, with a F substituent on the cyclo-octyl ring; or (b) ETX021 can consist essentially of molecules having linker and ligand portions essentially as depicted in FIG. 21 but having the F substituent as shown in FIG. 21 on the cyclo-octyl ring replaced by a substituent occurring as a result of hydrolytic displacement, such as an OH substituent, or (c) ETX021 can comprise a mixture of molecules as defined in (a) and/or (b).

Figure 22:
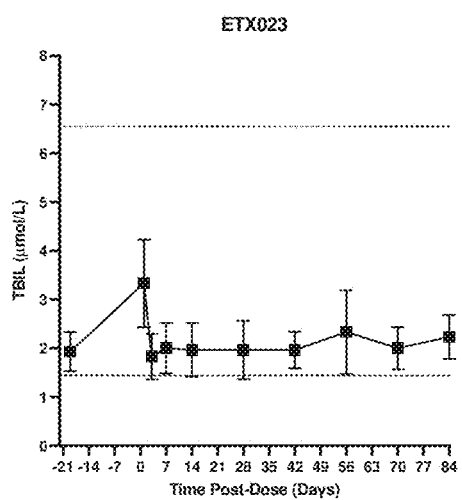

FIG. 22. Total bilirubin concentration in serum from animals treated with a single 1 mg/kg dose of ETX023. Each point represents the mean and standard deviation of 3 animals. The dotted lines show the range of values considered normal for this species (Park et al. 2016 Reference values of clinical pathology parameter in cynomolgus monkeys used in preclinical studies. Lab Anim Res 32:79-86.)

Figure 23:
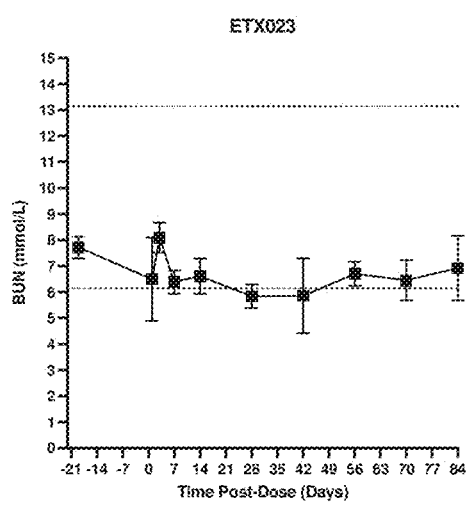

FIG. 23. Blood urea nitrogen (BUN) concentration from animals treated with a single 1 mg/kg dose of ETX023. Each point represents the mean and standard deviation of 3 animals. The dotted lines show the range of values considered normal for this species (Park et al. 2016 Reference values of clinical pathology parameter in cynomolgus monkeys used in preclinical studies. Lab Anim Res 32:79-86.)

Figure 24:
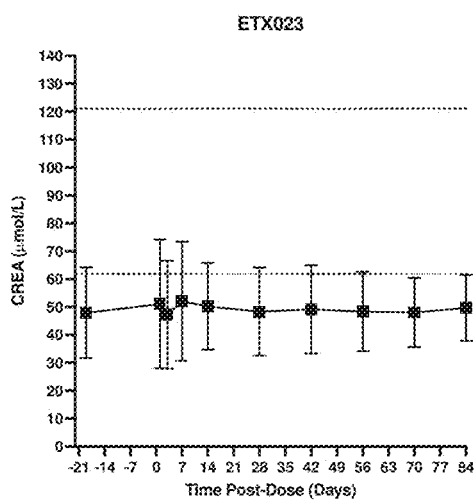

FIG. 24. Creatinine (CREA) concentration from animals treated with a single 1 mg/kg dose of ETX023. Each point represents the mean and standard deviation of 3 animals. The dotted lines show the range of values considered normal for this species (Park et al. 2016 Reference values of clinical pathology parameter in cynomolgus monkeys used in preclinical studies. Lab Anim Res 32:79-86.)

Figure 25A:
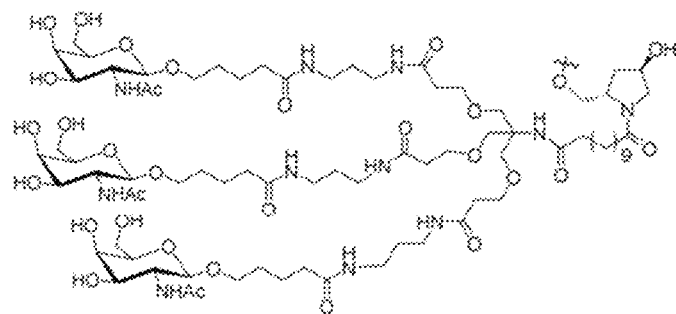
Figure 25B:
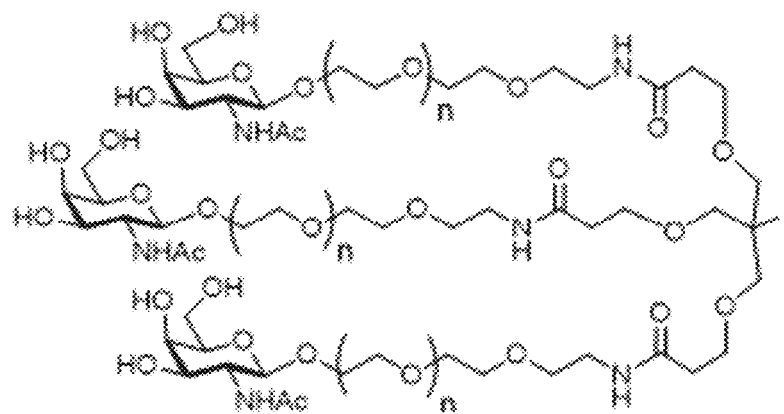
Figure 26A:
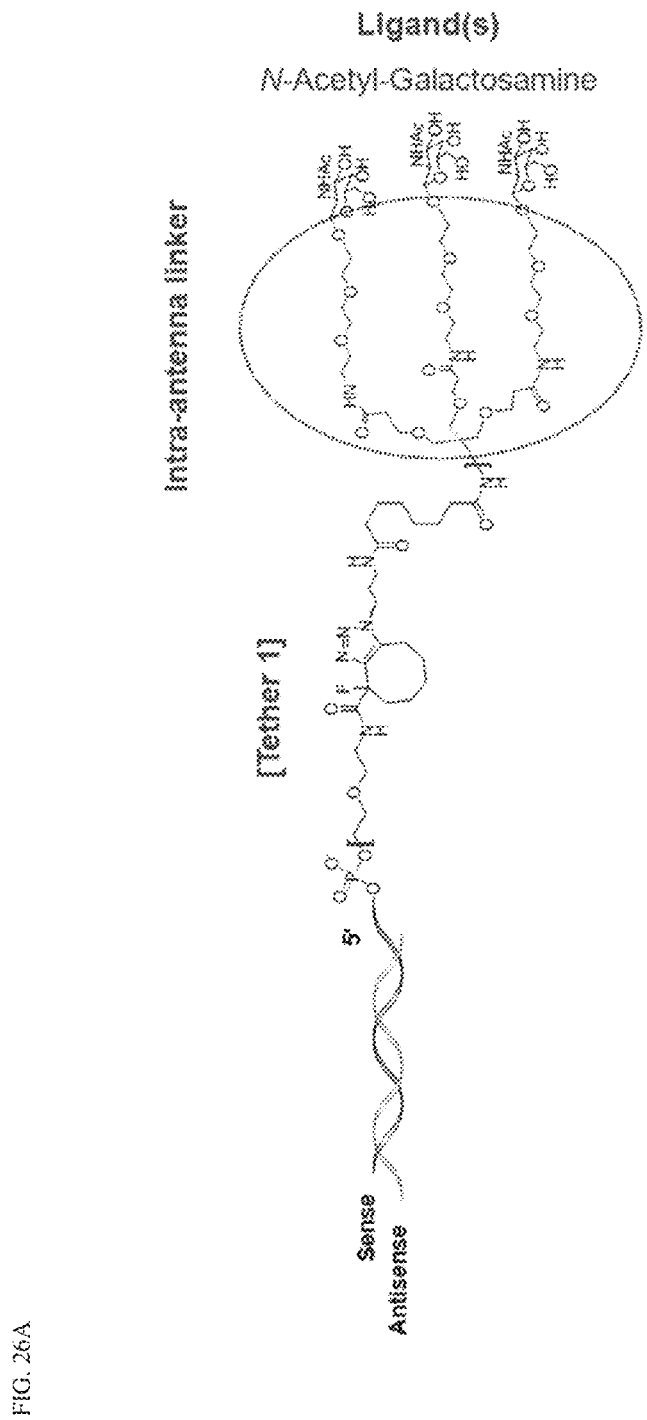
Figure 26B:
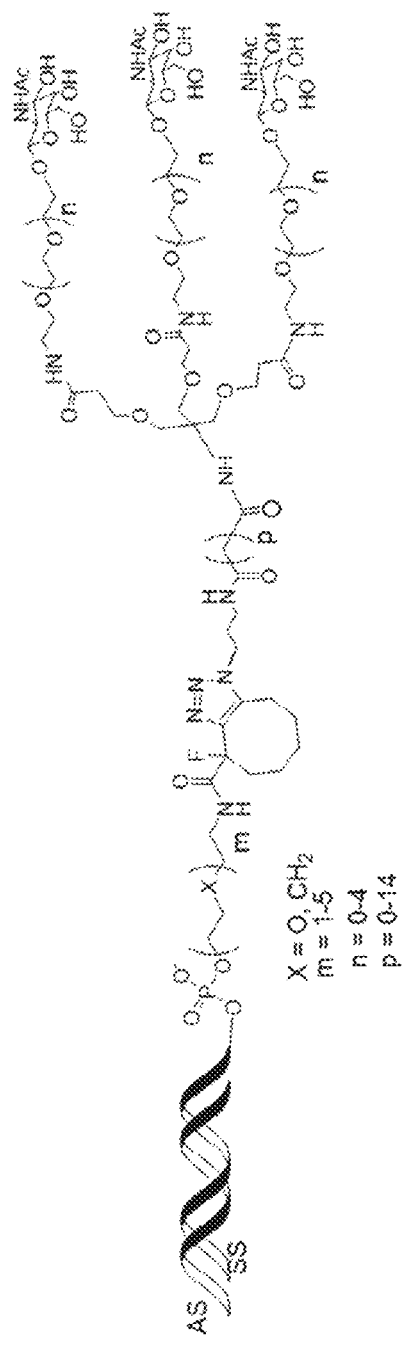
Figure 26C:
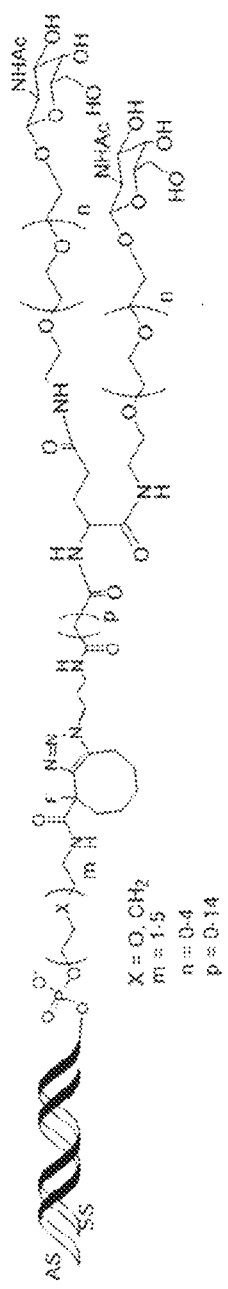
Figure 26D:
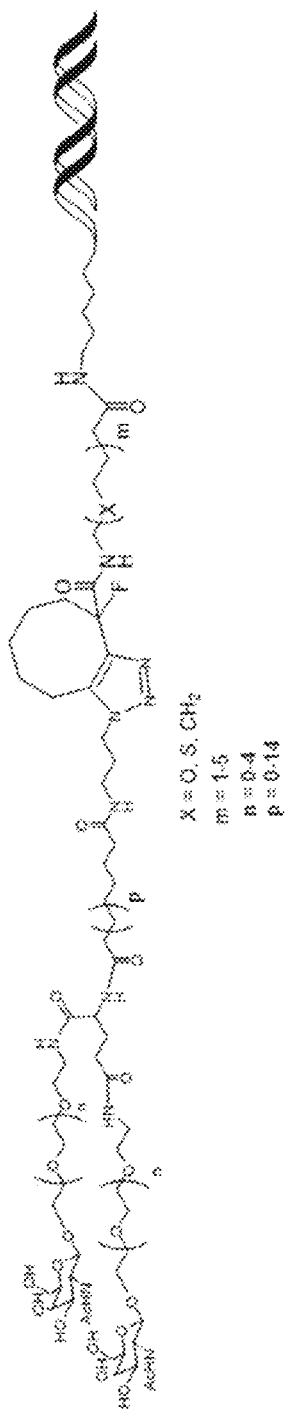
Figure 27A:
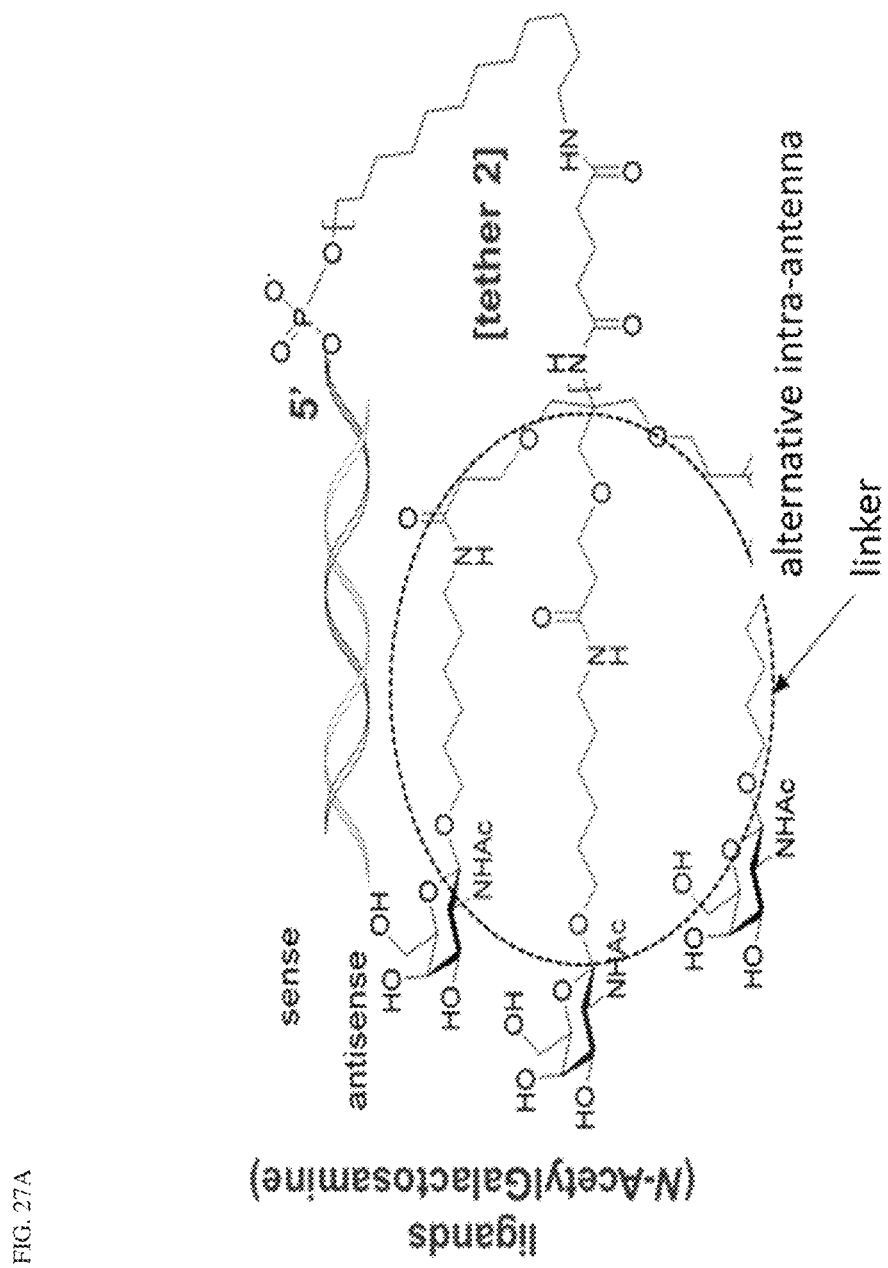
Figure 27B:
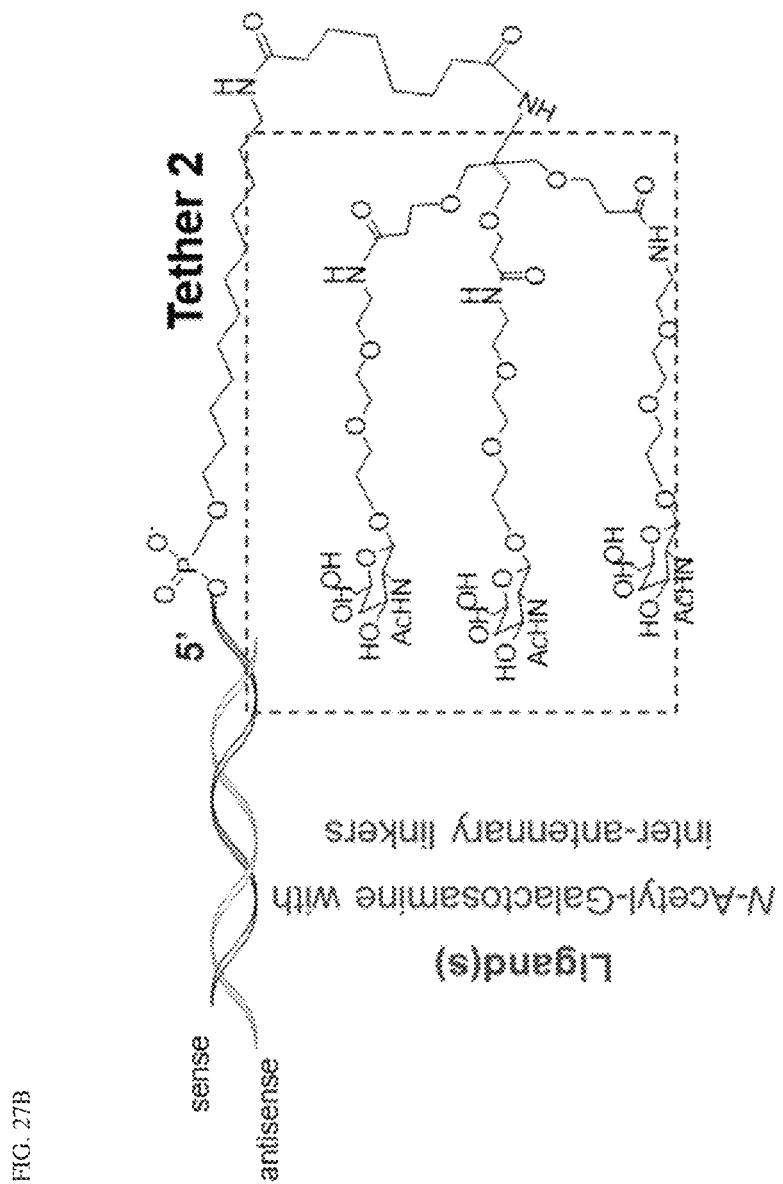
Figure 27C:
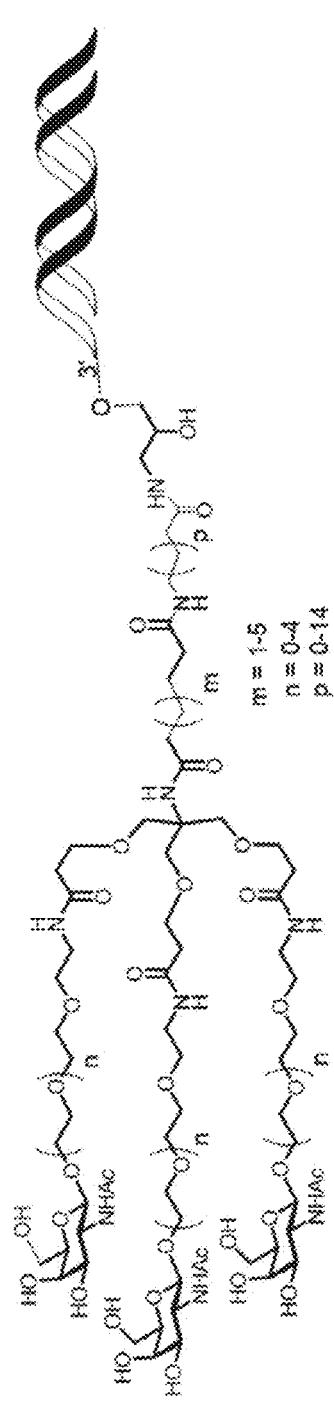
Figure 27D:
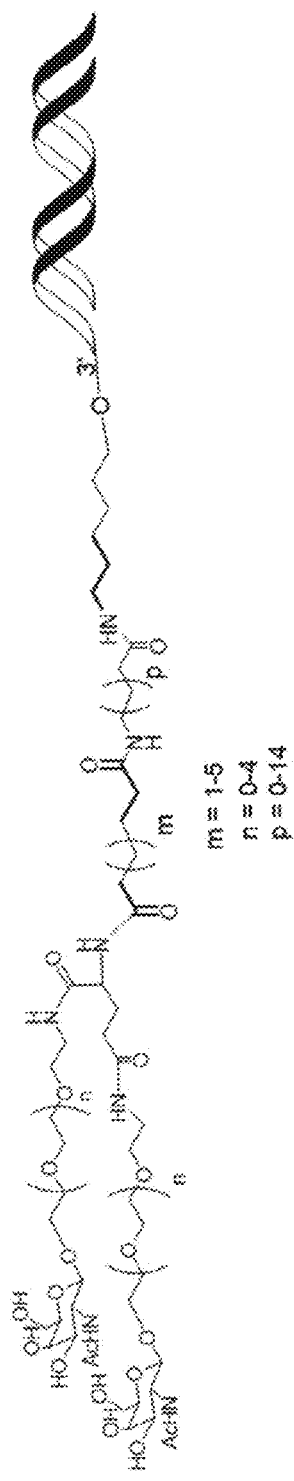

FIG. 25A depicts a tri-antennary GalNAc (N-acetylgalactosamine) unit. FIG. 25B depicts an alternative tri-antennary GalNAc according to one embodiment of the invention, showing variance in linking groups. FIG. 26A depicts tri-antennary GalNAc-conjugated siRNA according to the invention, showing variance in the linking groups. FIG. 26B depicts a genera of tri-antennary GalNAc-conjugated siRNAs according to one embodiment of the invention. FIG. 26C depicts a genera of bi-antennary GalNAc-conjugated siRNAs according to one embodiment of the invention, showing variance in the linking groups. FIG. 26D depicts a genera of bi-antennary GalNAc-conjugated siRNAs according to another embodiment of the invention, showing variance in the linking groups. FIG. 27A depicts another embodiment of the tri-antennary GalNAc-conjugated siRNA according to one embodiment of the invention. FIG. 27B depicts a variant shown in FIG. 27A, having an alternative branching GalNAc conjugate. FIG. 27C depicts a genera of tri-antennary GalNAc-conjugated siRNAs according to one embodiment of the invention, showing variance in the linking groups. FIG. 27D depicts a genera of bi-antennary GalNAc-conjugated siRNAs according to one embodiment the invention, showing variance in the linking groups.

Figure 28:
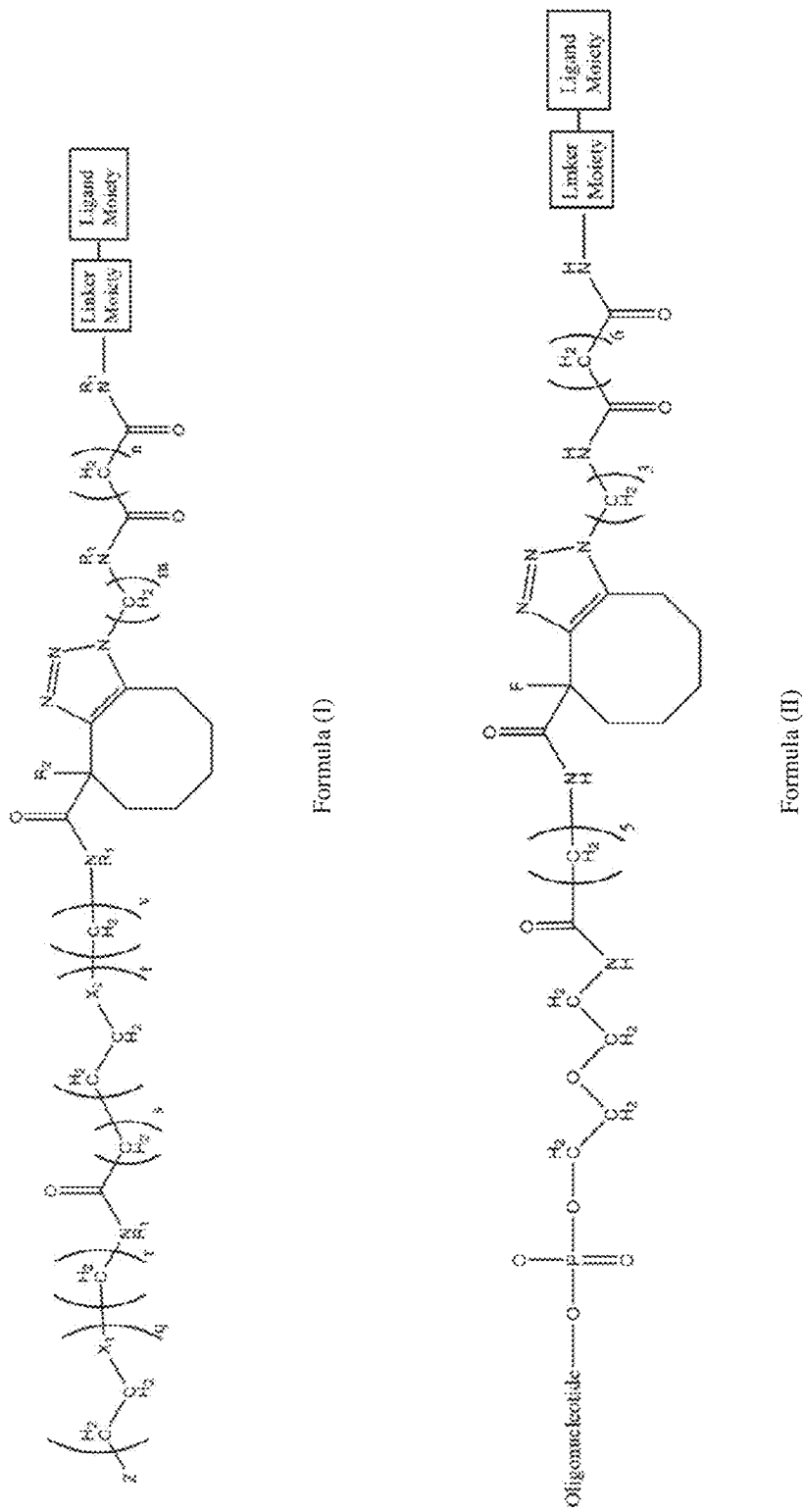
Figure 28:
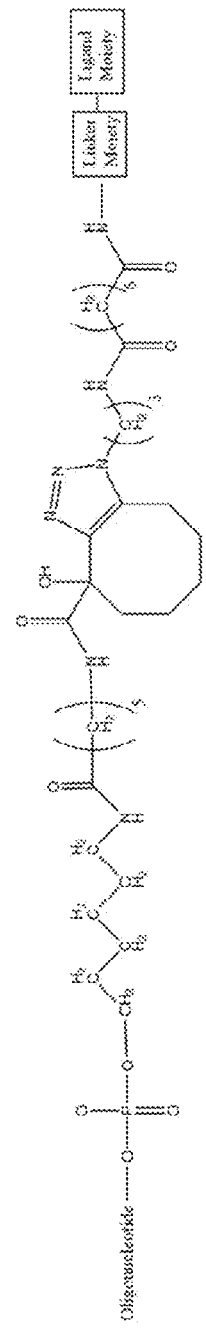
Figure 28:
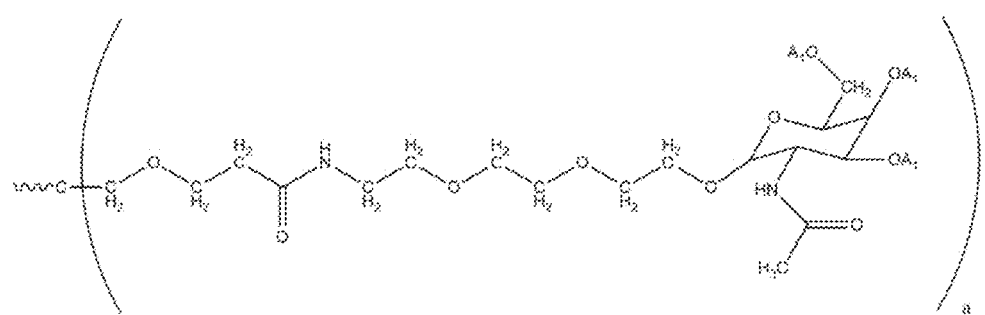
Figure 28:
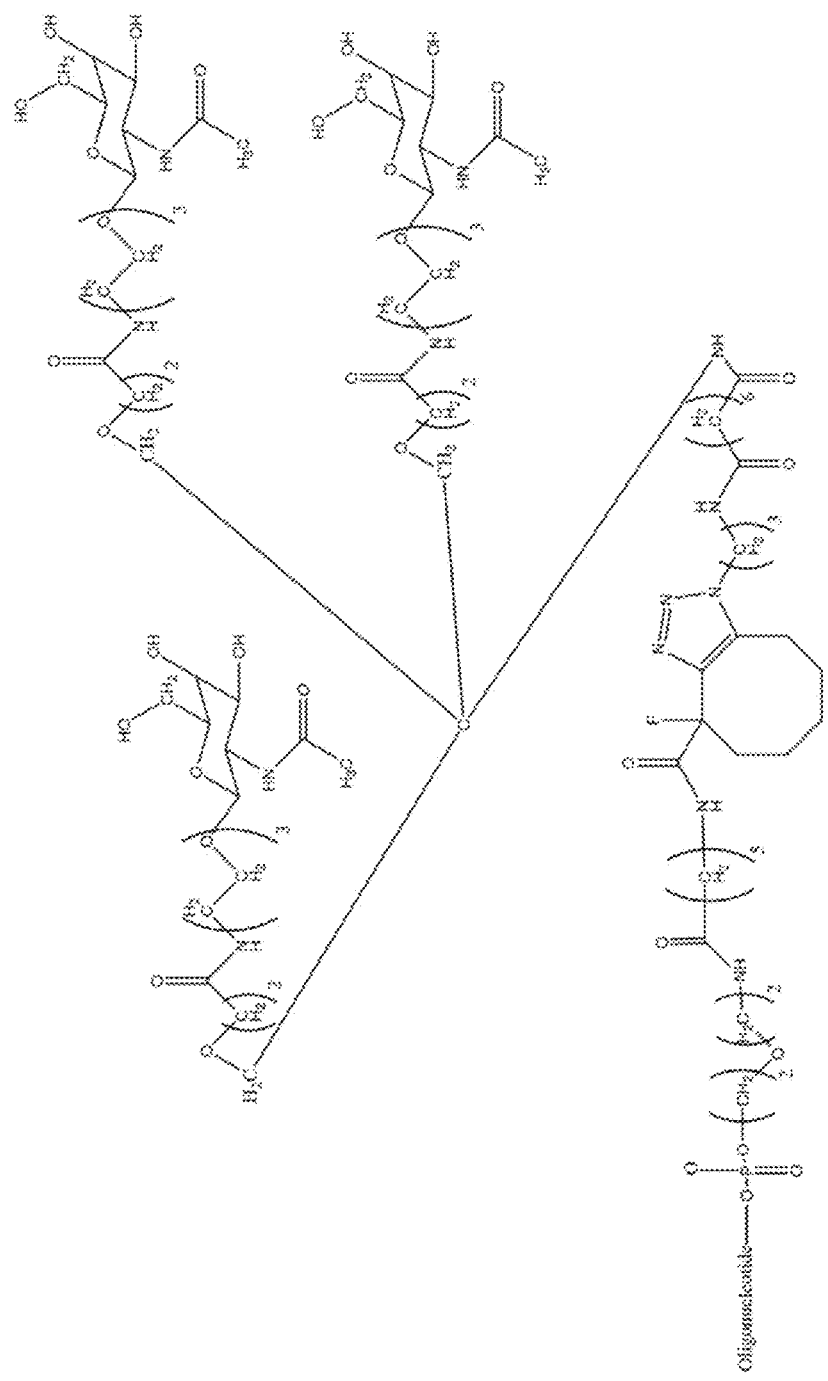
Figure 28:
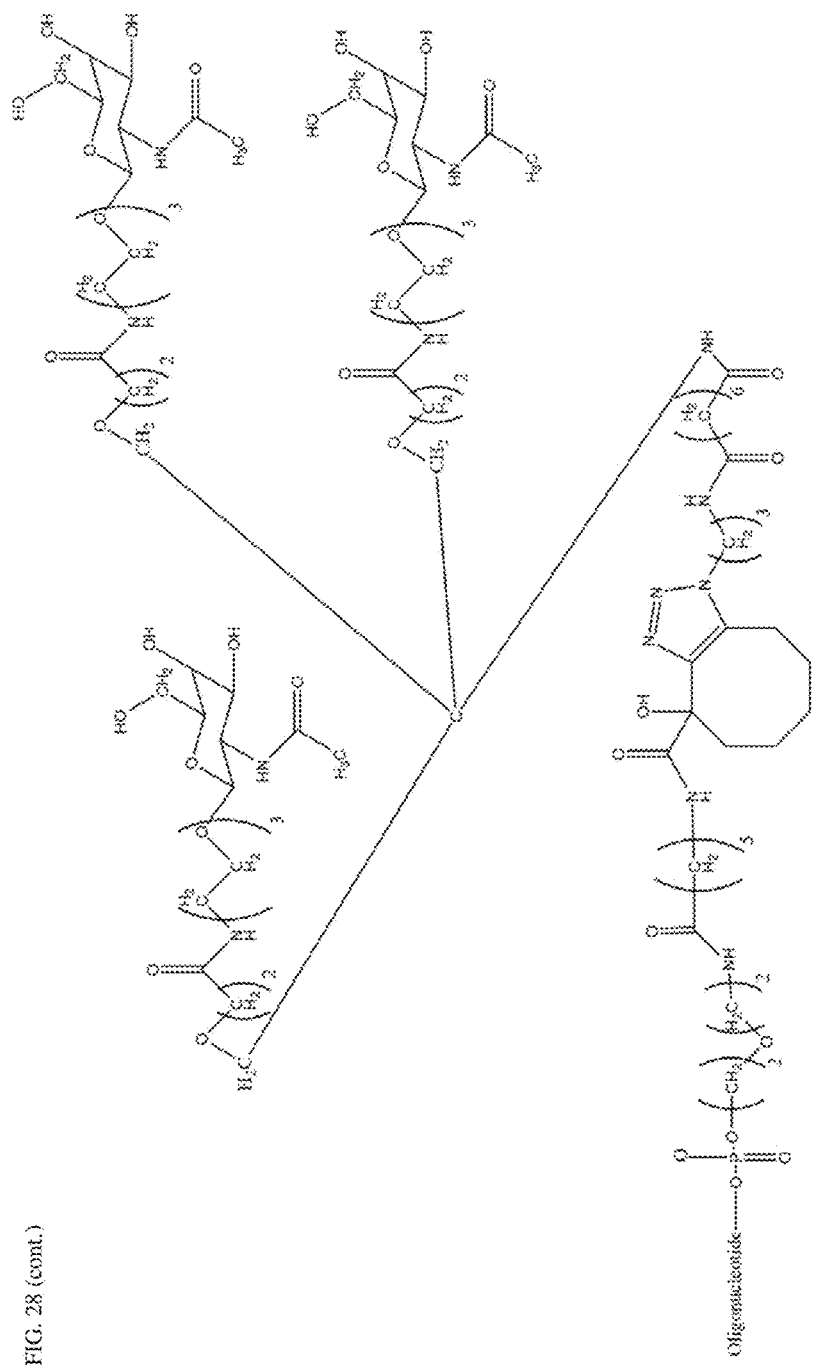
Figure 28:
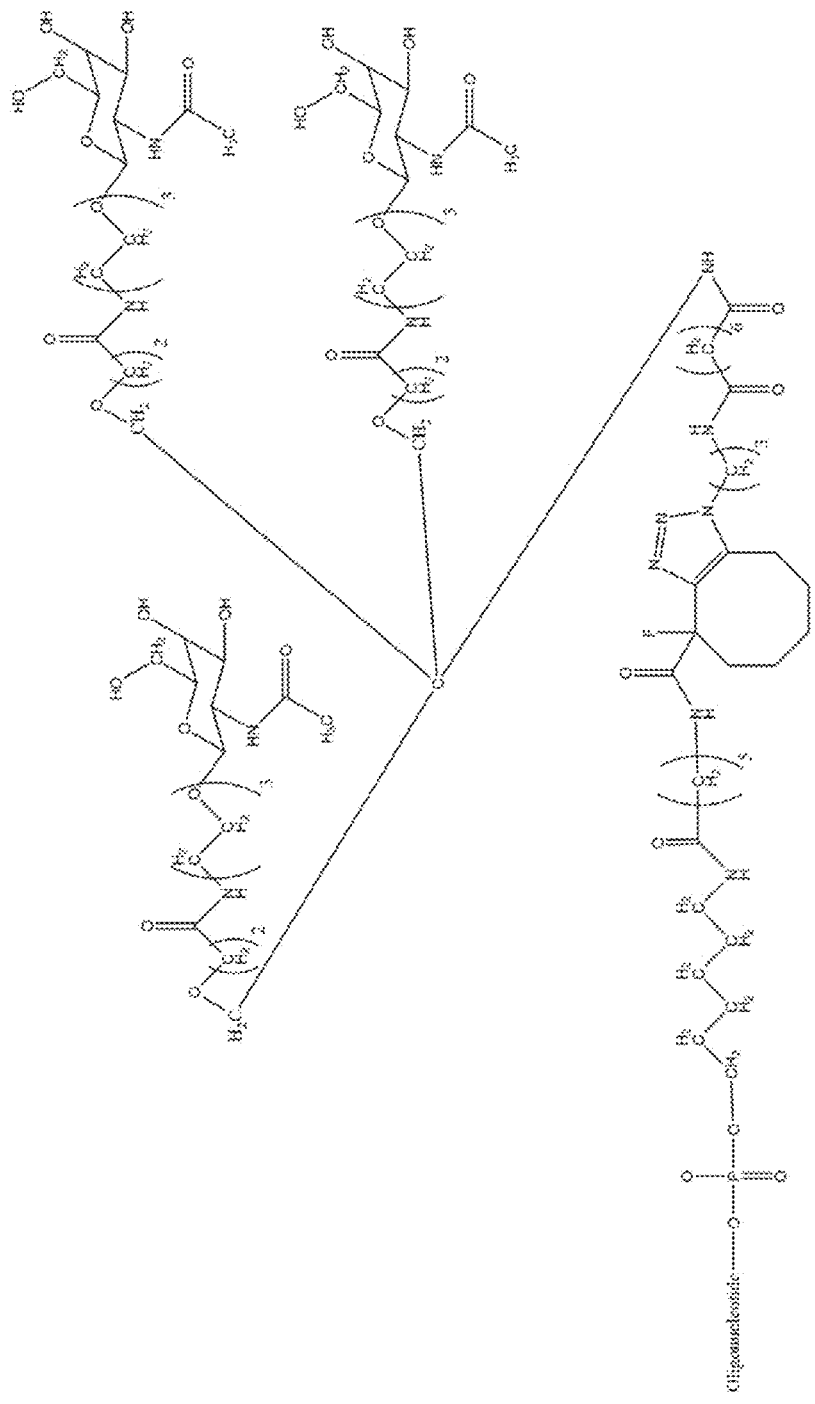
Figure 28:
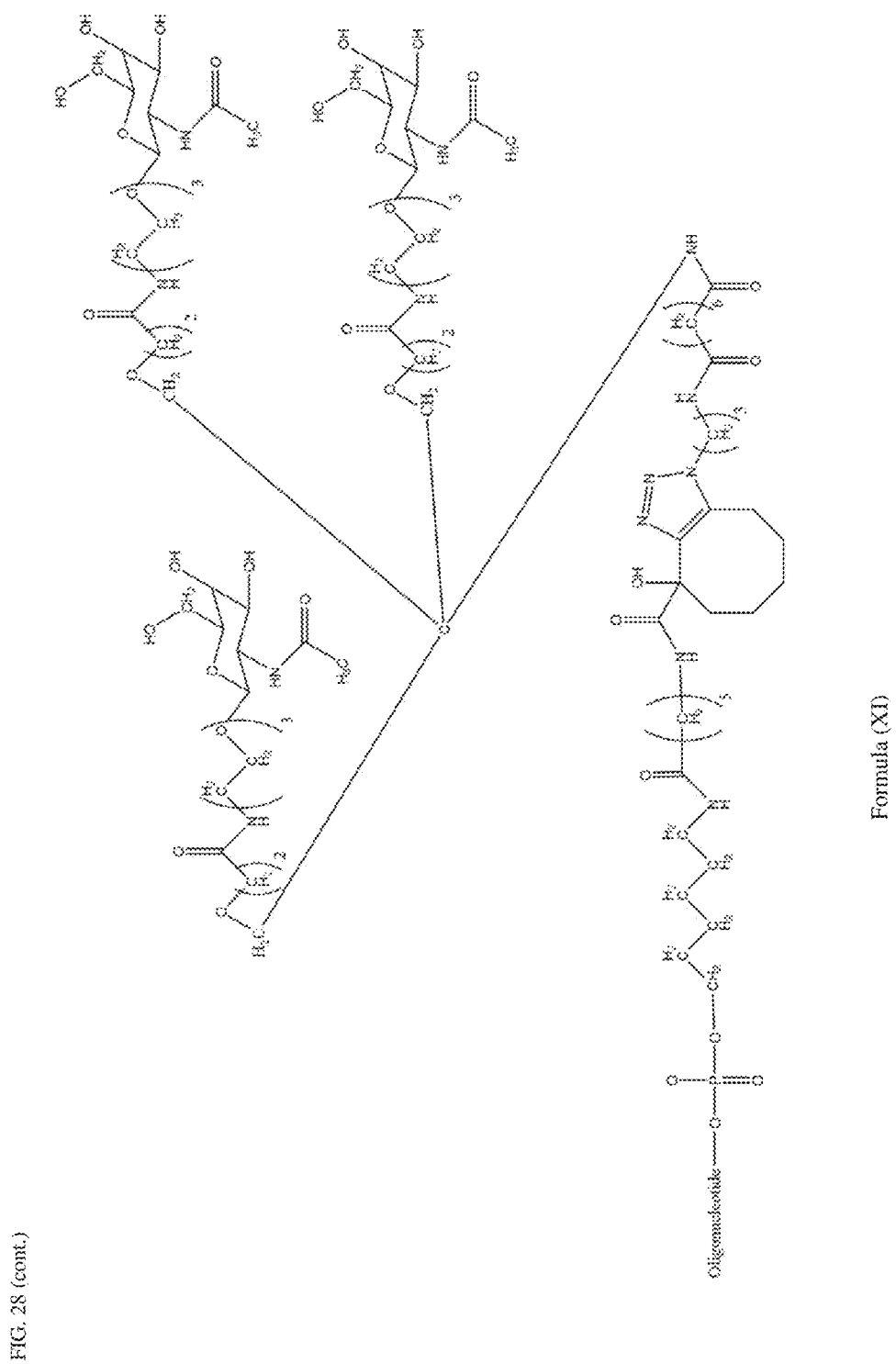
Figure 28:
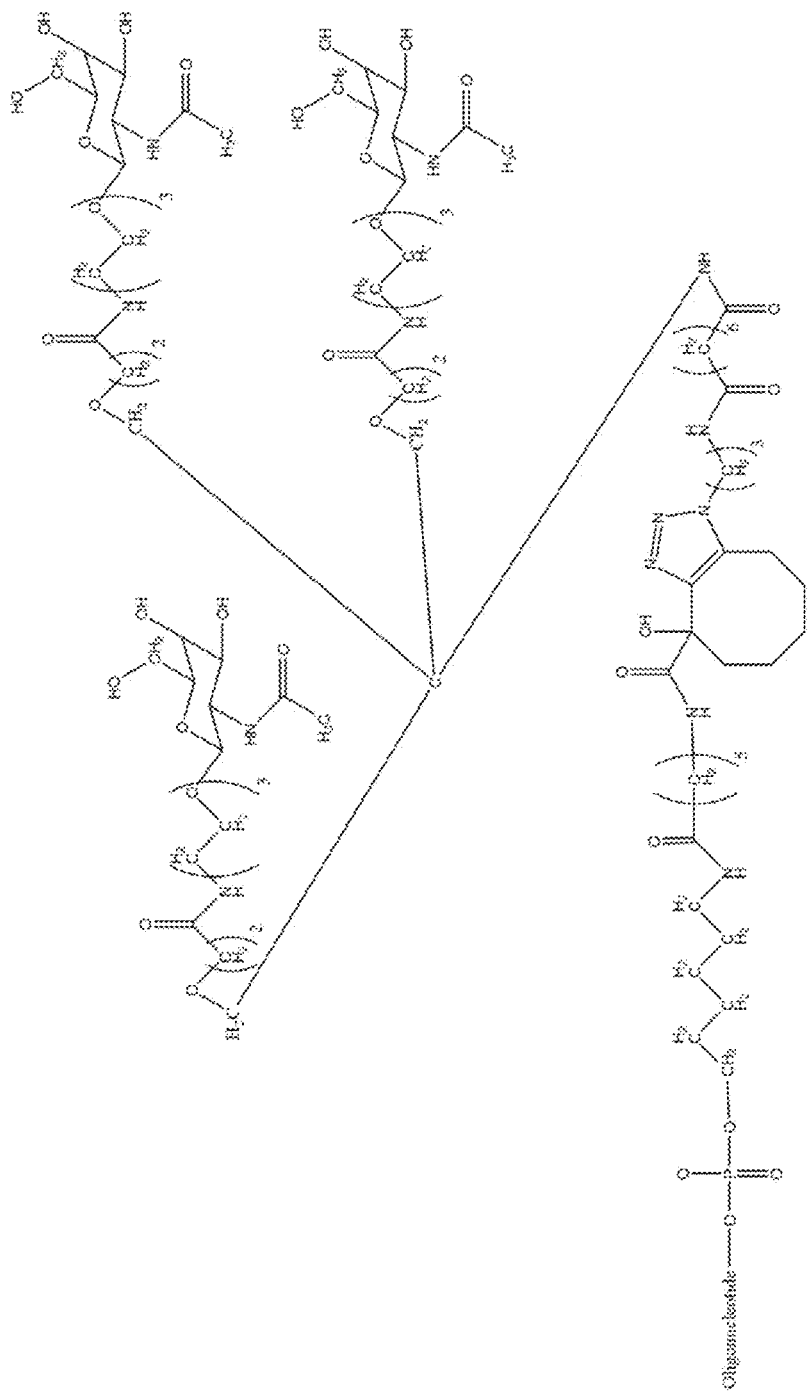

FIG. 28 shows the detail of formulae I to XV below.

FIG. 29A shows the underlying nucleotide sequences for the sense (SS) and antisense (AS) strands of construct ETX001 as described herein (SEQ ID NOs: 1 and 2, respectively). For ETX001 a galnac linker is attached to the 5' end region of the sense strand in use (not depicted in FIG. 29A). For ETX001 the galnac linker is attached and as shown in FIG. 21. Reference to FIG. 29A in the subsequent paragraphs is reference to the sequence, construct design and modification pattern of ETX001.

iaia as shown at the 3' end region of the sense strand in FIG. 29A represents (i) two abasic nucleotides provided as the penultimate and terminal nucleotides at the 3' end region of the sense strand, (ii) wherein a 3'-3' reversed linkage is provided between the antepenultimate nucleotide (namely A at position 21 of the sense strand, wherein position 1 is the terminal 5' nucleotide of the sense strand, namely terminal G at the 5'end region of the sense strand) and the adjacent penultimate abasic residue of the sense strand, and (iii) the linkage between the terminal and penultimate abasic nucleotides is 5'-3' when reading towards the 3' end region comprising the terminal and penultimate abasic nucleotides.

For the sense strand of FIG. 29A, when reading from position 1 of the sense strand (which is the terminal 5' nucleotide of the sense strand, namely terminal G at the 5'end region of the sense strand), then: (i) the nucleotides at positions 1 to 6, 8, and 12 to 21 have sugars that are 2' O-methyl modified, (ii) the nucleotides at positions 7, and 9 to 11 have sugars that are 2' F modified, (iii) the abasic nucleotides have sugars that have H at positions 1 and 2.

For the antisense strand of FIG. 29A, when reading from position 1 of the antisense strand (which is the terminal 5' nucleotide of the antisense strand, namely terminal U at the 5'end region of the antisense strand), then: (i) the nucleotides at positions 1, 3 to 5, 7, 10 to 13, 15, 17 to 23 have sugars that are 2' O-methyl modified, (ii) the nucleotides at positions 2, 6, 8, 9, 14, 16 have sugars that are 2' F modified.

ETX003 as described herein has the same underlying sequence and galnac linker and attachment as depicted for ETX001 in FIG. 29A, but without the terminal iaia motif and with a fully alternating 2' O-methyl/2'F modification pattern on the sugars of the nucleotides. For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

FIG. 29B shows the underlying nucleotide sequences for the sense (SS) and antisense (AS) strands of construct ETX005 as described herein (SEQ ID NOs: 7 and 8, respectively). For ETX005 a galnac linker is attached to the 3' end region of the sense strand in use (not depicted in FIG. 29B). For ETX005 the galnac linker is attached and as shown in FIG. 20. Reference to FIG. 29B in the subsequent paragraphs is reference to the sequence, construct design and modification pattern of ETX005.

iaia as shown at the 5' end region of the sense strand in FIG. 29B represents (i) two abasic nucleotides provided as the penultimate and terminal nucleotides at the 5' end region of the sense strand, (ii) wherein a 5'-5' reversed linkage is provided between the antepenultimate nucleotide (namely G at position 1 of the sense strand, not including the iaia motif at the 5' end region of the sense strand in the nucleotide position numbering on the sense strand) and the adjacent penultimate abasic residue of the sense strand, and (iii) the linkage between the terminal and penultimate abasic nucleotides is 3'-5' when reading towards the 5' end region comprising the terminal and penultimate abasic nucleotides.

For the sense strand of FIG. 29B, when reading from position 1 of the sense strand (which is the terminal 5' nucleotide of the sense strand, namely terminal G at the 5'end region of the sense strand, not including the iaia motif at the 5' end region of the sense strand in the nucleotide position numbering on the sense strand), then: (i) the nucleotides at positions 1 to 6, 8, and 12 to 21 have sugars that are 2' O-methyl modified, (ii) the nucleotides at positions 7, and 9 to 11 have sugars that are 2' F modified, (iii) the abasic nucleotides have sugars that have H at positions 1 and 2.

For the antisense strand of FIG. 29B, when reading from position 1 of the antisense strand (which is the terminal 5' nucleotide of the antisense strand, namely terminal U at the 5'end region of the antisense strand), then: (i) the nucleotides at positions 1, 3 to 5, 7, 10 to 13, 15, 17 to 23 have sugars that are 2' O-methyl modified, (ii) the nucleotides at positions 2, 6, 8, 9, 14, 16 have sugars that are 2' F modified.

ETX007 as described herein has the same underlying sequence and galnac linker and attachment as depicted for ETX005 in FIG. 29B, but without the terminal iaia motif and with a fully alternating 2' O-methyl/2'F modification pattern on the sugars of the nucleotides. For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

FIG. 30A shows the underlying nucleotide sequences for the sense (SS) and antisense (AS) strands of construct ETXO10 as described herein (SEQ ID NOs: 3 and 4, respectively). For ETXO10 a galnac linker is attached to the 5' end region of the sense strand in use (not depicted in FIG. 30A). For ETXO10 the galnac linker is attached and as shown in FIG. 21. Reference to FIG. 30A in the subsequent paragraphs is reference to the sequence, construct design and modification pattern of ETXO10.

iaia as shown at the 3' end region of the sense strand in FIG. 30A represents (i) two abasic nucleotides provided as the penultimate and terminal nucleotides at the 3' end region of the sense strand, (ii) wherein a 3'-3' reversed linkage is provided between the antepenultimate nucleotide (namely A at position 21 of the sense strand, wherein position 1 is the terminal 5' nucleotide of the sense strand, namely terminal A at the 5'end region of the sense strand) and the adjacent penultimate abasic residue of the sense strand, and (iii) the linkage between the terminal and penultimate abasic nucleotides is 5'-3' when reading towards the 3' end region comprising the terminal and penultimate abasic nucleotides.

For the sense strand of FIG. 30A, when reading from position 1 of the sense strand (which is the terminal 5' nucleotide of the sense strand, namely terminal A at the 5'end region of the sense strand), then: (i) the nucleotides at positions 1, 2, 4, 6, 8, 12, 14, 15, 17, 19 to 21 have sugars that are 2' O-methyl modified, (ii) the nucleotides at positions 3, 5, 7, 9 to 11, 13, 16, 18 have sugars that are 2' F modified, (iii) the abasic nucleotides have sugars that have H at positions 1 and 2.

For the antisense strand of FIG. 30A, when reading from position 1 of the antisense strand (which is the terminal 5' nucleotide of the antisense strand, namely terminal U at the 5'end region of the antisense strand), then: (i) the nucleotides at positions 1, 4, 6, 7, 9, 11 to 13, 15, 17, 19 to 23 have sugars that are 2' O-methyl modified, (ii) the nucleotides at positions 2, 3, 5, 8, 10, 14, 16, 18 have sugars that are 2' F modified, (iii) the penultimate and terminal T nucleotides at positions 24, 25 at the 3' end region of the antisense strand have sugars that have H at position 2.

ETX012 as described herein has the same underlying sequence and galnac linker and attachment as depicted for ETXO10 in FIG. 30A, but without the terminal iaia motif and with a fully alternating 2' O-methyl/2'F modification pattern on the sugars of the nucleotides (with the exception of the terminal T nucleotides that have H at position 2). For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

FIG. 30B shows the underlying nucleotide sequences for the sense (SS) and antisense (AS) strands of construct ETX014 as described herein (SEQ ID NOs: 9 and 10, respectively). For ETX014 a galnac linker is attached to the 3' end region of the sense strand in use (not depicted in FIG. 30B). For ETX014 the galnac linker is attached and as shown in FIG. 20. Reference to FIG. 30B in the subsequent paragraphs is reference to the sequence, construct design and modification pattern of ETX014.

iaia as shown at the 5' end region of the sense strand in FIG. 30B represents (i) two abasic nucleotides provided as the penultimate and terminal nucleotides at the 5' end region of the sense strand, (ii) wherein a 5'-5' reversed linkage is provided between the antepenultimate nucleotide (namely A at position 1 of the sense strand, not including the iaia motif at the 5' end region of the sense strand in the nucleotide position numbering on the sense strand) and the adjacent penultimate abasic residue of the sense strand, and (iii) the linkage between the terminal and penultimate abasic nucleotides is 3'-5' when reading towards the 5' end region comprising the terminal and penultimate abasic nucleotides.

For the sense strand of FIG. 30B, when reading from position 1 of the sense strand (which is the terminal 5' nucleotide of the sense strand, namely terminal A at the 5'end region of the sense strand, not including the iaia motif at the 5' end region of the sense strand in the nucleotide position numbering on the sense strand), then: (i) the nucleotides at positions 1, 2, 4, 6, 8, 12, 14, 15, 17, 19 to 21 have sugars that are 2' O-methyl modified, (ii) the nucleotides at positions 3, 5, 7, 9 to 11, 13, 16, 18 have sugars that are 2' F modified, (iii) the abasic nucleotides have sugars that have H at positions 1 and 2.

For the antisense strand of FIG. 30B, when reading from position 1 of the antisense strand (which is the terminal 5' nucleotide of the antisense strand, namely terminal U at the 5'end region of the antisense strand), then: (i) the nucleotides at positions 1, 4, 6, 7, 9, 11 to 13, 15, 17, 19 to 23 have sugars that are 2' O-methyl modified, (ii) the nucleotides at positions 2, 3, 5, 8, 10, 14, 16, 18 have sugars that are 2' F modified, (iii) the penultimate and terminal T nucleotides at positions 24, 25 at the 3' end region of the antisense strand have sugars that have H at position 2.

ETX016 as described herein has the same underlying sequence and galnac linker and attachment as depicted for ETX014 in FIG. 30B, but without the terminal iaia motif and with a fully alternating 2' O-methyl/2'F modification pattern on the sugars of the nucleotides (with the exception of the terminal T nucleotides that have H at position 2). For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

FIG. 31A shows the underlying nucleotide sequences for the sense (SS) and antisense (AS) strands of construct ETX019 as described herein (SEQ ID NOs: 5 and 6, respectively). For ETX019 a galnac linker is attached to the 5' end region of the sense strand in use (not depicted in FIG. 31A). For ETX019 the galnac linker is attached and as shown in FIG. 21. Reference to FIG. 31A in the subsequent paragraphs is reference to the sequence, construct design and modification pattern of ETX019.

iaia as shown at the 3' end region of the sense strand in FIG. 31A represents (i) two abasic nucleotides provided as the penultimate and terminal nucleotides at the 3' end region of the sense strand, (ii) wherein a 3'-3' reversed linkage is provided between the antepenultimate nucleotide (namely A at position 21 of the sense strand, wherein position 1 is the terminal 5' nucleotide of the sense strand, namely terminal U at the 5'end region of the sense strand) and the adjacent penultimate abasic residue of the sense strand, and (iii) the linkage between the terminal and penultimate abasic nucleotides is 5'-3' when reading towards the 3' end region comprising the terminal and penultimate abasic nucleotides.

For the sense strand of FIG. 31A, when reading from position 1 of the sense strand (which is the terminal 5' nucleotide of the sense strand, namely terminal U at the 5'end region of the sense strand), then: (i) the nucleotides at positions 1 to 6, 8, and 12 to 21 have sugars that are 2' O-methyl modified, (ii) the nucleotides at positions 7, and 9 to 11 have sugars that are 2' F modified, (iii) the abasic nucleotides have sugars that have H at positions 1 and 2.

For the antisense strand of FIG. 31A, when reading from position 1 of the antisense strand (which is the terminal 5' nucleotide of the antisense strand, namely terminal U at the 5'end region of the antisense strand), then: (i) the nucleotides at positions 1, 3 to 5, 7, 8, 10 to 13, 15, 17 to 23 have sugars that are 2' O-methyl modified, (ii) the nucleotides at positions 2, 6, 9, 14, 16 have sugars that are 2' F modified.

ETX021 as described herein has the same underlying sequence and galnac linker and attachment as depicted for ETX019 in FIG. 31A, but without the terminal iaia motif and with a fully alternating 2' O-methyl/2'F modification pattern on the sugars of the nucleotides. For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

FIG. 31B shows the underlying nucleotide sequences for the sense (SS) and antisense (AS) strands of construct ETX023 as described herein (SEQ ID NOs: 11 and 12, respectively). For ETX023 a galnac linker is attached to the 3' end region of the sense strand in use (not depicted in FIG. 31B). For ETX023 the galnac linker is attached and as shown in FIG. 20. Reference to FIG. 31B in the subsequent paragraphs is reference to the sequence, construct design and modification pattern of ETX023.

iaia as shown at the 5' end region of the sense strand in FIG. 31B represents (i) two abasic nucleotides provided as the penultimate and terminal nucleotides at the 5' end region of the sense strand, (ii) wherein a 5'-5' reversed linkage is provided between the antepenultimate nucleotide (namely U at position 1 of the sense strand, not including the iaia motif at the 5' end region of the sense strand in the nucleotide position numbering on the sense strand) and the adjacent penultimate abasic residue of the sense strand, and (iii) the linkage between the terminal and penultimate abasic nucleotides is 3'-5' when reading towards the 5' end region comprising the terminal and penultimate abasic nucleotides.

For the sense strand of FIG. 31B, when reading from position 1 of the sense strand (which is the terminal 5' nucleotide of the sense strand, namely terminal U at the 5'end region of the sense strand, not including the iaia motif at the 5' end region of the sense strand in the nucleotide position numbering on the sense strand), then: (i) the nucleotides at positions 1 to 6, 8, and 12 to 21 have sugars that are 2' O-methyl modified, (ii) the nucleotides at positions 7, and 9 to 11 have sugars that are 2' F modified, (iii) the abasic nucleotides have sugars that have H at positions 1 and 2.

For the antisense strand of FIG. 31B, when reading from position 1 of the antisense strand (which is the terminal 5' nucleotide of the antisense strand, namely terminal U at the 5'end region of the antisense strand), then: (i) the nucleotides at positions 1, 3 to 5, 7, 8, 10 to 13, 15, 17 to 23 have sugars that are 2' O-methyl modified, (ii) the nucleotides at positions 2, 6, 9, 14, 16 have sugars that are 2' F modified.

ETX025 as described herein has the same underlying sequence and galnac linker and attachment as depicted for ETX023 in FIG. 31B, but without the terminal iaia motif and with a fully alternating 2' O-methyl/2'F modification pattern on the sugars of the nucleotides. For the sense strand, the fully alternating modification pattern starts with a 2'F modification at position 1 at the 5' end region of the sense strand. For the antisense strand, the fully alternating modification pattern starts with a 2' O-methyl modification at position 1 at the 5' end region of the antisense strand.

Figure 32:
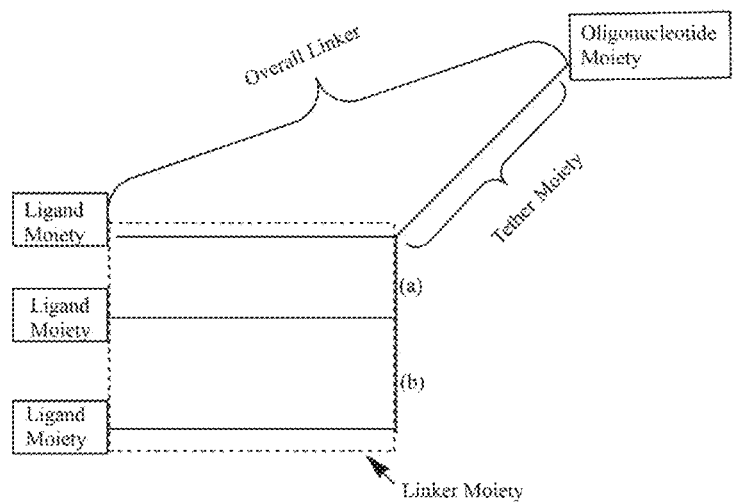

Exemplary linear configuration is shown in FIG. 32, wherein (a) and/or (b) can typically represent connecting bonds or groups, such as phosphate or phosphorothioate groups.

Figure 33:
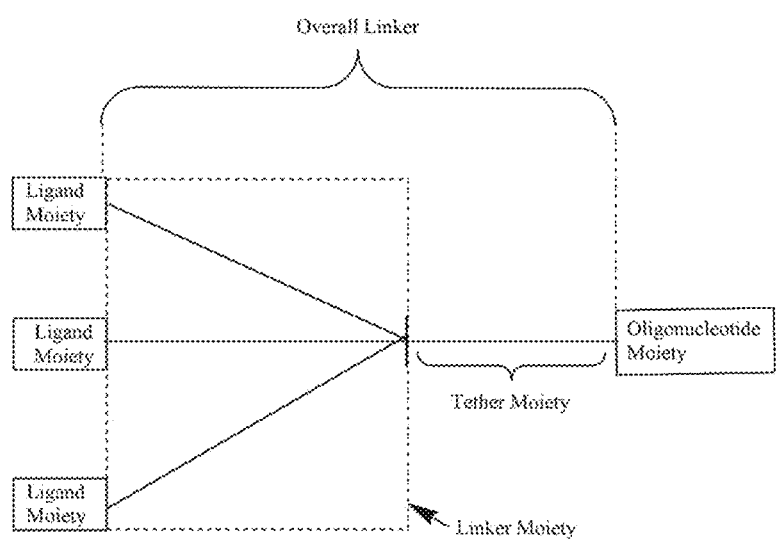

Exemplary branched configuration is shown in FIG. 33.

DETAILED DESCRIPTION

The present invention provides novel, ligand-conjugated oligonucleotide compounds, methods of making these compounds and uses thereof.

Compounds of the invention comprise an oligonucleotide moiety and/or a linker and/or a ligand moiety, or parts thereof, as disclosed herein. Preferably, compounds of the invention comprise an oligonucleotide moiety, a linker and a ligand moiety. These moieties may be covalently bonded together, such that the oligonucleotide moiety is covalently bonded to the ligand moiety via the linker.

It will be understood that compounds of the invention can combine any oligonucleotide moiety as described anywhere herein, and/or any linker as described anywhere herein, and/or any ligand moiety as described anywhere herein.

Exemplary compounds of the invention comprise the following general structure:

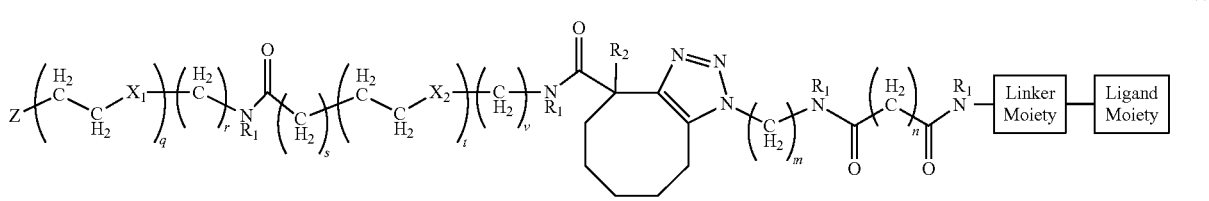

Formula (I)

wherein:
R$_1$ at each occurrence is independently selected from the group consisting of hydrogen, methyl and ethyl;
R$_2$ is selected from the group consisting of hydrogen, hydroxy, —OC$_{1-3}$alkyl, —C(=O)OC$_{1-3}$alkyl, halo and nitro;
X$_1$ and X$_2$ at each occurrence are independently selected from the group consisting of methylene, oxygen and sulfur;
m is an integer of from 1 to 6;
n is an integer of from 1 to 10;
q, r, s, t, v are independently integers from 0 to 4, with the proviso that:
(i) q and r cannot both be 0 at the same time; and
(ii) s, t and v cannot all be 0 at the same time;
Z is an oligonucleotide moiety.

1. Ligand Moiety

Exemplary compounds of the invention comprise a 'ligand moiety', as depicted in Formula (I).

In some embodiments, the ligand moiety as depicted in Formula (I) comprises one or more ligands.

In some embodiments, the ligand moiety as depicted in Formula (I) comprises one or more carbohydrate ligands.

In some embodiments, the one or more carbohydrates can be a monosaccharide, disaccharide, trisaccharide, tetrasaccharide, oligosaccharide and/or polysaccharide.

In some embodiments, the one or more carbohydrates comprise one or more galactose moieties, one or more lactose moieties, one or more N-AcetylGalactosamine moieties, and/or one or more mannose moieties.

In some embodiments, the one or more carbohydrates comprise one or more N-AcetylGalactosamine moieties.

In some embodiments, the compounds as described anywhere herein comprise two or three N-AcetylGalactosamine moieties.

In some embodiments, the one or more ligands are attached in a linear configuration, or in a branched configuration, for example each configuration being respectively attached to a branch point in an overall linker.

Exemplary linear configuration, or branched configurations, of ligand moieties can be depicted as follows, using the nomenclature as further explained in sections 2, 3 and 4 hereinafter.

Exemplary linear configuration is shown in FIG. 32, wherein (a) and/or (b) can typically represent connecting bonds or groups, such as phosphate or phosphorothioate groups.

Exemplary branched configuration is shown in FIG. 33.

In some embodiments, the one or more ligands are attached as a biantennary or triantennary branched configuration. Typically, a triantennary branched configuration can be preferred, such as an N-AcetylGalactosamine triantennary branched configuration.

2. Linker

Exemplary compounds of the invention comprise a 'linker moiety', as depicted in Formula (I), that is part of an overall 'linker'.

As will be further understood in the art, exemplary compounds of the invention comprise an overall linker that is located between the oligonucleotide moiety and the ligand moiety of these compounds. The overall linker, thereby 'links' the oligonucleotide moiety and the ligand moiety to each other.

The overall linker is often notionally envisaged as comprising one or more linker building blocks. For example, there is a linker portion that is depicted as the 'linker moiety' as represented in Formula (I) positioned adjacent the ligand moiety and attaching the ligand moiety, typically via a branch point, directly or indirectly to the oligonucleotide moiety. The linker moiety as depicted in Formula (I) can also often be referred to as the 'ligand arm or arms' of the overall linker. There can also, but not always, be a further linker portion between the oligonucleotide moiety and the branch point, that is often referred to as the 'tether moiety' of the overall linker, 'tethering' the oligonucleotide moiety to the remainder of the conjugated compound. Such 'ligand arms' and/or 'linker moieties' and/or 'tether moieties' can be envisaged by reference to the linear and/or branched configurations as set out above.

As can be seen from the claims, and the reminder of the patent specification, the scope of the present invention extends to linear or branched configurations, and with no limitation as to the number of individual ligands that might be present. Furthermore, the addressee will also be aware that there are many structures that could be used as the linker moiety, based on the state of the art and the expertise of an oligonucleotide chemist.

The remainder of the overall linker (other than the linker moiety) as set out in the claims, and the remainder of the patent specification, is shown by its chemical constituents in Formula (I), which the inventors consider to be particularly unique to the current invention. In more general terms, however, these chemical constituents could be described as a 'tether moiety' as hereinbefore described, wherein the 'tether moiety' is that portion of the overall linker which comprises the group of atoms between Z, namely the oligonucleotide moiety, and the linker moiety as depicted in Formula (I).

2.1 Tether Moiety

In relation to Formula (I), the 'tether moiety' comprises the group of atoms between Z, namely the oligonucleotide moiety, and the linker moiety.

In some embodiments, R$_1$ is hydrogen at each occurrence. In some embodiments, R$_1$ is methyl. In some embodiments, R$_1$ is ethyl.

In some embodiments, $R_2$ is hydroxy. In some embodiments, $R_2$ is halo. In some embodiments, $R_2$ is fluoro. In some embodiments, $R_2$ is chloro. In some embodiments, $R_2$ is bromo. In some embodiments, $R_2$ is iodo. In some embodiments, $R_2$ is nitro.

In some embodiments, $X_1$ is methylene. In some embodiments, $X_1$ is oxygen. In some embodiments, $X_1$ is sulfur.

In some embodiments, $X_2$ is methylene. In some embodiments, $X_2$ is oxygen. In some embodiments, $X_2$ is sulfur.

In some embodiments, m=3.

In some embodiments, n=6.

In some embodiments, $X_1$ is oxygen and $X_2$ is methylene. In some embodiments, both $X_1$ and $X_2$ are methylene.

In some embodiments, q=1, r=2, s=1, t=1, v=1. In some embodiments, q=1, r=3, s=1, t=1, v=1.

In some embodiments, $R_1$ is hydrogen at each occurrence, n=6, m=3, $R_2$ is fluoro, $X_2$ is methylene, v=1, t=1, s=1, $X_1$ is methylene, q=1 and r=2.

Thus, in some embodiments, exemplary compounds of the invention comprise the following structure:

Formula (IV)

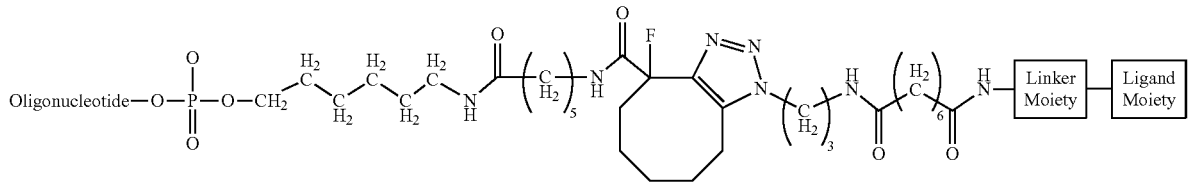

In some embodiments, $R_1$ is hydrogen at each occurrence, n=6, m=3, $R_2$ is fluoro, $X_2$ is methylene, v=1, t=1, s=1, $X_1$ is oxygen, q=1 and r=2.

Thus, in some embodiments, exemplary compounds of the invention comprise the following structure:

Formula (II)

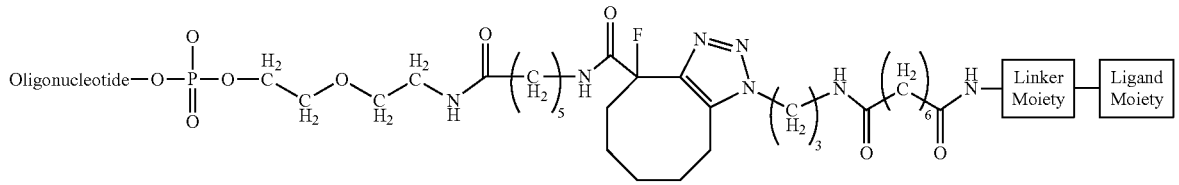

2.1.1 Alternative Tether Moieties

During the synthesis of compounds of the present invention, alternative tether moiety structures may arise. In some embodiments, alternative tether moieties have a change of one or more atoms in the tether moiety of the overall linker compared to tether moieties described anywhere herein.

In some embodiments, the alternative tether moiety is a compound of Formula (I) as described anywhere herein, wherein $R_2$ is hydroxy.

In some embodiments, $R_1$ is hydrogen at each occurrence, n=6, m=3, $R_2$ is hydroxy, $X_2$ is methylene, v=1, t=1, s=1, $X_1$ is methylene, q=1 and r=2.

Thus, in some embodiments, compounds of the invention comprise the following structure:

Formula (V)

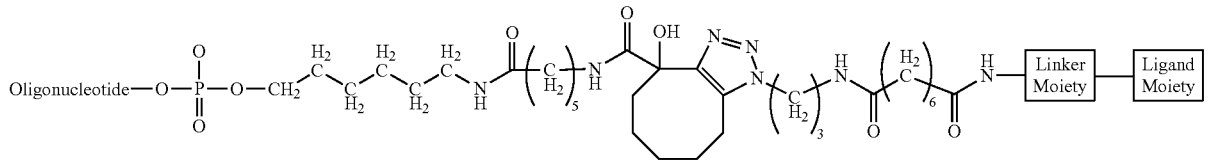

In some embodiments, $R_1$ is hydrogen at each occurrence, n=6, m=3, $R_2$ is hydroxy, $X_2$ is methylene, v=1, t=1, s=1, $X_1$ is oxygen, q=1 and r=2.

Thus, in some embodiments, compounds of the invention comprise the following structure:

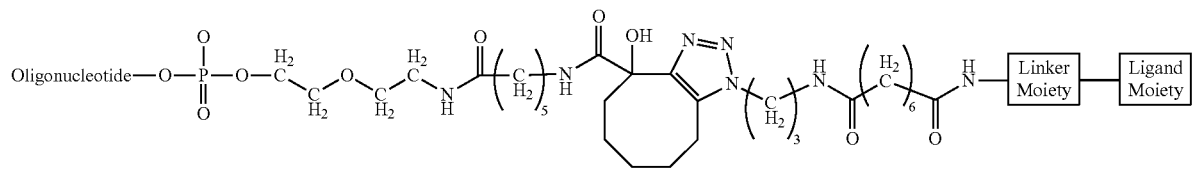

Formula (III)

2.2 Linker Moiety

In relation to Formula (I), the 'linker moiety' as depicted in Formula (I) comprises the group of atoms located between the tether moiety as described anywhere herein, and the ligand moiety as described anywhere herein.

In some embodiments:

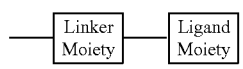

as depicted in Formula (I) as described anywhere herein is any of Formulae (VIa), (VIb) or (VIc), preferably Formula (VIa):

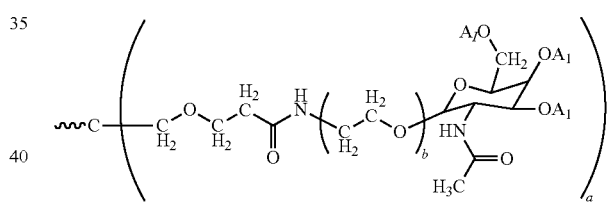

Formula (VIa)

wherein:
$A_1$ is hydrogen, or a suitable hydroxy protecting group;
a is an integer of 2 or 3; and
b is an integer of 2 to 5; or

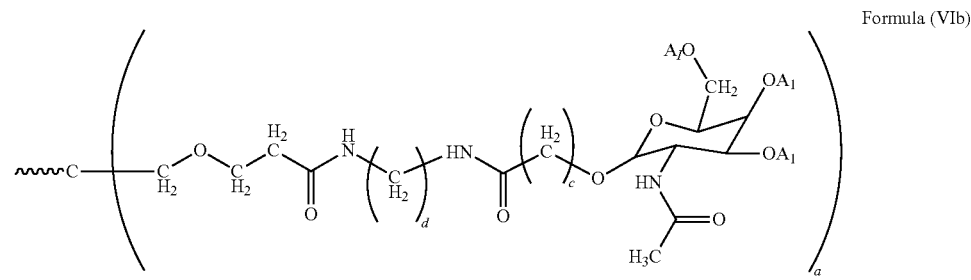

Formula (VIb)

wherein:
A₁ is hydrogen, or a suitable hydroxy protecting group;
a is an integer of 2 or 3; and
c and d are independently integers of 1 to 6; or

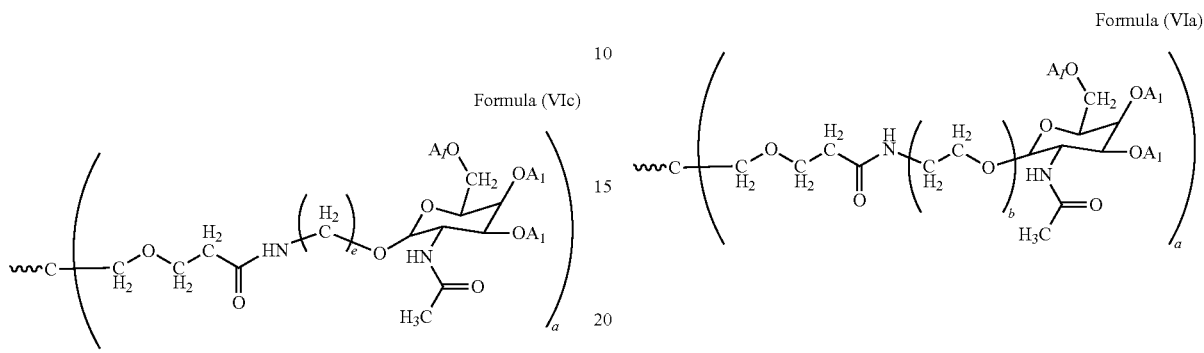

Formula (VIc)

wherein:
A₁ is hydrogen, or a suitable hydroxy protecting group;
a is an integer of 2 or 3; and
e is an integer of 2 to 10.
In some embodiments, the moiety:

as depicted in Formula (I) is Formula (VIa):

Formula (VIa)

wherein:
A₁ is hydrogen, or a suitable hydroxy protecting group;
a is 3; and
b is an integer of 3.
In some embodiments, the moiety:

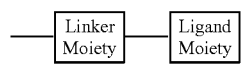

as depicted in Formula (I) as described anywhere herein is Formula (VII):

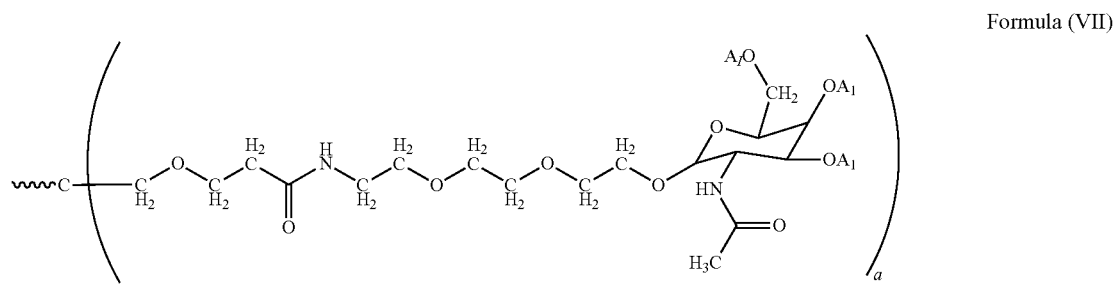

Formula (VII)

wherein:
A₁ is hydrogen;
a is an integer of 2 or 3, preferably 3.

3. Oligonucleotide Moiety

Exemplary compounds of the present invention comprise an oligonucleotide moiety, depicted as 'Z' in Formula (I). In some embodiments, Z is:

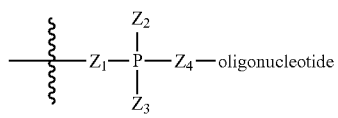

wherein:

$Z_1$, $Z_2$, $Z_3$, $Z_4$ are independently at each occurrence oxygen or sulfur; and one the bonds between P and $Z_2$, and P and $Z_3$ is a single bond and the other bond is a double bond.

In some embodiments, the oligonucleotide is an RNA compound capable of modulating expression of a target gene. In some embodiments, the oligonucleotide is an RNA compound capable of inhibiting expression of a target gene.

In some embodiments, the RNA compound comprises an RNA duplex comprising first and second strands, wherein the first strand is at least partially complementary to an RNA sequence of a target gene, and the second strand is at least partially complementary to said first strand, and wherein each of the first and second strands have 5' and 3' ends.

In some embodiments, the first strand is at least 80% complementary to an RNA sequence of a target gene, such as at least 85%, at least 90%, at least 91%, at least 92% at least 93%, at least 94%, at least 95%, at least 96%, at least 97%, at least 98%, or at least 99% complementary, such as 100% complementary over the length of the first strand.

In some embodiments, the RNA compound is attached at the 5' end of its second strand to the adjacent phosphate.

In some embodiments, the RNA compound is attached at the 3' end of its second strand to the adjacent phosphate.

It will be understood that where the RNA compound is attached at the 5'end of the second strand, the phosphate group connecting the oligonucleotide to the linker moiety (i.e. the 'P' connected to $Z_1$, $Z_2$, $Z_3$ and $Z_4$) is the naturally occurring phosphate group from the 5' terminal ribose of the oligonucleotide.

It will be understood that where the RNA compound is attached at the 3'end of the second strand, the phosphate group connecting the oligonucleotide to the linker moiety (i.e. the 'P' connected to $Z_1$, $Z_2$, $Z_3$ and $Z_4$) is engineered on to the 3' terminal ribose of the oligonucleotide, to substitute the naturally occurring hydroxy group at the 3' position.

In some embodiments, the oligonucleotide comprises an RNA duplex which further comprises one or more riboses modified at the 2' position. In some embodiments, the RNA duplex comprises a plurality of riboses modified at the 2' position. In some embodiments, the modifications are selected from 2'-O-methyl, 2'-deoxy-fluoro, and 2'-deoxy.

In some embodiments, the oligonucleotide further comprises one or more degradation protective moieties at one or more ends. In some embodiments, said one or more degradation protective moieties are not present at the end of the oligonucleotide strand that carries the ligand moieties. In some embodiments, said one or more degradation protective moieties are not present at the end of the oligonucleotide strand that is adjacent the remainder of the compound as shown in Formula (I), (VII), (IX), (X) or (XI). In some embodiments, said one or more degradation protective moieties is selected from phosphorothioate internucleotide linkages, phosphorodithioate internucleotide linkages and inverted abasic nucleotides, wherein said inverted abasic nucleotides are present at the distal end of the strand that carries the ligand moieties.

4. Exemplary Compounds

Compounds of the invention combine any oligonucleotide moiety as described anywhere herein, any linker as described anywhere herein, and/or any ligand moiety as described anywhere herein, or parts thereof.

In some embodiments, the compound comprises Formula (VIII):

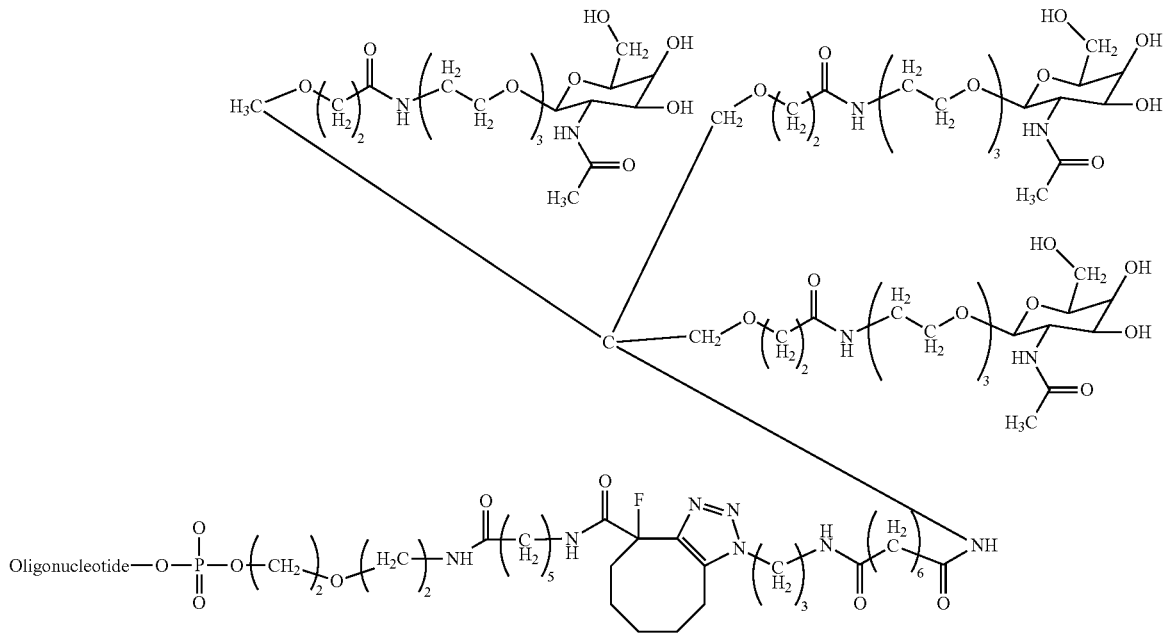

In some embodiments, the compound comprises Formula (IX):
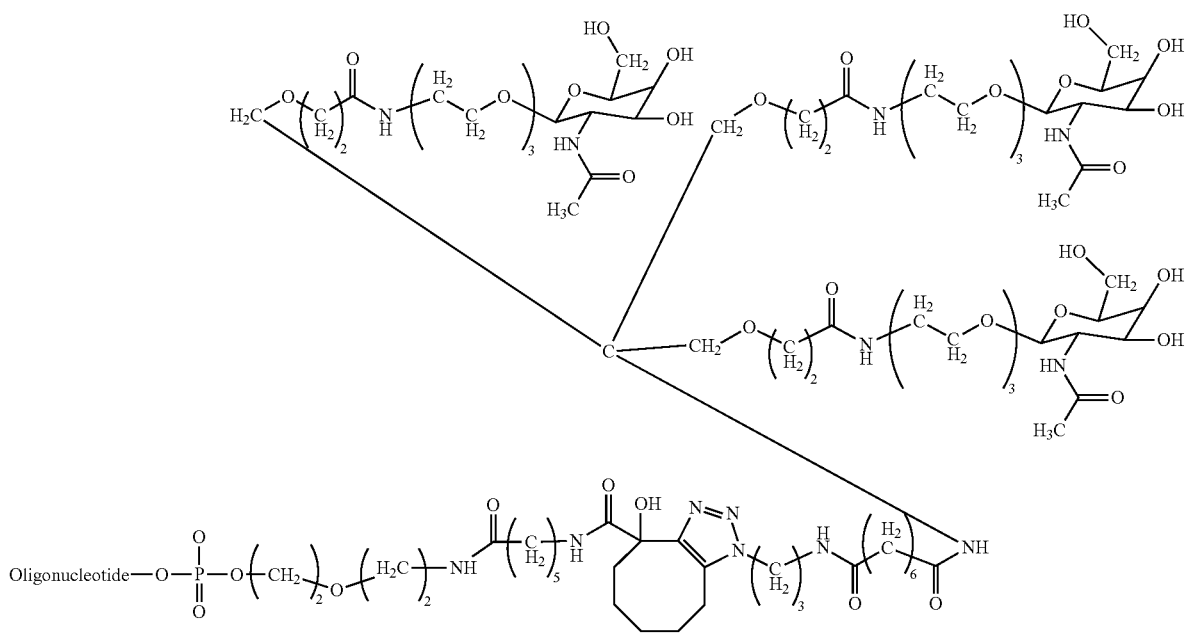
In some embodiments, the compound comprises Formula (X):
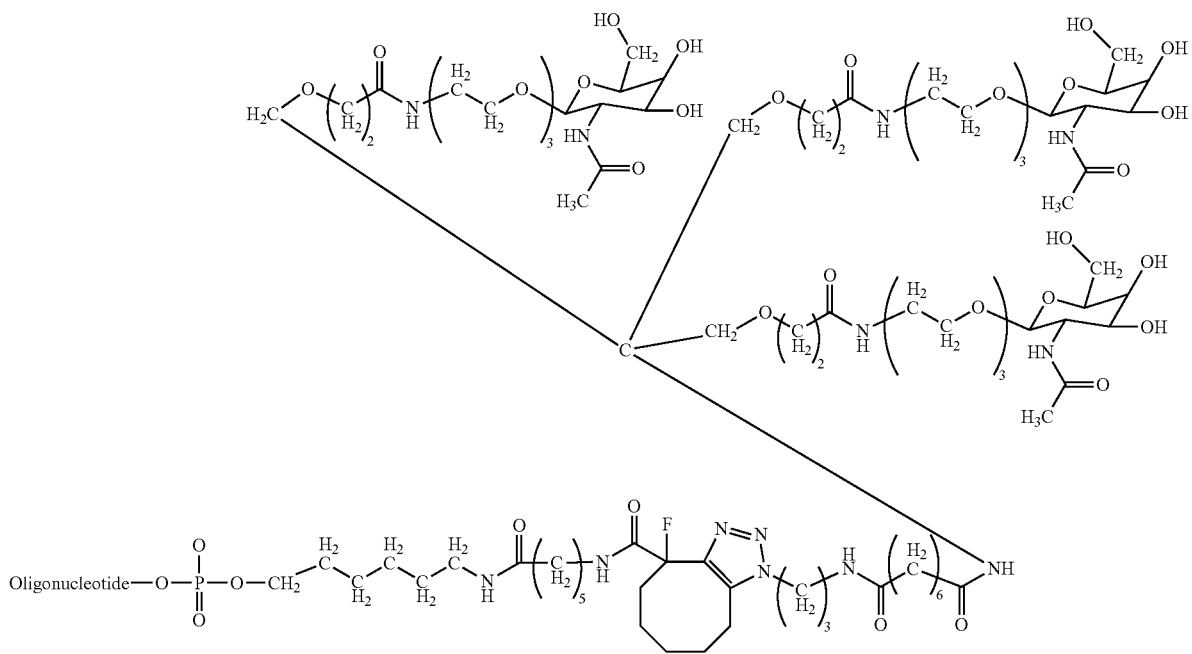

In some embodiments, the compound comprises Formula (XI):

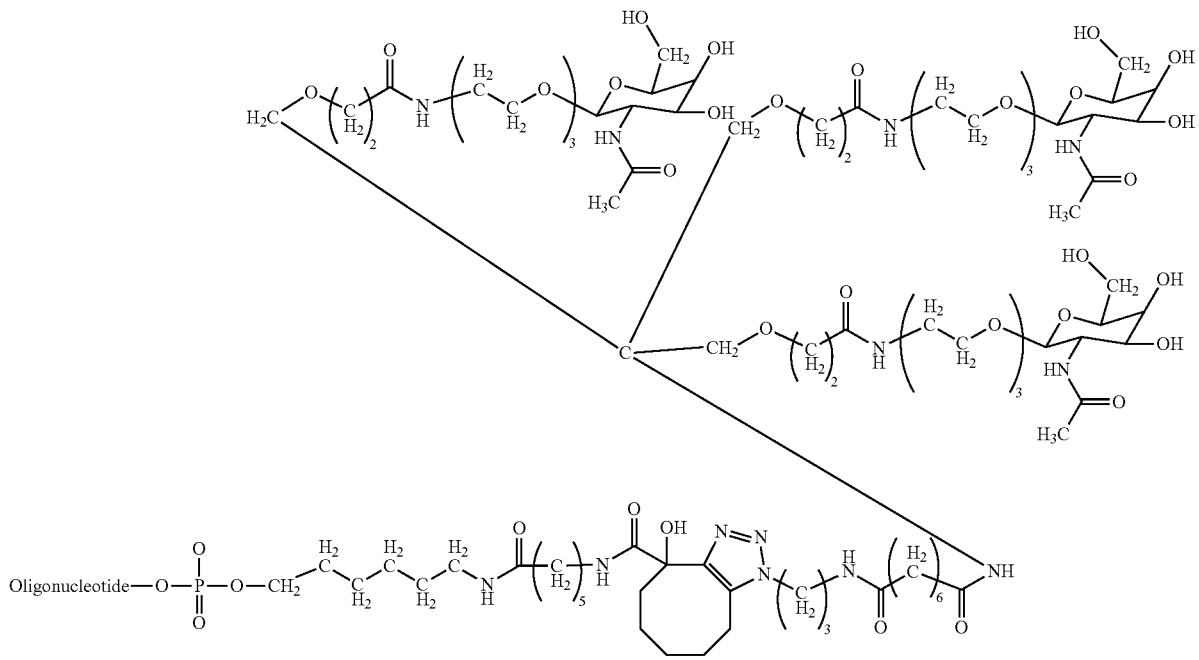

4.1 Intermediate Compounds

Compounds of the invention also include intermediate compounds produced or used during the production processes of the invention as described anywhere herein, for the production of compounds as described anywhere herein.

Thus, in some embodiments, the compound comprises Formula (XII):

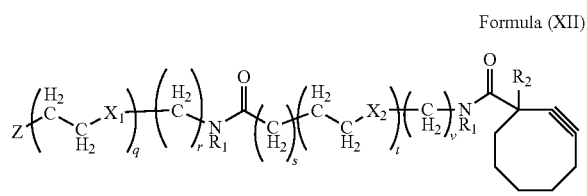

Formula (XII)

wherein:

$R_1$ at each occurrence is independently selected from the group consisting of hydrogen, methyl and ethyl;

$R_2$ is selected from the group consisting of hydroxy, halo and nitro;

$X_1$ and $X_2$ at each occurrence are independently selected from the group consisting of methylene, oxygen and sulfur;

q, r, s, t, v are independently integers from 0 to 4, with the proviso that:

(i) q and r cannot both be 0 at the same time; and (ii) s, t and v cannot all be 0 at the same time;

Z is an oligonucleotide moiety.

In some embodiments, the compound comprises Formula (XIIa):

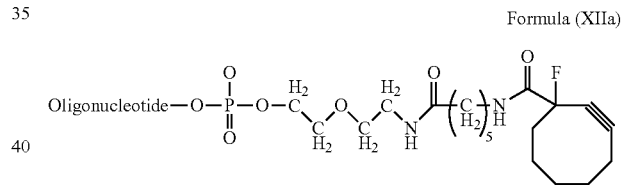

Formula (XIIa)

In some embodiments, the compound comprises Formula (XIIb):

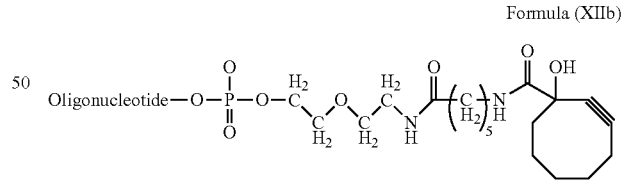

Formula (XIIb)

In some embodiments, the compound comprises Formula (XIIc):

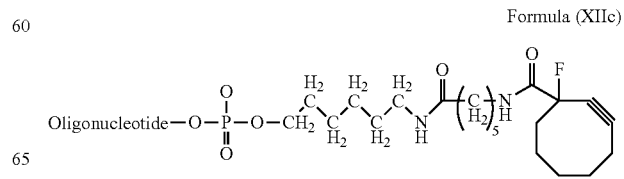

Formula (XIIc)

In some embodiments, the compound comprises Formula (XIId):

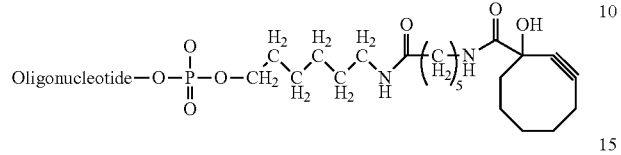

Formula (XIId)

In some embodiments, the compound comprises Formula (XIII):

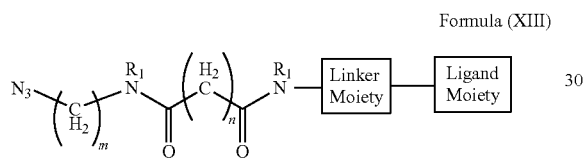

Formula (XIII)

wherein:

R₁ at each occurrence is independently selected from the group consisting of hydrogen, methyl and ethyl;

m is an integer of from 1 to 6;

n is an integer of from 1 to 10.

In some embodiments, the compound comprises Formula (XIIIa):

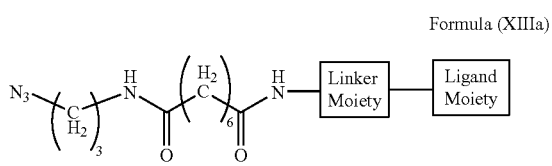

Formula (XIIIa)

In some embodiments, the compound comprises Formula (XIIIb):

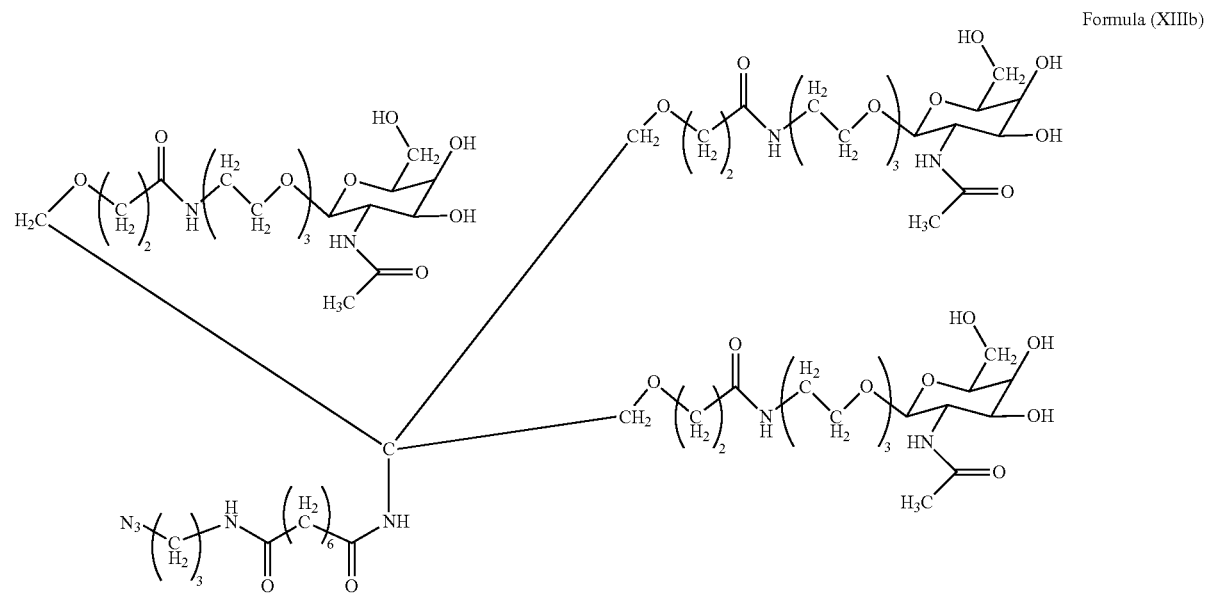

Formula (XIIIb)

In some embodiments, the compound comprises Formula (XIV):

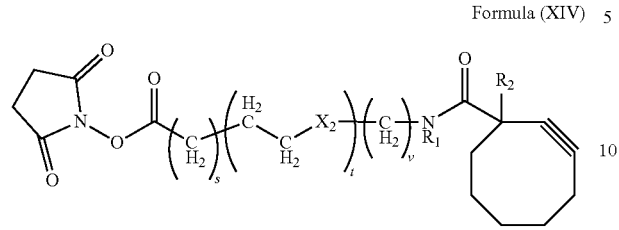

Formula (XIV)

wherein:
$R_1$ is selected from the group consisting of hydrogen, methyl and ethyl;
$R_2$ is selected from the group consisting of hydroxy, halo and nitro;
$X_2$ is selected from the group consisting of methylene, oxygen and sulfur;
s, t, v are independently integers from 0 to 4, with the proviso that s, t and v cannot all be 0 at the same time.

In some embodiments, the compound comprises Formula (XIVa):

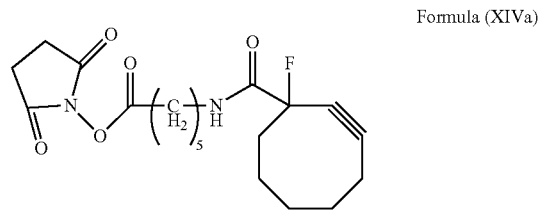

Formula (XIVa)

In some embodiments, the compound comprises Formula (XIVb):

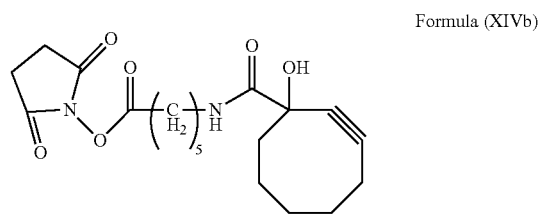

Formula (XIVb)

In some embodiments, the compound comprises Formula (XV):

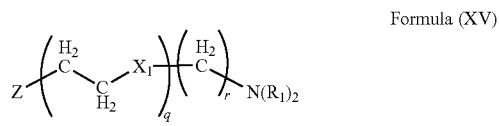

Formula (XV)

wherein:
$R_1$ at each occurrence is independently selected from the group consisting of hydrogen, methyl and ethyl;
$X_1$ is selected from the group consisting of methylene, oxygen and sulfur;
q and r are independently integers from 0 to 4, with the proviso that q and r cannot both be 0 at the same time;
Z is an oligonucleotide moiety.

In some embodiments, the compound comprises Formula (XVa):

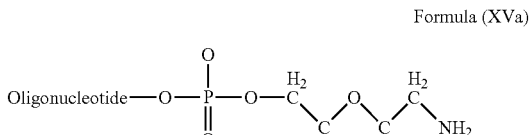

Formula (XVa)

In some embodiments, the compound comprises Formula (XVb):

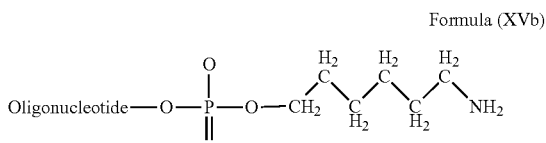

Formula (XVb)

5. Compositions

The invention relates to compositions comprising a combination of compounds of the invention.

In some embodiments, the combination comprises a compound comprising an alternative moiety portion as described anywhere herein.

In some embodiments, the compound in the composition comprising the alternative tether moiety as described anywhere herein is present in an amount of 10% by weight or less of said composition.

In some embodiments, the compound in the composition comprising the alternative tether moiety as described anywhere herein is present in an amount in the range of 10 to 15% by weight of said composition.

In some embodiments, the composition comprises a compound of Formula (IV) as described anywhere herein, and a compound of Formula (V) as described anywhere herein. In some embodiments, the compound of Formula (V) as described anywhere herein is present in an amount in the range of 10 to 15% by weight of said composition.

In some embodiments, the composition comprises a compound of Formula (X) as described anywhere herein, and a compound of Formula (XI) as described anywhere herein. In some embodiments, the compound of Formula (XI) as described anywhere herein is present in an amount in the range of 10 to 15% by weight of said composition.

In some embodiments, the composition comprises a compound of Formula (II) as described anywhere herein, and a compound of Formula (III) as described anywhere herein. In some embodiments, the compound of Formula (III) as described anywhere herein is present in an amount in the range of 10 to 15% by weight of said composition.

In some embodiments, the composition comprises a compound of Formula (VIII) as described anywhere herein, and a compound of Formula (IX) as described anywhere herein.

In some embodiments, the compound of Formula (IX) as described anywhere herein is present in an amount in the range of 10 to 15% by weight of said composition.

6. Production Processes

The invention further provides a process of preparing a compound as described anywhere herein. The invention further provides a process of preparing a composition as described anywhere herein.

In some embodiments, the process comprises reacting compounds of Formulae (XII) and (XIII):

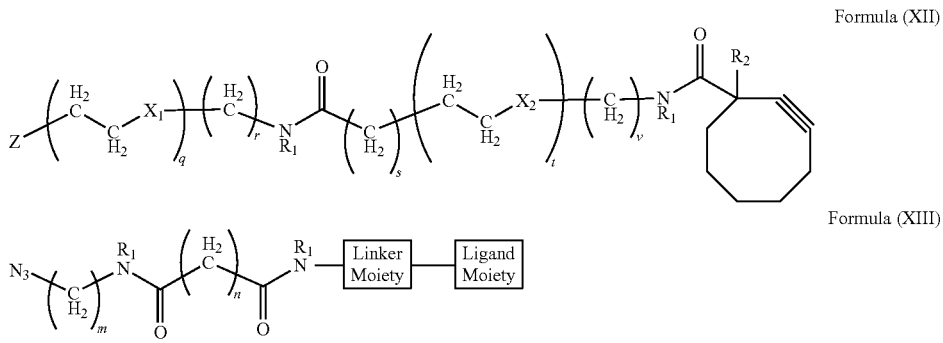

Formula (XII)

Formula (XIII)

wherein:
- $R_1$ at each occurrence is independently selected from the group consisting of hydrogen, methyl and ethyl;
- $R_2$ is selected from the group consisting of hydrogen, hydroxy, —$OC_{1-3}$alkyl, —$C(=O)OC_{1-3}$alkyl, halo and nitro;
- $X_1$ and $X_2$ at each occurrence are independently selected from the group consisting of methylene, oxygen and sulfur;
- m is an integer of from 1 to 6;
- n is an integer of from 1 to 10;
- q, r, s, t, v are independently integers from 0 to 4, with the proviso that:
  (i) q and r cannot both be 0 at the same time; and
  (ii) s, t and v cannot all be 0 at the same time;
- Z is oligonucleotide moiety;

and where appropriate carrying out deprotection of the ligand and/or annealing of a second strand for the oligonucleotide moiety.

In some embodiments, compound of Formula (XII) is Formula (XIIa):

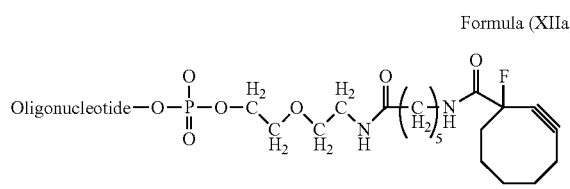

Formula (XIIa)

and compound of Formula (XIII) is Formula (XIIIa):

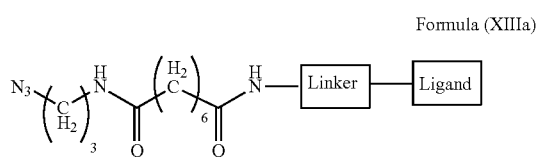

Formula (XIIIa)

wherein the oligonucleotide comprises an RNA duplex comprising first and second strands, wherein the first strand is at least partially complementary to an RNA sequence of a target gene, and the second strand is at least partially complementary to said first strand, and wherein each of the first and second strands have 5' and 3' ends, and wherein said RNA duplex is attached at the 5' end of its second strand to the adjacent phosphate.

In some embodiments, Formula (XII) is Formula (XIIb):

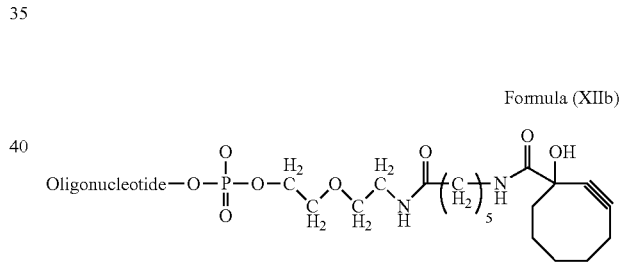

Formula (XIIb)

and compound of Formula (XIII) is Formula (XIIIa):

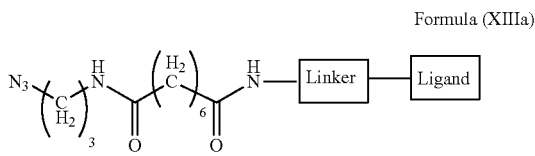

Formula (XIIIa)

wherein the oligonucleotide comprises an RNA duplex comprising first and second strands, wherein the first strand is at least partially complementary to an RNA sequence of a target gene, and the second strand is at least partially complementary to said first strand, and wherein each of the first and second strands have 5' and 3' ends, and wherein said RNA duplex is attached at the 5' end of its second strand to the adjacent phosphate.

In some embodiments, compound of Formula (XII) is Formula (XIIc):

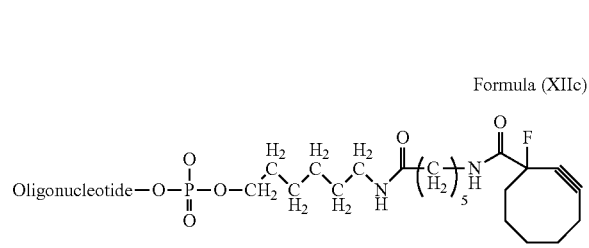

Formula (XIIc)

and compound of Formula (XIII) is Formula (XIIIa):

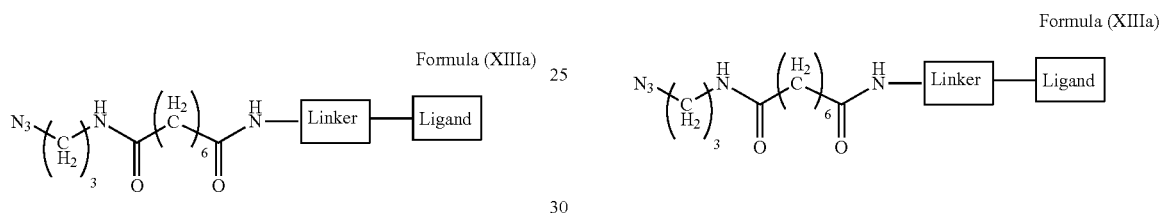

Formula (XIIIa)

wherein the oligonucleotide comprises an RNA duplex comprising first and second strands, wherein the first strand is at least partially complementary to an RNA sequence of a target gene, and the second strand is at least partially complementary to said first strand, and wherein each of the first and second strands have 5' and 3' ends, and wherein said RNA duplex is attached at the 3' end of its second strand to the adjacent phosphate.

In some embodiments, compound of Formula (XII) is Formula (XIId):

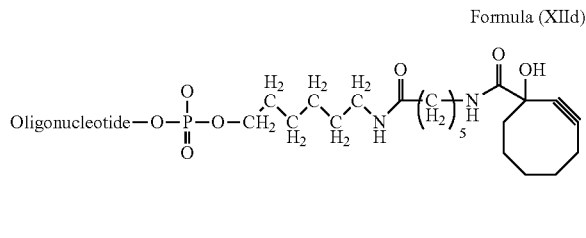

Formula (XIId)

and compound of Formula (XIII) is Formula (XIIIa):

Formula (XIIIa)

wherein the oligonucleotide comprises an RNA duplex comprising first and second strands, wherein the first strand is at least partially complementary to an RNA sequence of a target gene, and the second strand is at least partially complementary to said first strand, and wherein each of the first and second strands have 5' and 3' ends, and wherein said RNA duplex is attached at the 3' end of its second strand to the adjacent phosphate.

In some embodiments, compound of Formula (XIIIa) is Formula (XIIIb):

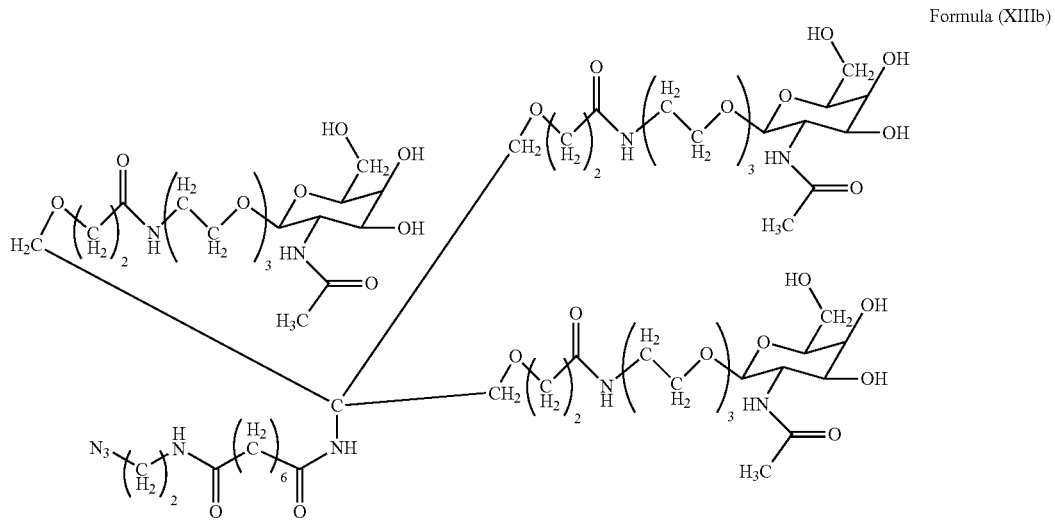

Formula (XIIIb)

In some embodiments, a compound of Formula (XII) is prepared by reacting compounds of Formulae (XIV) and (XV):

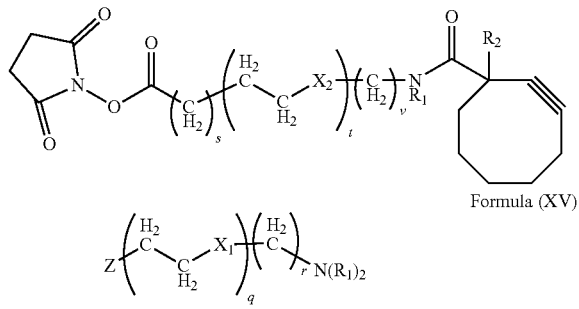

Formula (XIV)

Formula (XV)

R₁ at each occurrence is independently selected from the group consisting of hydrogen, methyl and ethyl;

R₂ is selected from the group consisting of hydrogen, hydroxy, —OC$_{1-3}$alkyl, —C(=O)OC$_{1-3}$alkyl, halo and nitro;

X₁ and X₂ at each occurrence are independently selected from the group consisting of methylene, oxygen and sulfur;

q, r, s, t, v are independently integers from 0 to 4, with the proviso that:

(i) q and r cannot both be 0 at the same time; and
(ii) s, t and v cannot all be 0 at the same time;

Z is an oligonucleotide moiety.

In some embodiments, compound of Formula (XIV) is either Formula (XIVa) or Formula (XIVb):

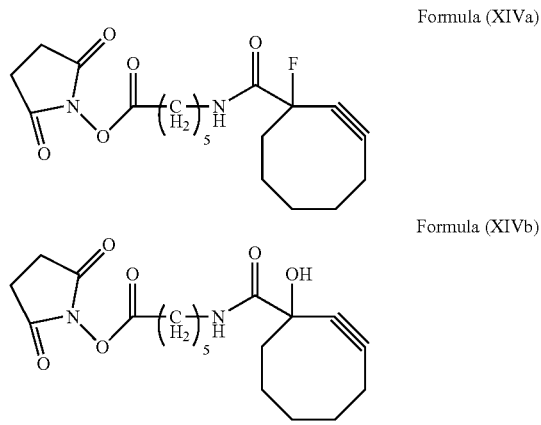

Formula (XIVa)

Formula (XIVb)

and compound of Formula (XV) is either Formula (XVa) or Formula (XIVb):

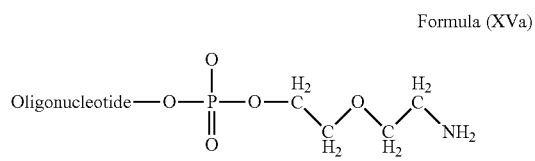

Formula (XVa)

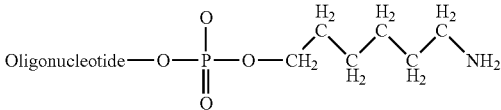

Formula (XVb)

wherein the oligonucleotide comprises an RNA duplex comprising first and second strands, wherein the first strand is at least partially complementary to an RNA sequence of a target gene, and the second strand is at least partially complementary to said first strand, and wherein each of the first and second strands have 5' and 3' ends, and wherein (i) said RNA duplex is attached at the 5' end of its second strand to the adjacent phosphate in Formula (XVa), or (ii) said RNA duplex is attached at the 3' end of its second strand to the adjacent phosphate in Formula (XVb).

7. Uses

The invention relates to use of the compounds and compositions as described anywhere herein.

The present invention also relates to uses of a compound as described anywhere herein, for the preparation of another compound as described anywhere herein.

The present invention further relates to uses of a composition as described anywhere herein, for the preparation of another composition as described anywhere herein.

In some embodiments, the use is for the preparation of a compound or a composition as described anywhere herein, wherein R₂=F.

In some embodiments, the use is for the preparation of a compound or a composition as described anywhere herein, comprising an alternative tether moiety as described anywhere herein. In some embodiments, the use is for the preparation of a compound or a composition as described anywhere herein, wherein R₂=OH.

The present invention relates to use of a compound of Formula (XII) as described anywhere herein, for the preparation of a compound as described anywhere herein, and/or a composition as described anywhere herein. The present invention relates to use of a compound of Formula (XIII) as described anywhere herein, for the preparation of a compound as described anywhere herein, and/or a composition as described anywhere herein. The present invention relates to use of a compound of Formula (XIV) as described anywhere herein, for the preparation of a compound as described anywhere herein, and/or a composition as described anywhere herein. The present invention relates to use of a compound of Formula (XV) as described anywhere herein, for the preparation of a compound as described anywhere herein, and/or a composition as described anywhere herein.

The present invention relates to use of a compound of Formula (XIIa) as described anywhere herein, for the preparation of a compound as described anywhere herein, and/or a composition as described anywhere herein. The present invention relates to use of a compound of Formula (XIIb) as described anywhere herein, for the preparation of a compound as described anywhere herein, and/or a composition as described anywhere herein. The present invention relates to use of a compound of Formula (XIIc) as described anywhere herein, for the preparation of a compound as described anywhere herein and/or a composition as described anywhere herein. The present invention relates to use of a compound of Formula (XIId) as described anywhere herein, for the preparation of a compound as described anywhere herein, and/or a composition as described anywhere herein. The present invention relates to use of a compound of Formula (XIIIa) as described anywhere herein, for the preparation of a compound as described anywhere herein, and/or a composition as described anywhere herein. The present invention relates to use of a compound of Formula (XIIIb) as described anywhere herein, for the preparation of a compound as described anywhere herein, and/or a composition as described anywhere herein. The present invention relates to use of a compound of Formula (XIVa) as described anywhere herein, for the preparation of a compound as described anywhere herein, and/or a composition as described anywhere herein. The present invention relates to use of a compound of Formula (XIVb) as described anywhere herein, for the preparation of a compound as described anywhere herein, and/or a composition as described anywhere herein. The present invention relates to use of a compound of Formula (XVa) as described anywhere herein, for the preparation of a compound as described anywhere herein, and/or a composition as described anywhere herein. The present invention relates to use of a compound of Formula (XVb) as described anywhere herein, for the preparation of a compound as described anywhere herein, and/or a composition as described anywhere herein.

The invention relates to a compound or composition obtained, or obtainable by a process as described anywhere herein.

The invention relates to therapeutic uses of the compounds and compositions described anywhere herein.

Thus, the present invention relates to a pharmaceutical composition comprising a compound as described anywhere herein, together with a pharmaceutically acceptable carrier, diluent or excipient. The present invention relates to a pharmaceutical composition comprising a composition as described anywhere herein, together with a pharmaceutically acceptable carrier, diluent or excipient.

The present invention also relates to a compound as described anywhere herein, for use in therapy. The present invention also relates to a composition as described anywhere herein, for use in therapy.

Suitable dosages, formulations, administration routes, compositions, dosage forms, combinations with other therapeutic agents, pro-drug formulations are also encompassed by the present invention.

The compounds of the invention may be utilized as research reagents for, for example, diagnostics, therapeutics and prophylaxis.

In therapy, compounds of the invention may be used to specifically modulate the synthesis of a target protein in a cell. This can be achieved by degrading, silencing or inhibiting the mRNA of said target protein, thereby preventing the formation of said protein. Alternatively, compounds of the invention may be used to modulate a non-coding DNA or RNA molecule exerting a regulatory effect on mechanisms within a cell in cells and experimental animals thereby facilitating functional analysis of the target or an appraisal of its usefulness as a target for therapeutic intervention.

In preferred embodiments, target protein is in a target cell that comprises asialoglycoprotein receptors (ASPGR) on the surface, such as liver cells, in particular hepatocytes.

Thus, compounds of the invention may be used as a therapy in an animal or a human, suspected of having a disease or disorder, which can be alleviated or treated by modulating a DNA or RNA encoding a mammalian target polypeptide in said animal or human.

In preferred embodiments the target nucleic acid is a gene, a messenger RNA (mRNA) or micro RNA (miRNA).

Further provided are methods of treating a mammal, such as treating a human, suspected of having or being prone to a disease or condition, by administering a therapeutically or prophylactically effective amount of one or more of the compounds or compositions of the invention.

The invention also provides for the use of the compound or conjugate of the invention as described for the manufacture of a medicament for the treatment of a disorder or for a method of the treatment of as a disorder affected by the modulation of a target nucleic acid.

The invention also provides for a method for treating a disorder, said method comprising administering a compound according to the invention and/or a pharmaceutical composition according to the invention to a patient in need thereof.

Examples of disorders to be treated are liver diseases such as hepatitis (including viral hepatitis, such as HBV or HCV), hepatic steatosis, atherosclerosis, hyperlipidemia, hypercholesterolemia, familiar hypercholesterolemia e.g. gain of function mutations in Apolipoprotein B, HDL/LDL cholesterol imbalance, dyslipidemias, e.g., familial hyperlipidemia (FCHL), acquired hyperlipidemia, statin-resistant hypercholesterolemia, coronary artery disease (CAD), and coronary heart disease (CHD), cirrhosis and cancer.

8. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

It is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, the term "and/or" refers to any one of the items, any combination of the items, or all of the items with which the term is associated. For instance, the phrase "A, B, and/or C" is intended to encompass each of the following embodiments: A, B, and C; A, B, or C; A or B; A or C; B or C; A and B; A and C; B and C; A and B or C; B and A or C; C and A or B; A (alone); B (alone); and C (alone).

9. EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

The following constructs are used in the examples:

20 and FIG. 21 herein. This correspondence of abbreviation to actual linker structure similarly applies to all other references of the above abbreviations herein.

Reference to (invabasic)(invabasic) refers to nucleotides in an overall polynucleotide which are the terminal 2 nucleotides which have sugar moieties that are (i) abasic, and (ii) in an inverted configuration, whereby the bond between the

TABLE 1

| Target | ID | Sense Sequence 5' → 3' | Antisense Sequence 5' → 3' |
|---|---|---|---|
| hsHAO1 | ETX003 | (ET-GalNAc-T1N3)(MFCO)(NH-DEG)GfaCfuUfuCfaUfcCfuGfgAfaAfuAfsusAf (SEQ ID NO: 13) | usAfsuAfuUfuCfcAfgGfaUfgAfaAfg UfcsCfsa (SEQ ID NO: 14) |
| hsHAO1 | ETX005 | (invabasic)(invabasic)gsascuuuCfaUfCfCfuggaaauasusa (NHC6)(MFCO)(ET-GalNAc-T1N3) (SEQ ID NO: 7) | usAfsuauUfuCfCfaggaUfgAfaagucs csa (SEQ ID NO: 8) |
| hsHAO1 | ETX001 | (ET-GalNAc-T1N3)(MFCO)(NH-DEG)gacuuuCfaUfCfCfuggaaauasusa(invabasic)(invabasic) (SEQ ID NO: 1) | usAfsuauUfuCfCfaggaUfgAfaagucs csa (SEQ ID NO: 2) |
| hsHAO1 | ETX007 | GfsasCfuUfuCfaUfcCfuGfgAfaAfuAfuAf(NHC6)(MFCO)(ET-GalNAc-T1N3) (SEQ ID NO: 19) | usAfsuAfuUfuCfcAfgGfaUfgAfaAfg UfcsCfsa (SEQ ID NO: 20) |
| hsC5 | ETX014 | (invabasic)(invabasic)asasGfcAfaGfaUfAfUfuUfuuAfuAfaua (NHC6)(MFCO)(ET-GalNAc-T1N3) (SEQ ID NO: 9) | usAfsUfuAfuaAfaAfauaUfcUfuGfcu ususudTdT (SEQ ID NO: 10) |
| hsC5 | ETX010 | (ET-GalNAc-T1N3)(MFCO)(NH-DEG)aaGfcAfaGfaUfAfUfuUfuuAfuAfasusa(invabasic)(invabasic) (SEQ ID NO: 3) | usAfsUfuAfuaAfaAfauaUfcUfuGfcu ususudTdT (SEQ ID NO: 4) |
| hsC5 | ETX012 | (ET-GalNAc-T1N3)(MFCO)(NH-DEG)AfaGfcAfaGfaUfaUfuUfuUfaUfaAfsusAf (SEQ ID NO: 15) | usAfsuUfaUfaAfaAfaUfaUfcUfuGfc UfusUfsudTdT (SEQ ID NO: 16) |
| hsC5 | ETX012 (pure FLP) | (ET-GalNAc-T1N3)(MFCO)(NH-DEG)AfaGfcAfaGfaUfaUfuUfuUfaUfaAfsusAf (SEQ ID NO: 15) | usAfsuUfaUfaAfaAfaUfaUfcUfuGfc UfusUfsudTdT (SEQ ID NO: 16) |
| hsC5 | ETX012 (pure-2Da) | (ET-GalNAc-T1N3)(MFCO)(NH-DEG)AfaGfcAfaGfaUfaUfuUfuUfaUfaAfsusAf (SEQ ID NO: 15) | usAfsuUfaUfaAfaAfaUfaUfcUfuGfc UfusUfsudTdT (SEQ ID NO: 16) |
| hsC5 | ETX016 | AfsasGfcAfaGfaUfaUfuUfuUfaUfaAfuAf(NHC6)(MFCO)(ET-GalNAc-T1N3) (SEQ ID NO: 21) | usAfsuUfaUfaAfaAfaUfaUfcUfuGfc UfusUfsudTdT (SEQ ID NO: 22) |
| hsTTR | ETX019 | (ET-GalNAc-T1N3)(MFCO)(NH-DEG)ugggauUfuCfAfUfguaaccaasgsa(invabasic)(invabasic) (SEQ ID NO: 5) | usCfsuugGfuuAfcaugAfaAfucccasu sc (SEQ ID NO: 6) |
| hsTTR | ETX021 | (ET-GalNAc-T1N3)(MFCO)(NH-DEG)UfgGfgAfuUfuCfaUfgUfaAfcCfaAfsgsAf (SEQ ID NO: 17) | usCfsuUfgGfuUfaCfaUfgAfaAfuCfc CfasUfsc (SEQ ID NO: 18) |
| hsTTR | ETX023 | (invabasic)(invabasic)usgsggauUfuCfAfUfguaaccaaga (NHC6)(MFCO)(ET-GalNAc-T1N3) (SEQ ID NO: 11) | usCfsuugGfuuAfcaugAfaAfucccasu sc (SEQ ID NO: 12) |
| hsTTR | ETX025 | UfsgsGfgAfuUfuCfaUfgUfaAfcCfaAfgAf(NHC6)(MFCO)(ET-GalNAc-T1N3) (SEQ ID NO: 23) | usCfsuUfgGfuUfaCfaUfgAfaAfuCfc CfasUfsc (SEQ ID NO: 24) |

In Table 1 the components in brackets having the following nomenclature (ET-GalNAc-T1N3), (MFCO), and (NH-DEG) are descriptors of elements of the linkers, and the complete corresponding linker structures are shown in FIG. 20 and FIG. 21 herein. penultimate nucleotide and the antepenultimate nucleotide has a reversed linkage, namely either a 5-5 or a 3-3 linkage. Again, this similarly applies to all other references to (invabasic)(invabasic) herein.

TABLE 1A

| Target | ID | Short Descriptor | Linker plus ligand SiRNA as Table 1 |
|---|---|---|---|
| hsHAO1 | ETX003 | 5'-GalNAc T1b alternating | Linker + ligand as FIG. 21 |
| hsHAO1 | ETX005 | 3'-GalNAc T1a inverted abasic | Linker + ligand as FIG. 20 |
| hsHAO1 | ETX001 | 5'-GalNAc T1b inverted abasic | Linker + ligand as FIG. 21 |
| hsHAO1 | ETX007 | 3'-GalNAc T1a alternating | Linker + ligand as FIG. 20 |
| hsC5 | ETX014 | 3'-GalNAc T1a inverted abasic | Linker + ligand as FIG. 20 |
| hsC5 | ETX010 | 5'-GalNAc T1b inverted abasic | Linker + ligand as FIG. 21 |
| hsC5 | ETX012 | 5'-GalNAc T1b alternating | Linker + ligand as FIG. 21 |
| hsC5 | ETX012 (pure FLP) | 5'-GalNAc T1b alternating | Linker + ligand as FIG. 21 |
| hsC5 | ETX012 (pure - 2Da) | 5'-GalNAc T1b alternating | Linker + ligand as FIG. 21 |
| hsC5 | ETX016 | 3'-GalNAc T1a alternating | Linker + ligand as FIG. 20 |
| hsTTR | ETX019 | 5'-GalNAc T1b inverted abasic | Linker + ligand as FIG. 21 |
| hsTTR | ETX021 | 5'-GalNAc T1b alternating | Linker + ligand as FIG. 21 |
| hsTTR | ETX023 | 3'-GalNAc T1a inverted abasic | Linker + ligand as FIG. 20 |
| hsTTR | ETX025 | 3'-GalNAc T1a alternating | Linker + ligand as FIG. 20 |

It should also be understood as already explained herein with reference to FIG. 20/FIG. 21, that where appropriate for the linker portions as shown in FIG. 20/FIG. 21 which can be present in any of products ETX001, ETX003, ETX005, ETX007, ETXO10, ETX012, ETX014, ETX016, ETX019, ETX021, ETX023 and ETX025 according to the present invention, that while these products can include molecules based on the linker and ligand portions as specifically depicted in FIG. 20/FIG. 21 attached to an oligonucleotide moiety as also depicted herein, these products may alternatively further comprise, or consist essentially of, molecules wherein the linker and ligand portions are essentially as depicted in FIG. 20/FIG. 21 attached to an oligonucleotide moiety but having the F substituent as shown in FIG. 20/FIG. 21 on the cyclo-octyl ring replaced by a substituent occurring as a result of hydrolytic displacement, such as an OH substituent. In this way, (a) these products can consist essentially of molecules having linker and ligand portions specifically as depicted in FIG. 20/FIG. 21, with a F substituent on the cyclo-octyl ring; or (b) these products can consist essentially of molecules having linker and ligand portions essentially as depicted in FIG. 20/FIG. 21 but having the F substituent as shown in FIG. 20/FIG. 21 on the cyclo-octyl ring replaced by a substituent occurring as a result of hydrolytic displacement, such as an OH substituent, or (c) these products can comprise a mixture of molecules as defined in (a) or (b).

The following control constructs are also used in the examples:

bp base-pair
C5 complement C5
conc. concentration
ctrl. control
CV coefficient of variation
dG, dC, dA, dT DNA residues
F Fluoro
FCS fetal calf serum
GalNAc N-Acetylgalactosamine
GAPDH Glyceraldehyde 3-phosphate dehydrogenase
G, C, A, U RNA residues
g, c, a, u 2'-O-Methyl modified residues
Gf, Cf, Af, Uf 2'-Fluoro modified residues
h hour
HAO1 Hydroxyacid Oxidase 1
HPLC High performance liquid chromatography
Hs *Homo sapiens*
IC50 concentration of an inhibitor where the response is reduced by 50%
ID identifier
KD knockdown
LF2000 Lipofectamine2000
M molar
Mf *Macaca fascicularis*
min minute
MV mean value
n.a. or N/A not applicable
NEAA non-essential amino acid
nt nucleotide

TABLE 2

| Target | ID | Sense Sequence 5' → 3' | Antisense Sequence 5' → 3' |
|---|---|---|---|
| F-Luc | XD-00914 | cuuAcGcuGAGuAcuucGAdTsdT (SEQ ID NO: 37) | UCGAAGuACUcAGCGuAAGdTsdT (SEQ ID NO: 38) |
| hsFVII | XD-03999 | AGAuAuGcAcAcAcAcGGAdTsdT (SEQ ID NO: 39) | UCCGUGUGUGUGcAuAUCUdTsdT (SEQ ID NO: 40) |
| hsAHSA1 | XD-15421 | uscsUfcGfuGfgCfcUfuAfaUfgAfaAf(invdT) (SEQ ID NO: 41) | UfsUfsuCfaUfuAfaGfgCfcAfcGfaGfasusu (SEQ ID NO: 42) |

ABBREVIATIONS

AHSA1 Activator of heat shock protein ATPase1
ASGR1 Asialoglycoprotein Receptor 1
ASO Antisense oligonucleotide
bDNA branched DNA
QC Quality control
QG2.0 QuantiGene 2.0
RLU relative light unit
RNAi RNA interference
RT room temperature s Phosphorothioate backbone modification
SAR structure-activity relationship
SD standard deviation
siRNA small interfering RNA
TTR Transthyretin

9.1 Example 1

Summary

GalNAc-siRNAs targeting either hsHAO1, hsC5 or hsTTR mRNA were synthesized and QC-ed. The entire set of siRNAs (except siRNAs targeting HAG1) was first studied in a dose-response setup in HepG2 cells by transfection using RNAiMAX, followed by a dose-response analysis in a gymnotic free uptake setup in primary human hepatocytes.

Direct incubation of primary human hepatocytes with GalNAc-siRNAs targeting hsHAO1, hsC5 or hsTTR mRNA resulted in dose-dependent on-target mRNA silencing to varying degrees.

Aim of Study

The aim of this set of experiments was to analyze the in vitro activity of different GalNAc-ligands in the context of siRNAs targeting three different on-targets, namely hsHAO1, hsC5 or hsTTR mRNA.

Work packages of this study included (i) assay development to design, synthesize and test bDNA probe sets specific for each and every individual on-target of interest, (ii) to identify a cell line suitable for subsequent screening experiments, (iii) dose-response analysis of potentially all siRNAs (by transfection) in one or more human cancer cell lines, and (iv) dose-response analysis of siRNAs in primary human hepatocytes in a gymnotic, free uptake setting. In both settings, IC50 values and maximal inhibition values should be calculated followed by ranking of the siRNA study set according to their potency.

Material and Methods

Oligonucleotide Synthesis

Standard solid-phase synthesis methods were used to chemically synthesize siRNAs of interest (see Table 1) as well as controls (see Table 2).

Cell Culture and In-Vitro Transfection Experiments

Cell culture, transfection and QuantiGene2.0 branched DNA assay are described below, and siRNA sequences are listed in Tables 1 and 2. HepG2 cells were supplied by American Tissue Culture Collection (ATCC) (HB-8065, Lot #: 63176294) and cultured in ATCC-formulated Eagle's Minimum Essential Medium supplemented to contain 10% fetal calf serum (FCS). Primary human hepatocytes (PHHs) were sourced from Primacyt (Schwerin, Germany) (Lot #: CyHufl9009HEc). Cells are derived from a malignant glioblastoma tumor by explant technique. All cells used in this study were cultured at 37° C. in an atmosphere with 5% $CO_2$ in a humidified incubator.

For transfection of HepG2 cells with hsC5 or hsTTR targeting siRNAs (and controls), cells were seeded at a density of 20.000 cells/well in regular 96-well tissue culture plates. Transfection of cells with siRNAs was carried out using the commercially available transfection reagent RNAiMAX (Invitrogen/Life Technologies) according to the manufacturer's instructions. 10 point dose-response experiments of 20 candidates (11× hsC5, 9× hsTTR) were done in HepG2 cells with final siRNA concentrations of 24, 6, 1.5, 0.4, 0.1, 0.03, 0.008, 0.002, 0.0005 and 0.0001 nM, respectively.

Dose response analysis in PHHs was done by direct incubation of cells in a gymnotic, free uptake setting starting with 1.5 µM highest final siRNA concentration, followed by 500 nM and from there on going serially down in twofold dilution steps.

Control wells were transfected into HepG2 cells or directly incubated with primary human hepatocytes at the highest test siRNA concentrations studied on the corresponding plate. All control siRNAs included in the different project phases next to mock treatment of cells are summarized and listed in Table 2. For each siRNA and control, at least four wells were transfected/directly incubated in parallel, and individual data points were collected from each well.

After 24 h of incubation with siRNA post-transfection, media was removed and HepG2 cells were lysed in Lysis Mixture (1 volume of lysis buffer plus 2 volumes of nuclease-free water) and then incubated at 53° C. for at least 45 minutes. In the case of PHHs, plating media was removed 5 h post treatment of cells followed by addition of 50 µl of complete maintenance medium per well. Media was exchanged in that way every 24 h up to a total incubation period of 72 h. At either 4 h or 72 h time point, cell culture supernatant was removed followed by addition of 200 µl of Lysis Mixture supplemented with 1:1000 v/v of Proteinase K.

The branched DNA (bDNA) assay was performed according to manufacturer's instructions. Luminescence was read using a 1420 Luminescence Counter (WALLAC VICTOR Light, Perkin Elmer, Rodgau-Jügesheim, Germany) following 30 minutes incubation in the presence of substrate in the dark. For each well, the on-target mRNA levels were normalized to the hsGAPDH mRNA levels. The activity of any siRNA was expressed as percent on-target mRNA concentration (normalized to hsGAPDH mRNA) in treated cells, relative to the mean on-target mRNA concentration (normalized to hsGAPDH mRNA) across control wells.

Assay Development

QuantiGene2.0 branched DNA (bDNA) probe sets were designed and synthesised specific for *Homo sapiens* GAPDH, AHSA1, hsHAO1, hsC5 and hsTTR. bDNA probe sets were initially tested by bDNA analysis according to manufacturer's instructions, with evaluation of levels of mRNAs of interest in two different lysate amounts, namely 10 µl and 50 µl, of the following human and monkey cancer cell lines next to primary human hepatocytes: SJSA-1, TF1, NCI-H1650, Y-79, Kasumi-1, EAhy926, Caki-1, Colo205, RPTEC, A253, HeLaS3, Hep3B, BxPC3, DU145, THP-1, NCI-H460, IGR37, LS174T, Be(2)-C, SW 1573, NCI-H358, TC71, 22Rv1, BT474, HeLa, KBwt, Panc-1, U87MG, A172, C42, HepG2, LNCaP, PC3, SupT11, A549, HCT116, HuH7, MCF7, SH-SY5Y, HUVEC, C33A, HEK293, HT29, MOLM 13 and SK-MEL-2. Wells containing only bDNA probe set without the addition of cell lysate were used to monitor technical background and noise signal.

Results

Identification of Suitable Cell Types for Screening of GalNAc-siRNAs

Figure 1:
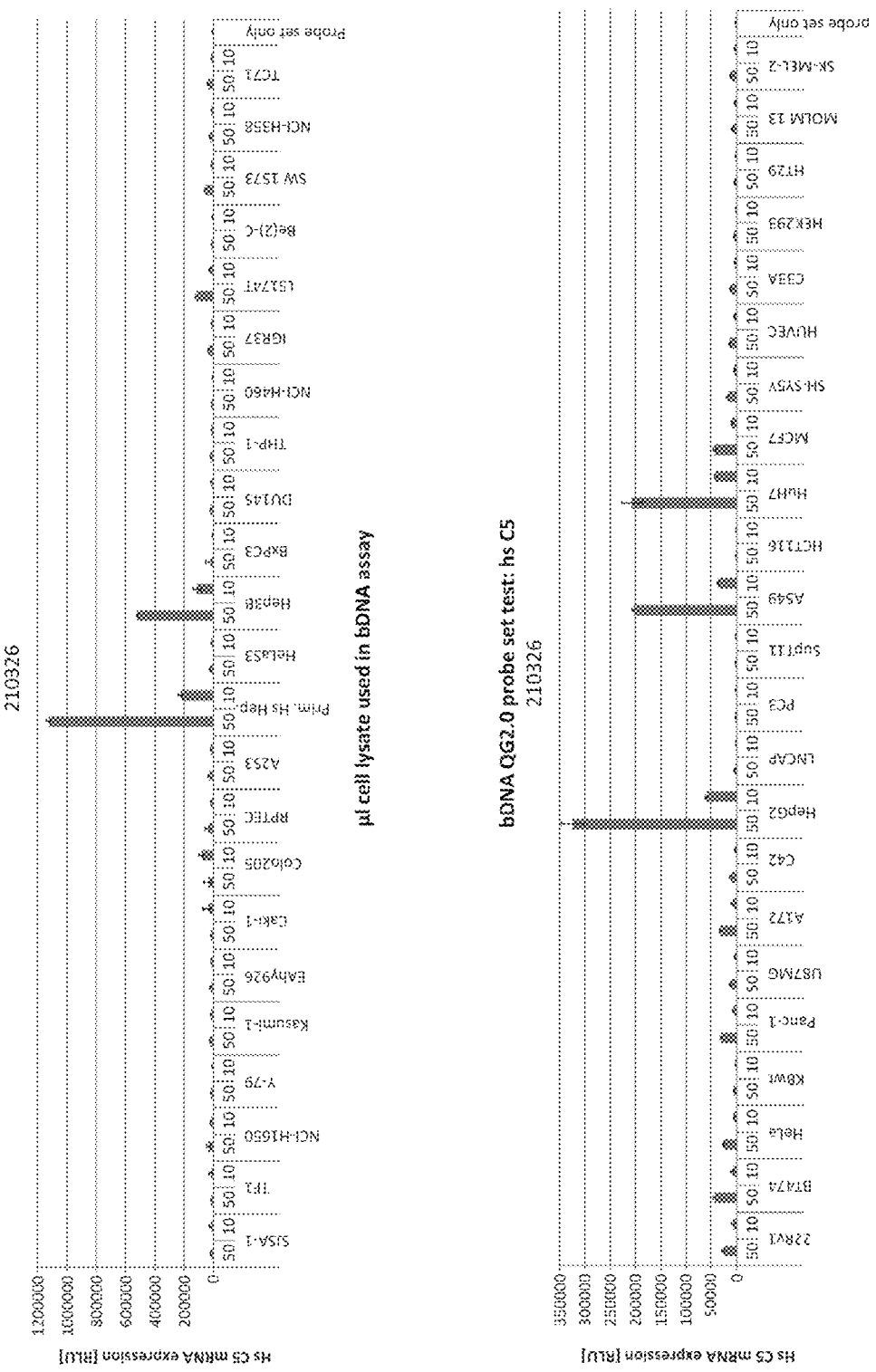
FIG. 1 shows analysis of hsC5 mRNA expression levels in a total of 45 human-derived cancer cell lysates and lysates of primary human hepatocytes (PHHs). mRNA expression levels are shown in relative light units [RLUs].
Figure 2:
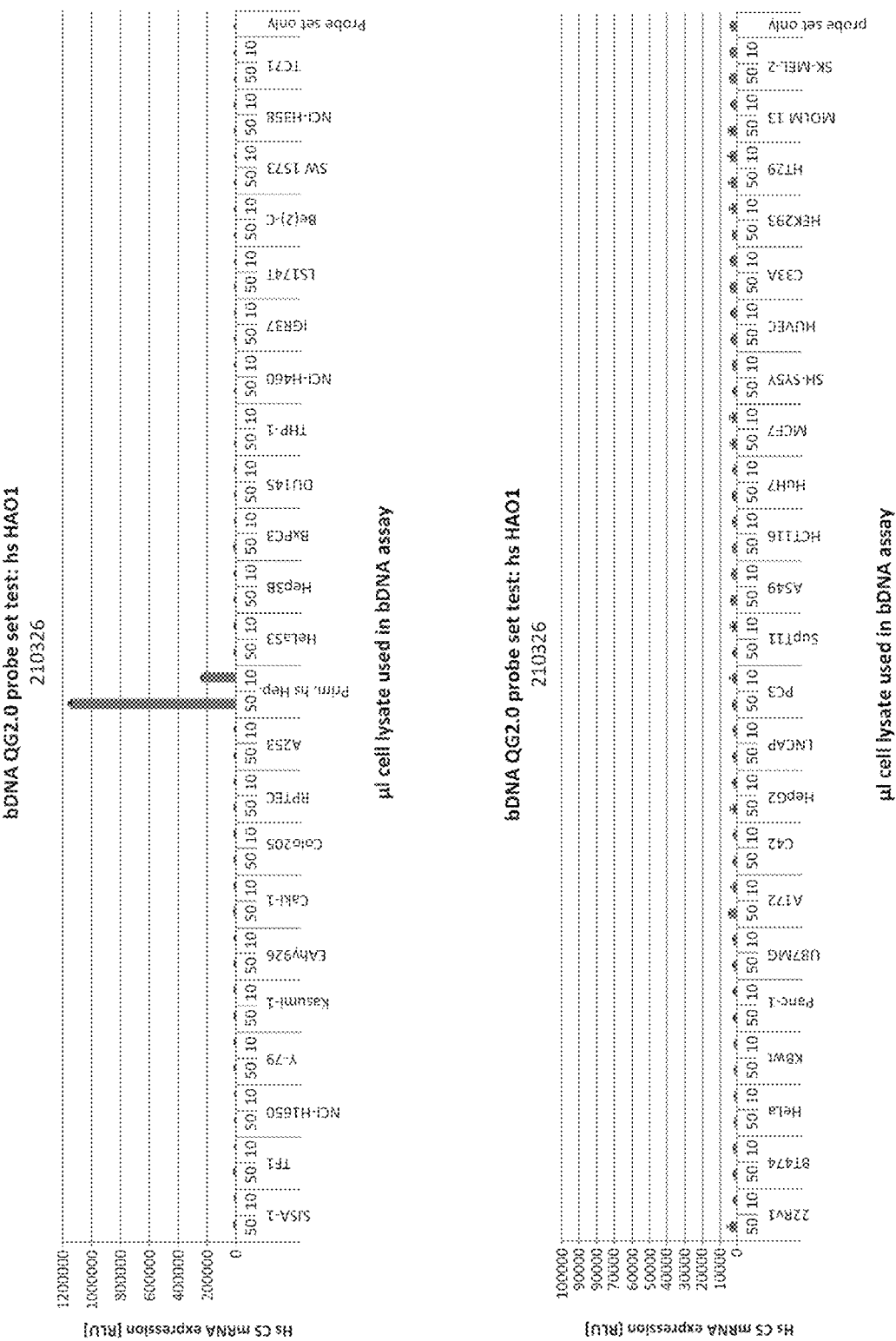
FIG. 2 shows analysis of hsHAO1 mRNA expression levels in a total of 45 human-derived cancer cell lysates and lysates of primary human hepatocytes (PHHs). mRNA expression levels are shown in relative light units [RLUs].
Figure 3:
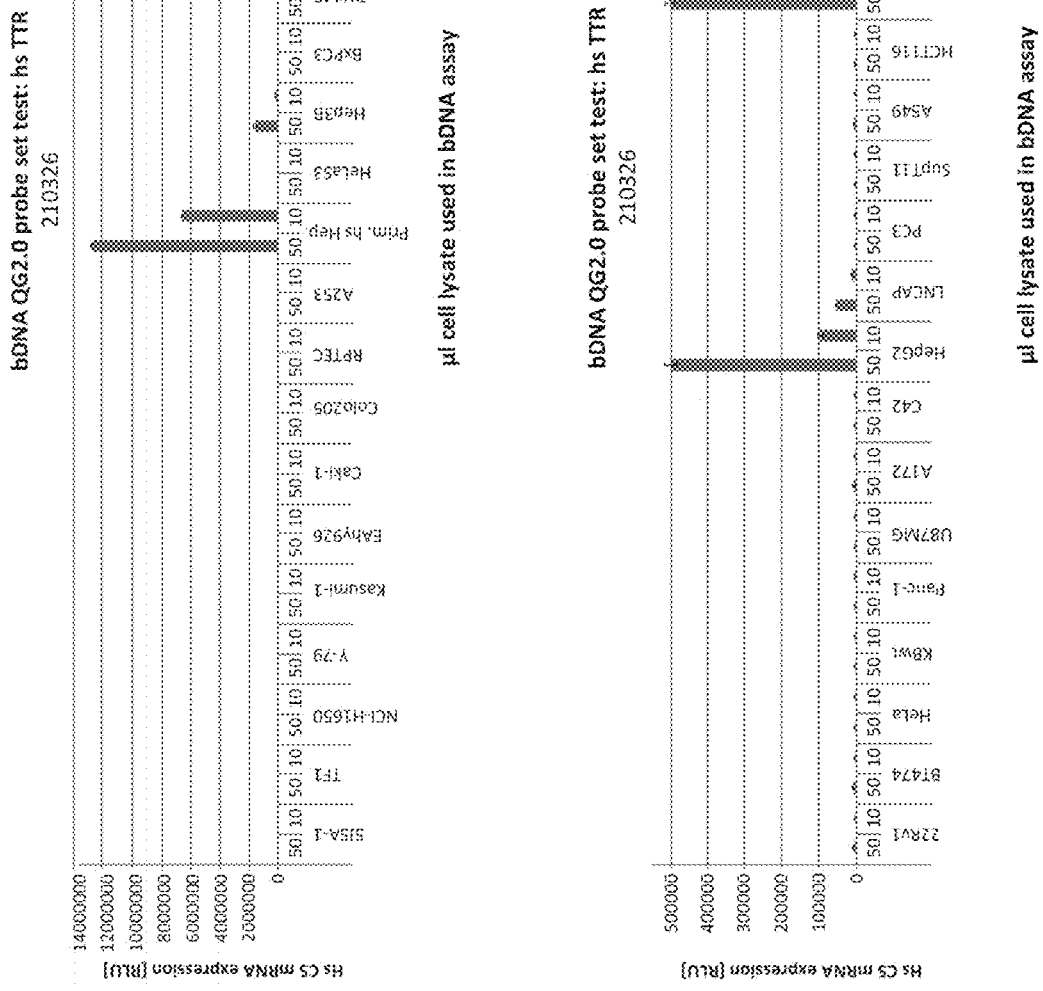
FIG. 3 shows analysis of hsTTR mRNA expression levels in a total of 45 human-derived cancer cell lysates and lysates of primary human hepatocytes (PHHs). mRNA expression levels are shown in relative light units [RLUs].
Figure 4A:
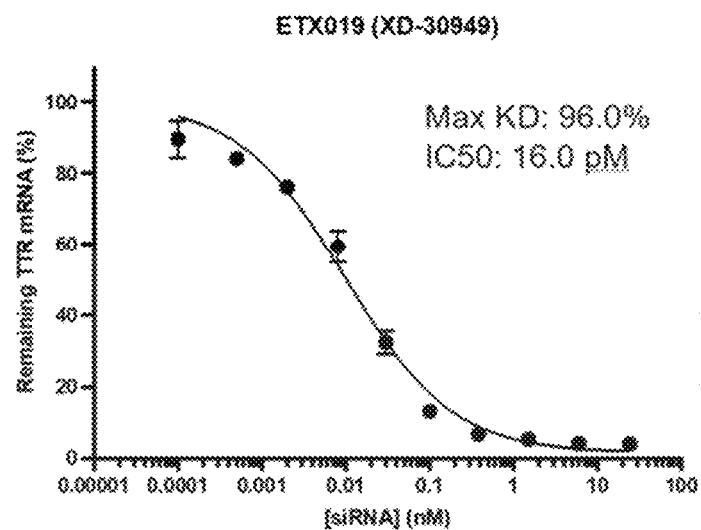
FIGS. 4A-4D shows the results from the dose-response analysis of hsTTR targeting GalNAc-siRNAs in HepG2 cells in Example 1.
Figure 4B:
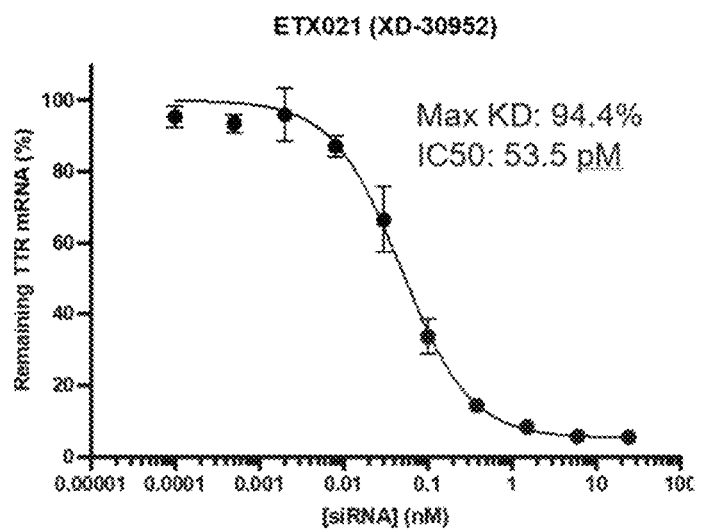
Figure 4C:
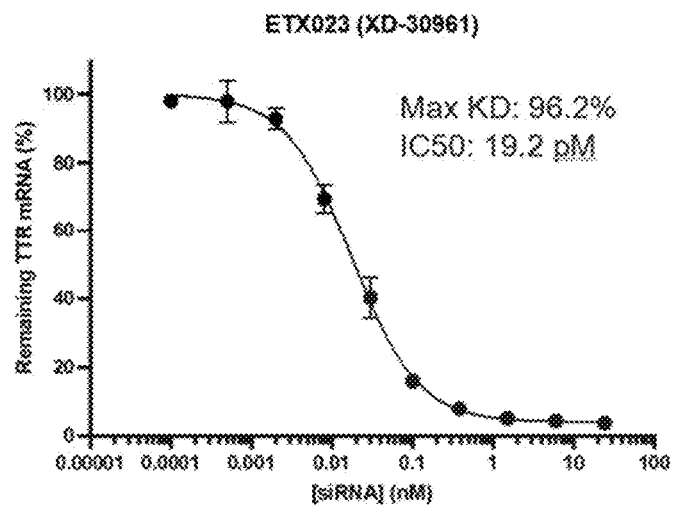
Figure 4D:
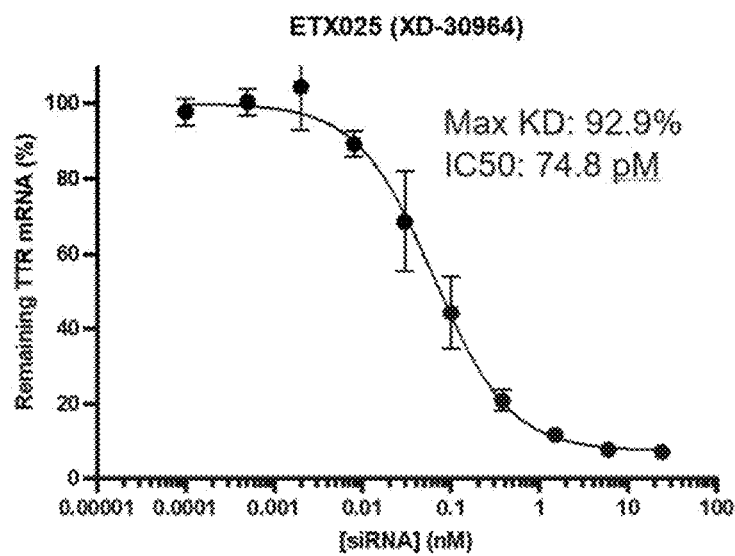
Figure 5A:
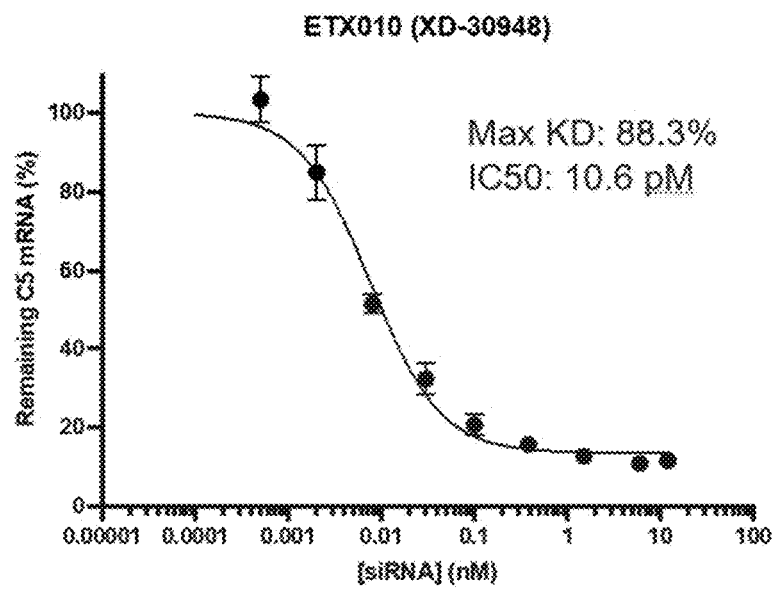
FIGS. 5A-5D shows the results from the dose-response analysis of hsC5 targeting GalNAc-siRNAs in HepG2 cells in Example 1.
Figure 5B:
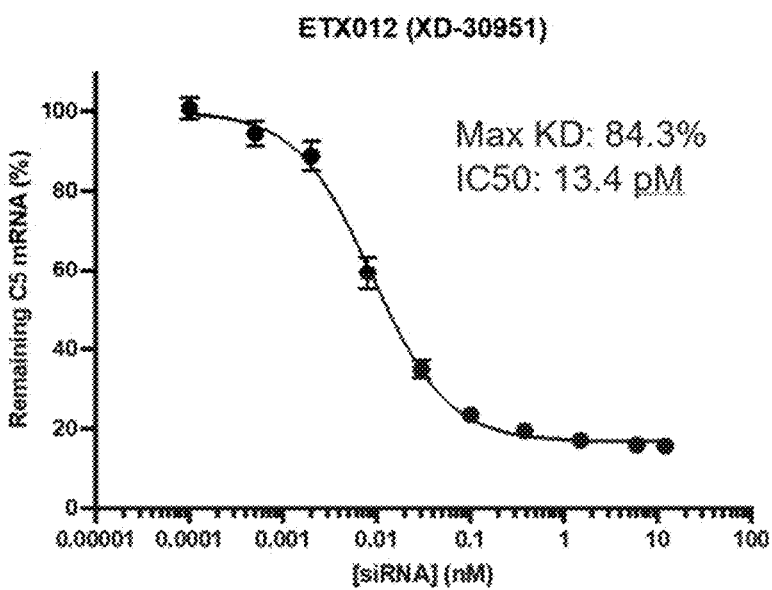
Figure 5C:
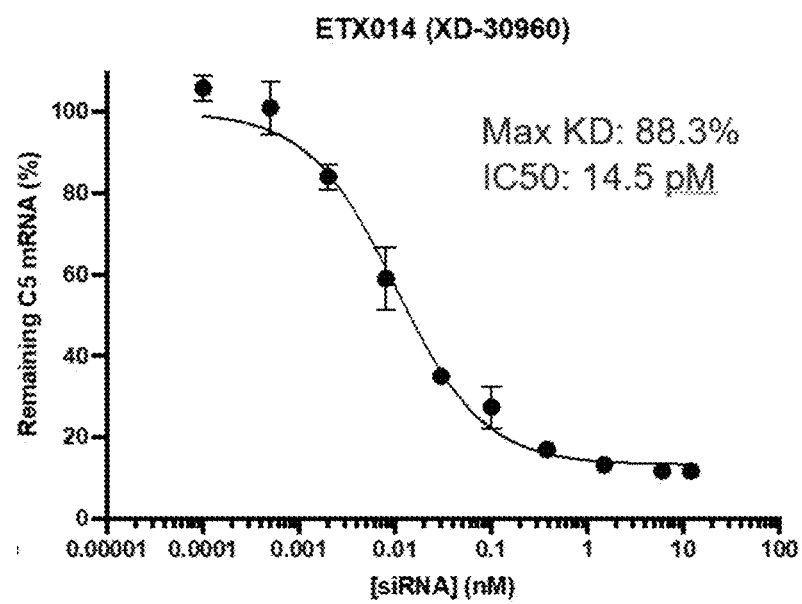
Figure 5D:
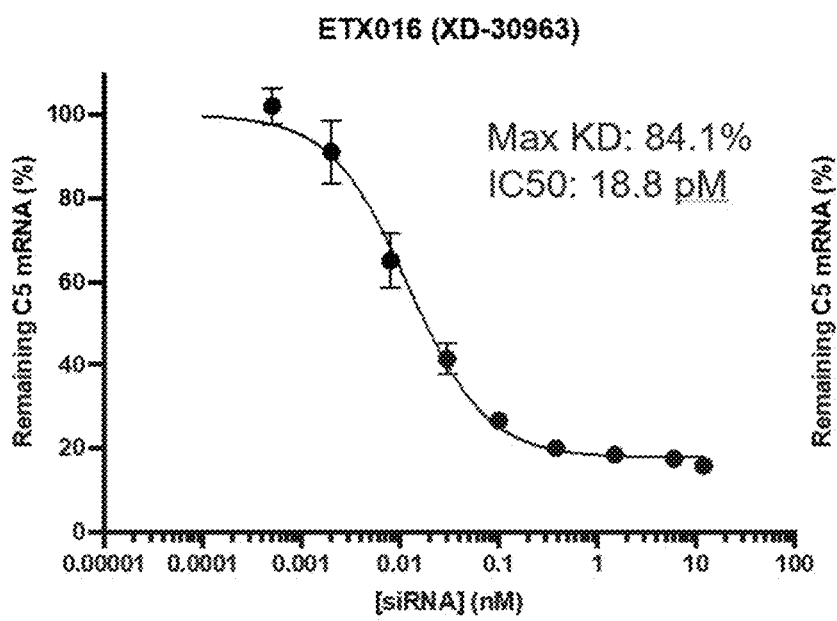

FIGS. 1-3 show mRNA expression data for the three on-targets of interest, namely hsC5, hsHAO1 and hsTTR, in lysates of a diverse set of human cancer cell lines plus primary human hepatocytes. Cell numbers per lysate volume are identical with each cell line tested, this is necessary to allow comparisons of expression levels amongst different cell types. FIG. 1 shows hsC5 mRNA expression data for all cell types tested.

The identical type of cells were also screened for expression of hsHAO1 mRNA, results are shown in bar diagrams as part of FIG. 2.

Lastly, suitable cell types were identified which would allow for screening of GalNAc-siRNAs targeting hsTTR, respective data are part of FIG. 3.

In summary, mRNA expression levels for all three on-targets of interest are high enough in primary human hepatocytes (PHHs). Further, HepG2 cells could be used to screen GasNAc-siRNAs targeting hsC5 and hsTTR mRNAs, in contrast, no cancer cell line could be identified which would be suitable to test siRNAs specific for hsHAO1 mRNA.

Dose-Response Analysis of hsTTR Targeting GaNAc-siRNAs in HepG2 Cells

Following transfection optimization, HepG2 cells were transfected with the entire set of hsTTR targeting GaNAc-siRNAs (see Table 1) in a dose-response setup using RNAiMAX. The highest final siRNA test concentration was 24 nM, going down in nine fourfold dilution steps. The experiment ended at 4 h and 24 h post transfection of HepG2 cells. Table 3 lists activity data for all hsTTR targeting GalNAC-siRNAs studied.

TABLE 3

Target, incubation time, external ID, IC20/IC50/IC80 values and maximal inhibition of hsTTR targeting siRNAs in HepG2 cells. The listing is ordered according to external ID, with 4 h of incubation listed on top and 24 h of incubation on the bottom.

| Target | Incubation [h] | External ID | IC20 [nM] | IC50 [nM] | IC80 [nM] | Max. Inhib. [%] |
|---|---|---|---|---|---|---|
| hsTTR | 4 | ETX019 | 0.206 | 3.769 | #N/A | 58.4 |
| hsTTR | 4 | ETX021 | #N/A | #N/A | #N/A | 3.2 |
| hsTTR | 4 | ETX023 | 1.338 | #N/A | #N/A | 45.9 |
| hsTTR | 4 | ETX025 | #N/A | #N/A | #N/A | -1.8 |
| hsTTR | 24 | ETX019 | 0.002 | 0.016 | 0.143 | 96.0 |
| hsTTR | 24 | ETX021 | 0.014 | 0.053 | 0.236 | 94.4 |
| hsTTR | 24 | ETX023 | 0.005 | 0.019 | 0.081 | 96.2 |
| hsTTR | 24 | ETX025 | 0.018 | 0.075 | 0.392 | 92.9 |

Results for the 24 h incubation are also shown in FIGS. 4A-4D.

In general, transfection of HepG2 cells with hsTTR targeting siRNAs results in on-target mRNA silencing spanning in general the entire activity range from 0% silencing to maximal inhibition. Data generated 24 h post transfection are more robust with lower standard variations, as compared to data generated only 4 h post transfection. Further, the extent of on-target knockdown generally increases over time from 4 h up to 24 h of incubation. hsTTR GalNAc-siRNAs have been identified that silence the on-target mRNA >95% with IC50 values in the low double-digit pM range.

Dose-Response Analysis of hsC5 Targeting GalNAc-siRNAs in HepG2 Cells

The second target of interest, hsC5 mRNA, was tested in an identical dose-response setup (with minimally different final siRNA test concentrations, however) by transfection of HepG2 cells using RNAiMAX with GalNAc-siRNAs sharing identical linger/position/GalNAc-ligand variations as with hsTTR siRNAs, but sequences specific for the on-target hsC5 mRNA. Further, included in the test set of study molecules were two extra variants of siRNA XD-30951. One variant was a full-length product (FLP) minus 2 Da fraction, the other one was fractionated, pure FLP.

TABLE 4

Target, incubation time, external ID, IC20/IC50/IC80 values and maximal inhibition of hsC5 targeting siRNAs in HepG2 cells. The listing is ordered according to external ID, with 4 h of incubation listed on top and 24 h of incubation on the bottom.

| Target | Incubation [h] | External ID | IC20 [nM] | IC50 [nM] | IC80 [nM] | Max. Inhib. [%] |
|---|---|---|---|---|---|---|
| C5 | 4 | ETX010 | 0.125 | 0.445 | #N/A | 71.1 |
| C5 | 4 | ETX012 | 0.087 | 0.756 | #N/A | 67.2 |
| C5 | 4 | ETX012 (pure FLP variant) | 0.157 | 0.707 | #N/A | 62.9 |
| C5 | 4 | ETX012 (pure -2Da variant) | 0.347 | 2.795 | #N/A | 62.2 |
| C5 | 4 | ETX014 | 0.595 | 2.554 | #N/A | 52.7 |
| C5 | 4 | ETX016 | 0.466 | 2.180 | #N/A | 67.1 |
| C5 | 24 | ETX010 | 0.003 | 0.011 | 0.064 | 88.3 |
| C5 | 24 | ETX012 | 0.003 | 0.013 | 0.155 | 84.3 |
| C5 | 24 | ETX012 (pure FLP variant) | 0.001 | 0.007 | 0.115 | 84.0 |
| C5 | 24 | ETX012 (pure -2Da variant) | 0.003 | 0.014 | 0.142 | 85.5 |
| C5 | 24 | ETX014 | 0.003 | 0.014 | 0.130 | 88.3 |
| C5 | 24 | ETX016 | 0.004 | 0.019 | 0.220 | 84.1 |

Results for the 24 h incubation are also shown in FIGS. 5A-5D.

There is dose-dependent on-target hsC5 mRNA silencing upon transfection of HepG2 cells with the GalNAc-siRNA set specific for hsC5. Some knockdown can already be detected at 4 h post-transfection of cells, an even higher on-target silencing is observed after a longer incubation period, namely 24 h. hsC5 GalNAc-siRNAs have been identified that silence the on-target mRNA almost 90% with IC50 values in the low single-digit pM range.

Identification of a Primary Human Hepatocyte Batch Suitable for Testing of all GalNAc-siRNAs The dose-response analysis of the two GalNAc-siRNA sets in human cancer cell line HepG2 should demonstrate (and ensure) that all new GalNAc-/linker/position/cap variants are indeed substrates for efficient binding to AGO2 and loading into RISC, and in addition, able to function in RNAi-mediated cleavage of target mRNA. However, in order to test whether the targeting GalNAc-ligand derivatives allow for efficient uptake into hepatocytes, dose-response analysis experiments should be done in primary human hepatocytes by gymnotic, free uptake setup. Hepatocytes do exclusively express the Asialoglycoprotein receptor (ASGR1) to high levels, and this receptor generally is used by the liver to remove target glycoproteins from circulation. It is common knowledge by now, that certain types of oligonucleotides, e.g. siRNAs or ASOs, conjugated to GalNAc-ligands are recognized by this high turnover receptor and efficiently taken up into the cytoplasm via clathrin-coated vesicles and trafficking to endosomal compartments. Endosomal escape is thought to be the rate-limiting step for oligonucleotide delivery.

Figure 6:
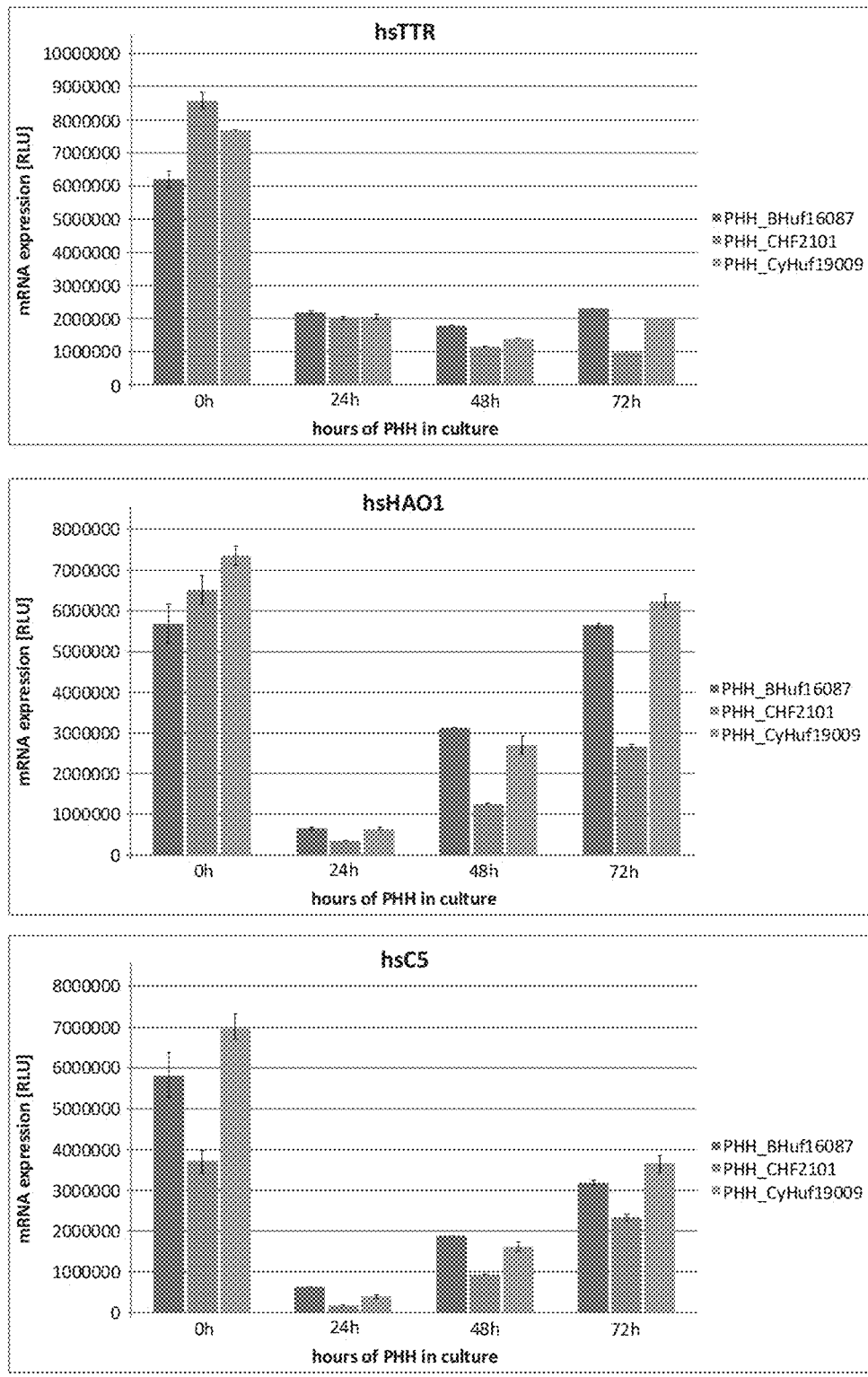
FIG. 6 shows the analysis of hsTTR (top), hsC5 (middle) and hsHAO1 (bottom) mRNA expression levels in all three batches of primary human hepatocytes BHuf16087 (left), CHF2101 (middle) and CyHuf19009 (right) each after 0 h, 24 h, 48 h and 72 h in culture. mRNA expression levels are shown in relative light units [RLUs].

An intermediate assay development experiment was done in which different batches of primary human hepatocytes were tested for their expression levels of relevant genes of interest, namely hsC5, hsTTR, hsHAO1, hsGAPDH and hsAHSA1. Primacyt (Schwerin, Germany) provided three vials of different primary human hepatocyte batches for testing, namely BHuf16087, CHF2101 and CyHufl9009. The cells were seeded on collagen-coated 96-well tissue culture plates, followed by incubation of cells for 0 h, 24 h, 48 h and 72 h before cell lysis and bDNA analysis to monitor mRNA levels of interest. FIG. 6 shows the absolute mRNA expression data for all three on-targets of interest—hsTTR, hsC5 and hsHAO1—in the primary human hepatocyte batches BHuf16087, CHF2101 and CyHufl9009. mRNA expression levels of hsGAPDH and hsAHSA1 are shown in FIG. 7.

Figure 7:
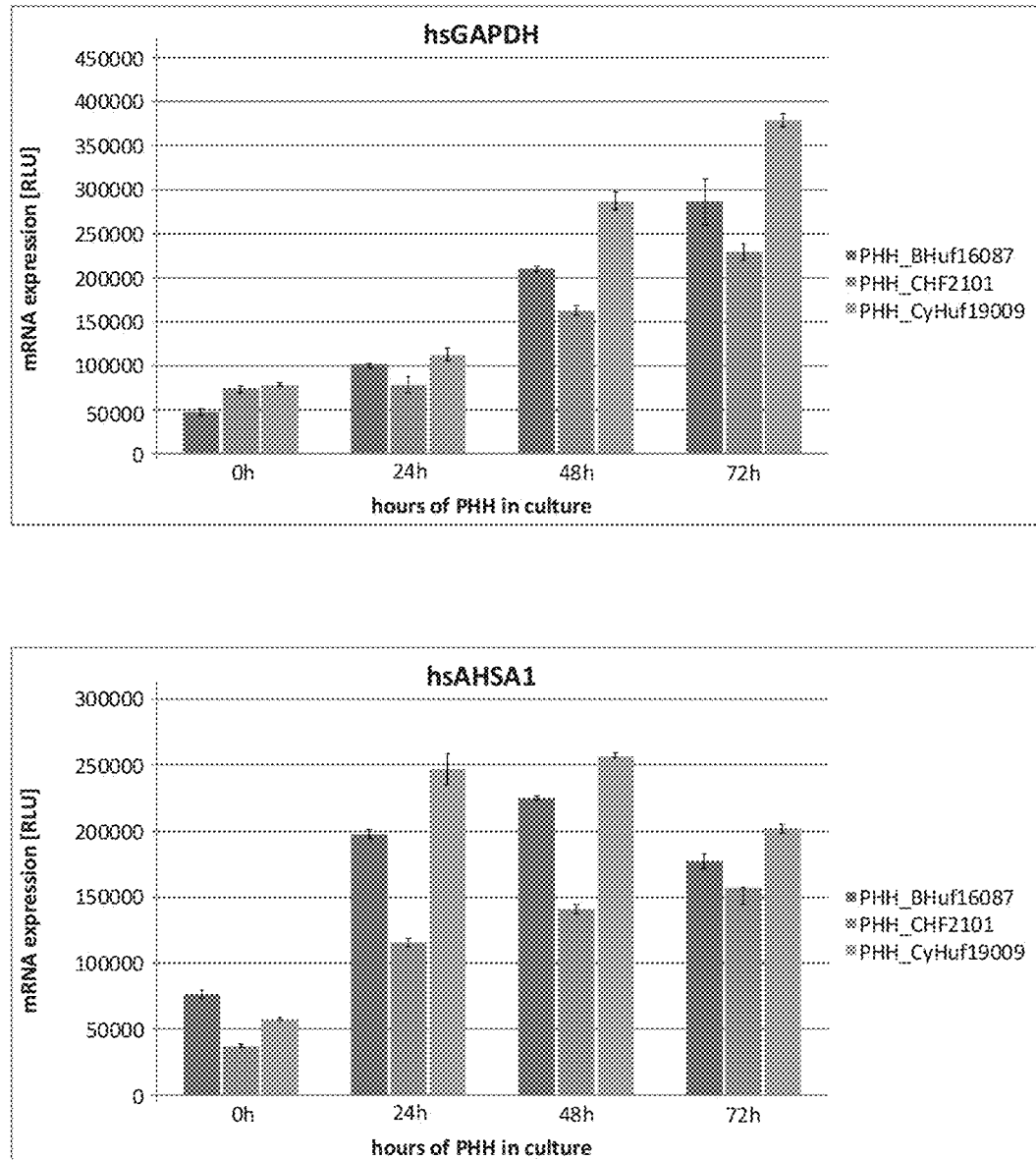
FIG. 7 shows the analysis of hsGAPDH (top) and hsAHSA1 (bottom) mRNA expression levels in all three batches of primary human hepatocytes BHuf16087 (left), CHF2101 (middle) and CyHuf19009 (right) each after 0 h, 24 h, 48 h and 72 h in culture. mRNA expression levels are shown in relative light units [RLUs].
Figure 8A:
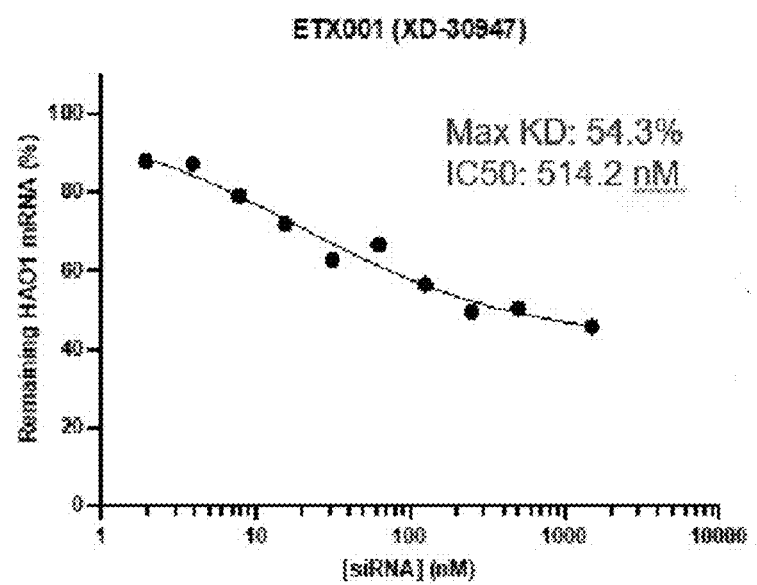
FIGS. 8A-8D shows the results from the dose-response analysis of hsHAO1 targeting GalNAc-siRNAs in PHHs in Example 1.
Figure 8B:
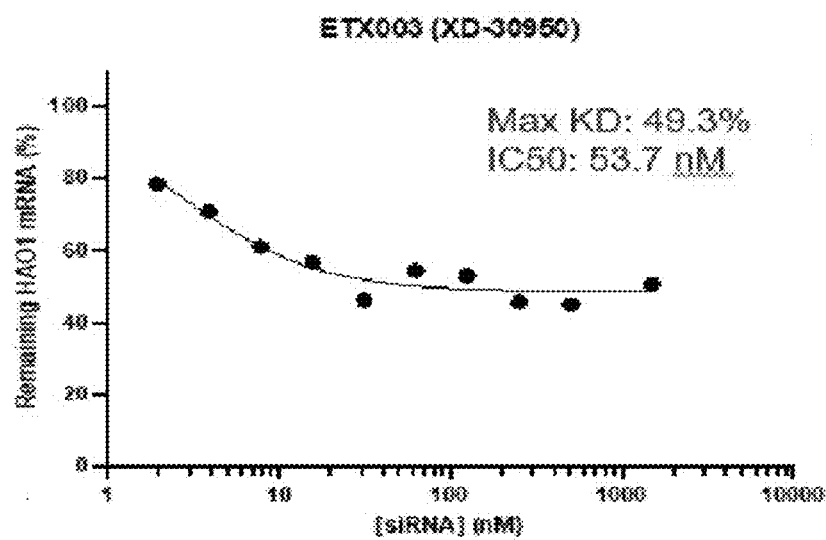
Figure 8C:
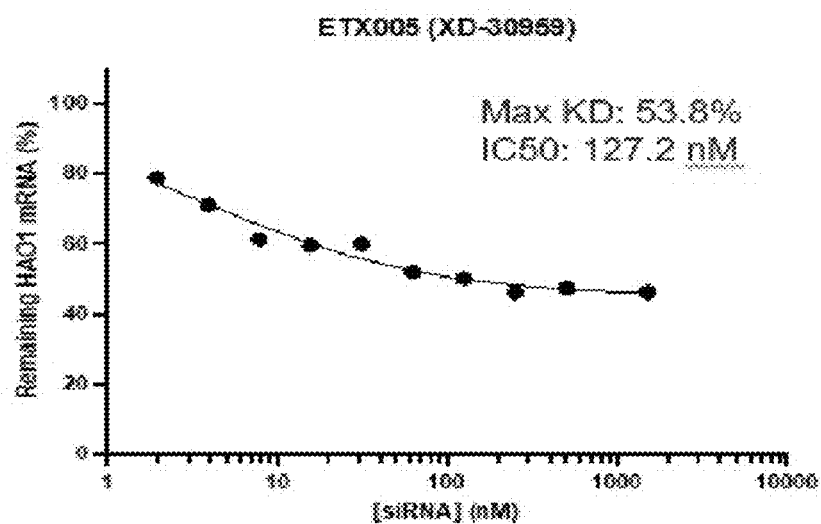
Figure 8D:
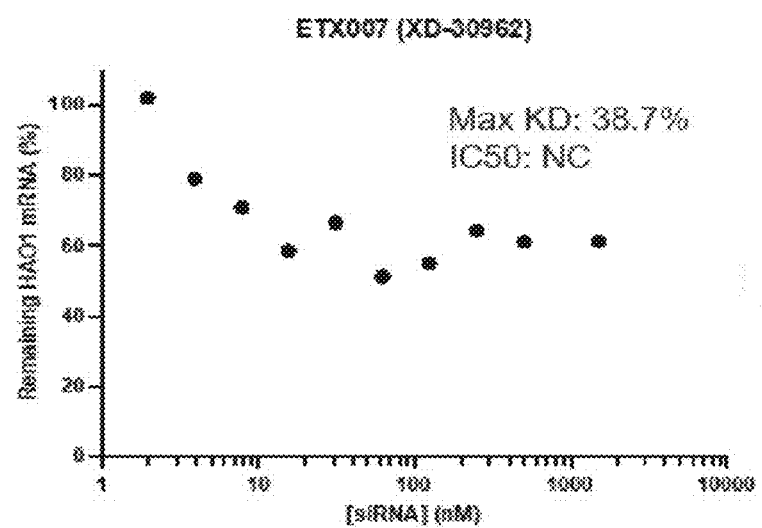
Figure 9A:
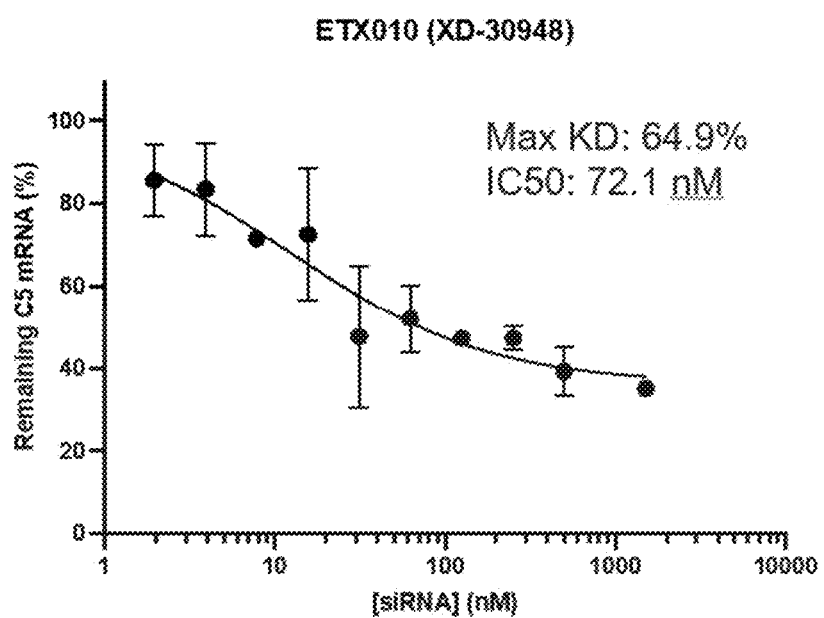
FIGS. 9A-9D shows the results from the dose-response analysis of hsC5 targeting GalNAc-siRNAs in PHHs in Example 1.
Figure 9B:
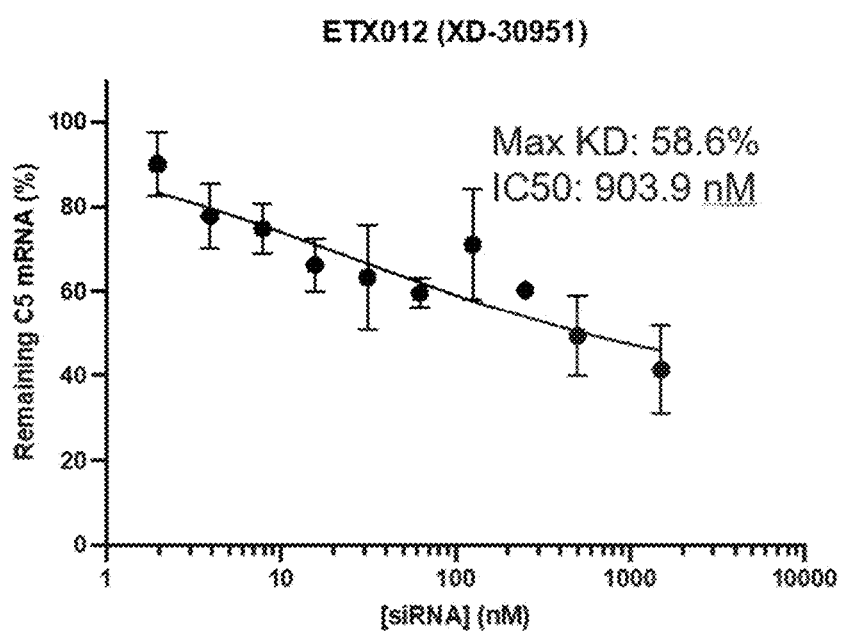
Figure 9C:
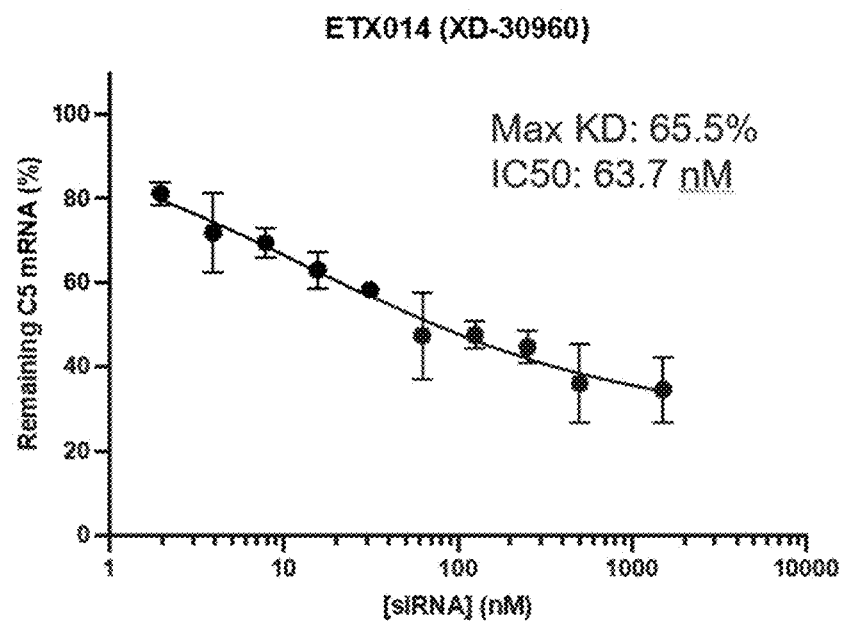
Figure 9D:
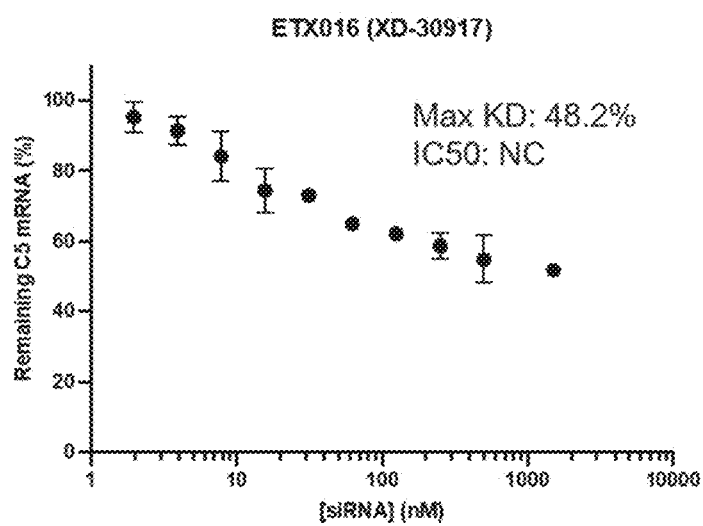
Figure 10A:
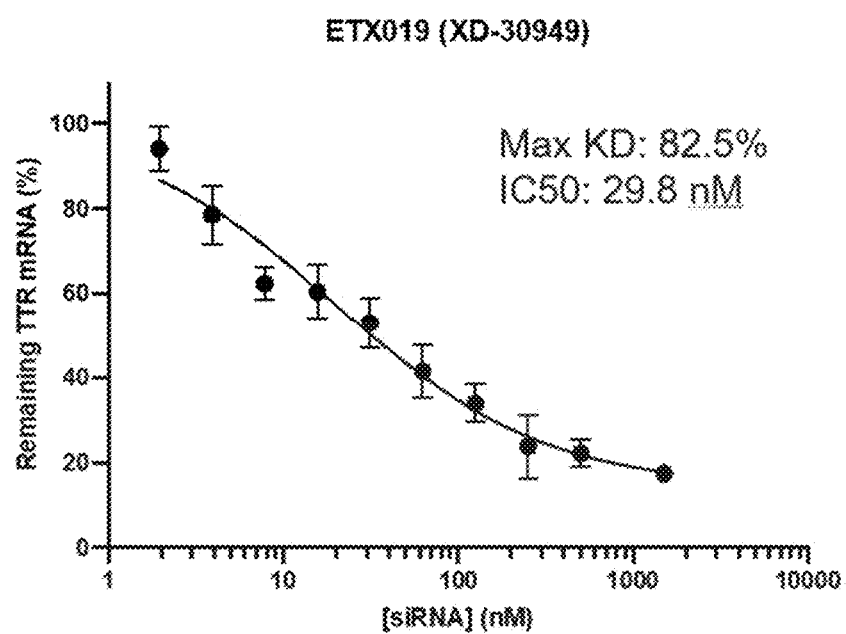
FIGS. 10A-10D shows the results from the dose-response analysis of hsTTR targeting GalNAc-siRNAs in PHHs in Example 1.
Figure 10B:
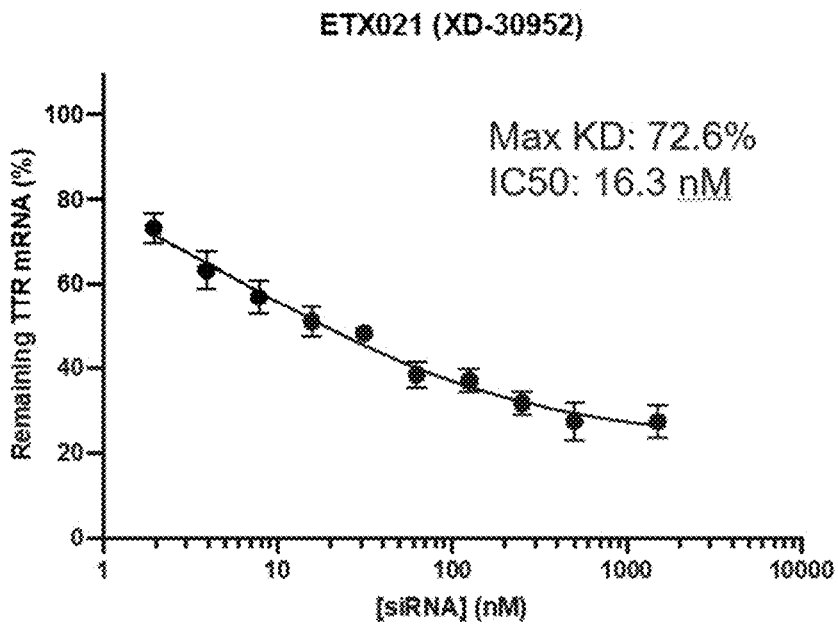
Figure 10C:
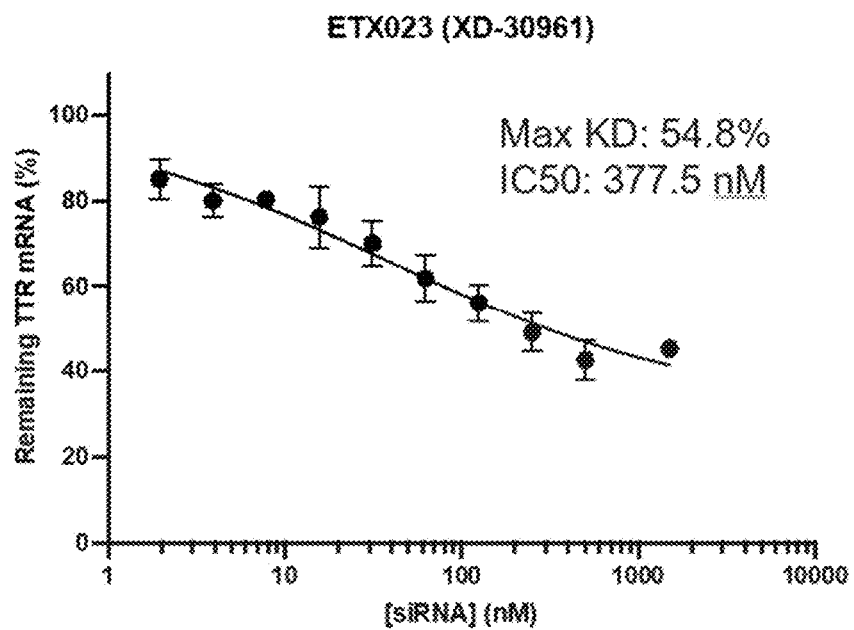
Figure 10D:
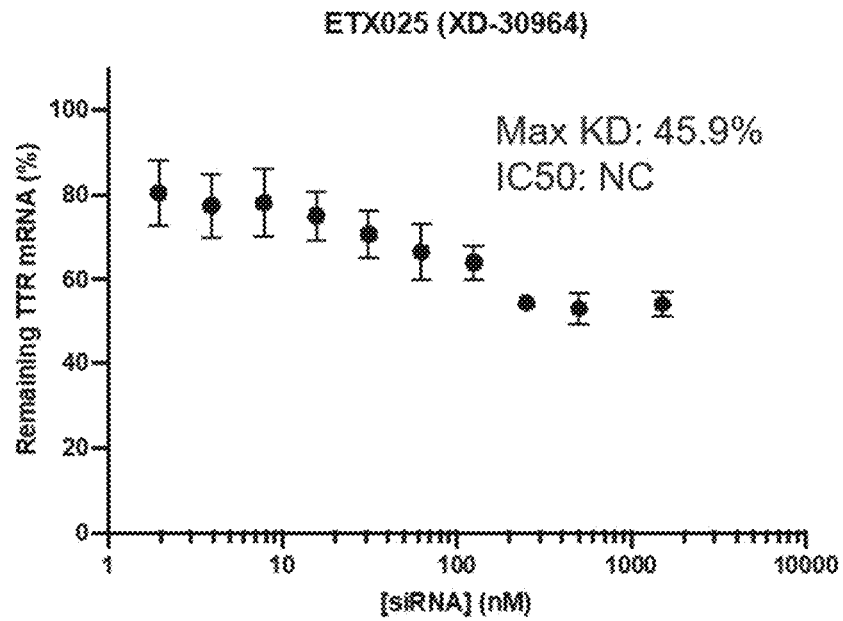

In FIGS. 6 and 7 the left hand column of each data set triplet is BHuf16087, the middle column is CHF2101 and the right hand column is CyHufl9009.

Overall, the mRNA expression of all three on-targets of interest in the primary human hepatocyte batches BHuf16087 and CyHufl9009 are high enough after 72 h to continue with the bDNA assay. Due to the total amount of vials available for further experiments, we continued the experiments with the batch CyHufl9009.

Dose-Response Analysis of hsHAO1 Targeting GalNAc-siRNAs in PHHs

Following the identification of a suitable batch (CyHufl9009) of primary human hepatocytes (PHHs), a gymnotic, free uptake analysis was performed of hsHAO1 targeting GalNAc-siRNAs, listed in Table 1. The highest tested final siRNA concentration was 1.5 µM, followed by 500 nM, going down in eight two-fold serial dilution steps to the lowest final siRNA concentration of 1.95 nM. The experiments ended at 4 h and 72 h post direct incubation of PHH cells. Table 5 lists activity data for all hsHAO1 targeting GalNAc-siRNAs studied. All control siRNAs included in this experiment are summarized and listed in Table 2.

TABLE 5

Target, incubation time, external ID, IC20/IC50/IC80 values and maximal inhibition of hsHAO1 targeting GalNAc-siRNAs in primary human hepatocytes (PHHs). The listing is organized according to external ID, with 4 h and 72 h incubation listed on top and bottom, respectively.

| Target | Incubation [h] | External ID | IC20 [nM] | IC50 [nM] | IC80 [nM] | Max. Inhib. [%] |
|---|---|---|---|---|---|---|
| hsHAO1 (hsGO1) | 4 | ETX001 | #N/A | #N/A | #N/A | 3.5 |
| hsHAO1 (hsGO1) | 4 | ETX003 | #N/A | #N/A | #N/A | 8.4 |
| hsHAO1 (hsGO1) | 4 | ETX005 | #N/A | #N/A | #N/A | 0.7 |
| hsHAO1 (hsGO1) | 4 | ETX007 | #N/A | #N/A | #N/A | 0.2 |
| hsHAO1 (hsGO1) | 72 | ETX001 | 7.1 | 514.2 | #N/A | 54.3 |
| hsHAO1 (hsGO1) | 72 | ETX003 | 1.5 | 53.7 | #N/A | 49.3 |
| hsHAO1 (hsGO1) | 72 | ETX005 | 1.5 | 127.2 | #N/A | 53.8 |

TABLE 5-continued

Target, incubation time, external ID, IC20/IC50/IC80 values and maximal inhibition of hsHAO1 targeting GalNAc-siRNAs in primary human hepatocytes (PHHs). The listing is organized according to external ID, with 4 h and 72 h incubation listed on top and bottom, respectively.

| Target | Incubation [h] | External ID | IC20 [nM] | IC50 [nM] | IC80 [nM] | Max. Inhib. [%] |
|---|---|---|---|---|---|---|
| hsHAO1 (hsGO1) | 72 | ETX007 | 4.0 | #N/A | #N/A | 38.7 |

Results for the 72 h incubation are also shown in FIGS. 8A-8D.

Gymnotic, free uptake of GalNAc-siRNAs targeting hsHAO1 did not lead to significant on-target silencing within 4 h, however after 72 h incubation on-target silencing was visible in a range of 35.5 to 58.1% maximal inhibition.

Dose-Response Analysis of hsC5 Targeting GalNAc-siRNAs in PHHs

The second target of interest, hsC5 mRNA, was tested in an identical dose-response setup by gymnotic, free uptake in PHHs with GalNAc-siRNAs sharing identical linker/position/GalNAc-ligand variations as with hsTTR and hsHAO1 tested in the assays before, but sequences specific for the on-target hsC5 mRNA. Sequences for the GalNAc-siRNAs targeting hsC5 and all sequences and information about control siRNAs are listed in Table 1 and Table 2, respectively. The experiment ended after 4 h and 72 h direct incubation of PHHs. Table 6 lists activity data for all hsC5 targeting GalNAc-siRNAs studied.

TABLE 6

Target, incubation time, external ID, IC20/IC50/IC80 values and maximal inhibition of hsC5 targeting GalNAc-siRNAs in PHHs. The listing is organized according to external ID, with 4 h and 72 h incubation listed on top and bottom, respectively.

| Target | Incubation [h] | External ID | IC20 [nM] | IC50 [nM] | IC80 [nM] | Max. Inhib. [%] |
|---|---|---|---|---|---|---|
| C5 | 4 | ETX010 | #N/A | #N/A | #N/A | −1.3 |
| C5 | 4 | ETX012 | #N/A | #N/A | #N/A | 19.3 |
| C5 | 4 | ETX012 (pure FLP variant) | #N/A | #N/A | #N/A | −6.8 |
| C5 | 4 | ETX012 (pure -2Da variant) | #N/A | #N/A | #N/A | 2.6 |
| C5 | 4 | ETX014 | 51.8 | #N/A | #N/A | 23.7 |
| C5 | 4 | ETX016 | #N/A | #N/A | #N/A | 4.5 |
| C5 | 72 | ETX010 | 4.3 | 72.1 | #N/A | 64.9 |
| C5 | 72 | ETX012 | 3.9 | 903.9 | #N/A | 58.6 |
| C5 | 72 | ETX012 (pure FLP variant) | 5.3 | 338.5 | #N/A | 61.2 |
| C5 | 72 | ETX012 (pure -2Da variant) | 2.9 | 151.0 | #N/A | 62.5 |
| C5 | 72 | ETX014 | 2.2 | 63.7 | #N/A | 65.6 |
| C5 | 72 | ETX016 | 11.4 | #N/A | #N/A | 48.2 |

Results for the 72 h incubation are also shown in FIGS. 9A-9D.

No significant on-target silencing of GalNAc-siRNAs is visible after 4 h incubation. Data generated after an incubation period of 72 h showed a more robust on-target silencing of up to 65.5% maximal inhibition.

Dose-Response Analysis of hsTTR Targeting GalNAc-siRNAs in PHHs

The last target of interest, hsTTR mRNA, was again tested in a gymnotic, free uptake in PHHs in an identical dose-response setup as for the targets hsHAO1 and hsC5, with the only difference being that specific siRNA sequences for the on-target hsTTR mRNA was used (see Table 1).

The experiment ended after 72 h of direct incubation of PHHs. Table 7 lists activity data for all hsTTR targeting GalNAc-siRNAs studied.

TABLE 7

Target, incubation time, external ID, IC20/IC50/IC80 values and maximal inhibition of hsTTR targeting GalNAc-siRNAs in primary human hepatocytes (PHHs). The listing is organized according to external ID.

| Target | Incubation [h] | External ID | IC20 [nM] | IC50 [nM] | IC80 [nM] | Max. Inhib. [%] |
|---|---|---|---|---|---|---|
| hsTTR | 72 | ETX019 | 3.9 | 29.8 | 1536.8 | 82.5 |
| hsTTR | 72 | ETX021 | 0.9 | 16.3 | #N/A | 72.6 |
| hsTTR | 72 | ETX023 | 6.7 | 377.5 | #N/A | 54.8 |
| hsTTR | 72 | ETX025 | 3.9 | #N/A | #N/A | 46.0 |

Results are also shown in FIGS. 10A-10D.

Gymnotic, free uptake of GalNAc-siRNAs targeting hsTTR did lead to significant on-target silencing within 72 h, ranging between 46 to 82.5% maximal inhibition. hsTTR GalNAc-siRNAs were identified that silence the on-target mRNA with IC50 values in the low double-digit nM range.

Conclusions and Discussion

The scope of this study was to analyze the in vitro activity of GalNAc-ligands according to the present invention when used in the context of siRNAs targeting three different on-targets, namely hsHAO1, hsC5 and hsTTR mRNA. siRNA sets specific for each target were composed of siRNAs with different linker/cap/modification/GalNAc-ligand chemistries in the context of two different antisense strands each.

For all targets, GalNAc-siRNAs from Table 1 were identified that showed a high overall potency and low IC50 value.

9.2 Example 2

Routes of Synthesis i) Synthesis of the conjugate building blocks TriGalNAc Thin layer chromatography (TLC) was performed on silica-coated aluminium plates with fluorescence indicator 254 nm from Macherey-Nagel. Compounds were visualized under UV light (254 nm), or after spraying with the 5% $H_2SO_4$ in methanol (MeOH) or ninhydrin reagent according to Stahl (from Sigma-Aldrich), followed by heating. Flash chromatography was performed with a Biotage Isolera One flash chromatography instrument equipped with a dual variable UV wavelength detector (200-400 nm) using Biotage Sfar Silica 10, 25, 50 or 100 g columns (Uppsala, Sweden).

All moisture-sensitive reactions were carried out under anhydrous conditions using dry glassware, anhydrous solvents and argon atmosphere. All commercially available reagents were purchased from Sigma-Aldrich and solvents from Carl Roth GmbH+Co. KG. D-Galactosamine pentaacetate was purchased from AK scientific.

HPLC/ESI-MS was performed on a Dionex UltiMate 3000 RS UHPLC system and Thermo Scientific MSQ Plus Mass spectrometer using an Acquity UPLC Protein BEH C4 column from Waters (300 Å, 1.7 μm, 2.1×100 mm) at 60° C. The solvent system consisted of solvent A with $H_2O$ containing 0.1% formic acid and solvent B with acetonitrile (ACN) containing 0.1% formic acid. A gradient from 5-100% of B over 15 min with a flow rate of 0.4 mL/min was employed. Detector and conditions: Corona ultra-charged aerosol detection (from esa). Nebulizer Temp.: 25° C. $N_2$ pressure: 35.1 psi. Filter: Corona.

$^1H$ and $^{13}C$ NMR spectra were recorded at room temperature on a Varian spectrometer at 500 MHz ($^1H$ NMR) and 125 MHz ($^{13}C$ NMR). Chemical shifts are given in ppm referenced to the solvent residual peak ($CDCl_3$—$^1H$ NMR: δ at 7.26 ppm and $^{13}C$ NMR δ at 77.2 ppm; DMSO-$d_6$-$^1H$ NMR: δ at 2.50 ppm and $^{13}C$ NMR δ at 39.5 ppm). Coupling constants are given in Hertz. Signal splitting patterns are described as singlet (s), doublet (d), triplet (t) or multiplet (m).

ii) Synthesis route for the conjugate building block TriGalNAc

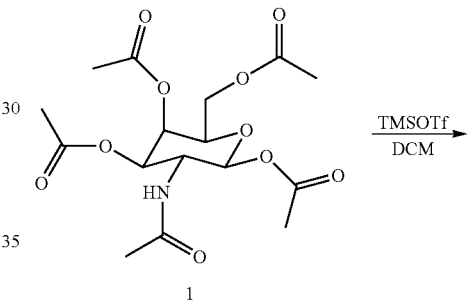

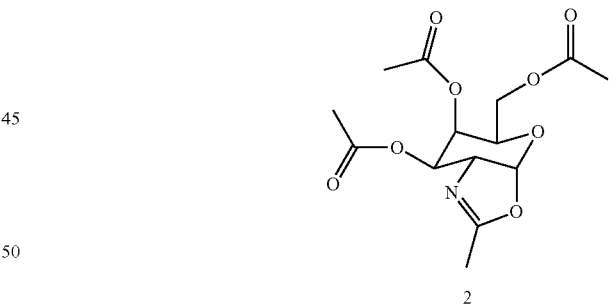

Preparation of compound 2: D-Galactosamine pentaacetate (3.00 g, 7.71 mmol, 1.0 eq.) was dissolved in anhydrous dichloromethane (DCM) (30 mL) under argon and trimethylsilyl trifluoromethanesulfonate (TMSOTf, 4.28 g, 19.27 mmol, 2.5 eq.) was added. The reaction was stirred at room temperature for 3 h. The reaction mixture was diluted with DCM (50 mL) and washed with cold saturated aq. $NaHCO_3$ (100 mL) and water (100 mL). The organic layer was separated, dried over Na2SO4 and concentrated to afford the title compound as yellow oil, which was purified by flash chromatography (gradient elution: 0-10% MeOH in DCM in 10 CV). The product was obtained as colourless oil (2.5 g, 98%, rf=0.45 (2% MeOH in DCM)).

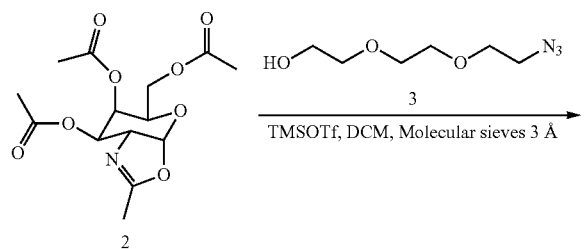

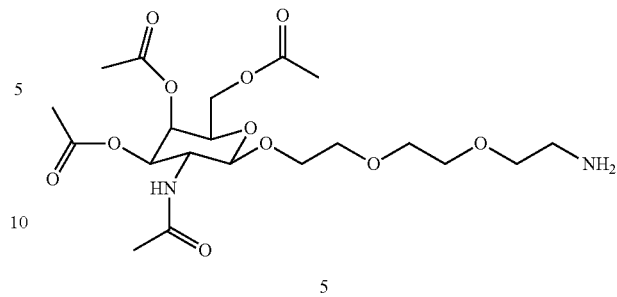

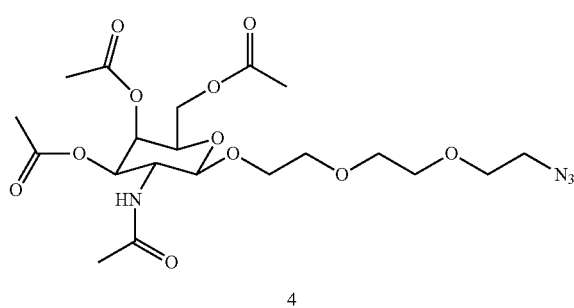

Preparation of compound 4: Compound 2 (2.30 g, 6.98 mmol, 1.0 eq.) and azido-PEG3-OH (1.83 g, 10.5 mmol, 1.5 eq.) were dissolved in anhydrous DCM (40 mL) under argon and molecular sieves 3 Å (5 g) was added to the solution. The mixture was stirred at room temperature for 1 h. TMSOTf (0.77 g, 3.49 mmol, 0.5 eq.) was then added to the mixture and the reaction was stirred overnight. The molecular sieves were filtered, the filtrate was diluted with DCM (100 mL) and washed with cold saturated aq. NaHCO$_3$ (100 mL) and water (100 mL). The organic layer was separated, dried over Na$_2$SO$_4$ and the solvent was removed under reduced pressure. The crude material was purified by flash chromatography (gradient elution: 0-3% MeOH in DCM in 10 CV) to afford the title product as light yellow oil (3.10 g, 88%, rf=0.25 (2% MeOH in DCM)). MS: calculated for C$_{20}$H$_{32}$N$_4$O$_{11}$, 504.21. Found 505.4. $^1$H NMR (500 MHz, CDCl$_3$) δ 6.21-6.14 (m, 1H), 5.30 (dd, J=3.4, 1.1 Hz, 1H), 5.04 (dd, J=11.2, 3.4 Hz, 1H), 4.76 (d, J=8.6 Hz, 1H), 4.23-4.08 (m, 3H), 3.91-3.80 (m, 3H), 3.74-3.59 (m, 9H), 3.49-3.41 (m, 2H), 2.14 (s, 3H), 2.02 (s, 3H), 1.97 (d, J=4.2 Hz, 6H). $^{13}$C NMR (125 MHz, CDCl$_3$) δ 170.6 (C), 170.5 (C), 170.4 (C), 170.3 (C), 102.1 (CH), 71.6 (CH), 70.8 (CH), 70.6 (CH), 70.5 (CH), 70.3 (CH$_2$), 69.7 (CH$_2$), 68.5 (CH$_2$), 66.6 (CH$_2$), 61.5 (CH$_2$), 23.1 (CH$_3$), 20.7 (3×CH$_3$).

Preparation of compound 5: Compound 4 (1.00 g, 1.98 mmol, 1.0 eq.) was dissolved in a mixture of ethyl acetate (EtOAc) and MeOH (30 mL 1:1 v/v) and Pd/C (100 mg) was added. The reaction mixture was degassed using vacuum/argon cycles (3×) and hydrogenated under balloon pressure overnight. The reaction mixture was filtered through celite and washed with EtOAc (30 mL). The solvent was removed under reduced pressure to afford the title compound as colourless oil (0.95 g, quantitative yield, rf=0.25 (10% MeOH in DCM)). The compound was used without further purification. MS: calculated for C$_{20}$H$_{34}$N$_2$O$_{11}$, 478.2. Found 479.4.

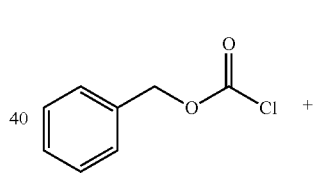

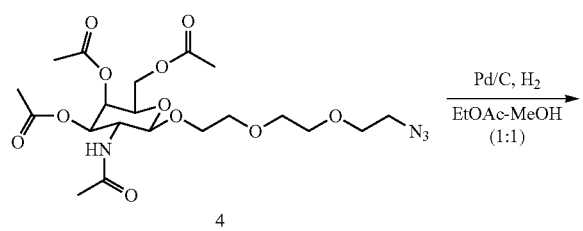

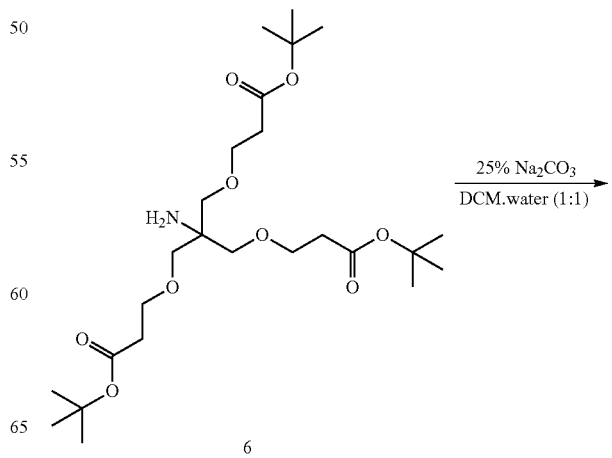

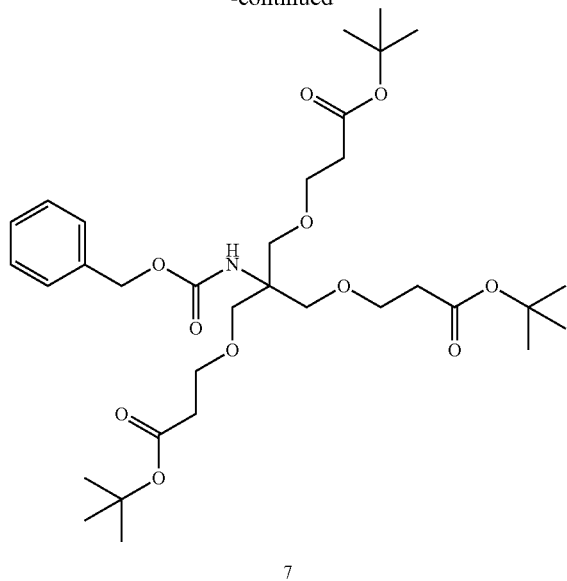

7

Preparation of compound 7: Tris{[2-(tert-butoxycarbonyl)ethoxy]methyl}-methylamine 6 (3.37 g, 6.67 mmol, 1.0 eq.) was dissolved in a mixture of DCM/water (40 mL 1:1 v/v) and $Na_2CO_3$ (0.18 g, 1.7 mmol, 0.25 eq.) was added while stirring vigorously. Benzyl chloroformate (2.94 mL, 20.7 mmol, 3.10 eq.) was added dropwise to the previous mixture and the reaction was stirred at room temperature for 24 h. The reaction mixture was diluted with $CH_2Cl_2$ (100 mL) and washed with water (100 mL). The organic layer was separated and dried over $Na_2SO_4$. The solvent was removed under reduced pressure and the resulting crude material was purified by flash chromatography (gradient elution: 0-10% EtOAc in cyclohexane in 12 CV) to afford the title compound as pale yellowish oil (3.9 g, 91%, rf=0.56 (10% EtOAc in cyclohexane)). MS: calculated for $C_{33}H_{53}NO_1$, 639.3. Found 640.9. $^1H$ NMR (500 MHz, DMSO-$d_6$) δ 7.38-7.26 (m, 5H), 4.97 (s, 2H), 3.54 (t, 6H), 3.50 (s, 6H), 2.38 (t, 6H), 1.39 (s, 27H). $^{13}C$ NMR (125 MHz, DMSO-$d_6$) δ 170.3 (3×C), 154.5 (C), 137.1 (C), 128.2 (2×CH), 127.7 (CH), 127.6 (2×CH), 79.7 (3×C), 68.4 (3×CH$_2$), 66.8 (3×CH$_2$), 64.9 (C), 58.7 (CH$_2$), 35.8 (3×CH$_2$), 27.7 (9×CH$_3$).

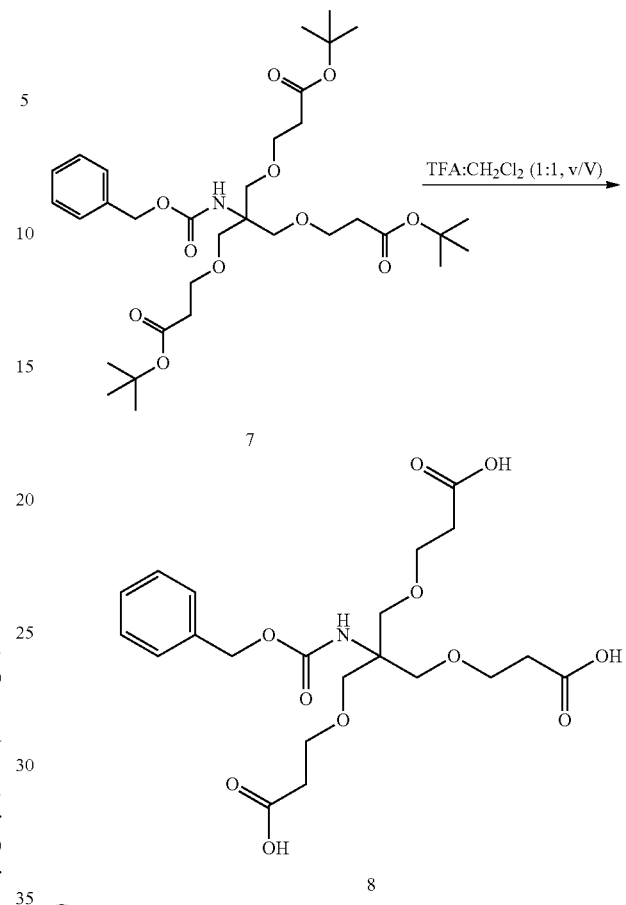

8

(?) indicates text missing or illegible when filed

Preparation of compound 8: Cbz-NH-tris-Boc-ester 7 (0.20 g, 0.39 mmol, 1.0 eq.) was dissolved in $CH_2Cl_2$ (1 mL) under argon, trifluoroacetic acid (TEA, 1 mL) was added and the reaction was stirred at room temperature for 1 h. The solvent was removed under reduced pressure, the residue was co-evaporated 3 times with toluene (5 mL) and dried under high vacuum to get the compound as its TEA salt (0.183 g, 98%). The compound was used without further purification. MS: calculated for $C_{21}H_{29}NO_{11}$, 471.6. Found 472.4.

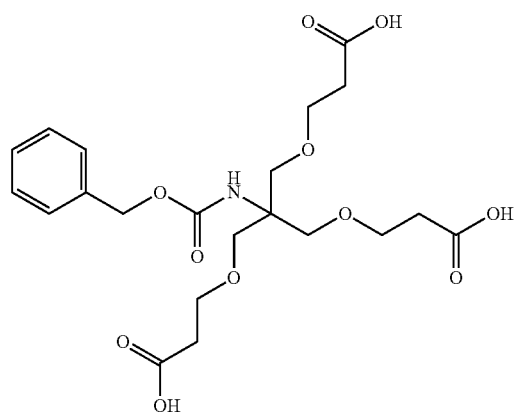

8

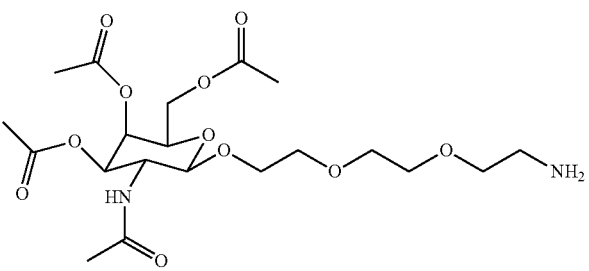

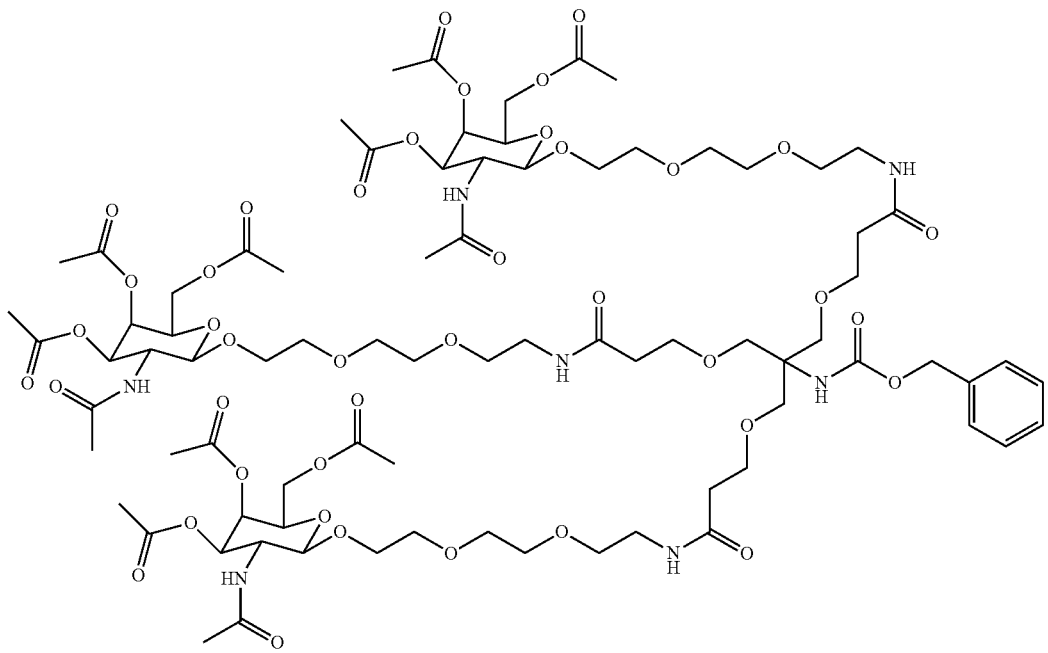

9

Preparation of compound 9: CbzNH-tris-COOH 8 (0.72 g, 1.49 mmol, 1.0 eq.) and GalNAc-PEG3-NH$_2$ 5 (3.56 g, 7.44 mmol, 5.0 eq.) were dissolved in N,N-dimethylformamide (DMF) (25 mL). Then N,N,N',N'-tetramethyl-O-(1H-benzotriazol-1-yl)uronium hexafluorophosphate (HBTU) (2.78 g, 7.44 mmol, 5.0 eq.), 1-hydroxybenzotriazole hydrate (HOBt) (1.05 g, 7.44 mmol, 5.0 eq.) and N,N-diisopropylethylamine (DIPEA) (2.07 mL, 11.9 mmol, 8.0 eq.) were added to the solution and the reaction was stirred for 72 h. The solvent was removed under reduced pressure, the residue was dissolved in DCM (100 mL) and washed with saturated aq. NaHCO$_3$ (100 mL). The organic layer was dried over Na$_2$SO$_4$, the solvent evaporated and the crude material was purified by flash chromatography (gradient elution: 0-5% MeOH in DCM in 14 CV). The product was obtained as pale yellowish oil (1.2 g, 43%, rf=0.20 (5% MeOH in DCM)). MS: calculated for C$_{81}$H$_{125}$N$_7$O$_{41}$, 1852.9. Found 1854.7. $^1$H NMR (500 MHz, DMSO-d$_6$) δ 7.90-7.80 (m, 10H), 7.65-7.62 (m, 4H), 7.47-7.43 (m, 3H), 7.38-7.32 (m, 8H), 5.24-5.22 (m, 3H), 5.02-4.97 (m, 4H), 4.60-4.57 (m, 3H), 4.07-3.90 (m 10H), 3.67-3.36 (m, 70H), 3.23-3.07 (m, 25H), 2.18 (s, 10H), 2.00 (s, 13H), 1.89 (s, 11H), 1.80-1.78 (m, 17H). $^{13}$C NMR (125 MHz, DMSO-d$_6$) δ 170.1 (C), 169.8 (C), 169.7 (C), 169.4 (C), 169.2 (C), 169.1 (C), 142.7 (C), 126.3 (CH), 123.9 (CH), 118.7 (CH), 109.7 (CH), 100.8 (CH), 70.5 (CH), 69.8 (CH), 69.6 (CH), 69.5 (CH), 69.3 (CH$_2$), 69.0 (CH$_2$), 68.2 (CH$_2$), 67.2 (CH$_2$), 66.7 (CH$_2$), 61.4 (CH$_2$), 22.6 (CH$_2$), 22.4 (3×CH$_3$), 20.7 (9×CH$_3$).

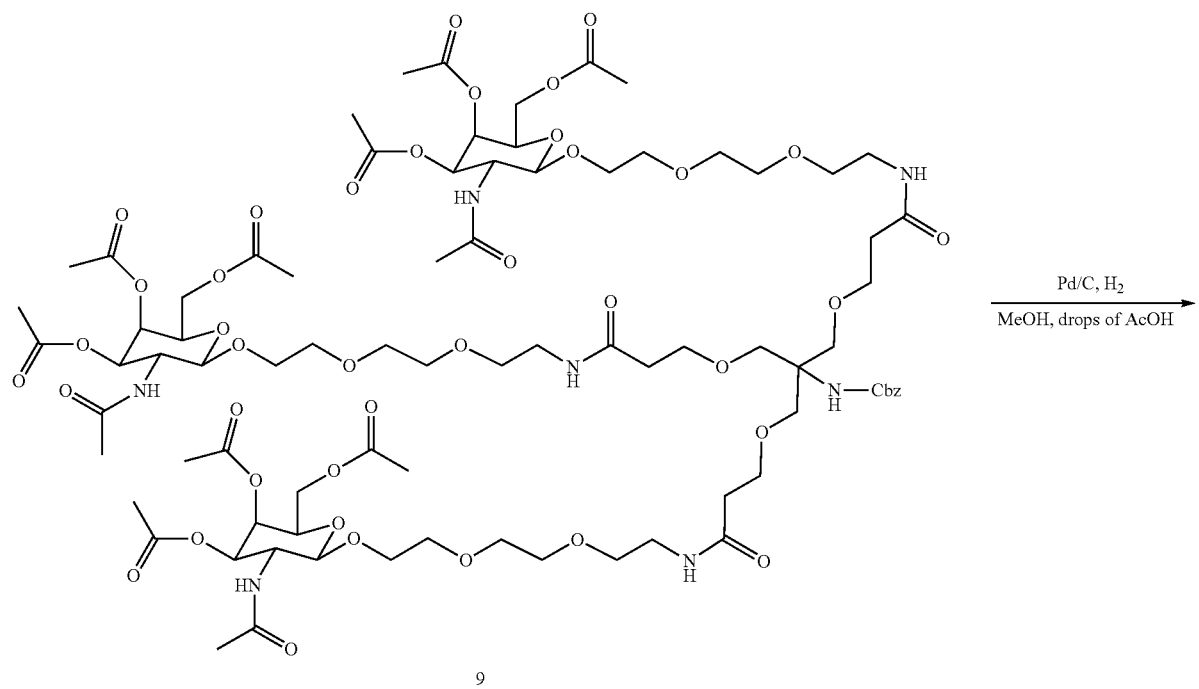

9

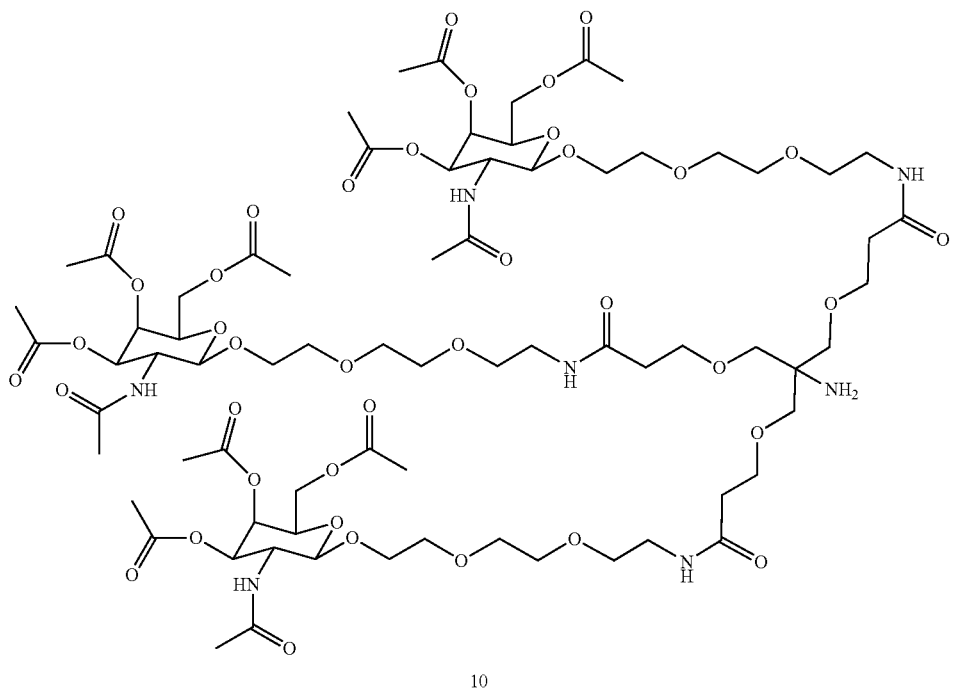

10

Preparation of compound 10: Triantennary GalNAc compound 9 (0.27 g, 0.14 mmol, 1.0 eq.) was dissolved in MeOH (15 mL), 3 drops of acetic acid (AcOH) and Pd/C (30 mg) was added. The reaction mixture was degassed using vacuum/argon cycles (3×) and hydrogenated under balloon pressure overnight. The completion of the reaction was followed by mass spectrometry and the resulting mixture was filtered through a thin pad of celite. The solvent was evaporated and the residue obtained was dried under high vacuum and used for the next step without further purification. The product was obtained as pale yellowish oil (0.24 g, quantitative yield). MS: calculated for $C_{73}H_{119}N_7O_{39}$, 1718.8. Found 1719.3.

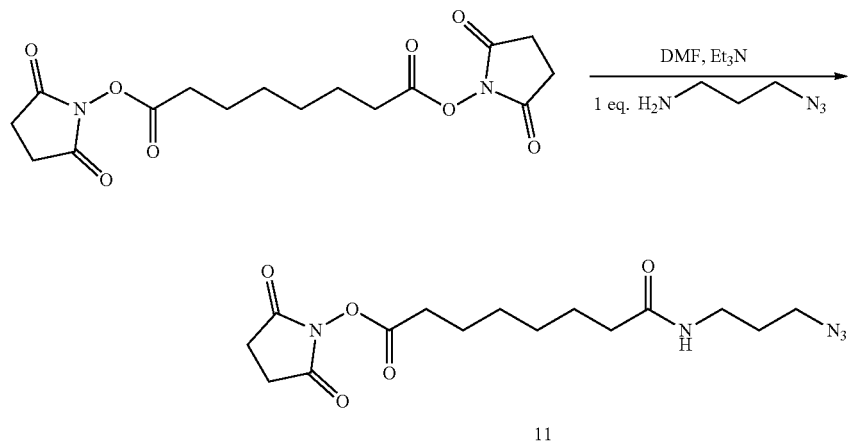

Preparation of compound 11: Commercially available suberic acid bis(N-hydroxysuccinimide ester) (3.67 g, 9.9 mmol, 1.0 eq.) was dissolved in DMF (5 mL) and triethylamine (1.2 mL) was added. To this solution was added dropwise a solution of 3-azido-1-propylamine (1.0 g, 9.9 mmol, 1.0 eq.) in DMF (5 mL). The reaction was stirred at room temperature for 3 h. The reaction mixture was diluted with EtOAc (100 mL) and washed with water (50 mL). The organic layer was separated, dried over $Na_2SO_4$ and the solvent was removed under reduced pressure. The crude material was purified by flash chromatography (gradient elution: 0-5% MeOH in DCM in 16 CV). The product was obtained as white solid (1.54 g, 43%, rf=0.71 (5% MeOH in DCM)). MS: calculated for $C_{15}H_{23}N_5O_5$, 353.4. Found 354.3.

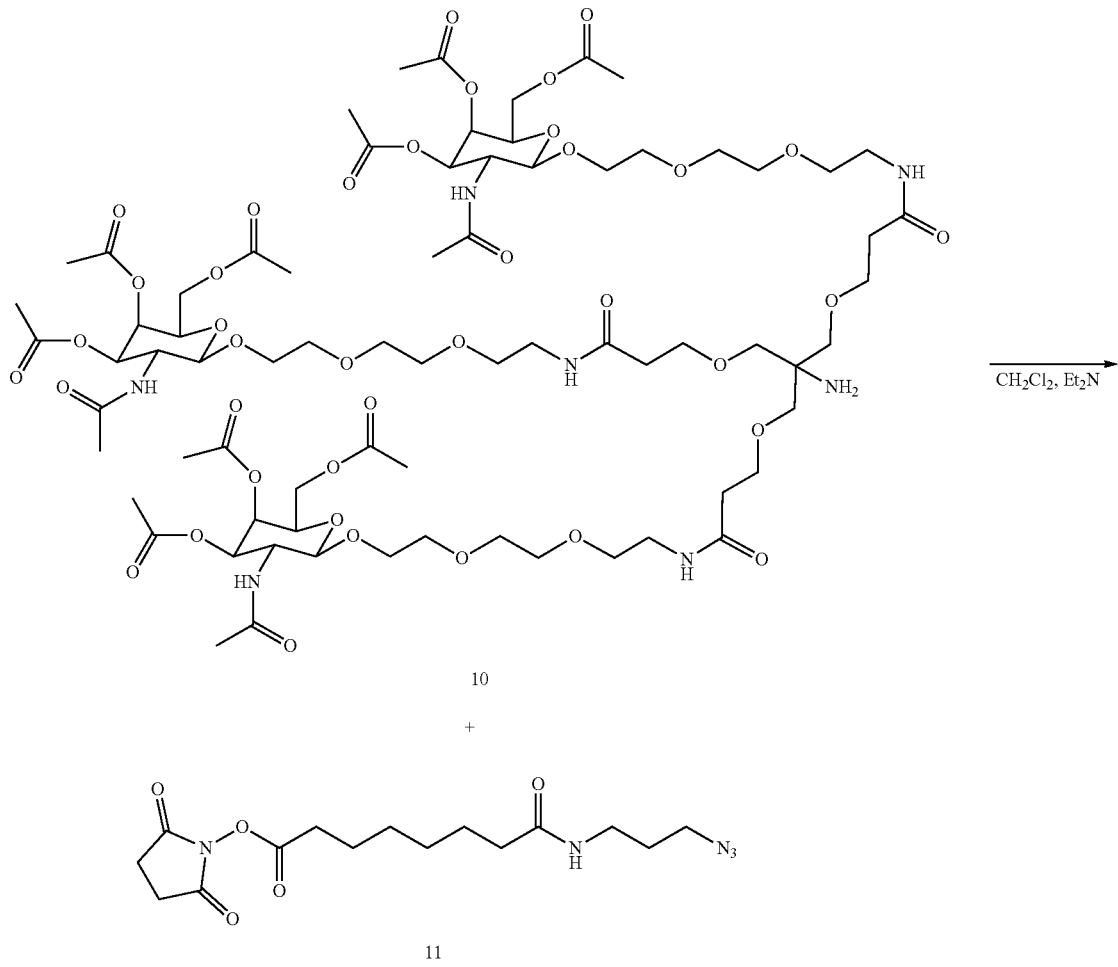

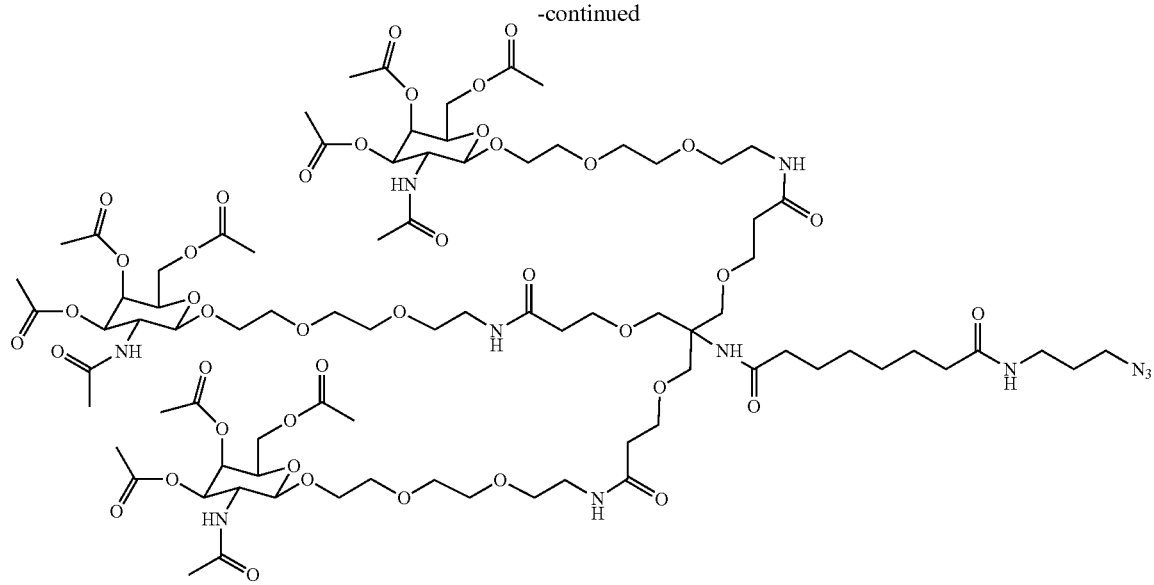

12

Preparation of TriGalNAc (12): Triantennary GalNAc compound 10 (0.35 g, 0.24 mmol, 1.0 eq.) and compound 11 (0.11 g, 0.31 mmol, 1.5 eq.) were dissolved in DCM (5 mL) under argon and triethylamine (0.1 mL, 0.61 mmol, 3.0 eq.) was added. The reaction was stirred at room temperature overnight. The solvent was removed under reduced pressure, the residue was dissolved in EtOAc (100 mL) and washed with water (100 mL). The organic layer was separated and dried over $Na_2SO_4$. The solvent was evaporated and the resulting crude material was purified by flash chromatography (elution gradient: 0-10% MeOH in DCM in 20 CV) to afford the title compound as white fluffy solid (0.27 g, 67%, rfR=0.5 (10% MeH in DCM)). MS: calculated for $C_{84}H_{137}N_{11}O_{41}$, 1957.1. Found 1959.6.

Compound 12 was used for subsequent oligonucleotide conjugate preparations employing "click chemistry".

iii) Oligonucleotide Synthesis

TABLE 8

| Single strand ID | Sequence 5' - 3' | Purity by RP HPLC (%) |
|---|---|---|
| X91382 | (NH2-DEG)gacuuuCfaUfCfCfuggaaauasusa(invabasic)(invabasic) (SEQ ID NO: 114) | 89.5 |
| X91383 | (NH2-DEG)aaGfcAfaGfaUfAfUfuUfuuAfuAfasusa(invabasic)(invabasic) (SEQ ID NO: 115) | 91.6 |
| X91384 | (NH2-DEG)ugggauUfuCfAfUfguaaccaasgsa(invabasic)(invabasic) (SEQ ID NO: 116) | 94.0 |
| X91385 | (NH2-DEG)GfaCfuUfuCfaUfcCfuGfgAfaAfuAfsusAf (SEQ ID NO: 117) | 90.6 |
| X91386 | (NH2-DEG)AfaGfcAfaGfaUfaUfuUfuUfaUfaAfsusAf (SEQ ID NO: 118) | 91.2 |
| X91387 | (NH2-DEG)UfgGfgAfuUfuCfaUfgUfaAfcCfaAfsgsAf (SEQ ID NO: 119) | 88.7 |
| X91403 | (NH2C12)gacuuuCfaUfCfCfuggaaauasusa(invabasic)(invabasic) (SEQ ID NO: 120) | 94.2 |
| X91404 | (NH2C12)aaGfcAfaGfaUfAfUfuUfuuAfuAfasusa(invabasic)(invabasic) (SEQ ID NO: 121) | 96.5 |
| X91405 | (NH2C12)ugggauUfuCfAfUfguaaccaasgsa(invabasic)(invabasic) (SEQ ID NO: 122) | 91.3 |

TABLE 8-continued

| Single strand ID | Sequence 5' - 3' | Purity by RP HPLC (%) |
|---|---|---|
| X91406 | (NH2C12)GfaCfuUfuCfaUfcCfuGfgAfaAfuAfsusAf (SEQ ID NO: 123) | 95.0 |
| X91407 | (NH2C12)AfaGfcAfaGfaUfaUfuUfuUfaUfaAfsusAf (SEQ ID NO: 124) | 97.0 |
| X91408 | (NH2C12)UfgGfgAfuUfuCfaUfgUfaAfcCfaAfsgsAf (SEQ ID NO: 125) | 90.0 |
| X91415 | (invabasic)(invabasic)gsascuuuCfaUfCfCfuggaaauasusa (NH2C6) (SEQ ID NO: 126) | 96.4 |
| X91416 | (invabasic)(invabasic)asasGfcAfaGfaUfAfUfuUfuuAfuAfaua (NH2C6) (SEQ ID NO: 127) | 77.4 |
| X91417 | (invabasic)(invabasic)usgsggauUfuCfAfUfguaaccaaga(NH2C6) (SEQ ID NO: 128) | 96.7 |
| X91418 | GfsasCfuUfuCfaUfcCfuGfgAfaAfuAfuAf(NH2C6) (SEQ ID NO: 129) | 96.0 |
| X91419 | AfsasGfcAfaGfaUfaUfuUfuUfaUfaAfuAf(NH2C6) (SEQ ID NO: 130) | 91.8 |
| X91420 | UfsgsGfgAfuUfuCfaUfgUfaAfcCfaAfgAf(NH2C6) (SEQ ID NO: 131) | 93.1 |
| X91379 | gsascuuuCfaUfCfCfuggaaauaua(GalNAc) (SEQ ID NO: 132) | 92.8 |
| X91380 | asasGfcAfaGfaUfAfUfuUfuuAfuAfaua(GalNAc) (SEQ ID NO: 133) | 95.7 |
| X91446 | usgsggauUfuCfAfUfguaaccaaga(GalNAc) (SEQ ID NO: 134) | 92.1 |
| X38483 | usAfsuauUfuCfCfaggaUfgAfaagucscsa (SEQ ID NO: 135) | 91.0 |
| X91381 | usAfsUfuAfuaAfaAfauaUfcUfuGfcuususudTdT (SEQ ID NO: 136) | 90.0 |
| X38104 | usCfsuugGfuuAfcaugAfaAfucccasusc (SEQ ID NO: 137) | 95.4 |
| X91398 | usAfsuAfuUfuCfcAfgGfaUfgAfaAfgUfcsCfsa (SEQ ID NO: 138) | 90.0 |
| X91400 | usAfsuUfaUfaAfaAfaUfaUfcUfuGfcUfusUfsudTdT (SEQ ID NO: 139) | 88.7 |
| X91402 | usCfsuUfgGfuUfaCfaUfgAfaAfuCfcCfasUfsc (SEQ ID NO: 140) | 89.6 |

Af, Cf, Gf, Uf: 2'-F RNA nucleotides
a, c, g, u: 2'-O-Me RNA nucleotides
dT: DNA nucleotides
s: Phosphorothioate
invabasic: 1,2-dideoxyribose
NH2-DEG: Aminoethoxyethyl linker
NH2C12: Aminododecyl linker
NH2C6: Aminohexyl linker Oligonucleotides were synthesized on solid phase according to the phosphoramidite approach. Depending on the scale either a Mermade 12 (BioAutomation Corporation) or an ÄKTA Oligopilot (GE Healthcare) was used.

Syntheses were performed on commercially available solid supports made of controlled pore glass either loaded with invabasic (CPG, 480 Å, with a loading of 86 µmol/g; LGC Biosearch cat. #BCG-1047-B) or 2'-F A (CPG, 520 Å, with a loading of 90 µmol/g; LGC Biosearch cat. #BCG-1039-B) or NH2C6 (CPG, 520 Å, with a loading of 85 µmol/g LGC Biosearch cat. #BCG-1397-B) or GalNAc (CPG, 500 Å, with a loading of 57 µmol/g; Primetech) or 2'-O-Methyl C (CPG, 500 Å, with a loading of 84 µmol/g LGC Biosearch cat. #BCG-10-B) or 2'-O-Methyl A (CPG, 497 Å, with a loading of 85 µmol/g, LGC Biosearch, Cat. #BCG-1029-B) or dT (CPG, 497 Å, with a loading of 87 µmol/g LGC Biosearch, cat. #BCG-1055-B).

2'-O-Me, 2'-F RNA phosphoramidites and ancillary reagents were purchased from SAFC Proligo (Hamburg, Germany).

Specifically, the following 2-O-Methyl phosphoramidites were used: 5'-(4,4'-dimethoxytrityl)-N-benzoyl-adenosine 2'-O-methyl-3'-[(2-cyanoethyl)-(N,N-diisopropyl)]-phosphoramidite, 5'-(4,4'-dimethoxytrityl)-N-benzoyl-cytidine 2'-O-methyl-3'-[(2-cyanoethyl)-(N,N-diisopropyl)]-phosphoramidite, 5'-(4,4'-dimethoxytrityl)-N-dimethylformamidine-guanosine 2'-O-methyl-3'-[(2-cyanoethyl)-(N,N-diisopropyl)]-phosphoramidite, 5'-(4,4'-dimethoxytrityl)-uridine 2'-O-methyl-3'-[(2-cyanoethyl)-(N,N-diisopropyl)]-phosphoramidite.

The following 2'-F phosphoramidites were used: 5'-dimethoxytrityl-N-benzoyl-deoxyadenosine 2'-fluoro-3'-[(2-cyanoethyl)-(N,N-diisopropyl)]-phosphoramidite, 5'-dimethoxytrityl-N-acetyl-deoxycytidine 2'-fluoro-3'-[(2-cyanoethyl)-(N,N-diisopropyl)]-phosphoramidite, 5'-dimethoxytrityl-N-isobutyryl-deoxyguanosine 2'-fluoro-3'-[(2-cyanoethyl)-(N,N-diisopropyl)]-phosphoramidite and 5'-dimethoxytrityl-deoxyuridine 2'-fluoro-3'-[(2-cyanoethyl)-(N,N-diisopropyl)]-phosphoramidite.

In order to introduce the required amino linkers at the 5'-end of the oligonucleotides the 2-[2-(4-Monomethoxytrityl)aminoethoxy]ethyl-(2-cyanoethyl)-N,N-diisopropyl)-phosphoramidite (Glen Research Cat. #1905) and the 12-(trifluoroacetylamino)dodecyl-[(2-cyanoethyl)-(N,N-diisopropyl)]-phosphoramidite (ChemGenes Cat. #CLP-1575) were employed. The invabasic modification was introduced using 5-O-dimethoxytrityl-1,2-dideoxyribose-3-[(2-cyanoethyl)-(N,N-diisopropyl)]-phosphoramidite (ChemGenes Cat. #ANP-1422).

All building blocks were dissolved in anhydrous acetonitrile (100 mM (Mermade12) or 200 mM (ÄKTA Oligopilot)) containing molecular sieves (3 Å) except 2'-O-methyl-uridine phosphoramidite which was dissolved in 50% anhydrous DCM in anhydrous acetonitrile. Iodine (50 mM in pyridine/H$_2$O 9:1 v/v) was used as oxidizing reagent. 5-Ethyl thiotetrazole (ETT, 500 mM in acetonitrile) was used as activator solution. Thiolation for introduction of phosphorthioate linkages was carried out using 100 mM xanthane hydride (TCI, Cat. #6846-35-1) in acetonitrile/pyridine 4:6 v/v.

Coupling times were 5.4 minutes except when stated otherwise. 5' amino modifications were incorporated into the sequence employing a double coupling step with a coupling time of 11 minutes per each coupling (total coupling time 22 min). The oxidizer contact time was set to 1.2 min and thiolation time was 5.2 min.

Sequences were synthesized with removal of the final DMT group, with exception of the MMT group from the NH2DEG sequences.

At the end of the synthesis, the oligonucleotides were cleaved from the solid support using a 1:1 volume solution of 28-30% ammonium hydroxide (Sigma-Aldrich, Cat. #221228) and 40% aqueous methylamine (Sigma-Aldrich, Cat. #8220911000) for 16 hours at 6° C. The solid support was then filtered off, the filter was thoroughly washed with H$_2$O and the volume of the combined solution was reduced by evaporation under reduced pressure. The pH of the resulting solution was adjusted to pH 7 with 10% AcOH (Sigma-Aldrich, Cat. #A6283).

The crude materials were purified either by reversed phase (RP) HPLC or anion exchange (AEX) HPLC.

RP HPLC purification was performed using a XBridge C18 Prep 19×50 mm column (Waters) on an ÄKTA Pure instrument (GE Healthcare). Buffer A was 100 mM triethylammonium acetate (TEAAc, Biosolve) pH 7 and buffer B contained 95% acetonitrile in buffer A. A flow rate of 10 mL/min and a temperature of 60° C. were employed. UV traces at 280 nm were recorded. A gradient of 0% B to 100% B within 120 column volumes was employed. Appropriate fractions were pooled and precipitated in the freezer with 3 M sodium acetate (NaOAc) (Sigma-Aldrich), pH 5.2 and 85% ethanol (VWR). Pellets were isolated by centrifugation, redissolved in water (50 mL), treated with 5 M NaCl (5 mL) and desalted by Size exclusion HPLC on an Akta Pure instrument using a 50×165 mm ECO column (YMC, Dinslaken, Germany) filled with Sephadex G25-Fine resin (GE Healthcare).

AEX HPLC purification was performed using a TSK gel SuperQ-5PW 20×200 mm (BISCHOFF Chromatography) on an ÄKTA Pure instrument (GE Healthcare). Buffer A was 20 mM sodium phosphate (Sigma-Aldrich) pH 7.8 and buffer B was the same as buffer A with the addition of 1.4 M sodium bromide (Sigma-Aldrich). A flow rate of 10 mL/min and a temperature of 60° C. were employed. UV traces at 280 nm were recorded. A gradient of 10% B to 100% B within 27 column volumes was employed. Appropriate fractions were pooled and precipitated in the freezer with 3 M NaOAc, pH 5.2 and 85% ethanol. Pellets were isolated by centrifugation, redissolved in water (50 mL), treated with 5 M NaCl (5 mL) and desalted by size exclusion chromatography.

The MMT group was removed with 25% acetic acid in water. Once the reaction was complete the solution was neutralized and the samples were desalted by size exclusion chromatography.

Single strands were analyzed by analytical LC-MS on a 2.1×50 mm XBridge C18 column (Waters) on a Dionex Ultimate 3000 (Thermo Fisher Scientific) HPLC system combined either with a LCQ Deca XP-plus Q-ESI-TOF mass spectrometer (Thermo Finnigan) or with a Compact ESI-Qq-TOF mass spectrometer (Bruker Daltonics). Buffer A was 16.3 mM triethylamine, 100 mM 1,1,1,3,3,3-hexafluoro-2-propanol (HFIP) and 1% MeOH in H$_2$O and buffer B contained buffer A in 95% MeOH. A flow rate of 250 µL/min and a temperature of 60° C. were employed. UV traces at 260 and 280 nm were recorded. A gradient of 1-40% B within 0.5 min followed by 40 to 100% B within 13 min was employed. Methanol (LC-MS grade), water (LC-MS grade), 1,1,1,3,3,3-hexafluoro-2-propanol (puriss. p.a.) and triethylamine (puriss. p.a.) were purchased from Sigma-Aldrich.

iv) Monofluoro cyclooctyne (MFCO) conjugation at 5'- or 3'-end

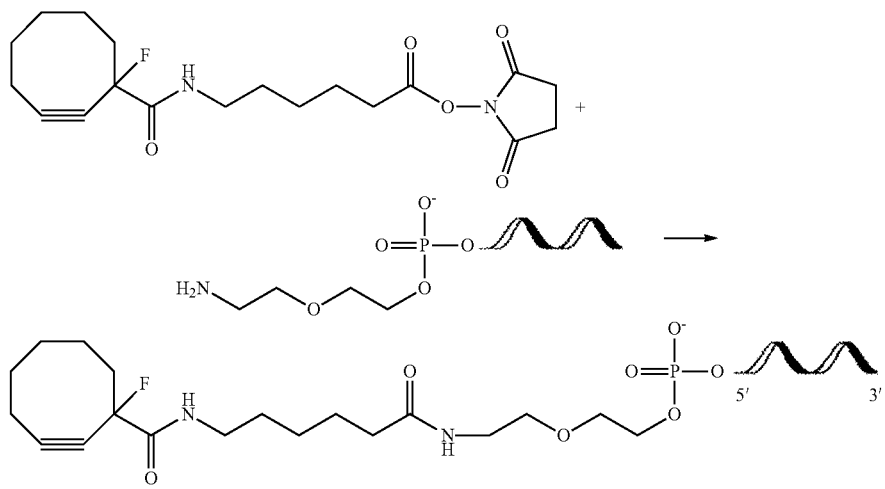

5'-end MFCO conjugation

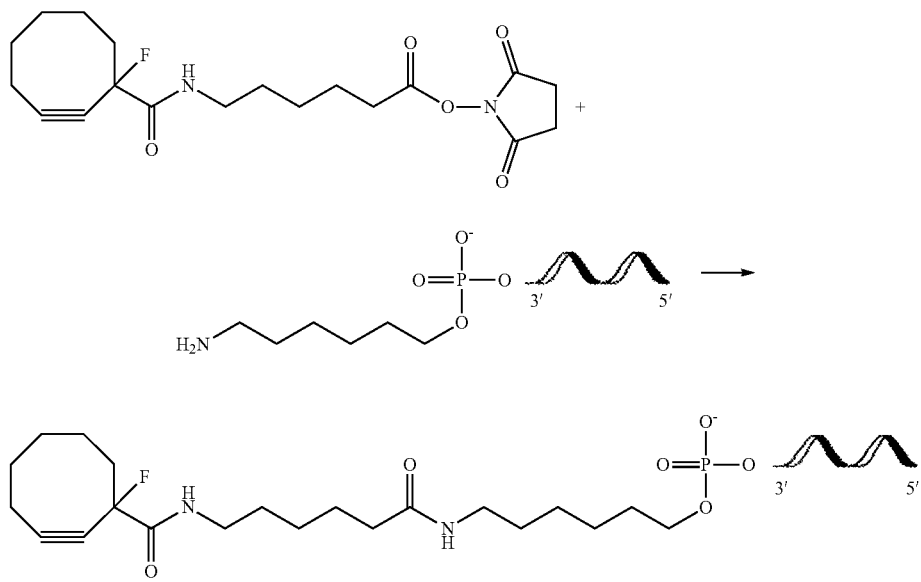

3'-end MFCO conjugation

General conditions for MFCO conjugation: Amine-modified single strand was dissolved at 700 OD/mL in 50 mM carbonate/bicarbonate buffer pH 9.6/dimethyl sulfoxide (DMSO) 4:6 (v/v) and to this solution was added one molar equivalent of a 35 mM solution of MFCO-C6-NHS ester (Berry&Associates, Cat. #LK 4300) in DMF. The reaction was carried out at room temperature and after 1 h another molar equivalent of the MFCO solution was added. The reaction was allowed to proceed for an additional hour and was monitored by LC/MS. At least two molar equivalent excess of the MFCO NHS ester reagent relative to the amino modified oligonucleotide were needed to achieve quantitative consumption of the starting material. The reaction mixture was diluted 15-fold with water, filtered through a 1.2 μm filter from Sartorius and then purified by reserve phase (RP HPLC) on an Akta Pure instrument (GE Healthcare).

Purification was performed using a XBridge C18 Prep 19×50 mm column from Waters. Buffer A was 100 mM TEAAc pH 7 and buffer B contained 95% acetonitrile in buffer A. A flow rate of 10 mL/min and a temperature of 60° C. were employed. UV traces at 280 nm were recorded. A gradient of 0-100% B within 60 column volumes was employed.

Fractions containing full length conjugated oligonucleotide were pooled, precipitated in the freezer with 3 M NaOAc, pH 5.2 and 85% ethanol and the collected pellet was dissolved in water. Samples were desalted by size exclusion chromatography and concentrated using a speed-vac concentrator to yield the conjugated oligonucleotide in an isolated yield of 40-80%.

TABLE 9

| Sense strand ID | Sense strand sequence 5' - 3' | Purity by RP HPLC (%) |
|---|---|---|
| X91388 | (MFCO)(NH-DEG)gacuuuCfaUfCfCfuggaaauasusa(invabasic)(invabasic) (SEQ ID NO: 58) | 89.0 |
| X91389 | (MFCO)(NH-DEG)aaGfcAfaGfaUfAfUfuUfuuAfuAfasusa(invabasic)(invabasic) (SEQ ID NO: 59) | 91.0 |
| X91390 | (MFCO)(NH-DEG)ugggauUfuCfAfUfguaaccaasgsa(invabasic)(invabasic) (SEQ ID NO: 60) | 90.0 |
| X91391 | (MFCO)(NH-DEG)GfaCfuUfuCfaUfcCfuGfgAfaAfuAfsusAf (SEQ ID NO: 177) | 86.0 |
| X91392 | (MFCO)(NH-DEG)AfaGfcAfaGfaUfaUfuUfuUfaUfaAfsusAf (SEQ ID NO: 178) | 87.0 |
| X91393 | (MFCO)(NH-DEG)UfgGfgAfuUfuCfaUfgUfaAfcCfaAfsgsAf (SEQ ID NO: 179) | 86.0 |
| X91421 | (invabasic)(invabasic)gsascuuuCfaUfCfCfuggaaauasusa(NHC6)(MFCO) (SEQ ID NO: 61) | 94.0 |
| X91422 | (invabasic)(invabasic)asasGfcAfaGfaUfAfUfuUfuuAfuAfaua(NHC6)(MFCO) (SEQ ID NO: 62) | 89.0 |
| X91423 | (invabasic)(invabasic)usgsggauUfuCfAfUfguaaccaaga(NHC6)(MFCO) (SEQ ID NO: 63) | 89.0 |
| X91424 | GfsasCfuUfuCfaUfcCfuGfgAfaAfuAfuAf(NHC6)(MFCO) (SEQ ID NO: 180) | 90.0 |
| X91425 | AfsasGfcAfaGfaUfaUfuUfuUfaUfaAfuAf(NHC6)(MFCO) (SEQ ID NO: 181) | 89.0 |
| X91426 | UfsgsGfgAfuUfuCfaUfgUfaAfcCfaAfgAf(NHC6)(MFCO) (SEQ ID NO: 182) | 89.0 | v) TriGalNAc (GalNAc-T1) conjugation at 5'- or 3'-end
5'-GalNAc-T1 conjugates

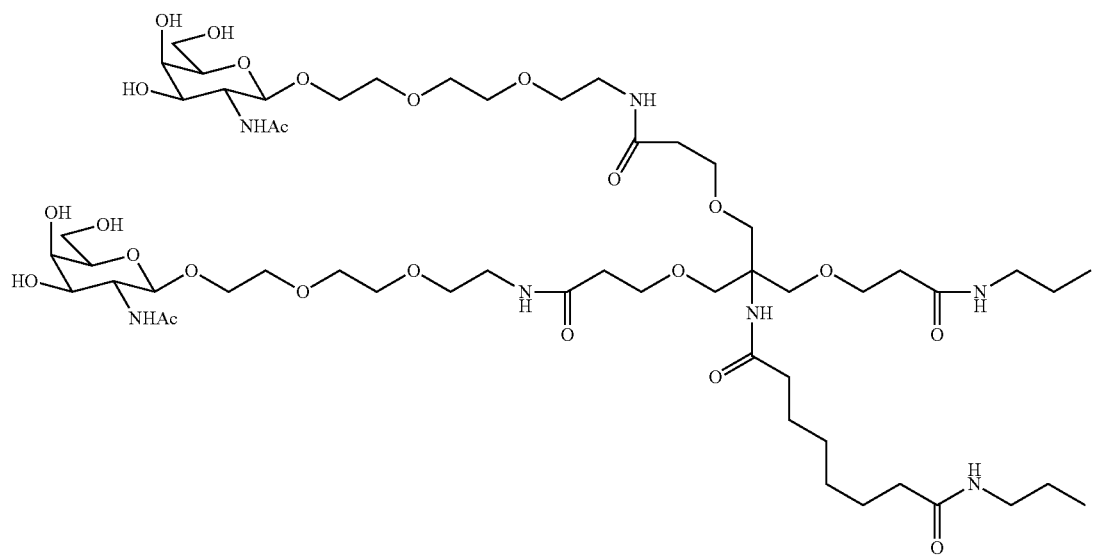

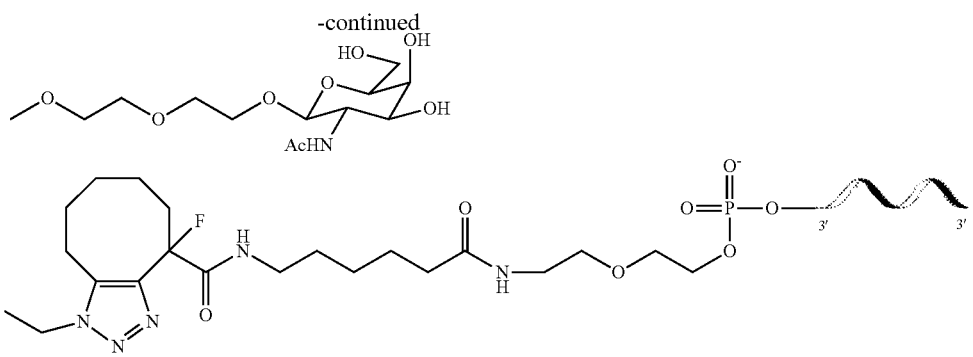

3'-GalNAc-T1 conjugates

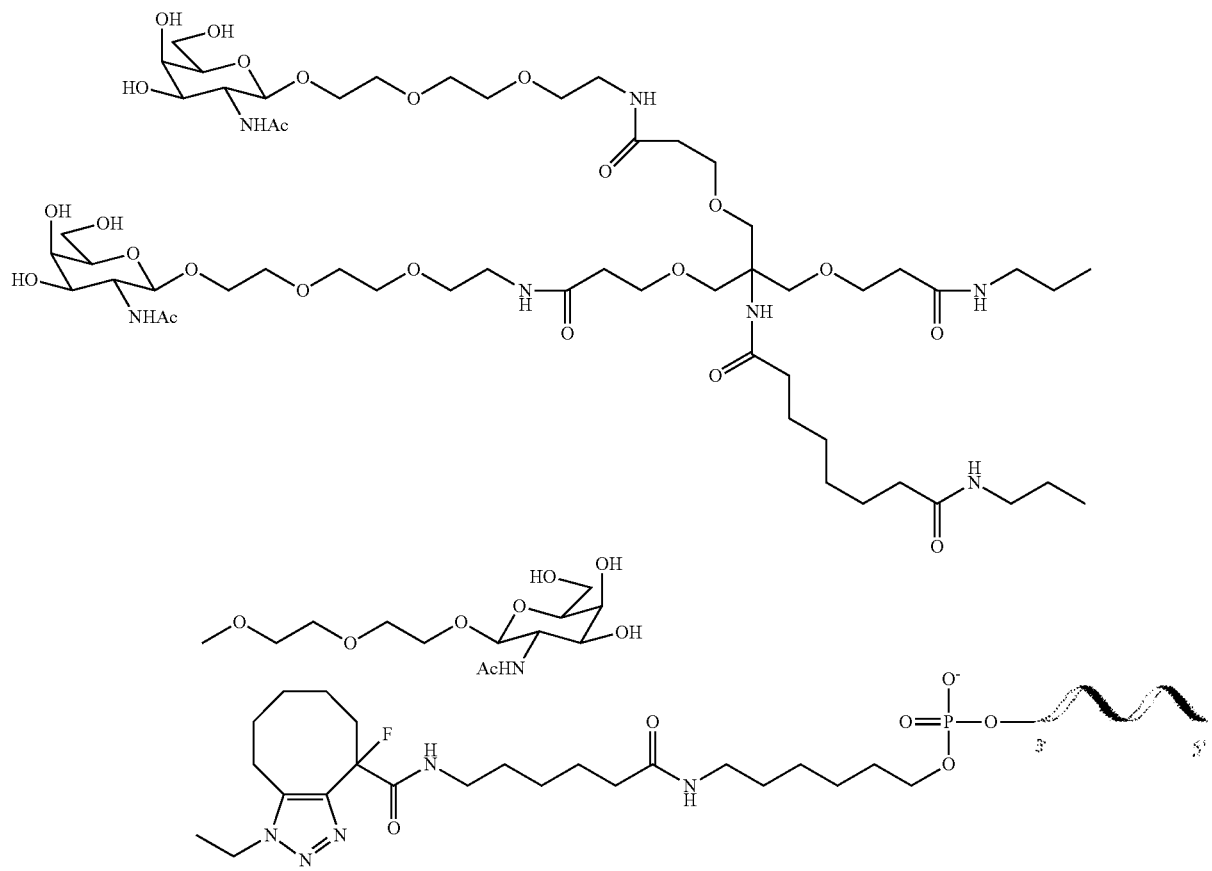

General procedure for TriGalNAc conjugation: MFCO-modified single strand was dissolved at 2000 OD/mL in water and to this solution was added one equivalent solution of compound 12 (10 mM) in DMF. The reaction was carried out at room temperature and after 3 h 0.7 molar equivalent of the compound 12 solution was added. The reaction was allowed to proceed overnight and completion was monitored by LCMS. The conjugate was diluted 15-fold in water, filtered through a 1.2 μm filter from Sartorius and then purified by RP HPLC on an Akta Pure instrument (GE Healthcare).

RP HPLC purification was performed using a XBridge C18 Prep 19×50 mm column from Waters. Buffer A was 100 mM triethylammonium acetate pH 7 and buffer B contained 95% acetonitrile in buffer A. A flow rate of 10 mL/min and a temperature of 60° C. were employed. UV traces at 280 nm were recorded. A gradient of 0-100% B within 60 column volumes was employed.

Fractions containing full-length conjugated oligonucleotide were pooled, precipitated in the freezer with 3 M NaOAc, pH 5.2 and 85% ethanol and the collected pellet was dissolved in water to give an oligonucleotide solution of about 1000 OD/mL. The O-acetates were removed by adding 20% aqueous ammonia. Quantitative removal of these protecting groups was verified by LC-MS.

The conjugates were desalted by size exclusion chromatography using Sephadex G25 Fine resin (GE Healthcare) on an Akta Pure (GE Healthcare) instrument to yield the conjugated nucleotide in an isolated yield of 50-70%.

TABLE 10

| Sense strand ID | Sense strand sequence 5' - 3' | Purity by RP HPLC (%) |
|---|---|---|
| X91394 | (GalNAc-T1)(MFCO)(NH-DEG)gacuuuCfaUfCfCfuggaaauasusa(invabasic)(invabasic) (SEQ ID NO: 64) | 80.0 |
| X91395 | (GalNAc-T1)(MFCO)(NH-DEG)aaGfcAfaGfaUfAfUfuUfuuAfuAfasusa(invabasic)(invabasic) (SEQ ID NO: 65) | 87.8 |
| X91396 | (GalNAc-T1)(MFCO)(NH-DEG)ugggauUfuCfAfUfguaaccaasgsa(invabasic)(invabasic) (SEQ ID NO: 66) | 87.9 |
| X91397 | (GalNAc-T1)(MFCO)(NH-DEG)GfaCfuUfuCfaUfcCfuGfgAfaAfuAfsusAf (SEQ ID NO: 13) | 83.0 |
| X91399 | (GalNAc-T1)(MFCO)(NH-DEG) AfaGfcAfaGfaUfaUfuUfuUfaUfaAfsusAf (SEQ ID NO: 15) | 80.5 |
| X91401 | (GalNAc-T1)(MFCO)(NH-DEG)UfgGfgAfuUfuCfaUfgUfaAfcCfaAfsgsAf (SEQ ID NO: 17) | 81.7 |
| X91427 | (invabasic)(invabasic)gsascuuuCfaUfCfCfuggaaauasusa(NHC6)(MFCO)(GalNAc-T1) (SEQ ID NO: 67) | 88.0 |
| X91428 | (invabasic)(invabasic)asasGfcAfaGfaUfAfUfuUfuuAfuAfaua(NHC6)(MFCO)(GalNAc-T1) (SEQ ID NO: 68) | 82.6 |
| X91429 | (invabasic)(invabasic)usgsggauUfuCfAfUfguaaccaaga(NHC6)(MFCO)(GalNAc-T1) (SEQ ID NO: 69) | 82.9 |
| X91430 | GfsasCfuUfuCfaUfcCfuGfgAfaAfuAfuAf(NHC6)(MFCO)(GalNAc-T1) (SEQ ID NO: 19) | 83.0 |
| X91431 | AfsasGfcAfaGfaUfaUfuUfuUfaUfaAfuAf(NHC6)(MFCO)(GalNAc-T1) (SEQ ID NO: 21) | 82.6 |
| X91432 | UfsgsGfgAfuUfuCfaUfgUfaAfcCfaAfgAf(NHC6)(MFCO)(GalNAc-T1) (SEQ ID NO: 23) | 81.2 | vi) Duplex Annealing

To generate the desired siRNA duplex, the two complementary strands were annealed by combining equimolar aqueous solutions of both strands. The mixtures were placed into a water bath at 70° C. for 5 minutes and subsequently allowed to cool to ambient temperature within 2 h. The duplexes were lyophilized for 2 days and stored at −20° C.

The duplexes were analyzed by analytical SEC HPLC on Superdex™ 75 Increase 5/150 GL column 5×153-158 mm (Cytiva) on a Dionex Ultimate 3000 (Thermo Fisher Scientific) HPLC system. Mobile phase consisted of 1× PBS containing 10% acetonitrile. An isocratic gradient was run in 10 min at a flow rate of 1.5 mL/min at room temperature. UV traces at 260 and 280 nm were recorded. Water (LC-MS grade) was purchased from Sigma-Aldrich and Phosphate-buffered saline (PBS; 10×, pH 7.4) was purchased from GIBCO (Thermo Fisher Scientific).

GalNAc conjugates prepared are compiled in the table below. These were directed against 3 different target genes. siRNA coding along with the corresponding single strands, sequence information as well as purity for the duplexes is captured.

TABLE 11

| Target | Duplex ID | SSRN ID | ssRNA-Sequence 5'-3' | Duplex Purity by HPLC (%) |
|---|---|---|---|---|
| G0 | ETX001 | X91394 | (GalNAc-T1)(MFCO)(NHDEG)gacuuuCfaUfCfCfuggaaauasusa(invabasic)(invabasic) (SEQ ID NO: 1) | 96.8 |
| | | X38483 | usAfsuauUfuCfCfaggaUfgAfaagucscsa (SEQ ID NO: 2) | |
| | ETX003 | X91397 | (GalNAc-T1)(MFCO)(NH-DEG)GfaCfuUfuCfaUfcCfuGfgAfaAfuAfsusAf (SEQ ID NO: 13) | 97.6 |
| | | X91398 | usAfsuAfuUfuCfcAfgGfaUfgAfaAfgUfcsCfsa (SEQ ID NO: 14) | |
| | ETX005 | X91427 | (invabasic)(invabasic)gsascuuuCfaUfCfCfuggaaauasusa(NHC6)(MFCO)(GalNAc-T1) (SEQ ID NO: 7) | 92.8 |
| | | X38483 | usAfsuauUfuCfCfaggaUfgAfaagucscsa (SEQ ID NO: 8) | |
| | ETX007 | X91430 | GfsasCfuUfuCfaUfcCfuGfgAfaAfuAfuAf(NHC6)(MFCO)(GalNAc-T1) (SEQ ID NO: 19) | 96.8 |
| | | X91398 | usAfsuAfuUfuCfcAfgGfaUfgAfaAfgUfcsCfsa (SEQ ID NO: 20) | |
| C5 | ETX010 | X91395 | (GalNAc-T1)(MFCO)(NH-DEG)aaGfcAfaGfaUfAfUfuUfuuAfuAfasusa(invabasic)(invabasic) (SEQ ID NO: 3) | 96.4 |
| | | X91381 | usAfsUfuAfuaAfaAfauaUfcUfuGfcuususudTdT (SEQ ID NO: 4) | |
| | ETX012 | X91399 | (GalNAc-T1)(MFCO)(NH-DEG)AfaGfcAfaGfaUfaUfuUfuUfaUfaAfsusAf (SEQ ID NO: 15) | 97.1 |
| | | X91400 | usAfsuUfaUfaAfaAfaUfaUfcUfuGfcUfusUfsudTdT (SEQ ID NO: 16) | |
| | ETX014 | X91428 | (invabasic)(invabasic)asasGfcAfaGfaUfAfUfuUfuuAfuAfaua(NHC6)(MFCO)(GalNAc-T1) (SEQ ID NO: 9) | 97.2 |
| | | X91381 | usAfsUfuAfuaAfaAfauaUfcUfuGfcuususudTdT (SEQ ID NO: 10) | |
| | ETX016 | X91431 | AfsasGfcAfaGfaUfaUfuUfuUfaUfaAfuAf(NHC6)(MFCO)(GalNAc-T1) (SEQ ID NO: 21) | 96.8 |
| | | X91400 | usAfsuUfaUfaAfaAfaUfaUfcUfuGfcUfusUfsudTdT (SEQ ID NO: 22) | |
| TTR | ETX019 | X91396 | (GalNAc-T1)(MFCO)(NH-DEG)ugggauUfuCfAfUfguaaccaasgsa(invabasic)(invabasic) (SEQ ID NO: 5) | 97.2 |
| | | X38104 | usCfsuugGfuuAfcaugAfaAfucccasusc (SEQ ID NO: 6) | |
| | ETX021 | X91401 | (GalNAc-T1)(MFCO)(NH-DEG)UfgGfgAfuUfuCfaUfgUfaAfcCfaAfsgsAf (SEQ ID NO: 17) | 95.5 |
| | | X91402 | usCfsuUfgGfuUfaCfaUfgAfaAfuCfcCfasUfsc (SEQ ID NO: 18) | |
| | ETX023 | X91429 | (invabasic)(invabasic)usgsggauUfuCfAfUfguaaccaaga(NHC6)(MFCO)(GalNAc-T1) (SEQ ID NO: 11) | 96.3 |
| | | X38104 | usCfsuugGfuuAfcaugAfaAfucccasusc (SEQ ID NO: 12) | |
| | ETX025 | X91432 | UfsgsGfgAfuUfuCfaUfgUfaAfcCfaAfgAf(NHC6)(MFCO)(GalNAc-T1) (SEQ ID NO: 23) | 97.5 |
| | | X91402 | usCfsuUfgGfuUfaCfaUfgAfaAfuCfcCfasUfsc (SEQ ID NO: 24) | |

The following schemes further set out the routes of synthesis:
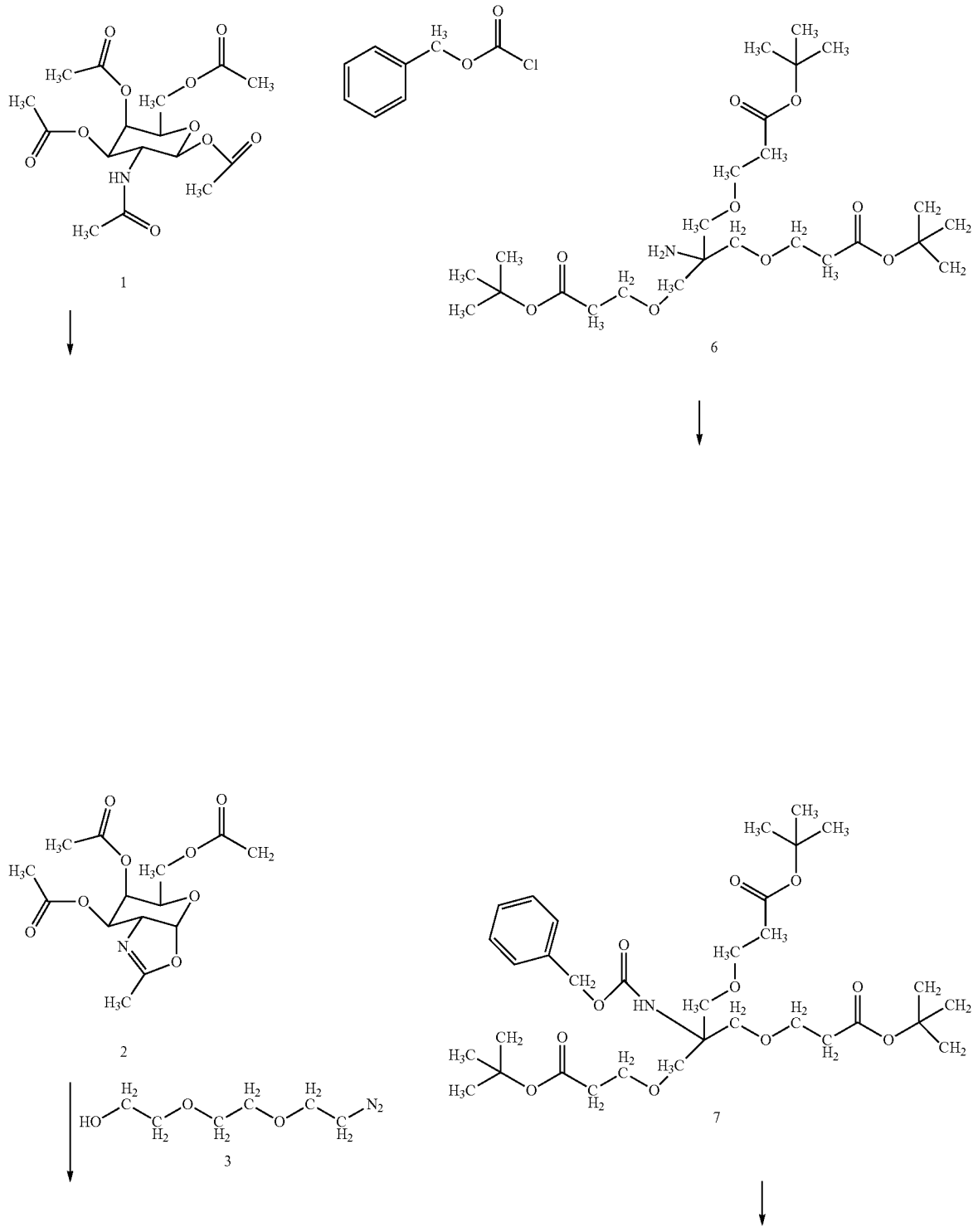

-continued
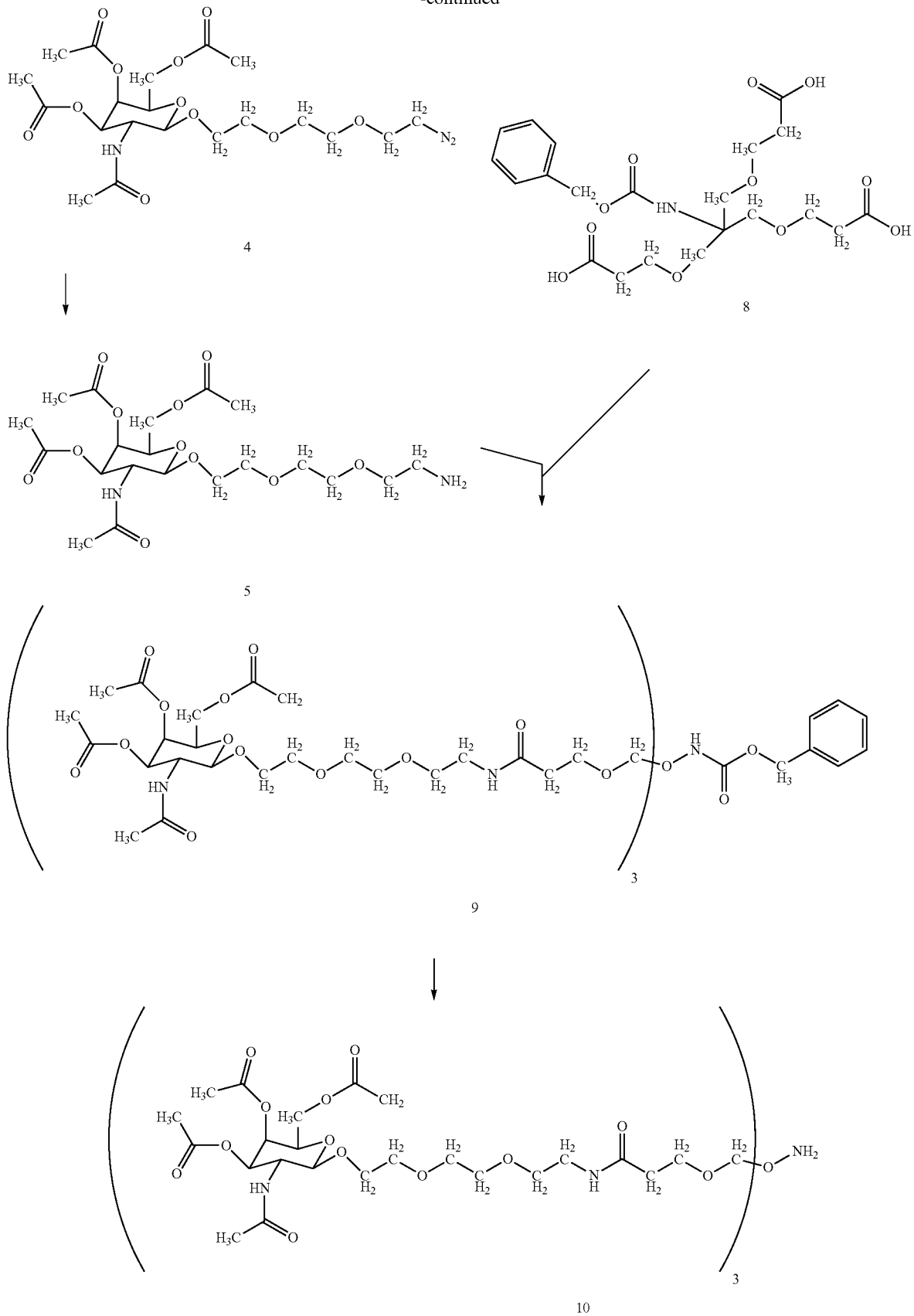

Scheme 2
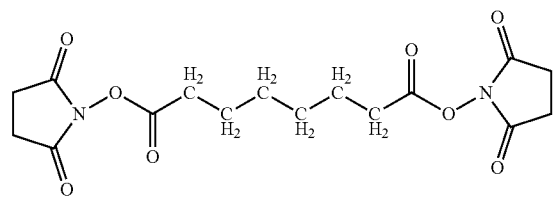
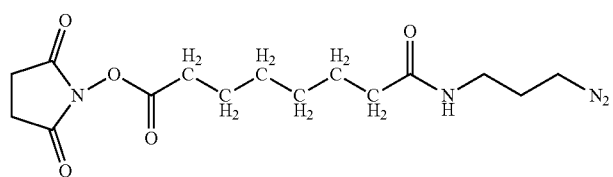
11
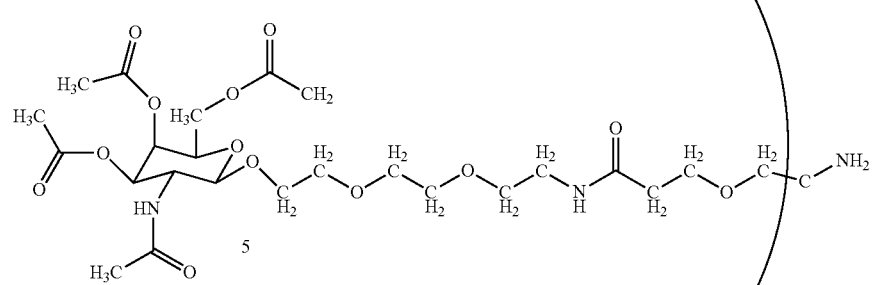
10
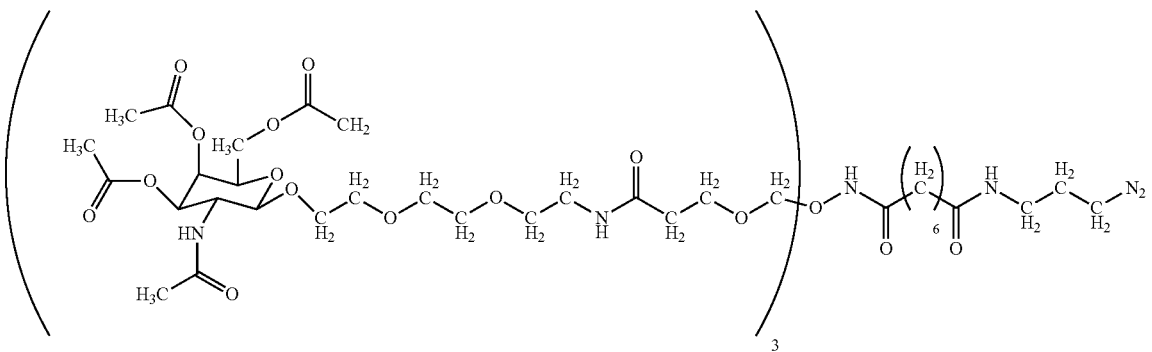
12

Scheme 3
5' end MFCO conjugation
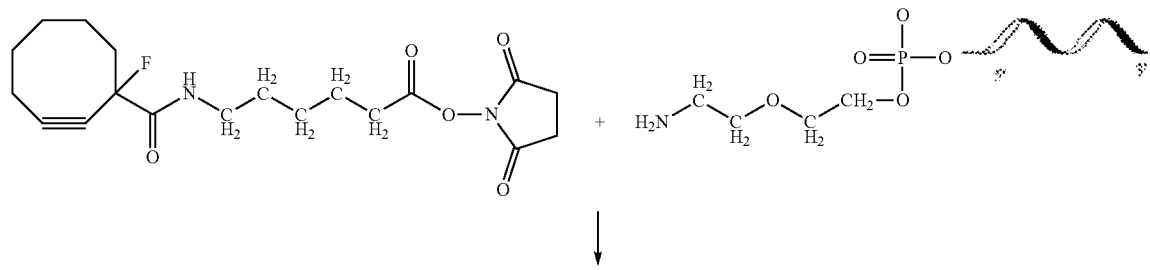
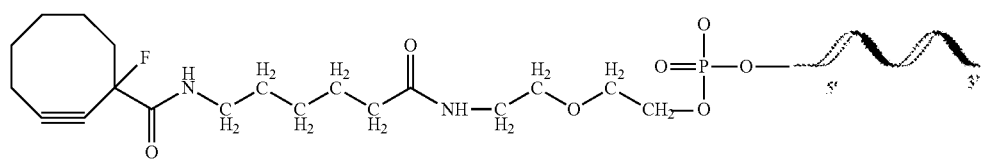
3' end MFCO conjugation
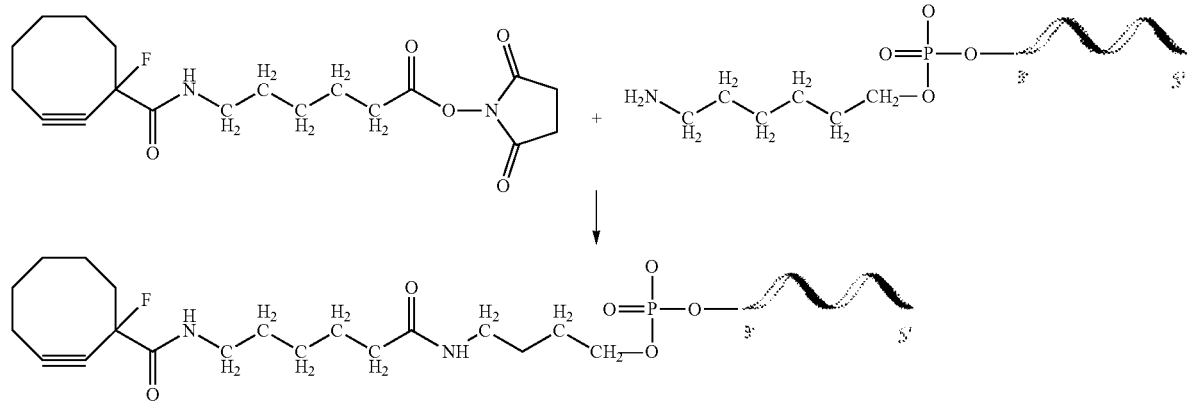
Scheme 4
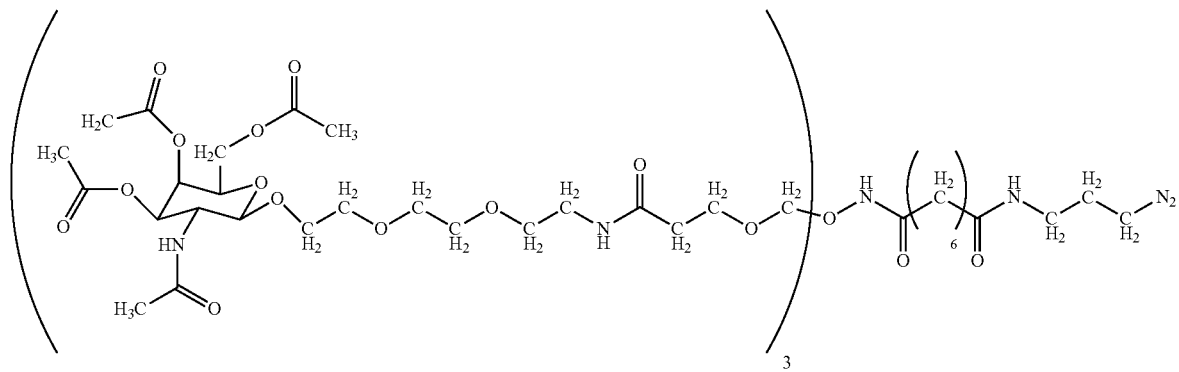
+

-continued
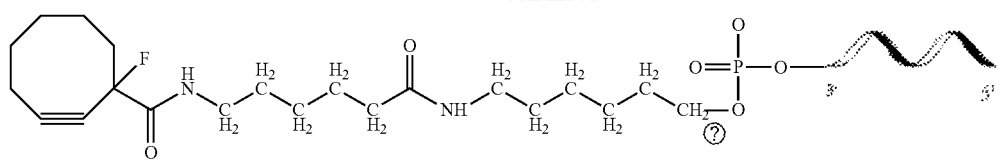
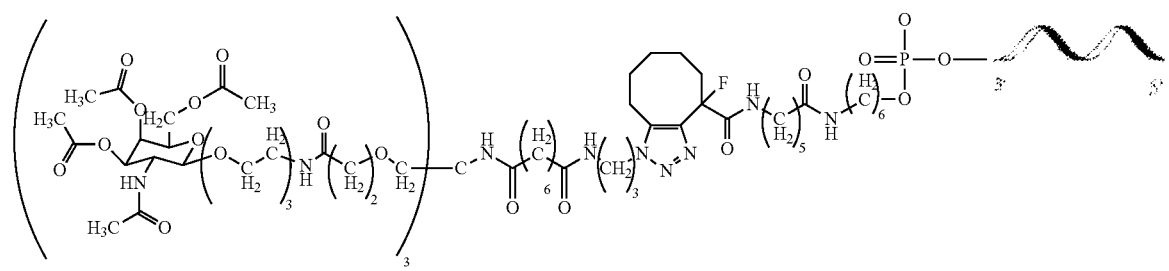
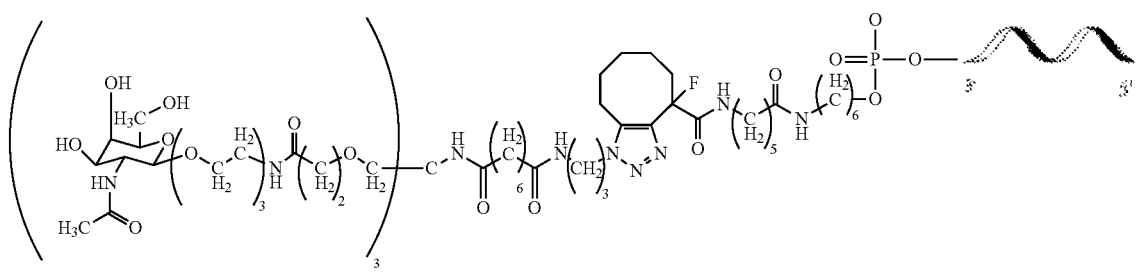
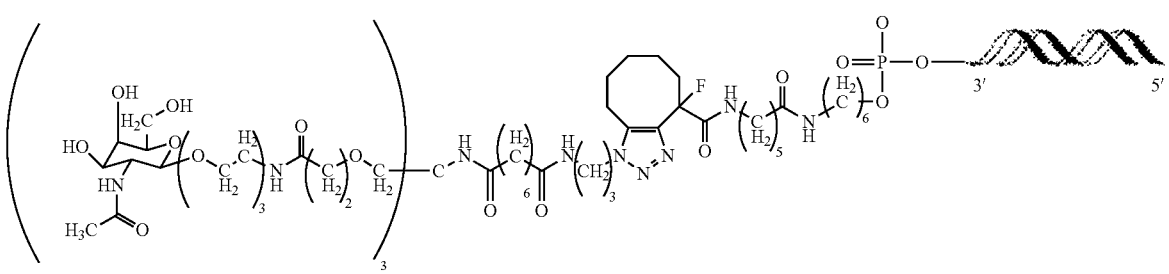

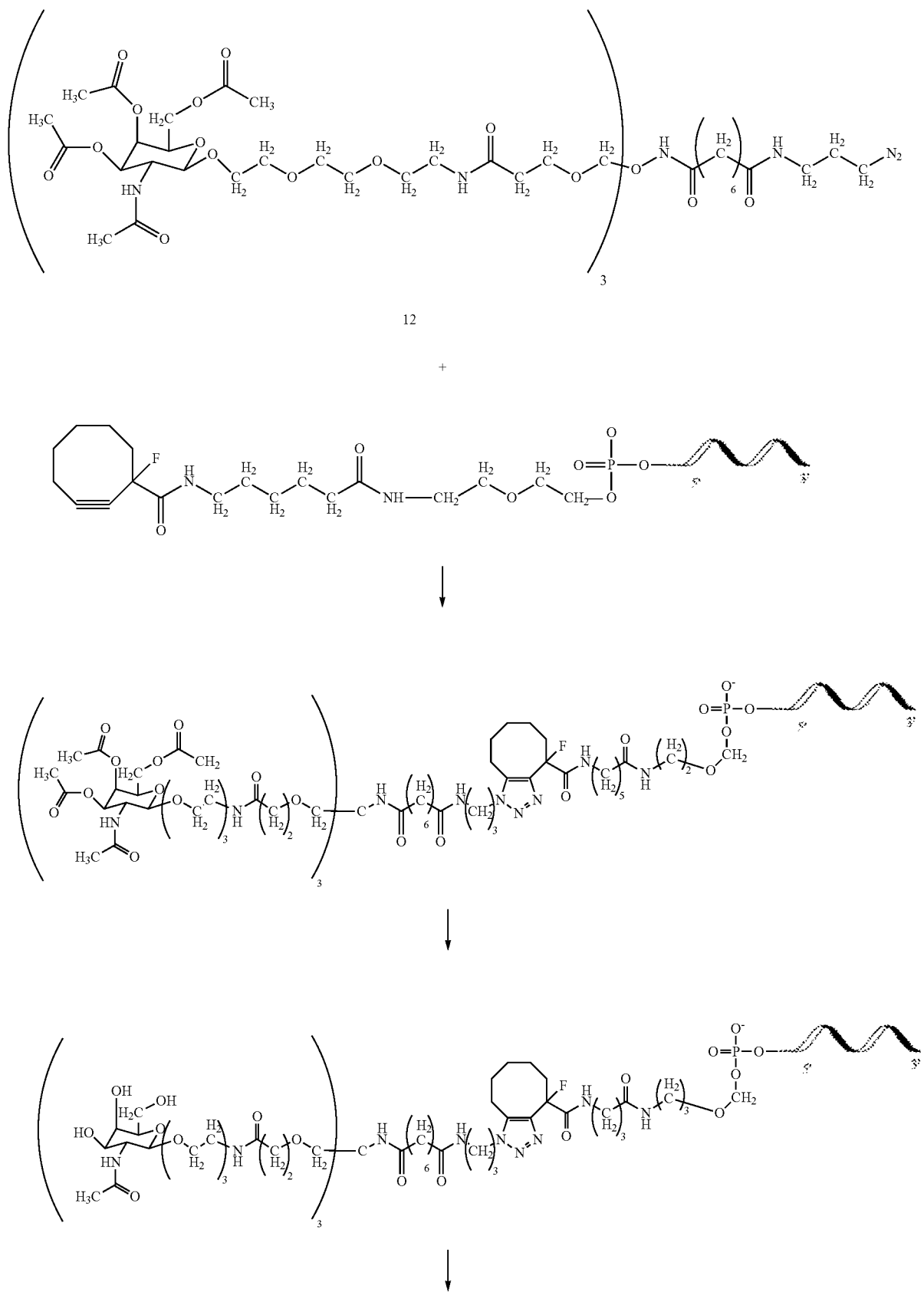
Scheme 5

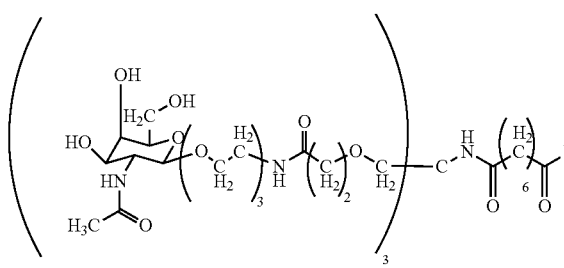
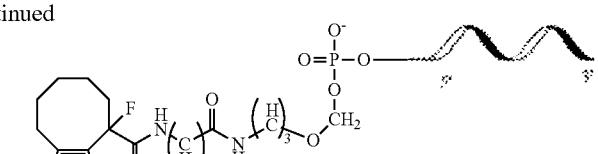

Example 3

Mouse Data for GalNAc-siRNA Constructs ETX005 and ETX014

ETX005 (Targeting HAO1 mRNA) T1a Inverted Abasic

An in vivo mouse pharmacology study was performed showing knockdown of HAO1 mRNA in liver tissue with an associated increase in serum glycolate level following a single subcutaneous dose of up to 3 mg/kg GalNAc conjugated modified siRNA ETX005.

Male C57BL/6 mice with an age of about 8 weeks were randomly assigned into groups of 21 mice. On day 0 of the study, the animals received a single subcutaneous dose of 0.3 or 3 mg/kg GalNAc-siRNA dissolved in saline (sterile 0.9% sodium chloride) or saline only as control. At day 1, day 2, day 4, day 7, day 14, day 21, and day 28 of the study, 3 mice from each group were euthanised and serum and liver samples taken.

Serum was taken from a group of 5 untreated mice at day 0 to provide a baseline measurement of glycolate concentration.

Serum was stored at −80° C. until further analysis. Liver sample (approximately 50 mg) were treated with RNAlater and stored overnight at 4° C., before being stored at −80° C.

Liver samples were analysed using quantitative real-time PCR for HAO1 mRNA (Thermo assay ID Mm00439249_m1) and the housekeeping gene GAPDH mRNA (Thermo assay ID Mm99999915_g1). The delta delta Ct method was used to calculated changes in HAO1 expression normalised to GAPDH and relative to the saline control group.

Figure 11:
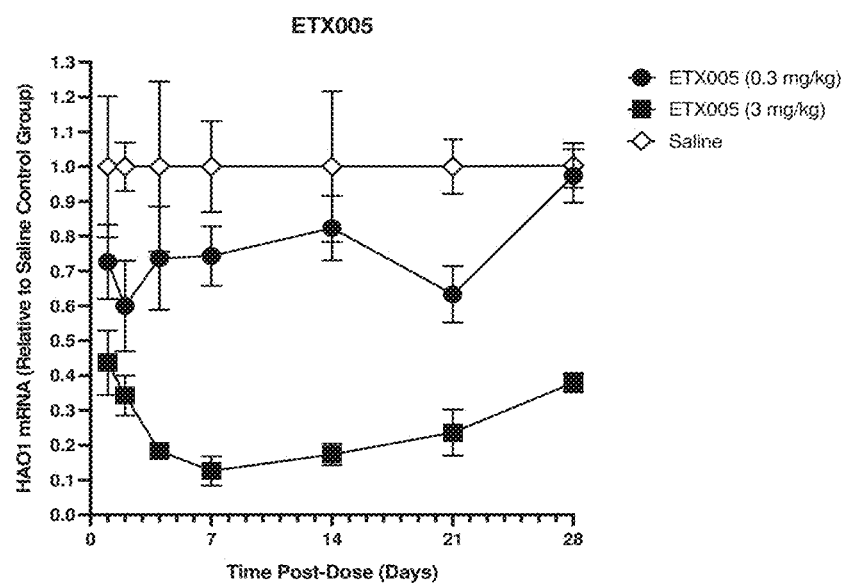
FIG. 11. Single dose mouse pharmacology of ETX005. HAO1 mRNA expression is shown relative to the saline control group. Each point represents the mean and standard deviation of 3 mice.

A single 3 mg/kg dose of ETX005 inhibited HAG1 mRNA expression by greater than 80% after 7 days (FIG. 11). The suppression of HAO1 expression was durable, with a single 3 mg/kg dose of ETX005 maintaining greater than 60% inhibition of HAO1 mRNA at the end of the study on day 28. A single dose of 0.3 mg/kg ETX005 also inhibited HAG1 expression when compared with the saline control group, with HAG1 expression levels reaching normal levels only at day 28 of the study.

Figure 12:
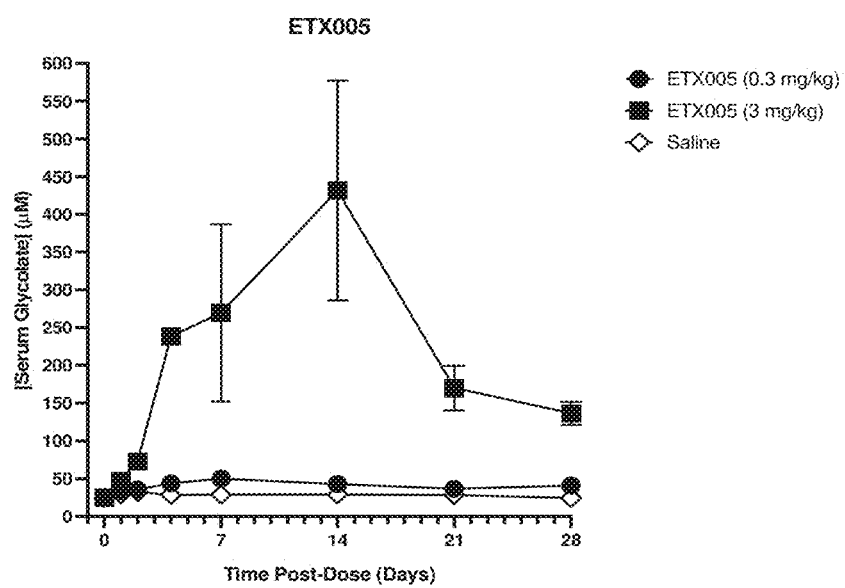
FIG. 12. Single dose mouse pharmacology of ETX005. Serum glycolate concentration is shown. Each point represents the mean and standard deviation of 3 mice, except for baseline glycolate concentration (day 0) which was derived from a group of 5 mice.

Suppression of HAG1 mRNA expression is expected to cause an increase in serum glycolate levels. Serum glycolate concentration was measured using LC-MS/MS (FIG. 12). A single 3 mg/kg dose of ETX005 caused a significant increase in serum glycolate concentration, reaching peak levels 14 days after dosing and remaining higher than baseline level (day 0) and the saline control group until the end of the study at day 28. A single 0.3 mg/kg dose of ETX005 showed a smaller and more transient increase in serum glycolate concentration above the level seen in a baseline and saline control group, demonstrating that a very small dose can suppress HAG1 mRNA at a magnitude sufficient to affect the concentration of a metabolic biomarker in serum.

ETX014 (Targeting C5 mRNA) T1a Inverted Abasic

An in vivo mouse pharmacology study was performed showing knockdown of C5 mRNA in liver tissue and the resulting decrease in serum C5 protein concentration following a single subcutaneous dose of up to 3 mg/kg GalNAc conjugated modified siRNA ETX014.

Male C57BL/6 mice with an age of about 8 weeks were randomly assigned into groups of 21 mice. On day 0 of the study, the animals received a single subcutaneous dose of 0.3, 1, or 3 mg/kg GalNAc-siRNA dissolved in saline (sterile 0.9% sodium chloride) or saline only as control. At day 1, day 2, day 4, day 7, day 14, day 21, and day 28 of the study, 3 mice from each group were euthanised and serum and liver samples taken.

Serum was stored at −80° C. until further analysis. Liver sample (approximately 50 mg) were treated with RNAlater and stored overnight at 4° C., before being stored at −80° C.

Liver samples were analysed using quantitative real-time PCR for C5 mRNA (Thermo assay ID Mm00439275_m1) and the housekeeping gene GAPDH mRNA (Thermo assay ID Mm99999915_g1). The delta delta Ct method was used to calculated changes in C5 expression normalised to GAPDH and relative to the saline control group.

Figure 13:
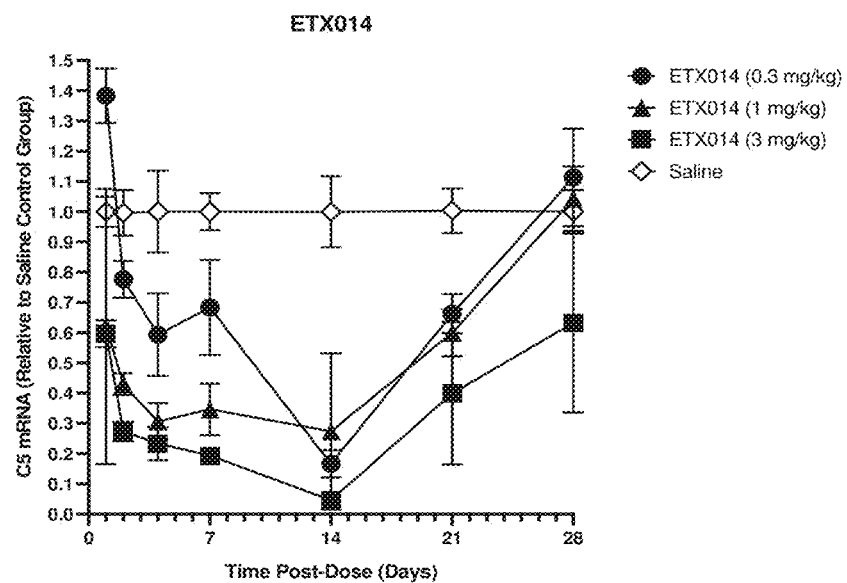
FIG. 13. Single dose mouse pharmacology of ETX014. C5 mRNA expression is shown relative to the saline control group. Each point represents the mean and standard deviation of 3 mice.

ETX014 inhibited C5 mRNA expression in a dose-dependent manner (FIG. 13) with the 3 mg/kg dose achieving greater than 90% reduction in C5 mRNA at day 14. The suppression of C5 expression by ETX014 was durable, with the 3 mg/kg dose of each molecule showing clear knockdown of C5 mRNA until the end of the study at day 28.

For C5 protein level analysis, serum samples were measured using a commercially available C5 ELISA kit (Abcam ab264609). Serum C5 levels were calculated relative to the saline group means at matching timepoints.

Figure 14:
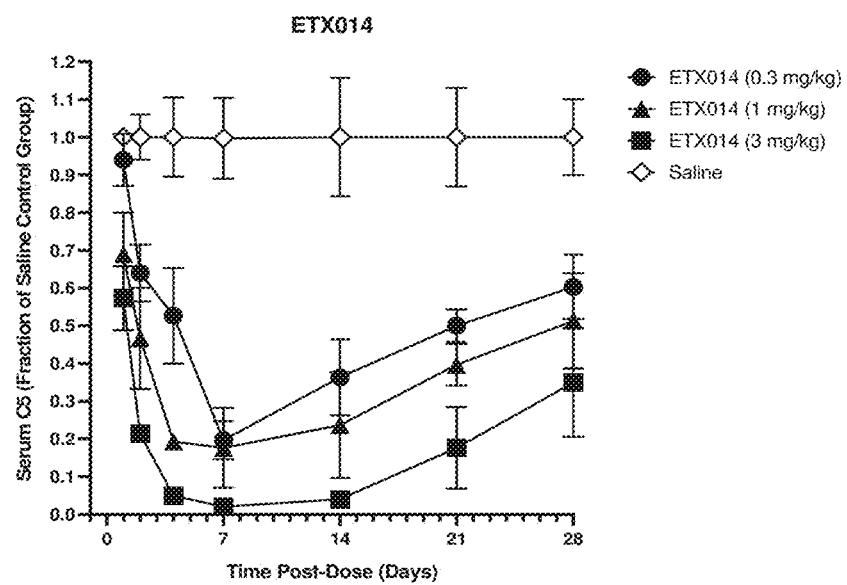
FIG. 14. Single dose mouse pharmacology of ETX0014. Serum C5 concentration is shown relative to the saline control group. Each point represents the mean and standard deviation of 3 mice.

Serum protein data support the mRNA analysis (FIG. 14). Treatment with ETX014 caused a dose-dependent decrease in serum C5 protein concentration. All doses of ETX014 reduced C5 protein levels by greater than 70%, with the 3 mg/kg dose reducing C5 levels to almost undetectable levels at day 7 of the study. Reduction of serum C5 was sustained by all doses until study termination, with even the lowest dose of 0.3 mg/kg still showing inhibition of approximately 40% at day 28.

Example 4 NHP Data for GalNAc-siRNA Construct ETX023

ETX023 (Targeting TTR mRNA) T1a Inverted Abasic

ETX023 pharmacology was evaluated in non-human primate (NHP) by quantifying serum transthyretin (TTR) protein levels. A single subcutaneous dose of 1 mg/kg GalNAc conjugated modified siRNA ETX023 demonstrated durable suppression of TTR protein expression.

Male cynomolgus monkeys (3-5 years old, 2-3 kg) were assigned into groups of 3 animals. Animals were acclimatised for 2 weeks, and blood taken 14 days prior to dosing to provide baseline TTR concentration. A liver biopsy was performed 18 or 38 days prior to dosing to provide baseline mRNA levels. On day 0 of the study, the animals received a single subcutaneous dose of 1 mg/kg GalNAc-siRNA ETX023 dissolved in saline (sterile 0.9% sodium chloride). At day 3, day 14, day 28, day 42, day 56, day 70 and day 84 of the study, a liver biopsy was taken and RNA extracted for measurement of TTR mRNA. At day 1, day 3, day 7, day 14, day 28, day 42, day 56, 70 and day 84 of the study, a blood sample was taken for measurement of serum TTR concentration and clinical blood chemistry analysis.

Figure 15:
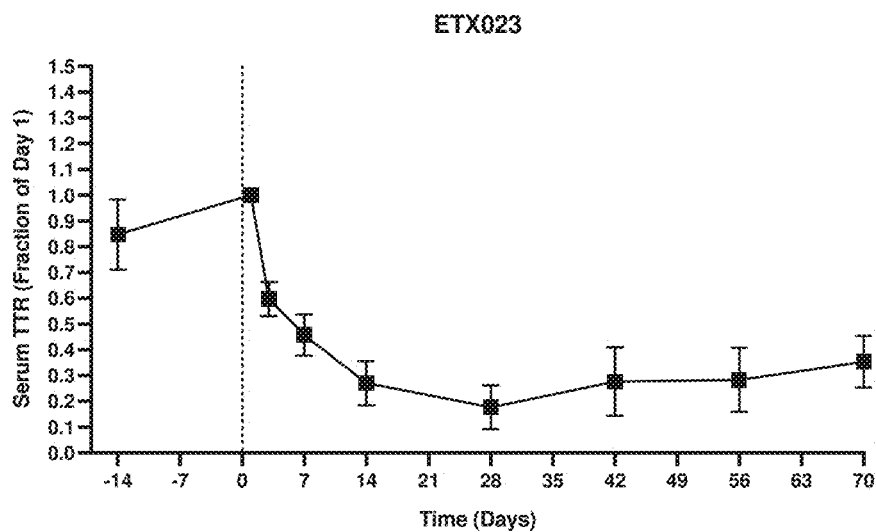
FIG. 15. Single dose NHP pharmacology of ETX023. Serum TTR concentration is shown relative to day 1 of the study. Each point represents the mean and standard deviation of 3 animals.
Figure 16:
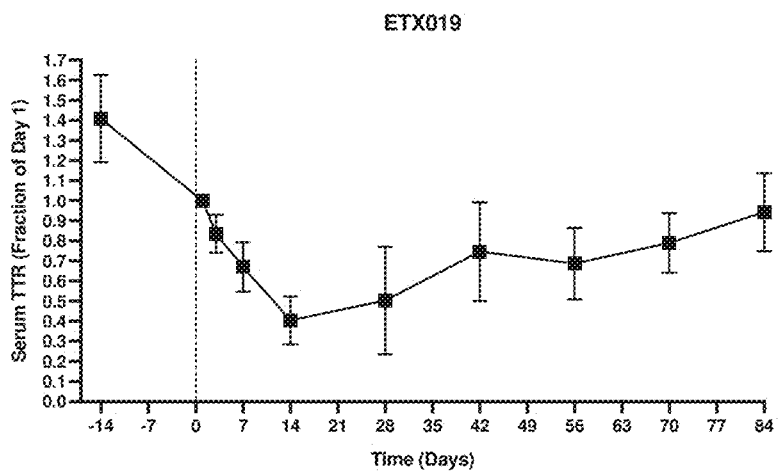
FIG. 16. Single dose NHP pharmacology of ETX019. Serum TTR concentration is shown relative to day 1 of the study and also pre-dose. Each point represents the mean and standard deviation of 3 animals. Time points up to 84 days are shown.
Figure 17:
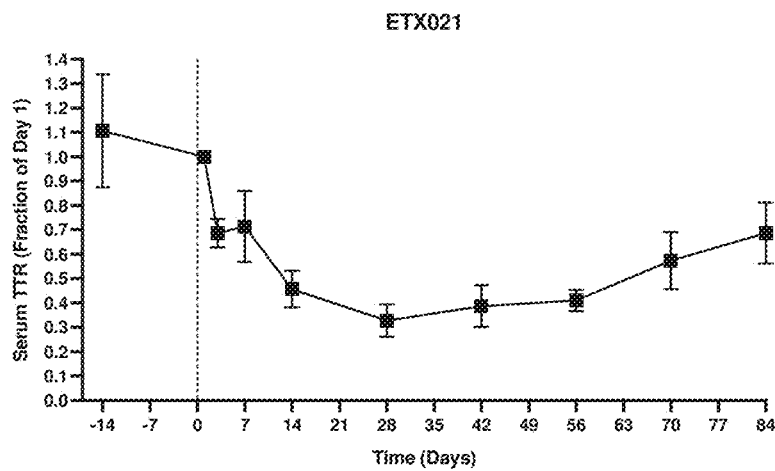
FIG. 17. Single dose NHP pharmacology of ETX021. Serum TTR concentration is shown relative to day 1 of the study and also pre-dose. Each point represents the mean and standard deviation of 3 animals. Time points up to 84 days are shown.

Suppression of TTR mRNA expression is expected to cause a decrease in serum TTR protein levels. Serum TTR protein concentration was measured by a commercially available ELISA kit (Abcam ab231920). TTR concentration as a fraction of day 1 was calculated for each individual animal and this was plotted as mean and standard deviation for the group of 3 animals (FIG. 15).

A single 1 mg/kg dose of ETX023 caused a rapid and significant reduction in serum TTR concentration, reaching nadir 28 days after dosing and remaining suppressed until day 70.

Data was further obtained until day 84. Identical experiments were carried out using ETX019, 021, 025. Data is provided for 84 days in FIGS. 16, 17, 18A and 19 (ETX019, 021, 023 and 025 respectively).

Figure 18A:
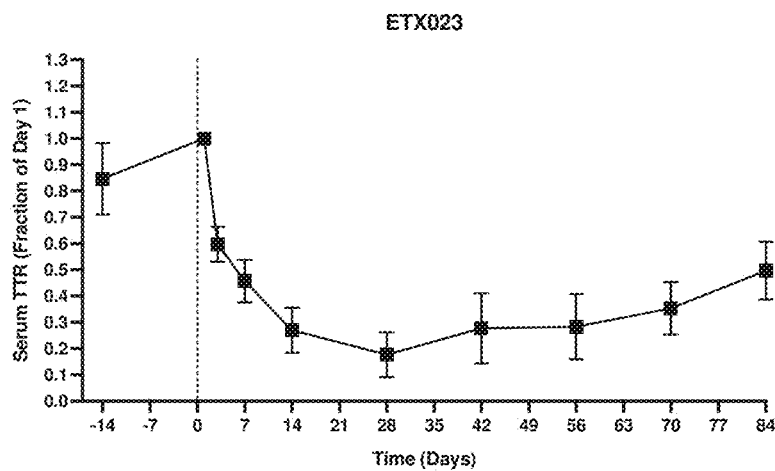
FIG. 18A. Single dose NHP pharmacology of ETX023. Serum TTR concentration is shown relative to day 1 of the study and also pre-dose. Each point represents the mean and standard deviation of 3 animals. Time points up to 84 days are shown.
Figure 18B:
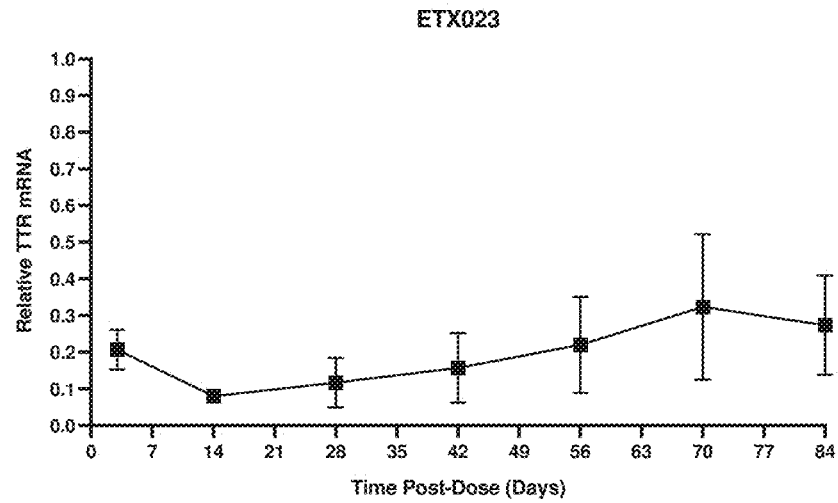
FIG. 18B. Sustained suppression of TTR gene expression in the liver after a single 1 mg/kg dose of ETX023. TTR mRNA is shown relative to baseline levels measured pre-dose. Each point represents the mean and standard deviation of 3 animals. Time points up to 84 days are shown.

TTR mRNA was measured by real-time quantitative PCR using a TaqMan Gene expression kit TTR (Thermo, assay ID Mf02799963_m1). GAPDH expression was also measured (Thermo, assay ID Mf04392546_g1) to provide a reference. Relative TTR expression for each animal was calculated normalised to GAPDH and relative to pre-dose levels by the DDCt method. A single 1 mg/kg dose of ETX023 also caused a rapid and significant reduction in liver TTR mRNA, reaching nadir 14 days after dosing and remaining suppressed until day 84 (FIG. 18B).

Figure 18C:
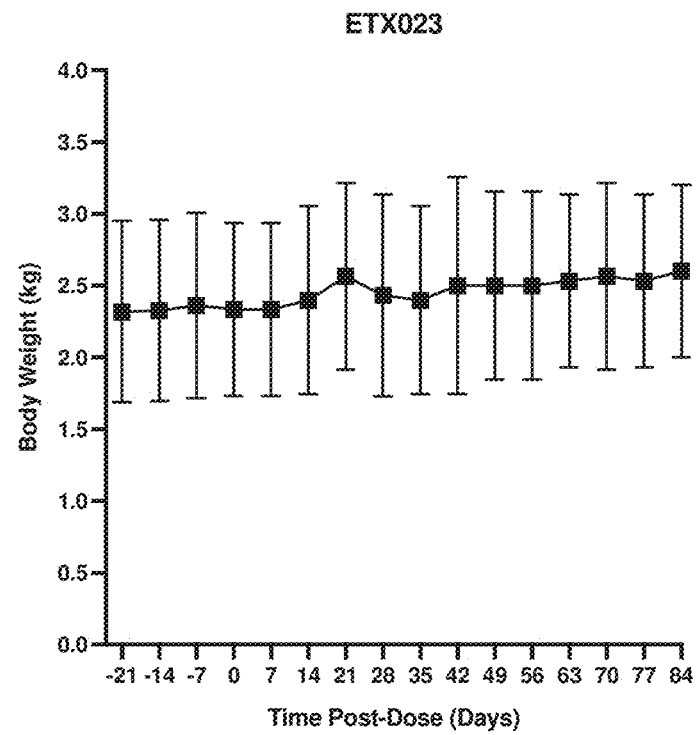
FIG. 18C. Body weight of animals dosed with a single 1 mg/kg dose of ETX023. Each point represents the mean and standard deviation of 3 animals. Time points up to 84 days are shown.

Animal body weight was measured once a week during the study. No fluctuations or decrease in body weight was associated with dosing ETX023 and animals continued to gain weight throughout the study (FIG. 18C).

Figure 18D:
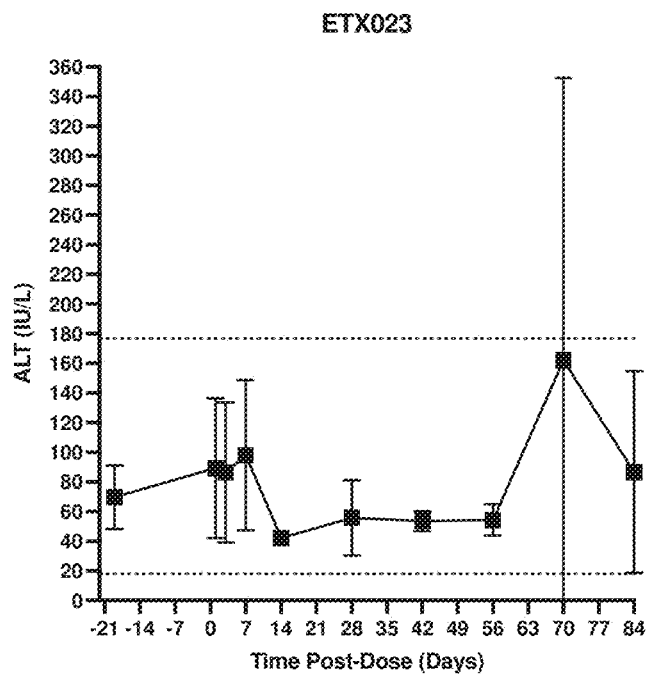
FIG. 18D. ALT concentration in serum from animals treated with a single 1 mg/kg dose of ETX023. Each point represents the mean and standard deviation of 3 animals. The shaded are shows the range of values considered normal at the facility used for the study. The dotted lines show values considered normal for this species (Park et al. 2016 Reference values of clinical pathology parameter in cynomolgus monkeys used in preclinical studies. Lab Anim Res 32:79-86.) Time points up to 84 days are shown.
Figure 18E:
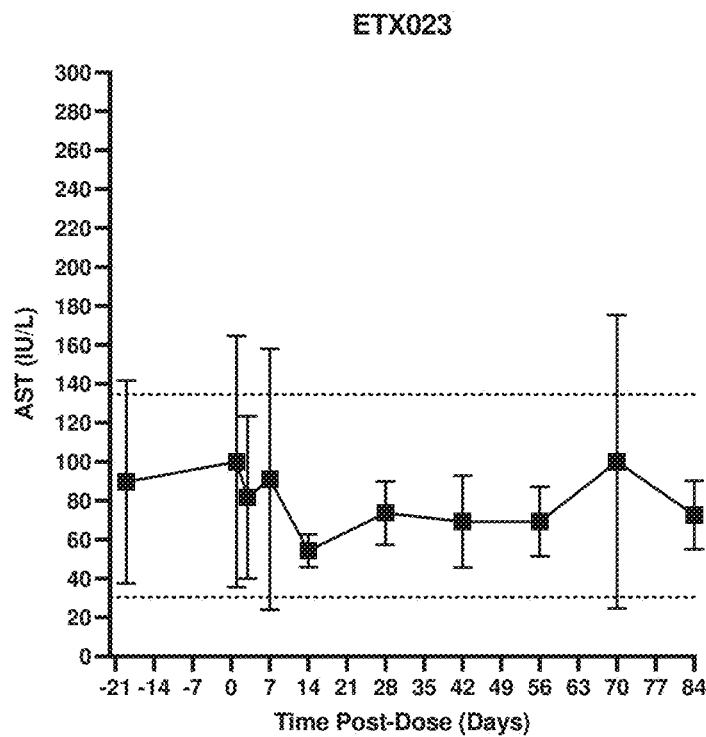
FIG. 18E. AST concentration in serum from animals treated with a single 1 mg/kg dose of ETX023. Each point represents the mean and standard deviation of 3 animals. The shaded are shows the range of values considered normal at the facility used for the study. The dotted lines show values considered normal for this species (Park et al. 2016 Reference values of clinical pathology parameter in cynomolgus monkeys used in preclinical studies. Lab Anim Res 32:79-86. Time points up to 84 days are shown.
Figure 19:
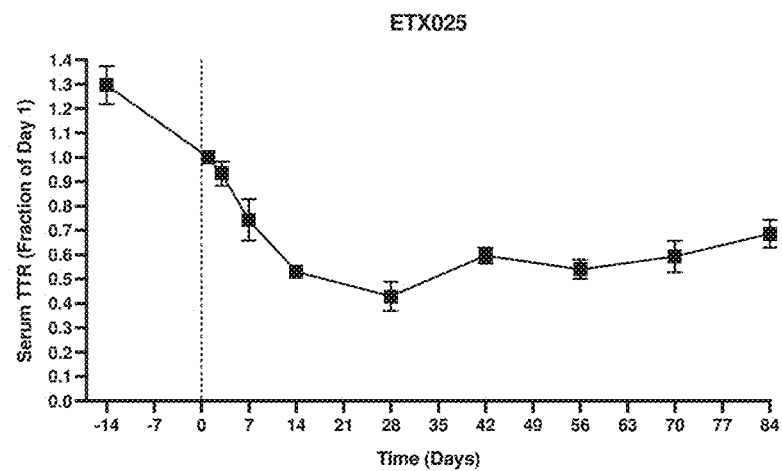
FIG. 19. Single dose NHP pharmacology of ETX025. Serum TTR concentration is shown relative to day 1 of the study and also pre-dose. Each point represents the mean and standard deviation of 3 animals. Time points up to 84 days are shown.

Serum was analysed within 2 hours using an automatic biochemical analyser. A significant increase in ALT (alanine transaminase) and AST (aspartate transaminase) are commonly used to demonstrate liver toxicity. No increase in ALT (FIG. 18D) or ALT (FIG. 18E) was associated with dosing of ETX023.

In preferred aspects, compounds of the invention are able to depress serum protein level of a target protein to a value below the initial (starting) concentration at day 0, over a period of up to at least about 14 days after day 0, up to at least about 21 days after day 0, up to at least about 28 days after day 0, up to at least about 35 days after day 0, up to at least about 42 days after day 0, up to at least about 49 days after day 0, up to at least about 56 days after day 0, up to at least about 63 days after day 0, up to at least about 70 days after day 0, up to at least about 77 days after day 0, or up to at least about 84 days after day 0, hereinafter referred to as the "dose duration". "Day 0" as referred to herein is the day when dosing of a compound of the invention to a patient is initiated, in other words the start of the dose duration or the time post dose.

In preferred aspects, compounds of the invention are able to depress serum protein level of a target protein to a value of at least about 90% or below of the initial (starting) concentration at day 0, such as at least about 85% or below, at least about 80% or below, at least about 75% or below, at least about 70% or below, at least about 65% or below, at least about 60% or below, at least about 55% or below, at least about 50% or below, at least about 45% or below, at least about 40% or below, at least about 35% or below, at least about 30% or below, at least about 25% or below, at least about 20% or below, at least about 15% or below, at least about 10% or below, at least about 5% or below, of the initial (starting) concentration at day 0. Typically such depression of serum protein can be maintained over a period of up to at least about 14 days after day 0, up to at least about 21 days after day 0, up to at least about 28 days after day 0, up to at least about 35 days after day 0, up to at least about 42 days after day 0, up to at least about 49 days after day 0, up to at least about 56 days after day 0, up to at least about 63 days after day 0, up to at least about 70 days after day 0, up to at least about 77 days after day 0, or up to at least about 84 days after day 0. More preferably, at a period of up to at least about 84 days after day 0, the serum protein can be depressed to a value of at least about 90% or below of the initial (starting) concentration at day 0, such as at least about 85% or below, at least about 80% or below, at least about 75% or below, at least about 70% or below, at least about 65% or below, at least about 60% or below, at least about 55% or below, at least about 50% or below, at least about 45% or below, at least about 40% or below, of the initial (starting) concentration at day 0.

In preferred aspects, compounds of the invention are able to achieve a maximum depression of serum protein level of a target protein to a value of at least about 50% or below of the initial (starting) concentration at day 0, such as at least about 45% or below, at least about 40% or below, at least about 35% or below, at least about 30% or below, at least about 25% or below, at least about 20% or below, at least about 15% or below, at least about 10% or below, at least about 5% or below, of the initial (starting) concentration at day 0. Typically such maximum depression of serum protein occurs at about day 14 after day 0, at about day 21 after day 0, at about day 28 after day 0, at about day 35 after day 0, or at about day 42 after day 0. More typically, such maximum depression of serum protein occurs at about day 14 after day 0, at about day 21 after day 0, or at about day 28 after day 0.

Specific compounds of the invention can typically achieve a maximum % depression of serum protein level of a target protein and/or a % depression over a period of up to at least about 84 days as follows:

ETX019 can typically achieve at least 50% depression of serum protein level of a target protein, typically TTR, typically at about 7 to 21 days after day 0, in particular at about 14 days after day 0, and/or can typically maintain at least 90% depression of serum protein level of a target protein, typically TTR, over a period of up to at least about 84 days after day 0 (as hereinbefore described, "day 0" as referred to herein is the day when dosing of a compound of the invention to a patient is initiated, and as such denotes the time post dose);

ETX021 can typically achieve at least 40% depression of serum protein level of a target protein, typically TTR, typically at about 7 to 21 days after day 0, in particular at about 14 days after day 0, and/or can typically maintain at least 80% depression of serum protein level of a target protein, typically TTR, over a period of up to at least about 84 days after day 0 (as hereinbefore described, "day 0" as referred to herein is the day when dosing of a compound of the invention to a patient is initiated, and as such denotes the time post dose);

ETX023 can typically achieve at least 20% depression of serum protein level of a target protein, typically TTR, typically at about 7 to 21 days after day 0, in particular at about 14 days after day 0, and/or can typically maintain at least 50% depression of serum protein level of a target protein, typically TTR, over a period of up to at least about 84 days after day 0 (as hereinbefore described, "day 0" as referred to herein is the day when dosing of a compound of the invention to a patient is initiated, and as such denotes the time post dose);

ETX025 can typically achieve at least 50% depression of serum protein level of a target protein, typically TTR, typically at about 7 to 21 days after day 0, in particular at about 14 days after day 0, and/or can typically maintain at least 70% depression of serum protein level of a target protein, typically TTR, over a period of up to at least about 84 days after day 0 (as hereinbefore described, "day 0" as referred to herein is the day when dosing of a compound of the invention to a patient is initiated, and as such denotes the time post dose). Suitably the depression of serum level is determined in non-human primates by delivering a single subcutaneous dose of 1 mg/kg of the relevant active agent, eg ETX0023, dissolved in saline (sterile 0.9% sodium chloride). Suitable methods are described herein. It will be appreciated that this is not limiting and other suitable methods with appropriate controls may be used.

Example 5 ETX023 (Targeting TTR mRNA) T1a Inverted Abasic

Total Bilirubin Levels Remained Stable Throughout the Study (FIG. 22)

Kidney health was monitored by assessment of urea (blood urea nitrogen, BUN) and creatinine concentration throughout the study. Both blood urea concertation (BUN) and creatinine levels remained stable and within the expected range after a single 1 mg/kg dose of ETX023 (FIGS. 23 and 24).

The present invention is not intended to be limited in scope to the particular disclosed embodiments, which are provided, for example, to illustrate various aspects of the invention. Various modifications to the compositions and methods described will become apparent from the DESCRIPTION and teachings herein. Such variations may be practiced without departing from the true scope and spirit of the disclosure and are intended to fall within the scope of the present disclosure.

A further aspect of the invention is described below, with non-limiting examples described in the following FIGS. 25-27 and Examples 6-15. The compounds described below are suitable for use in any of the aspects and embodiments disclosed above, for example in respect of the uses, nucleic acid lengths, definitions, pharmaceutically acceptable compositions, dosing, methods for inhibiting gene expression, and methods of treating or preventing diseases associated with gene expression, unless otherwise immediately apparent from the disclosure.

FIG. 25A depicts a tri-antennary GalNAc (N-acetylgalactosamine) unit

FIG. 25B depicts an alternative tri-antennary GalNAc according to one embodiment of the invention, showing variance in linking groups.

FIG. 26A depicts tri-antennary GalNAc-conjugated siRNA according to the invention, showing variance in the linking groups.

FIG. 26B depicts a genera of tri-antennary GalNAc-conjugated siRNAs according to one embodiment of the invention.

FIG. 26C depicts a genera of bi-antennary GalNAc-conjugated siRNAs according to one embodiment of the invention, showing variance in the linking groups.

FIG. 26D depicts a genera of bi-antennary GalNAc-conjugated siRNAs according to another embodiment of the invention, showing variance in the linking groups.

FIG. 27A depicts another embodiment of the tri-antennary GalNAc-conjugated siRNA according to one embodiment of the invention.

FIG. 27B depicts a variant shown in FIG. 27A, having an alternative branching GalNAc conjugate.

FIG. 27C depicts a genera of tri-antennary GalNAc-conjugated siRNAs according to one embodiment of the invention, showing variance in the linking groups.

FIG. 27D depicts a genera of bi-antennary GalNAc-conjugated siRNAs according to one embodiment the invention, showing variance in the linking groups.

The further aspect discloses forms of ASGP-R ligand-conjugated, chemically modified RNAi agents, and methods of making and uses of such conjugated molecules.

In certain embodiments, the ASGP-R ligand comprises N-acetylgalactosamine (GalNAc). In certain embodiments, the invention provides an siRNA conjugated to tri-antennary or biantennary units of GalNAc of the following formula (I):

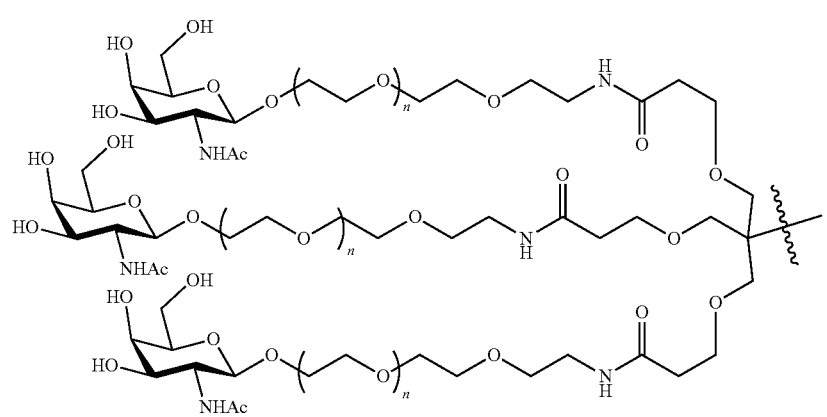

Formula I*

In Formula I*, n is 0, 1, 2, 3, or 4. In some embodiments, the number of the ethylene-glycol units may vary independently from each other in the different branches. For example, the middle branch may have n=4, while the side branches may have n=3, etc. Other embodiments my contain only two branches, as depicted in Formulae (II-a)

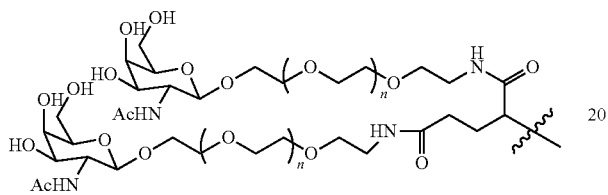

Formula II*-a

In Formulae II* and II*-a, n is chosen from 0, 1, 2, 3, or 4. In some embodiments, the number of the ethylene-glycol units may vary independently from each other in the different branches. For example, the one branch may have n=4 or 3, while the other branche(s) may have n=3 or 2, etc.

Additional GalNAc branches can also be added, for example, 4-, 5-, 6-, 7-, 8-, 9-branched GalNAc units may be used.

In related embodiments, the branched GalNAc can be chemically modified by the addition of another targeting moiety, e.g., a lipids, cholesterol, a steroid, a bile acid, targeting (poly)peptide, including polypeptides and proteins, (e.g., RGD peptide, transferrin, polyglutamate, polyaspartate, glycosylated peptide, biotin, asialoglycoprotein insulin and EGF.

Option 1. In further embodiments, the GalNAc units may be attached to the RNAi agent via a tether, such as the one shown in Formula (III*):

In Formula III*, m is chosen from 0, 1, 2, 3, 4, or 5, and p is chosen from 0, 1, 2, 3, 4, 5, 6, 7, 8, 9, 10, 11, 12, 13, or 14, independently of m, and X is either $CH_2$ or O.

In yet further embodiments, the tether can attach to the oligo via phosphate (Z=O) or a phosphorothioate group (Z=S), as shown in formula (IV*):

Formula IV*

Such an attachment of the GalNAc branched units via the specified tethers is preferably at a 3' or a 5' end of the sense strand of the RNAi agent. In one embodiment, the attachment to the 3' of RNAi agent is through C6 amino linker as shown in Formula (V*):

Formula V*

$H_2N$ ⌒⌒⌒⌒ $_{SS}$ ⌒⌒ $_{5'}$ —OH

This linker is the starting point of the synthesis as shown in Example 12.

The same linkers and tethers as described above can be used with alternative branched GalNAc structures as shown in Formulas VI* and VII*:

Formula III*

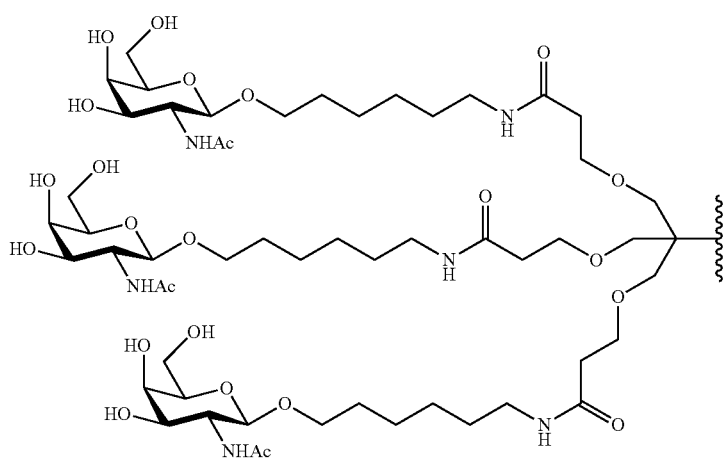

Formula VI*

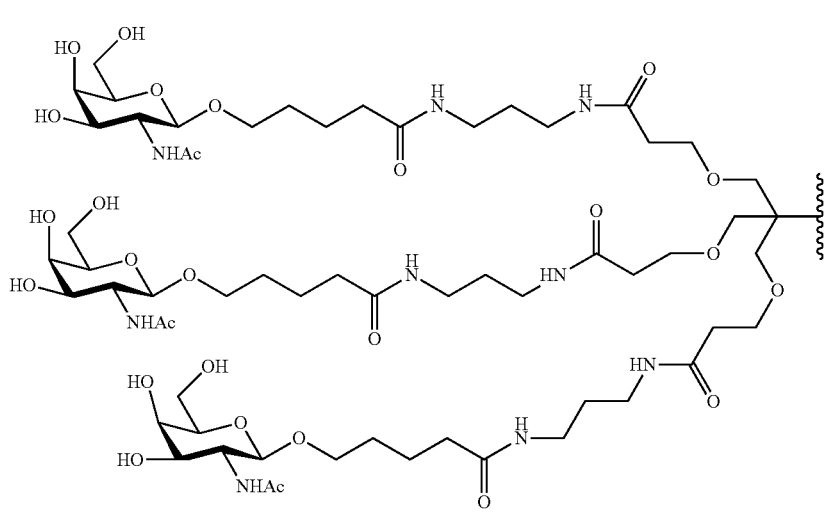

Formula VII*

Similarly to Formula II*-a, a bi-antennary form of ligand based on Formulae VI* and VII* can be used in the compositions of the invention.

Option 2. In further embodiments, the GalNAc units may be attached to the RNAi agent via a tether, such as the one shown in Formula (III*-2):

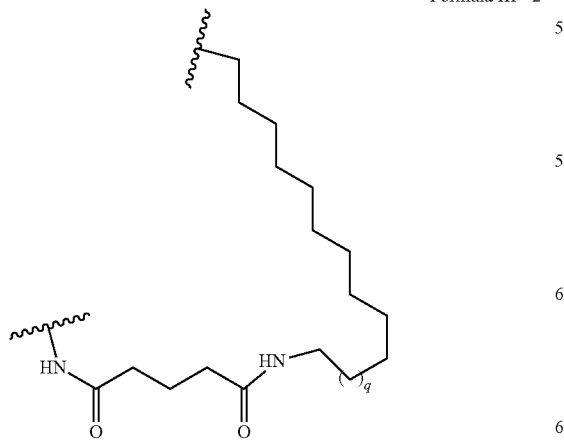

Formula III*-2

In Formula II*-2. q is chosen from 1, 2, 3, 4, 5, 6, 7 or 8,

In yet further embodiments, the tether can attach to the oligo via phosphate (Z=O) or a phosphorothioate group (Z=S), as shown in formula (WV*):

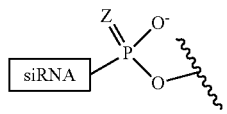

Formula IV*

Such an attachment of the GalNAc branched units via the specified tethers preferably at a 3' or a 5' end of the sense strand of the double stranded RNAi agent. In one embodiment, the attachment to the 3' of RNAi agent is as shown in Example 14. In one embodiment when the GalNAc tether is at attached to the 3' site, the transitional linker between the tether and the 3' end of the oligo comprises the structure of the formula (V*-a; see also FIG. 27C) or another suitable linker may be used, for example, C6 amino linker shown in Formula (V*-b):

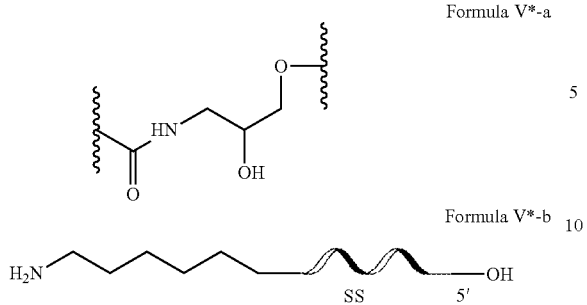

Formula V*-a

Formula V*-b

Additional and/or alternative conjugation sites may include any non-terminal nucleotide, including sugar residues, phosphate groups, or nucleic acid bases.

The same linkers and tether can be used with alternative branched GalNAc structures as shown in Formulas VI*-2 and VII*-2:

Characteristics of RNAi Agents of the Invention and their Chemical Modifications In certain embodiments, the conjugated oligomeric compound (referred herein as RNA interference compound (RNAi compound)) comprises two strands, each having sequence of from 8 to 55 linked nucleotide monomer subunits (including inverted abasic (ia) nucleotide(s)) in either the antisense strand or in the sense strand. In certain embodiments, the conjugated oligomeric compound strands comprise, for example, a sequence of 16 to 55, 53, 49, 40, 25, 24, 23, 21, 20, 19, 18, 17, or up to (about) 18-25, 18-23, 21-23 linked nucleotide monomer subunits. In certain embodiments, RNAi agent of the invention may have a hairpin structure, having a single strand of the combined lengths of both strands as described above. (The term "nucleotide" as used throughout, may also refer to nucleosides (i.e., nucleotides without phosphate/phosphonothioate groups) where context so requires.)

In certain embodiments, the double stranded RNAi agent is blunt-ended or has an overhang at one or both ends. In

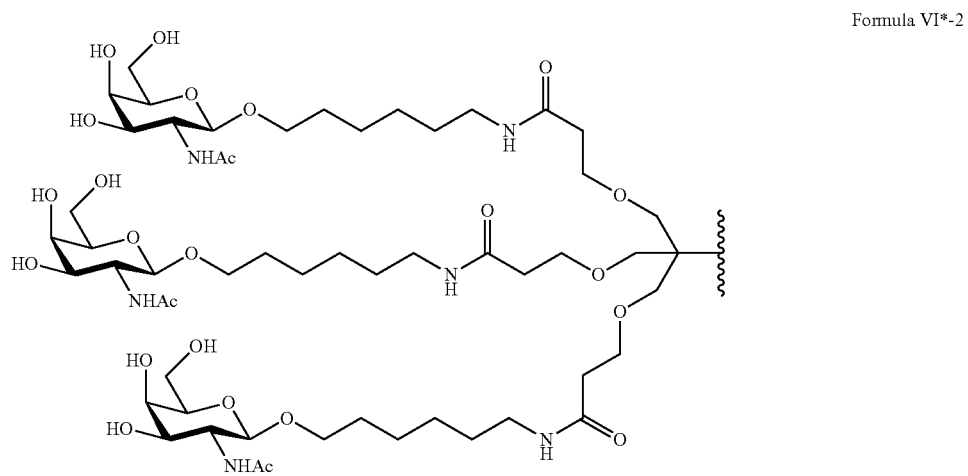

Formula VI*-2

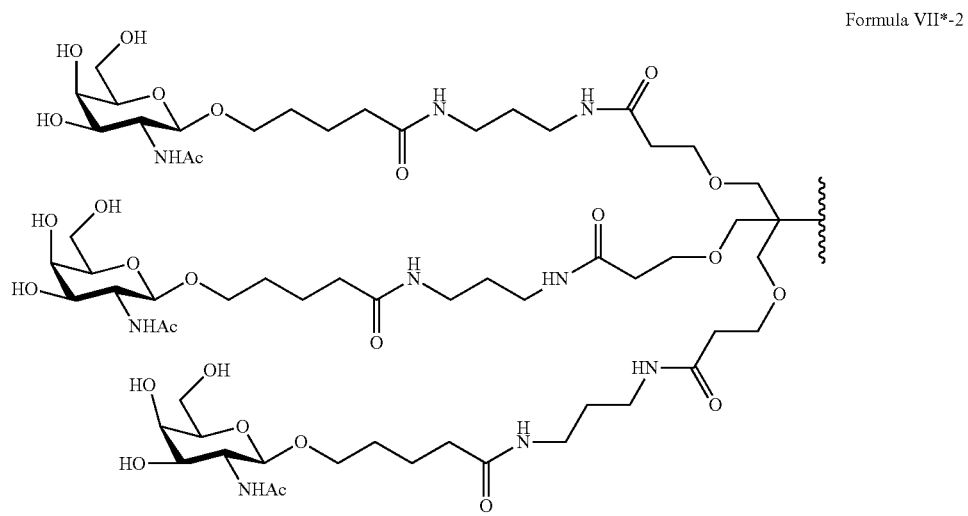

Formula VII*-2 some embodiments, the overhang is 1-6, 1-5, 1-4, 1-3, 2-4, 4, 3, 2 or 1 nucleotide(s) (at 3' end or at 5' end) of the antisense strand as well as 2-4, 3, or 2 or 1 nucleotide(s) (at 3' end or at 5' end) of the sense strand. In certain exemplary embodiments, see Ex.6, constructs 6.1, 6.2, and 6.3, the RNAi agent comprises 2 nucleotide overhang at the 3' end of the antisense strand and 2 nucleotide overhang at 3' end of the sense strand. In certain other exemplary embodiments, see Ex. 7, constructs 7.1 and 7.3, Ex. 8, constructs 8.1 and 8.3; and Ex. 9, constructs 9.1 and 9.3, the RNAi agents comprise 2 nucleotide overhang at the 3' end of the antisense strand and are blunt-ended on the other end. In certain other exemplary embodiment, see Ex. 7, construct 7.3, the construct is blunt-ended on both ends. In another exemplary embodiment, see Ex. 9, construct 9.2, the RNAi agent comprises 4 nucleotide overhang in the 3' end of the antisense strand and blunt-ended on the other end.

In certain embodiments, the constructs are modified with a degradation protective moiety that prevents or inhibits nuclease cleavage by using a terminal cap, one or more inverted abasic nucleotides, one or more phosphorothioate linkages, one of more deoxynucleotides (e.g., D-ribonucleotide, D-2'-deoxyribonucleotide or another modified nucleotide), or a combination thereof. Such degradation protective moieties may be present at any one or all ends that are not conjugated to the ASGP-R ligand. In certain embodiments, the degradation protective moiety is chosen alone or as any combination from a group consisting of 1-4, 1-3, 1-2, or 1 phosphorothioate linkages, 1-4 1-3, 1-2, or 1 deoxynucleotides, and 1-4, 1-3, 1-2, or 1 inverted abasic nucleotides. In certain exemplary embodiments, the degradation protective moieties are configured as in one of the constructs 6.1, 6.2, 6.3, 7.1, 7.2, 7.3, 8.1, 8.2, 8.3, 9.1, 9.2, and 9.3, as shown in the Examples 6-15. Such exemplary protective moieties' configurations can be used in conjunction with any RNAi agents of the invention.

In certain embodiments, all or some riboses of the nucleotides in the sense and/or antisense strand (s) are modified. In certain embodiments, at least 50%, 60%, 70%, 80%, 90% or more (e.g., 100%) of riboses in the RNAi agent are modified. In certain embodiments, 1, 2, 3, 4, 5, 6, 7, 8, 9, 10 or more riboses are not modified.

In preferred embodiments, ribose modifications include 2' substituent groups such as 2'-O-alkyl modifications, including 2'-O-methyl, and 2'-deoxyfluoro. Additional modifications are known in the art, including 2'-deoxy, LNA (e.g., 2'-O, 4'—C methylene bridge or 2'-O, 4'—C ethylene bridge), 2'-methoxythoxy (MOE), 2'-O—(CH$_2$)OCH$_3$, etc.

In certain embodiments, a number of modifications provide a distinct pattern of modifications, for example, as shown in constructs in the Examples 6-15, or as described in U.S. Pat. Nos. 7,452,987; 7,528,188; 8,273,866; 9,150,606; and 10,266,825; all of which are incorporated by reference herein.

In some embodiments, the siRNA comprises one or more thermally destabilizing nucleotides, e.g., GNA, ENA, etc., for example, at positions 11 (preferred), 12, 13 of the antisense strand and/or positions 9 and 10 (preferred) of the sense strand.

Additionally, nucleic acid bases could be modified, for example, at the C4 position as described in U.S. Pat. No. 10,119,136.

In general, the RNAi agents of the invention are directed against therapeutic targets, inhibition of which will result in prevention, alleviation, or treatment of a disease, including undesirable or pathological conditions. A great number of such targets is known in the art. Non-limiting examples of such targets include: ApoC, ApoB, ALAS1, TTR, GO, C5 (see Examples), etc. Generally, due to the abundant expression of ASGP-R on the surface of hepatocytes, such targets are preferably expressed in the liver, however, they could also be expressed in other tissues or organs. In preferred embodiments, targets are human, while the RNAi agent comprise an antisense strand fully or partially complementary to such a target. In certain embodiments, the RNAi agents may comprise two or more chemically linked RNAi agents directed against the same or different targets.

Example 6: Inverted Abasic Chemistry with 5'-GalNAc

In all RNAi agents depicted in the Examples, the following conventions are used:
  ia=inverted abasic nucleotide;
  m=2'-O-methyl nucleotide;
  f=2'-deoxy-2'-fluoro nucleotide;
  s=phosphorothioate internucleotide linkage;
  Xd=2'-deoxy-nucleotide;
  ~=tether.

Using standard synthesis techniques, the following constructs are synthesized in various versions, with tethers 1 and 2, and with various tri-antennary GalNAc units according to the invention, as described above or depicted in FIGS. 26A-27B.

```
6.1.
(Top strand (sense (ss)): SEQ ID NO: 1; bottom strand (antisense) SEQ ID NO: 2)
            1  2  3  4  5  6  7  8  9  10 11 12 13 14 15 16 17 18 19 20 21 22 23
5' GalNAc~Gm-Am-Cm-Um-Um-Um-Cf-Am-Uf-Cf-Cf-Um-Gm-Gm-Am-Am-Am-Um-Ams UmsAm-ia-
ia 3'
3' AmsCms-Cm-Um-Gm-Am-Am-Af-Gm-Uf-Am-Gm-Gm-Am-Cf-Cf-Um-Uf-Um-Am-UmsAfsUm 5'
   23 22   21 20 19 18 17 16 15 14 13 12 11 10 9  8  7  6  5  4  3  2  1

6.2.
(Top strand (sense (ss)): SEQ ID NO: 3; bottom strand (antisense) SEQ ID NO: 4)
            1  2  3  4  5  6  7  8  9  10 11 12 13 14 15 16 17 18 19 20 21 22 23
5' GalNAc~Am-Am-Gf-Cm-Af-Am-Gf-Am-Uf-Af-Uf-Um-Uf-Um-Um-Af-Um-Af-AmsUmsAm-ia-ia 3'
3' Td-Td-UmsUmsUm-Um-Cm-Gf-Um-Uf-Cm-Uf-Am-Um-Am-Af-Am-Af-Am-Um-Af-Um-UfsAfsUm 5'
   25 25  23 22 21 20 19 18 17 16 15 14 13 12 11 10 9  8  7  6  5  4  3  2  1

6.3.
(Top strand (sense (ss)): SEQ ID NO: 5; bottom strand (antisense) SEQ ID NO: 6)
            1  2  3  4  5  6  7  8  9  10 11 12 13 14 15 16 17 18 19 20 21 22 23
5' GalNAc~Um-Gm-Gm-Gm-Am-Um-Uf-Um-Cf-Af-Uf-Gm-Um-Am-Am-Cm-Cm-Am-AmsGmsAm-ia-ia 3'
3' CmsUmsAm-Cm-Cm-Cm-Um-Af-Am-Af-Gm-Um-Am-Cm-Af-Um-Um-Gf-Gm-Um-UmsCfsUm 5'
   23 22 21 20 19 18 17 16 15 14 13 12 11 10 9  8  7  6  5  4  3  2  1
```

Example 7: Inverted Abasic Chemistry with
3'-GalNAc

Using standard synthesis techniques, the following constructs are synthesized in various versions, with tethers 1 and 2 according to the invention, and with various tri-antennary GalNAc units according to the invention, as described above or depicted in FIGS. 26A-27B. Same sequences as in Example 6 are shown for consistency.

```
7.1
(Top strand (sense (ss)): SEQ ID NO: 7; bottom strand (antisense) SEQ ID NO: 8)
     1  2  3  4  5  6  7  8  9  10 11 12 13 14 15 16 17 18 19 20 21 22 23
5' ia-ia-GmsAmsCm-Um-Um-Um-Cf-Am-Uf-Cf-Cf-Um-Gm-Gm-Am-Am-Am-Um-Am-Um-Am~GalNAc 3'
3' AmsCmsCm-Um-Gm-Am-Am-Af-Gm-Uf-Am-Gm-Gm-Am-Cf-Cf-Um-Uf-Um-Am-UmsAfsUm 5'
   23 22 21 20 19 18 17 16 15 14 13 12 11 10 9  8  7  6  5  4  3  2  1

7.2
(Top strand (sense (ss)): SEQ ID NO: 9; bottom strand (antisense) SEQ ID NO: 10)
     1  2  3  4  5  6  7  8  9  10 11 12 13 14 15 16 17 18 19 20 21 22 23
5' ia-ia-AmsAmsGf-Cm-Af-Am-Gf-Am-Uf-Af-Uf-Um-Uf-Um-Um-Af-Um-Af-Am-Um-Am~GalNAc 3'
3' Td-Td-UmsUmsUm-Um-Cm-Gf-Um-Uf-Cm-Uf-Am-Um-Am-Af-Am-Af-Am-Um-Af-Um-UfsAfsUm 5'
   25 24 23 22 21 20 19 18 17 16 15 14 13 12 11 10 9  8  7  6  5  4  3  2  1

7.3.
(Top strand (sense (ss)): SEQ ID NO: 11; bottom strand (antisense) SEQ ID NO: 12)
     1  2  3  4  5  6  7  8  9  10 11 12 13 14 15 16 17 18 19 20 21 22 23
5' ia-ia-UmsGmsGm-Gm-Am-Um-Uf-Um-Cf-Af-Uf-Gm-Um-Am-Am-Cm-Cm-Am-Am-Gm-Am~GalNAc 3'
3' CmsUmsAm-Cm-Cm-Cm-Um-Af-Am-Af-Gm-Um-Am-Cm-Af-Um-Um-Gf-Gm-Um-UmsCfsUm 5'
   23 22 21 20 19 18 17 16 15 14 13 12 11 10 9  8  7  6  5  4  3  2  1
```

Example 8: Inverted Abasic Chemistry with
5'-GalNAc with Alternative Modification Patterns Using standard synthesis techniques, the following constructs are synthesized in various versions, with tethers 1 and 2 according to the invention, and with various tri-antennary GalNAc units according to the invention, as described above or depicted in FIGS. 26A-27B. Same sequences as in Example 6 are shown here for consistency.

```
8.1.
(Top strand (sense (ss)): SEQ ID NO: 13; bottom strand (antisense) SEQ ID NO: 14)
         1  2  3  4  5  6  7  8  9  10 11 12 13 14 15 16 17 18 19 20 21
5' GalNAc~Gf-Am-Cf-Um-Uf-Um-Cf-Am-Uf-Cm-Cf-Um-Gf-Gm-Af-Am-Af-Um-AfsUmsAf 3'
3' AmsCfsCm-Uf-Gm-Af-Am-Af-Gm-Uf-Am-Gf-Gm-Af-Cm-Cf-Um-Uf-Um-Af-UmsAfsUm 5'
   23 22 21 20 19 18 17 16 15 14 13 12 11 10 9  8  7  6  5  4  3  2  1

8.2
(Top strand (sense (ss)): SEQ ID NO: 15; bottom strand (antisense) SEQ ID NO: 16)
         1  2  3  4  5  6  7  8  9  10 11 12 13 14 15 16 17 18 19 20 21
5' GalNAc~Af-Am-Gf-Cm-Af-Am-Gf-Am-Uf-Am-Uf-Um-Uf-Um-Uf-Am-Uf-Am-AfsUmsAf 3'
3' Td-Td-UmsUfsUm-Uf-Cm-Gf-Um-Uf-Cm-Uf-Am-Uf-Af-Am-Af-Am-Uf-Am-Uf-UmsAfsUm 5'
   25 24 23 22 21 20 19 18 17 16 15 14 13 12 11 10 9  8  7  6  5  4  3  2  1

8.3.
(Top strand (sense (ss)): SEQ ID NO: 17; bottom strand (antisense) SEQ ID NO: 18)
         1  2  3  4  5  6  7  8  9  10 11 12 13 14 15 16 17 18 19 20 21
5' GalNAc~Uf-Gm-Gf-Gm-Af-Um-Uf-Um-Cf-Am-Uf-Gm-Uf-Am-Af-Cm-Cf-Am-AfsGmsAf 3'
3' CmsUfsAm-Cf-Cm-Cf-Um-Af-Am-Af-Gm-Uf-Am-Cf-Am-Uf-Um-Gf-Gm-Uf-UmsCfsUm 5'
   23 22 21 20 19 18 17 16 15 14 13 12 11 10 9  8  7  6  5  4  3  2  1
```

Example 9: Inverted Abasic Chemistry with 5'-GalNAc with Alternative Modification Patterns Using standard synthesis techniques, the following constructs are synthesized in various versions, with tethers 1 and 2 according to the invention, and with various tri-antennary GalNAc units according to the invention, as described above or depicted in FIGS. 26A-27B. Same sequences as in Example 6 are shown for consistency.

```
9.1.
(Top strand (sense (ss)): SEQ ID NO: 19; bottom strand (antisense) SEQ ID NO: 20)
      1  2  3  4  5  6  7  8  9 10 11 12 13 14 15 16 17 18 19 20 21
5' GfsAmsCf-Um-Uf-Um-Cf-Am-Uf-Cm-Cf-Um-Gf-Gm-Af-Am-Af-Um-Af-Um-Af~GalNAc 3'
3' AmsCfsCm-Uf-Gm-Af-Am-Af-Gm-Uf-Am-Gf-Gm-Af-Cm-Cf-Um-Uf-Um-Af-UmsAfsUm 5'
     23 22 21 20 19 18 17 16 15 14 13 12 11 10  9  8  7  6  5  4  3  2  1

9.2
(Top strand (sense (ss)): SEQ ID NO: 21; bottom strand (antisense) SEQ ID NO: 22)
      1  2  3  4  5  6  7  8  9 10 11 12 13 14 15 16 17 18 19 20 21
5' AfsAmsGf-Cm-Af-Am-Gf-Am-Uf-Am-Uf-Um-Uf-Um-Af-Uf-Am-Af-Um-Af~GalNAc 3'
3' Td-Td-UmsUfsUm-Uf-Cm-Gf-Um-Uf-Cm-Uf-Am-Uf-Am-Af-Am-Af-Am-Uf-Am-Uf-UmsAfsUm 5'
  25 24 23 22 21 20 19 18 17 16 15 14 13 12 11 10  9  8  7  6  5  4  3  2  1

9.3
(Top strand (sense (ss)): SEQ ID NO: 23; bottom strand (antisense) SEQ ID NO: 24)
      1  2  3  4  5  6  7  8  9 10 11 12 13 14 15 16 17 18 19 20 21
5' UfsGmsGf-Gm-Af-Um-Uf-Um-Cf-Am-Uf-Gm-Uf-Am-Af-Cm-Cf-Am-Af-Gm-Af~GalNAc 3'
3' CmsUfsAm-Cf-Cm-Cf-Um-Af-Am-Af-Gm-Uf-Am-Cf-Am-Uf-Um-Gf-Gm-Uf-UmsCfsUm 5'
     23 22 21 20 19 18 17 16 15 14 13 12 11 10  9  8  7  6  5  4  3  2  1
```

Example 10: Benchmarking of siRNA-GalNAc Conjugates

The constructs used in Examples 6-15 are referred to by their numbers and are listed in Table 12. Tether 1 and Tether 2 are shown in FIGS. 26 and 27 respectively.

TABLE 12

| Construct | Target A (GO) | Target B (C5) | Target C (TTR) |
|---|---|---|---|
| Tether 1 | 6.1 | 6.2 | 6.3 |
| Tether 2 | 6.1 | 6.2 | 6.3 |

TABLE 12-continued

| Construct | Target A (GO) | Target B (C5) | Target C (TTR) |
|---|---|---|---|
| Tether 1 | 8.1 | 8.2 | 8.3 |
| Tether 2 | 8.1 | 8.2 | 8.3 |
| Tether 1 | 7.1 | 7.2 | 7.3 |
| Tether 2 | 7.1 | 7.2 | 7.3 |
| Tether 1 | 9.1 | 9.2 | 9.3 |
| Tether 2 | 9.1 | 9.2 | 9.3 |
| 3'-GalNAc control (eg see FIG. 25A) | | | |

The following Table 13 reflects benchmarking to be performed with various select constructs of the invention.

TABLE 13

In vitro Experiments for Benchmarking siRNA-GalNAc

| Target | | A | | B | | C | |
|---|---|---|---|---|---|---|---|
| In Vitro siRNA Group | Benchmark RNAI agents | Human Primary hepatocyte uptake | ASPGR human hepatocyte binding | Human Primary hepatocyte uptake | ASPGR human hepatocyte binding | Human Primary hepatocyte uptake | ASPGR human hepatocyte binding |
| 1 | tether option 1 at 5'-end of sense strand Inverted abasic chemistry | 0, 4 (update), and 24 hr (silencing) incubations, or Hep3B Transfection w/RNAiMax for 24 h | Determine KD for ASPGR binding with siRNA-GalNAc | 0, 4 (update), and 24 hr (silencing) incubations, or Hep3B Transfection w/RNAiMax for 24 h | Determine KD for ASPGR binding with SIRNA-GalNAc | 0, 4 (update), and 24 hr (silencing) incubations, or Hep3B Transfection w/RNAiMax for 24 h | Determine KD for ASPGR binding with siRNA-GalNAc |
| 2 | tether option 2 at 5'-end of sense strand Inverted abasic chemistry | | | | | | |
| 3 | tether option 1 at 5' end of sense strand Alternating chemistry | | | | | | |
| 4 | tether option 2 at 5'-end of sense strand Alternating Chemistry | | | | | | |
| 5 | tether option 1 at 3'-end of sense strand Inverted abasic chemistry | | | | | | |
| 6 | tether option 2 at 3'-end of sense strand Inverted abasic chemistry | | | | | | |
| 7 | tether option 1 at 3'-end of sense strand Alternating chemistry | | | | | | |
| 8 | tether option 2 at 3' end of sense strand Alternating chemistry | | | | | | |
| 9 | 3'-GalNAc control (eg see FIG. 25A) | | | | | | |

In Vitro Pharmacodynamic Characterization

The in vitro pharmacodynamics activity, binding affinity, and liver uptake for 8 constructs, listed in Table 12 (GO1 siRNA-GalNAc, C5 siRNA-GalNAc, and TTR siRNA-GalNAc analogues) are benchmarked against the clinically validated versions of these molecules.

Human Liver Cell Line (HepG2 or Hep3B) Transfection Assay—Each GO1 siRNA-GalNAc, C5 siRNA-GalNAc, and TTR siRNA-GalNAc analogue molecule is incubated at 37° C. for 0 and 24 hours at 10 different concentrations in human liver cell line in the presence of transfection reagent (e.g RNAiMAX). All incubations at each concentration are run in quadruplicate. Following incubations, each sample is lysed and analyzed for HAG1 C5, TTR and housekeeping gene (such as GAPDH) mRNA concentrations by bDNA or RT-qPCR assay. mRNA concentrations data obtained is used for analysis to determine the silencing activity and $IC_{50}$ for each of the GO1 siRNA-GalNAc, C5 siRNA-GalNAc, and TTR siRNA-GalNAc molecules.

Primary Human Hepatocytes Uptake Assay—The liver uptake and silencing activity for each of the GO1 siRNA-GalNAc, C5 siRNA-GalNAc, and TTR siRNA-GalNAc molecules are evaluated in primary human hepatocytes. Each GO1 siRNA-GalNAc, C5 siRNA-GalNAc, and TTR siRNA-GalNAc analogues molecule is incubated at 37° C. for 0, 4, and 72 hours at 10 different concentrations in primary human hepatocytes. All incubations at each concentration are run in quadruplicate. Following incubations, each sample is lysed and analyzed for HAO1, C5, TTR and housekeeping gene(s) (such as GAPDH) mRNA concentrations by bDNA or RT-qPCR assay. mRNA concentrations data obtained are used for analysis to determine the silencing activity, uptake and $IC_{50}$ for each of the GO1 siRNA-GalNAc, C5 siRNA-GalNAc, and TTR siRNA-GalNAc molecules.

In Vivo Pharmacodynamic Characterization

The in vivo pharmacodynamics activity for 8 constructs each of GO1 siRNA-GalNAc, C5 siRNA-GalNAc, and TTR siRNA-GalNAc analogues is compared to the in vivo pharmacodynamic activity of clinically validated of each GO1siRNA-GalNAc, C5 siRNA-GalNAc, and TTR siRNA-GalNAc molecules following a single subcutaneous administration to male mice or cynomolgus monkeys.

For the in vivo mice pharmacology of GO1 siRNA-GalNAc of each of analogues is evaluated following a single subcutaneous dose at 0.3 or 3 mg/kg as provided in Table 14 below. There are 2 dose groups in which each of the GO1 siRNA-GalNAc analogues is administered subcutaneously to C57BL/6 male mice (n=3/timepoint/group) at 0.3 or 1 mg/kg. Blood samples to obtain serum samples and liver biopsy samples are obtained at various time points to determine the concentration of serum glycolate by LCMS and to determine the concentration of HAO1 mRNA by RT-qPCR or bDNA assay. The animals from each group at each specified time point are sacrificed and blood (approximately 0.5 mL/animal) and liver (approximately 100 mg) are collected. For Groups 1 through 9, blood (approximately 0.5 mL/animal) and liver (approximately 100 mg) are collected from 3 animals/time point/group at 24, 48, 96, 168, 336, 504, and 672 hours post-dosing. Group 10 (n=3) is a control group that is not dosed to provide baseline values for serum glycolate and mRNA HAO1 concentrations. The pharmacodynamic effect of the increase of serum glycolate and the silencing of HAO1 mRNA in the liver at various time points post-dosing is compared to the Group 10 control serum and liver samples.

TABLE 14

GO1 siRNA-GalNAc Analogues Mice Pharmacology Study Design

| Group | Number of Animals Male | Dose Route | Number of Doses/Animal | Target Dose Level (mg/kg) | Target Dose Concentration (mg/mL) | Target Dose Volume (mL/kg) |
|---|---|---|---|---|---|---|
| 1 | 21 | SC | 1 | 0.3 or 3 | 3 | 1.5 |
| 2 | 21 | SC | 1 | 0.3 or 3 | 3 | 1.5 |
| 3 | 21 | SC | 1 | 0.3 or 3 | 3 | 1.5 |
| 4 | 21 | SC | 1 | 0.3 or 3 | 3 | 1.5 |
| 5 | 21 | SC | 1 | 0.3 or 3 | 3 | 1.5 |
| 6 | 21 | SC | 1 | 0.3 or 3 | 3 | 1.5 |
| 7 | 21 | SC | 1 | 0.3 or 3 | 3 | 1.5 |
| 8 | 21 | SC | 1 | 0.3 or 3 | 3 | 1.5 |
| 9 | 21 | SC | 1 | 0.3 or 3 | 3 | 1.5 |
| 10[a] | 5 | NA | NA | NA | NA | NA |

Table Legend:

SC Subcutaneous

NA Not Applicable

[a]Group 10 animals are control animals and are not be dosed c Animals in Groups 1 to 9 are dosed on Day 1

Example 11: 5' Conjugation Using Click-Chemistry
(Option 1)
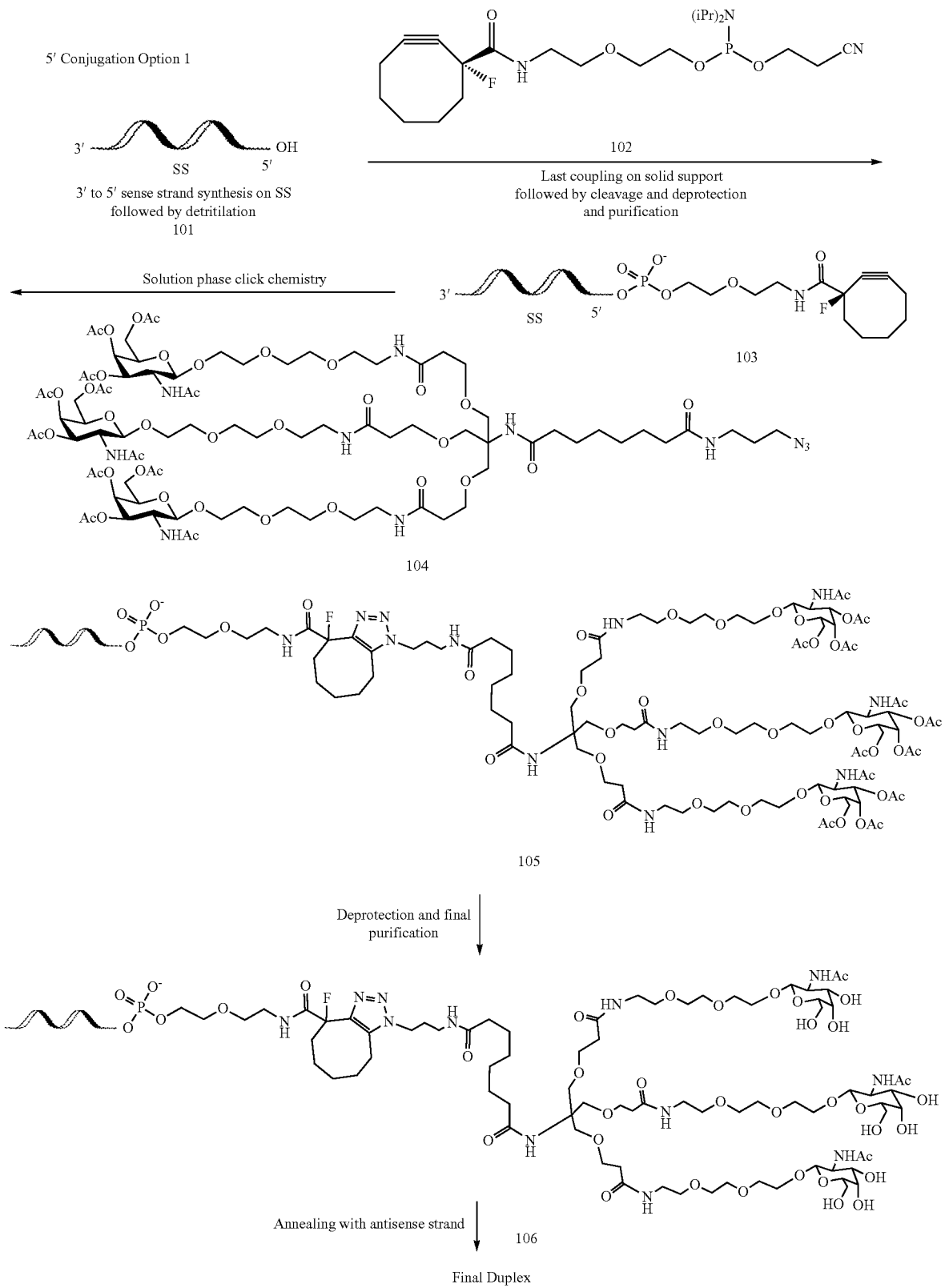
Final Duplex In this embodiment, the sense strand of the oligonucleotide 101 is synthesized on solid support and coupled with the commercially available octyne amidite 102 to give the required oligonucleotide with the click chemistry precursor on the solid support. This after standard cleavage and deprotection provides the pure oligo nucleotide 103. The azide 104 is dissolved in DMSO (150 μL/mg) and this solution is added to 10 OD of oligo 103 in 100 μL of water. The reaction mixture is then incubated at room temperature overnight. The conjugated oligo 105 is desalted on a Glen Gel-Pak™ to remove organics and the acetoxy protecting groups were removed by treating with methylamine followed by prep HPLC to give pure Oligo 106 which is annealed with an equimolar amount of sense strand to give the final duplex.

Example 12: 5' Conjugation (Option 2)

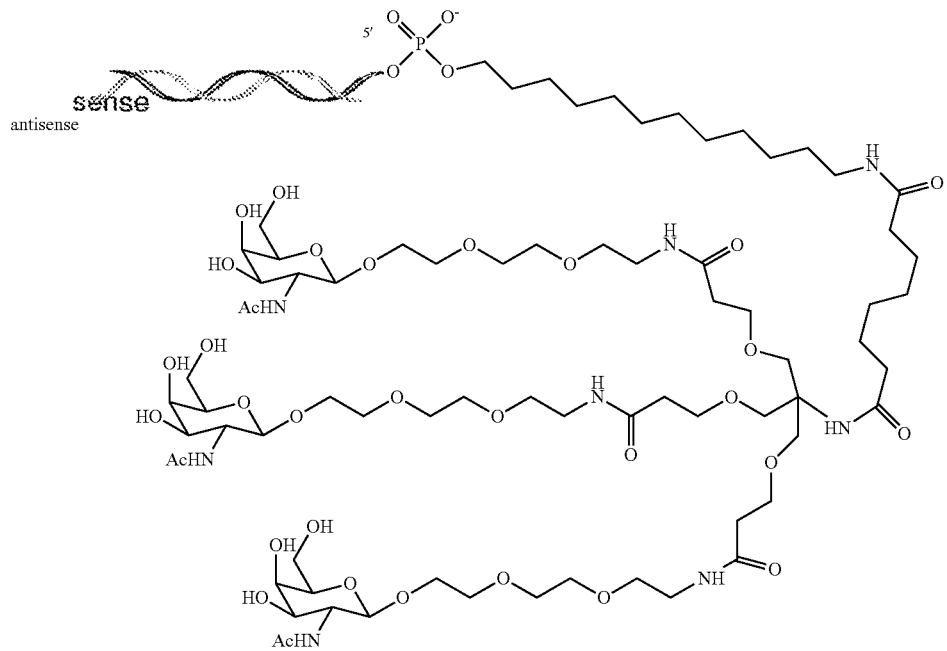 [SMILES: CC(=O)NC1C(OCCOCCOCCNC(=O)CCOCC(COCCC(=O)NCCOCCOCCOC2OC(CO)C(O)C(O)C2NC(C)=O)(COCCC(=O)NCCOCCOCCOC2OC(CO)C(O)C(O)C2NC(C)=O)NC(=O)CCCCCCC(=O)NCCCCCCCCCCCCOP(=O)([O-])O)OC(CO)C(O)C1O]

In this embodiment, the sense strand of the oligonucleotide 101 is synthesized on solid support and coupled with the commercially available amidite 108 to give the required oligonucleotide on the solid support. This after standard cleavage and deprotection provides the pure oligo nucleotide 109. The amine 109 is dissolved in water (15 μL/OD) and this solution is added to a solution of the acid 110 in DMSO (100 mL/mg) followed by 10 molar equivalents of EDC and 10 equivalents of HOBT and the reaction mixture is incubated at room temperature overnight. The conjugated oligo 111 is then desalted on a Glen Gel-Pak™ to remove organics and the acetoxy protecting groups were removed by treating with methylamine followed by prep HPLC to give pure Oligo 112 which is annealed with an equimolar amount of sense strand to give the final duplex.

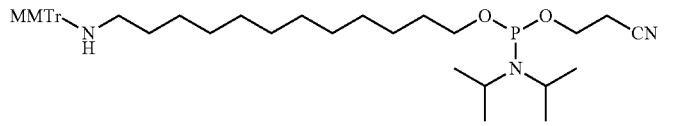

5' Conjugation Option 2

3' to 5' sense strand synthesis on SS
followed by detritilation
101

108

Last coupling on solid support
followed by cleavage and deprotection
and purification

127 128
-continued
Solution phase click chemistry
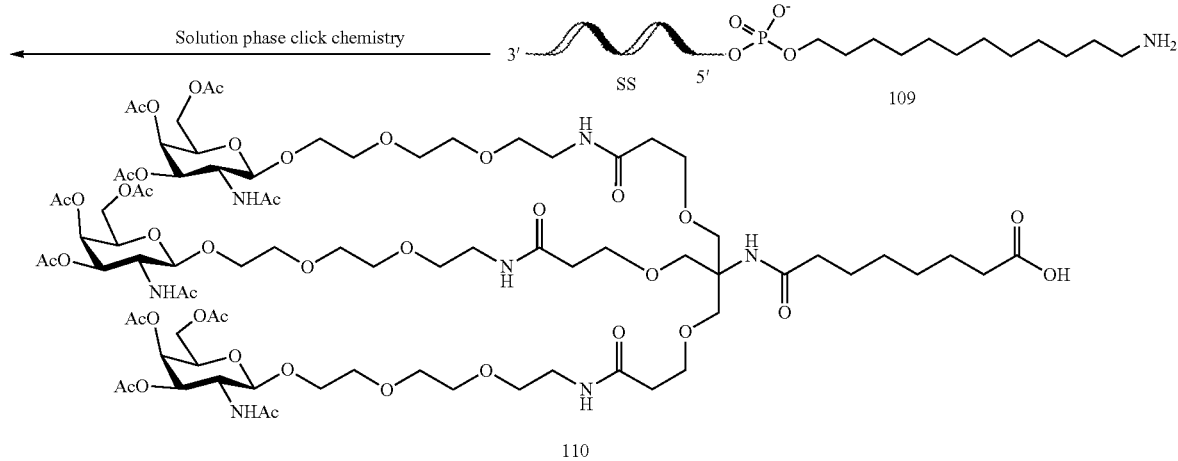
110
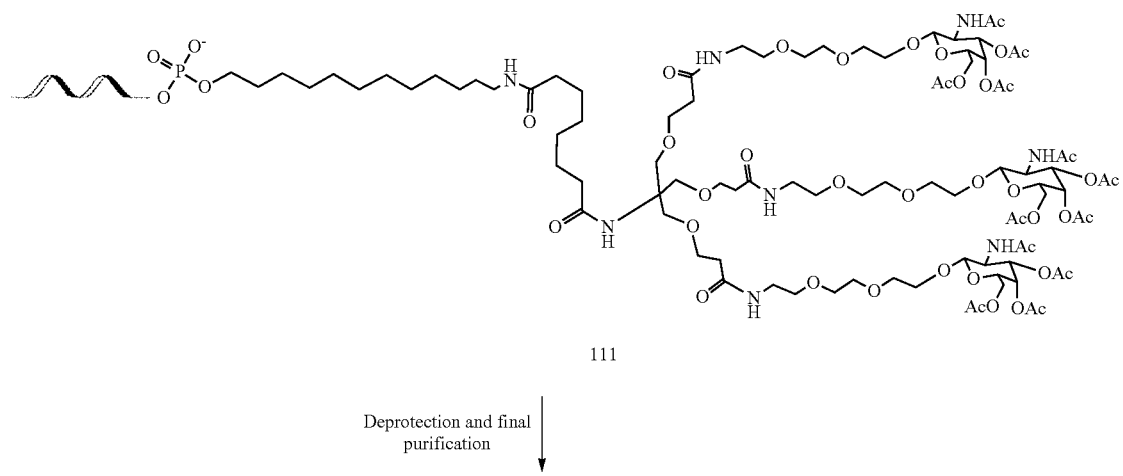
111
Deprotection and final purification
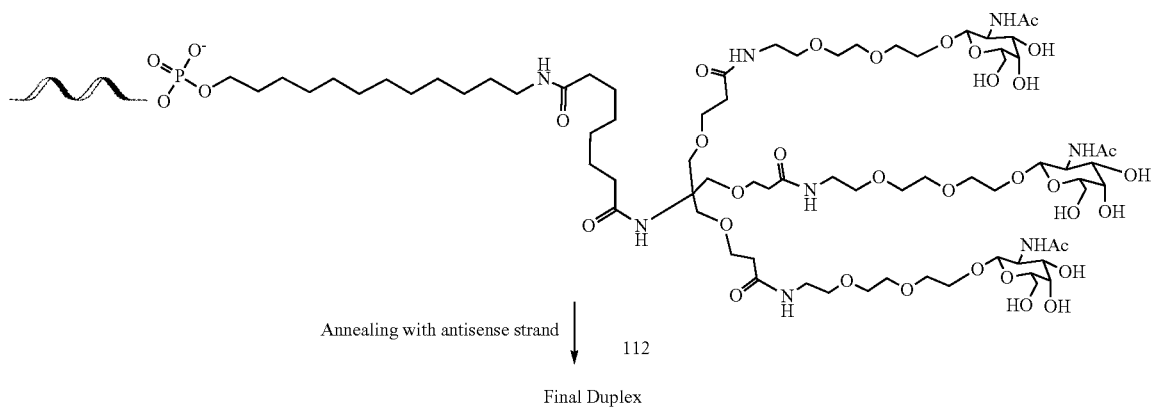
Annealing with antisense strand  112
Final Duplex Example 13: 5' Conjugation Using Click-Chemistry
(Option 1)
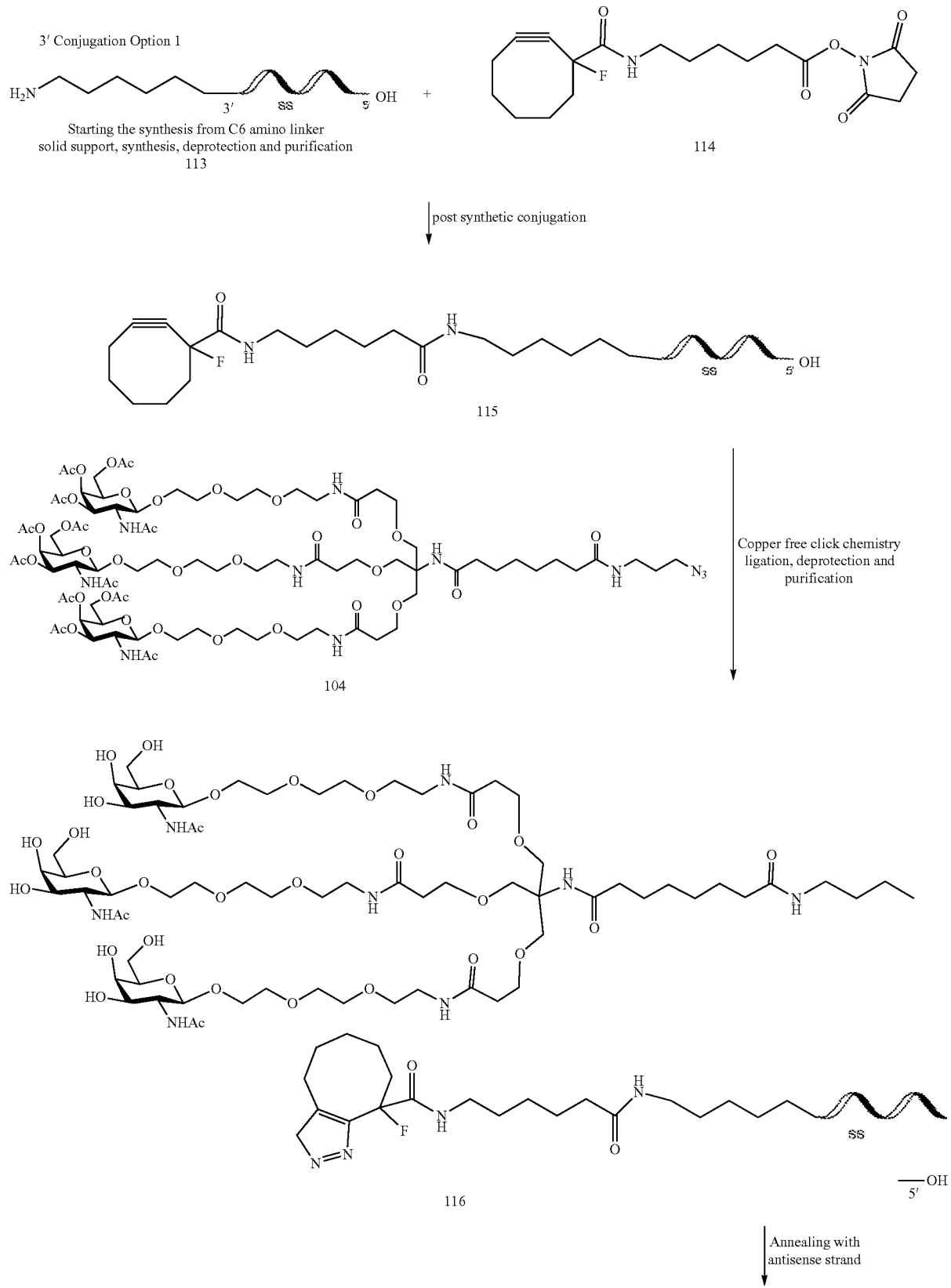

-continued

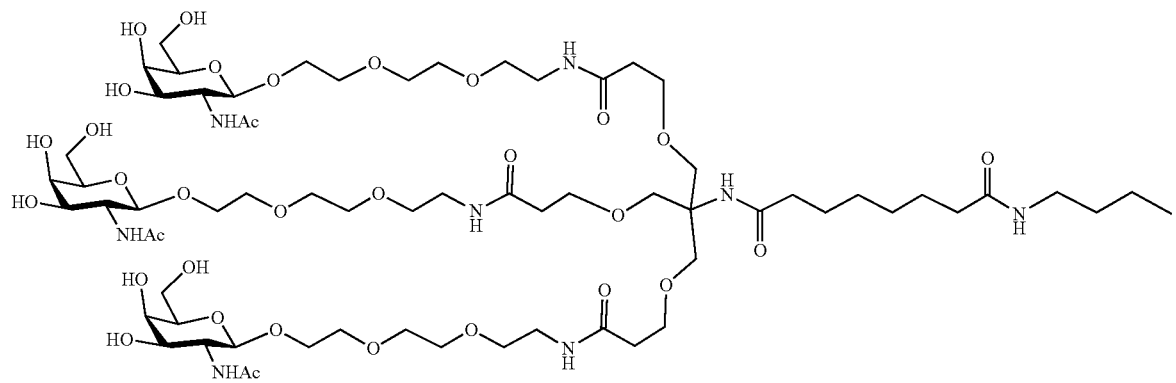

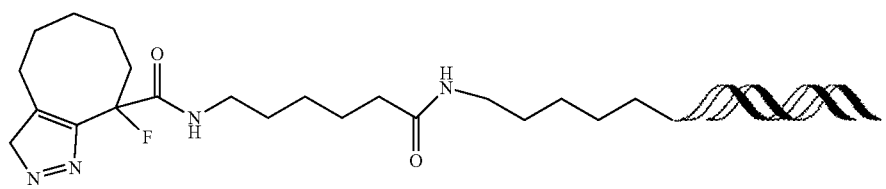

Final Duplex

For the synthesis of oligo construct 119 a similar approach is adapted where the triantennary GalNAc conjugate is loaded on to the solid support 118 (CPG) and the oligo synthesis is performed. After cleavage and deprotection and purification provides the pure oligo 119 which is annealed with antisense strand to give the required final duplex in a pure form. In another approach the 3' conjugate is also synthesized analogous to the synthesis of 116 starting from amino linked oligo 113 and post synthetically conjugating the GalNAc carboxylic acid to give the conjugated oligo 119.

Example 14: 3' Conjugation (Option 2)

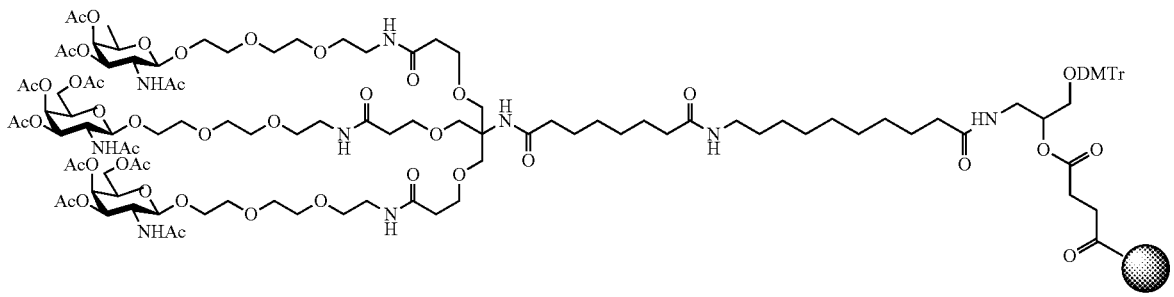

117

↓ Oligo synthesis

-continued

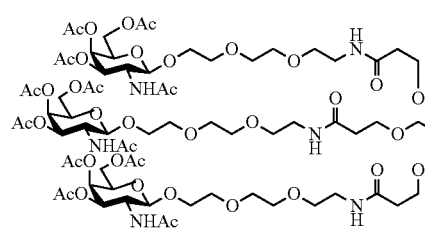 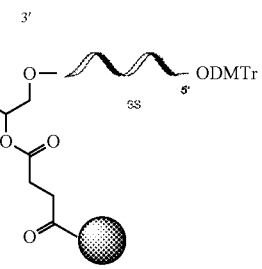

118

↓ Cleavage & Deprotection and purification

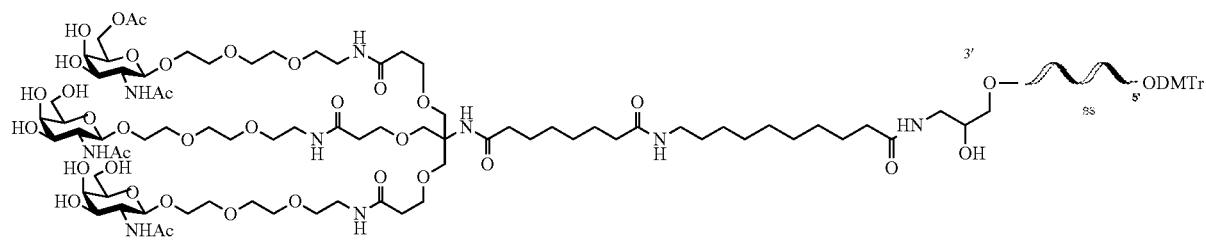

119

↓ Anealing with antisense strand

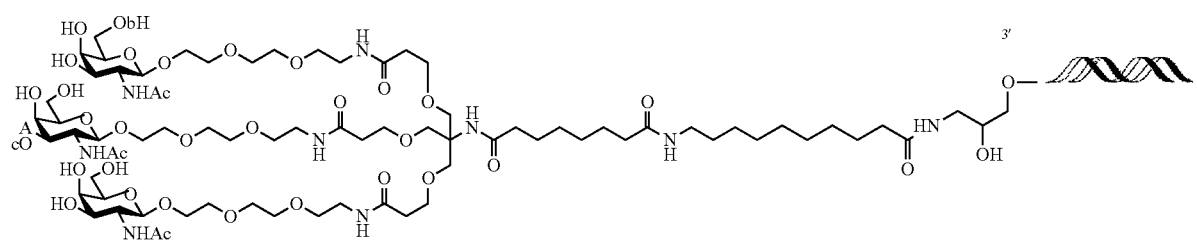

Fnal Duplex

For the synthesis of oligo construct 119 a similar approach is adapted where the tri-antennary GalNAc conjugate is loaded on to the solid support 118 (CPG) and the oligo synthesis is performed. After cleavage and deprotection and purification provided the pure oligo 119 which is annealed with antisense strand to give the required final duplex in a pure form. In another approach, the 3' conjugate is also synthesized analogous to the synthesis of 116 starting from amino linked oligo 113 and post synthetically conjugating the GalNAc carboxylic acid to give the conjugated oligo 119.

Example 15: Post-Synthetic Conjugation Approach

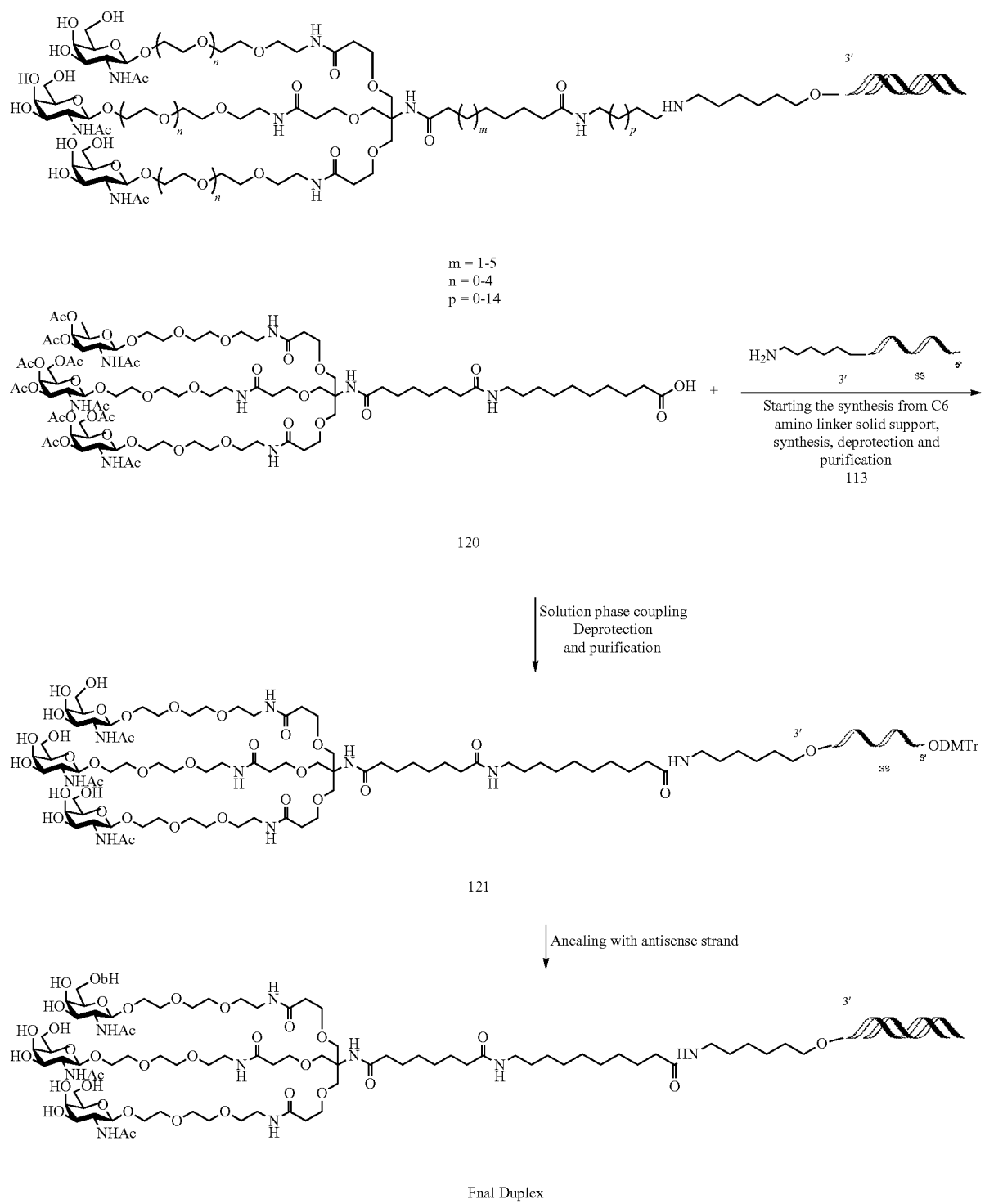

In this approach, the 3' conjugate is also synthesized analogous to the synthesis of 116 starting from amino linked oligo 113 and post synthetically conjugating the GalNAc carboxylic acid to give the conjugated oligo 121 which is annealed with antisense strand to give the required final duplex in a pure form.

The preceding Examples are not intended to be limiting. Those of skill in the art will, in light of the present disclosure, appreciate that many changes can be made in the specific materials and which are disclosed and still obtain a like or similar result without departing from the spirit and scope of the invention.

EXEMPLARY EMBODIMENTS

1. A modified RNAi agent comprising an RNA interference compound (RNAi compound) conjugated via a tether to an ASGP-R ligand, wherein the tether comprises:

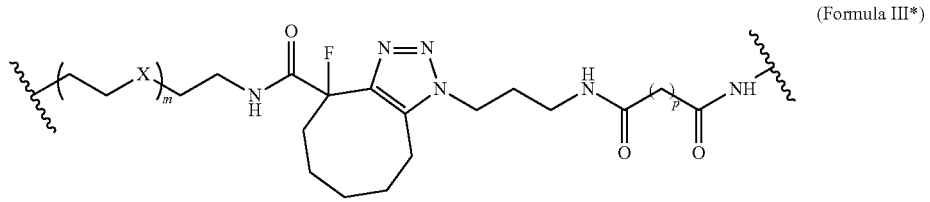

(Formula III*)

wherein m is chosen from 0, 1, 2, 3, 4, or 5, and p is chosen from 0, 1, 2, 3, 4, 5, 6, 7, 8, 9, 10, 11, 12, 13, or 14, independently of m; and X is chosen from O and $CH_2$.

2. The modified RNAi agent of statement 1, wherein m=1.
3. The modified RNAi agent of statement 1, wherein x is O.
4. The modified RNAi agent of statement 1, wherein p=6.
5. The modified RNAi agent of statement 1, wherein m=1, p=6, and x is O.
6. The modified RNAi agent of statement 1, wherein the ASGP-R ligand comprises a branched GalNAc.
7. The modified RNAi agent of statement 6, wherein the branched GalNAc is selected from the group consisting of:

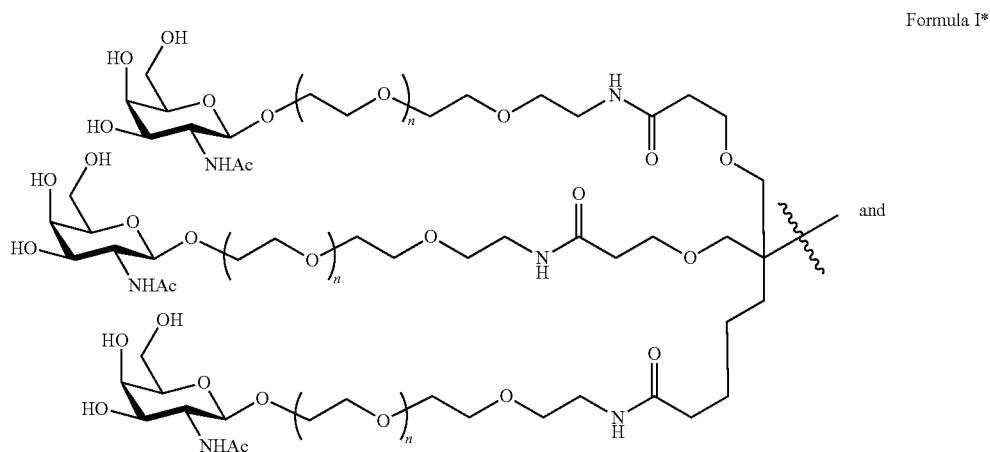

Formula I* and

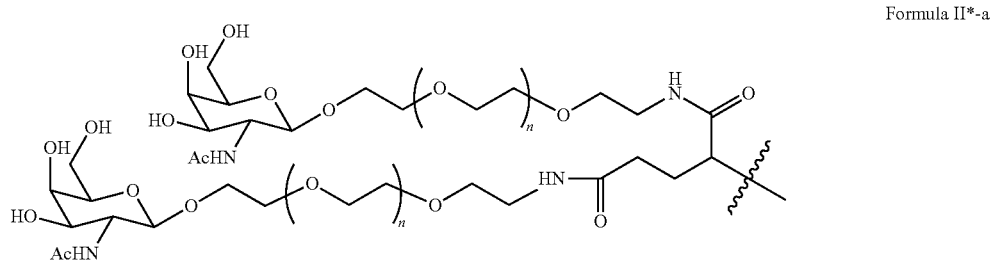

Formula II*-a wherein n is 0, 1, 2, 3, or 4.

8. The modified RNAi agent of statement 7, wherein n=1.
9. The modified RNAi agent of statement 6, wherein the branched GalNAc comprises Formula VI*

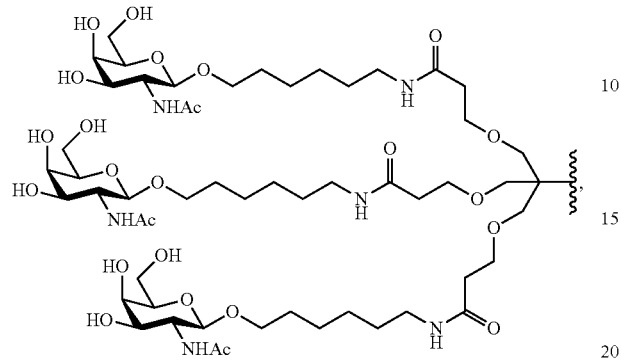

or a bi-antennary form thereof.

10. The modified RNAi agent of statement 6, wherein the branched GalNAc comprises or a bi-antennary form thereof.

Formula VII*

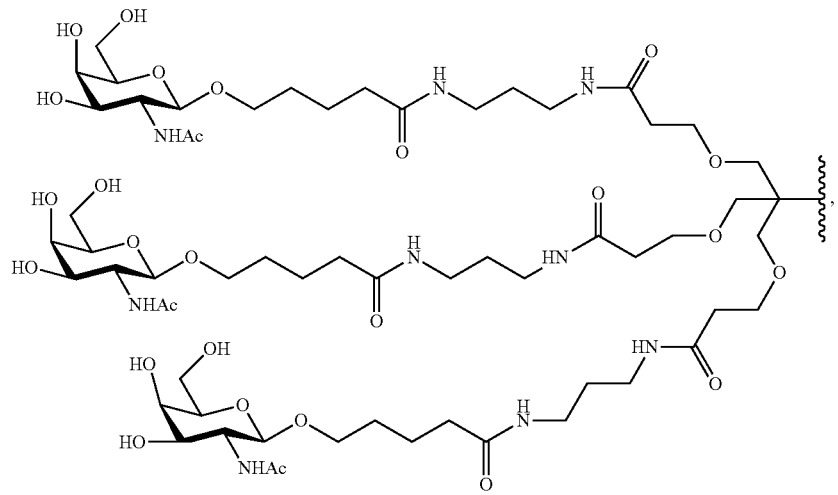

or a bi-antennary form thereof.

11. The modified RNAi agent of statement 1, wherein the tether is attached to the 5' end of the sense strand.

12. The modified RNAi agent of statement 11, wherein the tether is attached as shown in Formula IV*.

wherein Z is P or S.

13. The modified RNAi agent of statement 11, wherein the tether is attached to the 3' end of the sense strand.

14. The modified RNAi agent of statement 13, wherein the tether is attached as shown in Formulae V*-a or V*-b:

Formula V*-a

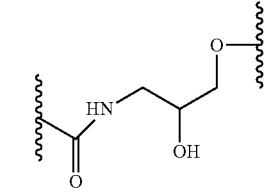

Formula V*-b

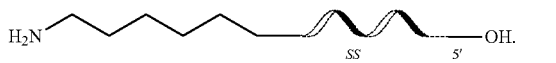

15. The modified RNAi agent of statement 1, as shown in FIG. 26A, 26B, 26C, or 26D.

16. The modified RNAi agent of statement 15, wherein the RNAi compound comprises modified riboses that are modified at the 2' position.

17. The modified RNAi agent of statement 16, wherein the modifications are chosen from 2'-O-methyl, 2'-deoxyfluoro, and 2'-deoxy.

18. The modified RNAi agent of statement 1, wherein RNAI compound contains one or more degradation protective moieties at any or all ends that are not conjugated to the ASGP-R ligand.

19. The modified RNAi agent of statement 18, wherein the degradation protective moiety is chosen alone or as any combination from a group consisting of 1-4 phosphorothioate linkages, 1-4 deoxynucleotides, and 1-4 inverted abasic nucleotides.

20. The modified RNAi agent of statement 19, wherein the degradation protective moieties are chosen from the configuration present in one of the following constructs 6.1, 6.2, 6.3, 7.1, 7.2, 7.3, 8.1, 8.2, 8.3, 9.1, 9.2, and 9.3.

21. A modified RNAi agent comprising an RNA interference compound (RNAi compound) conjugated via a tether to an ASGP-R ligand, wherein the tether comprises:

(Formula III*-2)

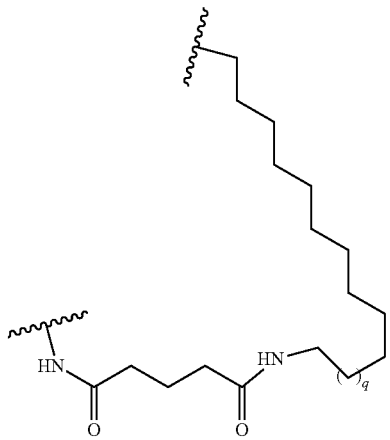

wherein q is chosen from 1, 2, 3, 4, 5, 6, 7, or 8.

22. The modified RNAi agent of statement 21, wherein q=1.

23. The modified RNAi agent of statement 21, wherein the ASGP-R ligand comprises a branched GalNAc.

24. The modified RNAi agent of statement 23, wherein the branched GalNAc is selected from the group consisting of:

Formula I*

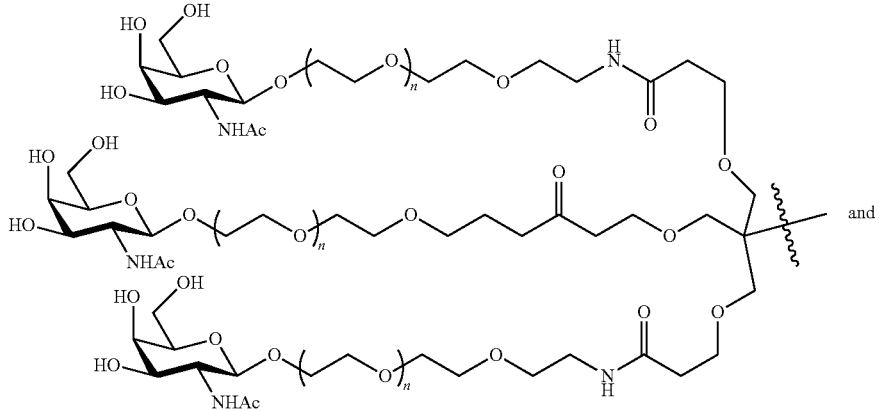

and

Formula II*-a

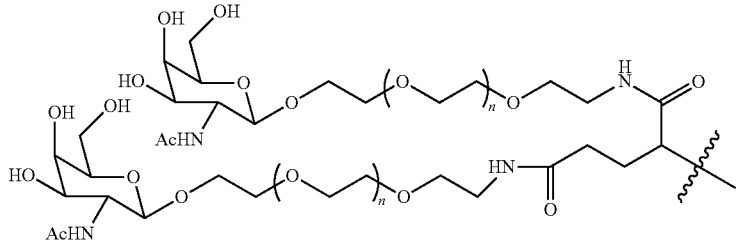

wherein n is 0, 1, 2, 3, or 4.

25. The modified RNAi agent of statement 24, wherein n=1.

26. The modified RNAi agent of statement 23, wherein the branched GalNAc comprises Formula VI*

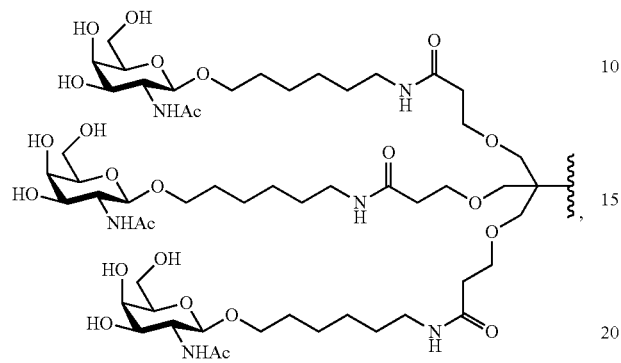

Formula VI* or a bi-antennary form thereof.

27. The modified RNAi agent of statement 23, wherein the branched GalNAc comprises or a bi-antennary form thereof.

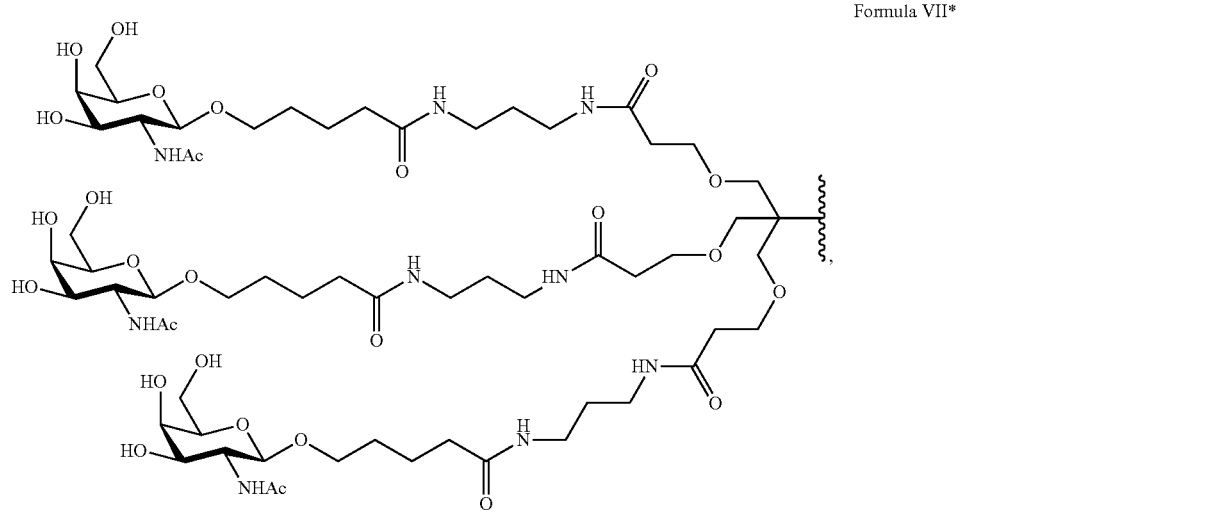

Formula VII* or a bi-antennary form thereof.

28. The modified RNAi agent of statement 21, wherein the tether is attached to the 5' end of the sense strand.

29. The modified RNAi agent of statement 28, wherein the tether is attached as shown in Formula IV*.

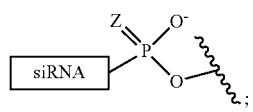

wherein Z is P or S.

30. The modified RNAi agent of statement 28, wherein the tether is attached to the 3' end of the sense strand.

31. The modified RNAi agent of statement 30, wherein the tether is attached as shown in Formulae V*-a or V*-b:

Formula V*-a

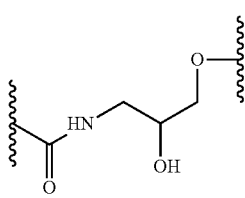

Formula V*-b

32. The modified RNAi agent of statement 31, as shown in FIG. 27A, 27B, 27C, or 27D.

33. The modified RNAi agent of statement 21, wherein the RNAi compound comprises modified riboses that are modified at the 2' position.

34. The modified RNAi agent of statement 33, wherein the modifications are chosen from 2'-O-methyl, 2'deoxy-fluoro, and 2'-deoxy.

35. The modified RNAi agent of statement 21, wherein siRNA contains one or more degradation protective moieties at any or all ends that are not conjugated to the ASGP-R ligand.

36. The modified RNAi agent of statement 35, wherein the degradation protective moiety is chosen alone or as any combination from a group consisting of 1-4 phosphorothioate linkages, 1-4 deoxynucleotides, and 1-4 inverted abasic nucleotides.

37. The modified RNAi agent of statement 36, wherein the degradation protective moieties are chosen from the configuration present in one of the following constructs 6.1, 6.2, 6.3, 7.1, 7.2, 7.3, 8.1, 8.2, 8.3, 9.1, 9.2, and 9.3.

39. A method of making the RNAi agent of statements 1 or 2, said method being shown in Examples 11-15.

40. A method of preventing, alleviating, or treating a disease in a subject, the method comprising administering, to the subject, the RNAi agent of statements 1 or 2 in a therapeutically amount effective to prevent, alleviate or treat the disease, thereby preventing, alleviating, or treating a disease.

41. The method of statement 40, wherein the subject is human.

TABLE A

Summary of Sequences

| Seq ID | Duplex ID | SSRN ID | Sense Sequence | Antisense Sequence | Clean Sequence |
|---|---|---|---|---|---|
| 1. | | | 5' GalNAc-Gm-Am-Cm-Um-Um-Cf-Am-Uf-Cf-Cf-Um-Gm-Gm-Am-Am-Um-AmsUmsAm-ia-ia 3' | | gacuuucauccuggaaauaua |
| 2. | | | | 3' AmsCms-Cm-Um-Gm-Am-Am-Af-Gm-Uf-Am-Gm-Gm-Am-Cf-Cf-Um-Uf-Um-Am-UmsAfsUm 5' | accugaaguaggaccuuuauau |
| 3. | | | 5' GalNAc-Am-Am-Gf-Cm-Af-Am-Gf-Am-Uf-Af-Uf-Um-Uf-Um-Af-Um-Af-AmsUmsAm-ia-ia 3' | | aagcaagauauuuuauauaua |
| 4. | | | | 3' Td-Td-UmsUmsUm-Um-Cm-Gf-Um-Uf-Cm-Uf-Am-Um-Am-Af-Am-Af-Am-Um-Af-Um-UfsAfsUm 5' | uuuucguucuauaaaauauau |
| 5. | | | 5'GalNAc-Um-Gm-Gm-Am-Um-Uf-Um-Cf-Af-Uf-Gm-Um-Am-Cm-Cm-Am-AmsGmsAm-ia-ia 3' | | ugggauuucauguaaccaaga |
| 6. | | | | 3' CmsUmsAm-Cm-Um-Cm-Um-Af-Am-Af-Gm-Um-Am-Cm-Af-Cf-Um-Gf-Gm-Um-UmsCfsUm 5' | cuacccuaaaguacauugguucu |
| 7. | | | 5' ia-ia-GmsAmsCm-Um-Um-Um-Cf-Am-Uf-Cf-Cf-Um-Gm-Gm-Am-Am-Um-Am-GalNAc 3' | | gacuuucauccuggaaauaua |
| 8. | | | | 3' AmsCmsCm-Cm-Um-Gm-Am-Am-Af-Gm-Uf-Am-Gm-Gm-Am-Cf-Cf-Um-Uf-Um-Am-UmsAfsUm 5' | accugaaguaggaccuuuauau |
| 9. | | | 5' ia-ia-AmsAmsGf-Cm-Af-Am-Gf-Am-Uf-Af-Uf-Um-Uf-Um-Af-Um-Af-Am-Um-Am-GalNAc 3' | | aagcaagauauuuuauauaua |
| 10. | | | | 3'Td-Td-UmsUmsUm-Um-Cm-Gf-Um-Uf-Cm-Uf-Am-Um-Am-Af-Am-Af-Am-Um-Af-Um-UfsAfsUm 5' | uuuucguucuauaaaauauau |
| 11. | | | 5' ia-ia-UmsGmsGm-Am-Um-Uf-Um-Cf-Af- | | ugggauuucauguaaccaaga |

TABLE A-continued

Summary of Sequences

| | | |
|---|---|---|
| 12. | Uf-Gm-Um-Am-Am-Cm-Am-Am-Gm-Am-GalNAc 3' | |
| 13. | 5'GalNAc-Gf-Am-Cf-Um-Uf-Um-Cf-Am-Uf-Cm-Cf-Um-Gf-Am-Af-Am-Af-Um-AfsUmsAf 3' | 3' CmsUmsAm-Cm-Cm-Cm-Um-Af-Gm-Af-Gm-Um-Am-Cm-Af-Um-Um-Gf-Gm-Um-UmsCfsUm 5' | cuacccuaaaguacauugguucu |
| 14. | | 3' AmsCfsCm-Uf-Gm-Af-Am-Af-Gm-Uf-Cm-Uf-Am-Af-Cm-Cf-Um-Uf-Um-Af-UmsAfsUm 5' | gacuucauccuggaaauaua |
| 15. | 5' GalNAc-Af-Am-Gf-Cm-Af-Am-Gf-Am-Uf-Am-Uf-Um-Uf-Um-Uf-Am-Uf-Am-AfsUmsAf 3' | | accugaaaguaggaccuuuauau |
| 16. | | 3' Td-Td-UmsUfsUm-Uf-Cm-Gf-Um-Uf-Cm-Uf-Am-Uf-Am-Af-Am-Af-Am-Uf-Am-UmsAfsUm 5' | aagcaagauauuuuauaaua |
| 17. | 5' GalNAc-Uf-Gm-Gf-Gm-Af-Um-Uf-Um-Cf-Am-Uf-Gm-Am-Cf-Am-Cf-Am-Af-AfsGmsAf 3' | | uuuucguucuauaaaauauau |
| 18. | | 3' CmsUfsAm-Cf-Cm-Cf-Um-Gf-Am-Af-Gm-Uf-Am-Cf-Am-Uf-Um-Gf-Gm-Uf-UmsCfsUm 5' | ugggauuucauguaaccaaga |
| 19. | 5' GfsAmsCf-Um-Uf-Um-Cf-Am-Uf-Cm-Cf-Um-Gf-Gm-Af-Am-Af-Um-Af-Um-Af-GalNAc 3' | | cuacccuaaaguacauugguucu |
| 20. | | 3' AmsCfsCm-Uf-Gm-Af-Am-Af-Gm-Uf-Cm-Uf-Am-Af-Cm-Cf-Um-Uf-Um-Af-UmsAfsUm 5' | gacuucauccuggaaauaua |
| 21. | 5' AfsAmsGf-Cm-Af-Am-Gf-Am-Uf-Am-Uf-Um-Uf-Um-Am-Uf-Am-Af-GalNAc 3' | | accugaaaguaggaccuuuauau |
| 22. | | 3' Td-Td-UmsUfsUm-Uf-Cm-Gf-Um-Uf-Cm-Uf-Am-Af-Am-Af-Am-Uf-UmsAfsUm 5' | aagcaagauauuuuauaaua |
| 23. | 5' UfsGmsGf-Gm-Af-Um-Uf-Um-Cf-Am-Uf- | | uuuucguucuauaaaauauau |

(continued)

ugggauuucauguaaccaaga

TABLE A-continued

Summary of Sequences

| # | ID | Sequence 1 | Sequence 2 |
|---|---|---|---|
| 24. | | Gm-Uf-Am-Af-Cm-Cf-Am-Af-Gm-Af-GalNAc 3' | 3' CmsUfsAm-Cf-Cm-Cf-Um-Af-Am-Af-Gm-Uf-Am-Cf-Am-Uf-Um-Gf-Gm-Uf-UmsCfsUm 5' | cuacccuaaaguacauuguucu |
| 25. | ETX005 | (invabasic)(invabasic)gsascuuuCfaUfCfCfuggaaauasusa(NHC6)(MFCO)(ET-GalNAc-T1N3) | | gacuuucauccuggaaauaua |
| 26. | ETX005 | | usAfsuauUfuCfCfaggaUfgAfaagucscsa | uauauuuccaggaugaaagucca |
| 27. | ETX001 | (ET-GalNAc-T1N3)(MFCO)(NH-DEG)gacuuuCfuCfCfCfuggaaauasusa(invabasic)(invabasic) | | gacuuucauccuggaaauaua |
| 28. | ETX001 | | usAfsuauUfuCfCfaggaUfgAfaagucscsa | uauauuuccaggaugaaagucca |
| 29. | ETX014 | (invabasic)(invabasic)asasGfcAfGfaUfAfUfuUfuuAfuAfaua(NHC6)(MFCO)(ET-GalNAc-T1N3) | | aagcaagauauuuuauaaua |
| 30. | ETX014 | | usAfsUfuAfuaAfaAfaAfauaUfcUfuGfcuususudTdT | uauuauaaaauaucuugcuuuu |
| 31. | ETX010 | (ET-GalNAc-T1N3)(MFCO)(NH-DEG)aaGfcAfaGfaUfAfUfuUfuuAfuAfasusa(invabasic)(invabasic) | | aagcaagauauuuuauaaua |
| 32. | ETX010 | | usAfsUfuAfuAfaAfaAfauaUfcUfuGfcuususudTdT | uauuauaaaauaucuugcuuuu |
| 33. | ETX019 | (ET-GalNAc-T1N3)(MFCO)(NH-DEG)ugggauUfuCfAfUfgua accasgsa(invabasic) | | ugggauuucauguaaccaaga |
| 34. | ETX019 | | usCfsuugGfuuAfcaugAfaAfucccasusc | ucuugguuacaugaaucccauc |
| 35. | ETX023 | (invabasic)(invabasic)usgsggauUfuCfAfUfguaaccaaga(NHC6)(MFCO)(ET-GalNAc-T1N3) | | ugggauuucauguaaccaaga |

TABLE A-continued

Summary of Sequences

| | | | |
|---|---|---|---|
| 36. | ETX023 | | usCfsuugGfuuAfcaugAfaAfucccasusc | ucuuguuacaugaaauccauc |
| 37. | XD-00914 | cuuAcGcuGAGuAcuucGAdTsdT | | cuuacgcugaguacuucga |
| 38. | XD-00914 | | UCGAAGuACUcAGCGuAAGdTsdT | ucgaaguacucagcguaag |
| 39. | XD-03999 | AGAuAuGcAcAcAcGGAdTsdT | | agauaugcacacacgga |
| 40. | XD-03999 | | UCCGUGUGUGCAuAUCUdTsdT | uccgugugugcauaucu |
| 41. | XD-15421 | uscsUfcGfuGfgCfcUfuAfaUfgAfaAf(invdT) | | ucucguggccuuaaugaa |
| 42. | XD-15421 | | UfsUfsuCfaUfuAfaGfgCfcAfcGfaGfasusu | uuucauuaaggccacgagauu |
| 43. | X91382 | (NH2-DEG)gacuuuCfaUfCfCfuggaauasusa(invabasic) | | gacuuucauccuggaauaua |
| 44. | X91383 | (NH2-DEG)aaGfcAfaGfaUfAfUfuUfuuAfuAfasusa(invabasic) | | aagcaagauauuuuauaaua |
| 45. | X91384 | (NH2-DEG)ugggauUfuCfAfUfguaaccaasgsa(invabasic) | | ugggauuucauguaaccaaga |
| 46. | X91403 | (NH2C12)gacuuuCfaUfCfCfuggaaauasusa(invabasic) | | gacuuucauccuggaauaua |
| 47. | X91404 | (NH2C12)aaGfcAfaGfaUfAfUfuUfuuAfuAfasusa(invabasic) | | aagcaagauauuuuauaaua |
| 48. | X91405 | (NH2C12)ugggauUfuCfAfUfguaaccaasgsa(invabasic) | | ugggauuucauguaaccaaga |
| 49. | X91415 | (invabasic)(invabasic)gsascuuucfaUfCfCfuggaaauasusa(NH2C6) | | gacuuucauccuggaauaua |

TABLE A-continued

Summary of Sequences

| | | | |
|---|---|---|---|
| 50. | X91416 | (invabasic)(invabasic)asasGf cAfaGfaUfAfUfuUfuuAfuA faua(NH2C6) | aagcaagauauuuuauaaua |
| 51. | X91417 | (invabasic)(invabasic)usgsg gauUfuCfAfUfguaaccaaga (NH2C6) | ugggauuucauguaaccaaga |
| 52. | X91379 | gsascuuuCfaUfCfcfuggaaau aua(GalNAc) | gacuuucauccuggaaauaua |
| 53. | X91380 | asasGfcAfaGfaUfAfUfuUfu uAfuAfaua(GalNAc) | aagcaagauauuuuauaaua |
| 54. | X91446 | usgsggauUfuCfAfUfguaacca aga(GalNAc) | ugggauuucauguaaccaaga |
| 55. | X38483 | usAfsuauUfuCfCfaggaUfgA faagucscsa | uauauuuccaggaugaagucca |
| 56. | X91381 | usAfUfuAfuaAfAfauaUfc UfuGfcuususudTdT | uauuauaaauaucuugcuuuu |
| 57. | X38104 | usCfsuugGfuuAfcaugAfaAf ucccasusc | ucuugguuacaugaauccauc |
| 58. | X91388 | (MFCO)(NH-DEG)gacuuuCfaUfCfCfugg aaauasusa(invabasic) (invabasic) | gacuuucauccuggaaauaua |
| 59. | X91389 | (MFCO)(NH-DEG)aaGfcAfaGfaUfAfUfu UfuuAfuAfasusa(invabasic) (invabasic) | aagcaagauauuuuauaaua |
| 60. | X91390 | (MFCO)(NH-DEG)ugggauUfuCfAfUfgua accaasgsa(invabasic) (invabasic) | ugggauuucauguaaccaaga |
| 61. | X91421 | (invabasic)(invabasic)gsascu uuCfaUfCfCfuggaaauasusa (NHC6)(MFCO) | gacuuucauccuggaaauaua |
| 62. | X91422 | (invabasic)(invabasic)asasGf cAfaGfaUfAfUfuUfuuAfuA faua(NHC6)(MFCO) | aagcaagauauuuuauaaua |
| 63. | X91423 | (invabasic)(invabasic)usgsg | ugggauuucauguaaccaaga |

TABLE A-continued

Summary of Sequences

| | | | |
|---|---|---|---|
| 64. | | gauUfuCfAfUfguaaccaaga(NHC6)(MFCO) | |
| 65. | X91394 | (GalNAc-T1)(MFCO)(NH-DEG)gacuuuCfaUfCfCfuggaaauasusa(invabasic) | gacuuucauccuggaaauaua |
| 66. | X91395 | (GalNAc-T1)(MFCO)(NH-DEG)aaGfcAfaGfaUfAfUfuUfuuAfuAfasusa(invabasic) | aagcaagauauuuuauaaua |
| 67. | X91396 | (GalNAc-T1)(MFCO)(NH-DEG)ugggauUfuCfAfUfguaaccasgsa(invabasic) | ugggauuucauguaaccaaga |
| 68. | X91427 | (invabasic)(invabasic)gsascuuuCfaUfCfCfuggaaauasusa(NHC6)(MFCO)(GalNAc-T1) | gacuuucauccuggaaauaua |
| 69. | X91428 | (invabasic)(invabasic)asasGfcAfaGfaUfAfUfuUfuuAfuAfaua(NHC6)(MFCO)(GalNAc-T1) | aagcaagauauuuuauaaua |
| 70. | X91429 | (invabasic)(invabasic)usgsggauUfuCfAfUfguaaccaaga(NHC6)(MFCO)(GalNAc-T1) | ugggauuucauguaaccaaga |
| 71. | ETX001 X91394 | (GalNAc-T1)(MFCO)(NHDEG)gacuuCfUfCfCfuggaaauasusa(invabasic)(invabasic) | gacuuucauccuggaaauaua |
| 72. | X38483 | usAfsuauUfuCfCfaggaUfgAfaagucscsa | uauauuuccaggaugaagucca |
| 73. | ETX005 X91427 | (invabasic)(invabasic)gsascuuuCfaUfCfCfuggaaauasusa(NHC6)(MFCO)(GalNAc-T1) | gacuuucauccuggaaauaua |
| 74. | X38483 | usAfsuauUfuCfCfaggaUfgAfaagucscsa | uauauuuccaggaugaagucca |
| | ETX010 X91395 | (GalNAc-T1)(MFCO)(NH-DEG)aaGfcAfaGfaUfAfUfuUfuuAfuAfasusa(invabasic) | aagcaagauauuuuauaaua |

TABLE A-continued

| Summary of Sequences | | | | | |
|---|---|---|---|---|---|
| 75. | | X91381 | usAfsUfuAfuaAfaAfauaUfc UfuGfcuususudTdT | | uauuauaaaaauaucuugcuuuu |
| 76. | ETX014 | X91428 | (invabasic)(invabasic)asasGf cAfaGfaUfAfUfuUfuuAfuA faua(NHC6)(MFCO) (GalNAc-T1) | | aagcaagauauuuuuauaaua |
| 77. | | X91381 | usAfsUfuAfuaAfaAfauaUfc UfuGfcuususudTdT | | uauuauaaaaauaucuugcuuuu |
| 78. | ETX019 | X91396 | (GalNAc-T1)(MFCO)(NH-DEG)ugggauUfuCfAfUfgua accaasgsa(invabasic) (invabasic) | | ugggauuucauguaaccaaga |
| 79. | | X38104 | usCfsuugGfuuAfcaugAfaAf ucccasusc | | ucuugguuacaugaaaucccauc |
| 80. | ETX023 | X91429 | (invabasic)(invabasic)usgsg gauUfuCfAfUfguaaccaaga (NHC6)(MFCO)(GalNAc-T1) | | ugggauuucauguaaccaaga |
| 81. | | X38104 | usCfsuugGfuuAfcaugAfaAf ucccasusc | | ucuugguuacaugaaaucccauc |
| 82. | ETX006 | | (invabasic)(invabasic)gsascu uuCfaUfCfCfuggaaauasusa (NHC6)(ET-GalNAc-T2CO) | | gacuuucauccuggaaauaua |
| 83. | ETX006 | | | usAfsuauUfuCfCfaggaUfgAfaagucscsa | uauauuuccaggaugaaagucca |
| 84. | ETX002 | | (ET-GalNAc-T2CO)(NH2C12)gacuuuCfa UfCfCfuggaaauasusa (invabasic)(invabasic) | | gacuuucauccuggaaauaua |
| 85. | ETX002 | | | usAfsuauUfuCfCfaggaUfgAfaagucscsa | uauauuuccaggaugaaagucca |
| 86. | ETX004 | | (ET-GalNAc-T2CO)(NH2C12)GfaCfuUf uCfaUfcCfuGfgAfaAfuAfsu sAf | | gacuuucauccuggaaauaua |
| 87. | ETX004 | | | usAfsuAfuUfuCfcAfgGfaUfgAfaAfgUf csCfsa | uauauuuccaggaugaaagucca |
| 88. | ETX008 | | GfsasCfuUfuCfaUfcCfuGfg AfaAfuAfuAf(NHC6)(ET-GalNAc-T2CO) | | gacuuucauccuggaaauaua |
| 89. | ETX008 | | | usAfsuAfuUfuCfcAfgGfaUfgAfaAfgUf csCfsa | uauauuuccaggaugaaagucca |

TABLE A-continued

| Summary of Sequences | | | | |
|---|---|---|---|---|
| 90. | ECX008 (lower purity) | GfsasCfuUfuCfaUfcCfuGfg AfaAfuAfuAf(NHC6)(ET-GalNAc-T2CO) | | gacuuucauccuggaaauaua |
| 91. | ECX008 (lower purity) | | usAfsuAfuUfuCfcAfgGfaUfgAfaAfgUf csCfsa | uauauuuccaggaugaaagucca |
| 92. | ETX011 | (ET-GalNAc-T2CO)(NH2C12)aaGfcAfa GfaUfAfUfuUfuuAfuAfasus a(invabasic)(invabasic) | | aagcaagauauuuuuauaaua |
| 93. | ETX011 | | usAfsUfuAfuaAfaAfauaUfcUfuGfcuus usudTdT | uauuauaaaaauaucuugcuuuu |
| 94. | ETX015 | (invabasic)(invabasic)asasGf cAfaGfaUfAfUfuUfuuAfuA faua(NHC6)(ET-GalNAc-T2CO) | | aagcaagauauuuuuauaaua |
| 95. | ETX015 | | usAfsUfuAfuaAfaAfauaUfcUfuGfcuus usudTdT | uauuauaaaaauaucuugcuuuu |
| 96. | ETX013 | (ET-GalNAc-T2CO)(NH2C12)AfaGfcAfa GfaUfaUfuUfuUfaUfaAfsus Af | | aagcaagauauuuuuauaaua |
| 97. | ETX013 | | usAfsuUfaUfaAfaAfaUfaUfcUfuGfcUf usUfsudTdT | uauuauaaaaauaucuugcuuuu |
| 98. | ETX017 | AfsasGfcAfaGfaUfaUfuUfu UfaUfaAfuAf(NHC6)(ET-GalNAc-T2CO) | | aagcaagauauuuuuauaaua |
| 99. | ETX017 | | usAfsuUfaUfaAfaAfaUfaUfcUfuGfcUf usUfsudTdT | uauuauaaaaauaucuugcuuuu |
| 100. | ETX020 | (ET-GalNAc-T2CO)(NH2C12)ugggauUfu CfAfUfguaaccaasgsa (invabasic)(invabasic) | | ugggauuucauguaaccaaga |
| 101. | ETX020 | | usCfsuugGfuuAfcaugAfaAfucccasusc | ucuugguuacaugaaaucccauc |
| 102. | ETX022 | (ET-GalNAc-T2CO)(NH2C12)UfgGfgAf uUfuCfaUfgUfaAfcCfaAfsg sAf | | ugggauuucauguaaccaaga |

TABLE A-continued

| | | Summary of Sequences | |
|---|---|---|---|
| 103. | ETX022 | usCfsuUfgGfuUfcCfaUfgAfaAfuCfccCfasUfsc | ucuugguuacaugaaaucccauc |
| 104. | ETX024

TABLE A-continued

Summary of Sequences

| | | | |
|---|---|---|---|
| 118. | | DEG)GfaCfuUfuCfaUfcCfu GfgAfaAfuAfsusAf | |
| 119. | X91386 | (NH2- DEG)AfaGfcAfaGfaUfu UfuUfaUfaAfsusAf | aagcagauauuuuauaaua |
| 120. | X91387 | (NH2- DEG)UfgGfgAfuUfuCfaUfg UfaAfcCfaAfsgsAf | ugggauuucauguaaccaaga |
| 121. | X91403 | (NH2C12)gacuuuCfaUfCfC fuggaaauasusa(invabasic) (invabasic) | gacuuucauccuggaaauaua |
| 122. | X91404 | (NH2C12)aaGfcAfaGfaUfA fUfuUfuuAfuAfasusa (invabasic)(invabasic) | aagcagauauuuuauaaua |
| 123. | X91405 | (NH2C12)ugggauUfuCfAfU fguaaccaasgsa(invabasic) (invabasic) | ugggauuucauguaaccaaga |
| 124. | X91406 | (NH2C12)GfaCfuUfuCfauf cCfuGfgAfaAfuAfsusAf | gacuuucauccuggaaauaua |
| 125. | X91407 | (NH2C12)AfaGfcAfaGfaUf aUfuUfuUfaUfaAfsusAf | aagcagauauuuuauaaua |
| 126. | X91408 | (NH2C12)UfgGfgAfuUfuCf aUfgUfaAfcCfaAfsgsAf | ugggauuucauguaaccaaga |
| 127. | X91415 | (invabasic)(invabasic)gsascu uuCfaUfcCfcfuggaaauasusa (NH2C6) | gacuuucauccuggaaauaua |
| 128. | X91416 | (invabasic)(invabasic)asasGf cAfaGfaUfAfUfuUfuuAfuA faua(NH2C6) | aagcagauauuuuauaaua |
| 129. | X91417 | (invabasic)(invabasic)usgsg gauUfuCfAfUfguaaccaaga (NH2C6) | ugggauuucauguaaccaaga |
| 130. | X91418 | GfsasCfuUfuCfcCfuGfg AfaAfuAfuAf(NH2C6) | gacuuucauccuggaaauaua |
| 131. | X91419 | AfsasGfcAfaGfaUfuUfu UfaUfaAfuAf(NH2C6) | aagcagauauuuuauaaua |
| | X91420 | UfsgsGfgAfuUfuCfaUfgUfa | ugggauuucauguaaccaaga |

TABLE A-continued

Summary of Sequences

| | | | |
|---|---|---|---|
| | | AfcCfaAfgAf(NH2C6) | |
| 132. | X91379 | gsascuuuCfaUfcCfuggaaau aua(GalNAc) | gacuuucauccuggaaauaua |
| 133. | X91380 | asasGfcAfaGfaUfAfUfuUfu uAfuAfaua(GalNAc) | aagcaagauauuuuauaaua |
| 134. | X91446 | usgsggauUfuCfAfUfguaacca aga(GalNAc) | ugggauuucauguaaccaaga |
| 135. | X38483 | usAfsuauUfuCfcfaggaUfgA faagucscsa | uauauuccaggaugaaagucca |
| 136. | X91381 | usAfsUfuAfuaAfaAfauaUfc UfuGfcuuususudTdT | uauuauaaaauaucuugcuuuu |
| 137. | X38104 | usCfsuugGfuuAfcaugAfaAf ucccasusc | ucuugguuacaugaaucccauc |
| 138. | X91398 | usAfsAfuUfuCfcAfgGfaUf gAfaAfgUfcsCfsa | uauauuccaggaugaaagucca |
| 139. | X91400 | usAfsuUfaAfaAfaAfauaUfaUf cUfuGfcUfus UfsudTdT | uauuauaaaauaucuugcuuuu |
| 140. | X91402 | usCfsuUfgGfuUfacfaUfgAf aAfuCfcfasUfsc | ucuugguuacaugaaucccauc |
| 141. | X91409 | (GalNAc-T2)(NH2C12)gacuuucfaUf CfCfuggaaauasusa(invabasic) (invabasic) | gacuuucauccuggaaauaua |
| 142. | X91410 | (GalNAc-T2)(NH2C12)aaGfcAfaGfa UfAfUfuUfuuAfuAfasusa (invabasic)(invabasic) | aagcaagauauuuuauaaua |
| 143. | X91411 | (GalNAc-T2)(NH2C12)ugggauUfuCf AfUfguaaccaasgsa(invabasic) (invabasic) | ugggauuucauguaaccaaga |
| 144. | X91412 | (GalNAc-T2)(NH2C12)GfaCfuUfuCf aUfcCfuGfgAfaAfuAfsusAf | gacuuucauccuggaaauaua |
| 145. | X91413 | (GalNAc-T2)(NH2C12)AfgGfcAfaGf aUfaUfuUfuUfaUfaAfsusAf | aagcaagauauuuuauaaua |

TABLE A-continued

Summary of Sequences

| | | | |
|---|---|---|---|
| 146. | X91414 | (GalNAc-T2)(NH2C12)UfgGfgAfuUf uCfaUfgUfaAfcCfaAfsgsAf | ugggauuucauguaaccaaga |
| 147. | X91433 | (invabasic)(invabasic)gsascu uuCfaUfcCfcfuggaaauasusa (NHC6)(GalNAc-T2) | gacuuucauccuggaaauaua |
| 148. | X91434 | (invabasic)(invabasic)asasGf cAfaGfaUfAfUfuUfuuAfuA faua(NHC6)(GalNAc-T2) | aagcaagauauuuuauaaua |
| 149. | X91435 | (invabasic)(invabasic)usgsg gauUfuCfAfUfguaaccaaga (NHC6)(GalNAc-T2) | ugggauuucauguaaccaaga |
| 150. | X91436 | GfsascfuUfuCfaUfcCfuGfg AfaAfuAf(NHC6) A(GalNc-T2) | gacuuucauccuggaaauaua |
| 151. | X91437 | AfsaaGfcAfaGfaUfaUfuUfu UfaUfaAfuAf(NHC6) (GalNAc-T2) | aagcaagauauuuuauaaua |
| 152. | X91438 | UfsgsGfgAfuUfuCfaUfgUfa AfcCfaAfgAf(NHC6) (GalNAc-T2) | ugggauuucauguaaccaaga |
| 153. | X91409 | (GalNAc-T2)(NH2C12)gacuuuCfaUf cCfcfuggaaauasusa(invabasic) (invabasic) | gacuuucauccuggaaauaua |
| 154. | ETX002 | usAfsuauUfuCfCfaggaUfgA fa TABLE A-continued Summary of Sequences

| | | | |
|---|---|---|---|
| 159. | ETX008 | X91436 | GfsasCfuUfuCfaUfcCfuGfg AfaAfuAfuAf(NHC6) (GalNAc-T2) | gacuuucauccuggaaauaua |
| 160. | | X91398 | usAfsuAfuUfuCfcAfgGfaUf gAfaAfgUfcsCfsa | uauauuccaggaugaaagucca |
| 161. | ETX011 | X91410 | (GalNAc-T2)(NH2C12)aaGfcAfaGfa UfAfUfuUfuuAfuAfasusa (invabasic) | aagcaagauauuuuaua TABLE A-continued Summary of Sequences

| | | |
|---|---|---|
| 172. | X91402 | usCfsuUfgGfuUfaCfaUfgAf aAfuCfcCfasUfsc<br>ucuugguuacaugaaauccauc |
| 173. | ETX024 X91435 | (invabasic)(invabasic)usgsg gauUfuCfaFfUfguaaccaaga (NHC6)(GalNAc-T2)<br>ugggauuucauguaaccaaga |
| 174. | X38104 | usCfsuugGfuuAfcaugAfaAf ucccasusc<br>ucuugguuacaugaaauccauc |
| 175. | ETX026 X91438 | UfsgsGfgAfuUfuCfaUfgUfa AfcCfaAfgAf(NHC6) (GalNAc-T2)<br>ugggauuucauguaaccaaga |
| 176. | X91402 | usCfsuUfgGfuUfaCfaUfgAf aAfuCfcCfasUfsc<br>ucuugguuacaugaaauccauc |

Key:
Key for SEQ ID NOs: 1-24
ia inverted abasic nucleotide (1,2-dideoxyribose)
m 2'-O-methyl nucleotide
f 2'-deoxy-2'-fluoro nucleotide
s phosphorothioate internucleotide linkage (Phosphorothioate backbone modification)
~ tether
Td Deoxythymidine
Key for SEQ ID NOs: 25-176
dG, dC, dA, dT DNA residues
GalNAc N-Acetylgalactosamine
G, C, A, U RNA residues
g, c, a, u 2'-O-Methyl modified residues
Gf, Cf, Af, Uf 2'-Fluoro modified residues
s Phosphorothioate backbone modification
siRNA small interfering RNA
MFCO Monofluoro cyclooctyne
invabasic 1,2-dideoxyribose
(invabasic)(invabasic) Nucleotides in an overall polynucleotide which are the terminal 2 nucleotides which have sugar moieties that are (i) abasic, and (ii) in an inverted configuration, whereby the bond between the penultimate nucleotide and the antepenultimate nucleotide has a reversed linkage, namely either a 5-5 or a 3-3 linkage
NH2-DEG/NHDEG Aminoethoxyethyl linker
NH2C12 Aminododecyl linker
NH2C6/NHC6 Aminohexyl linker
ET (E-therapeutics - company reference)
(ET-GalNAc-T1N3)(MFCO)(NH-DEG) tether T1b
(ET-GalNAc-T2CO)(NH2C12) tether T2b
(NHC6)(MFCO)(ET-GalNAc-T1N3)tether T1a
(NHC6)(ET-GalNAc-T2CO) tether T2a
T1N3 T1 tether
T2Co T2 tether
(GalNAc-)T1 GalNac T1 tether
(GalNAc-)T2 GalNac T2 tether
Note:
the key ref

The invention claimed is:

1. A compound of Formula (I):

Formula (I)

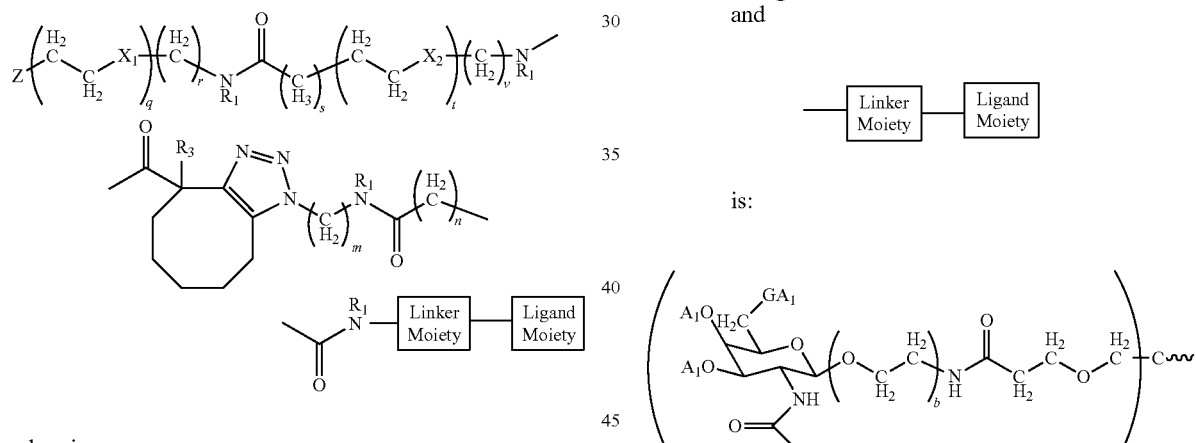

wherein:
R$_1$ at each occurrence is independently selected from the group consisting of hydrogen, methyl, and ethyl;
R$_2$ is fluoro or hydroxy;
X$_1$ and X$_2$ at each occurrence are independently selected from the group consisting of methylene, oxygen, and sulfur;
m is an integer of from 1 to 6;
n is an integer of from 1 to 10;
q, r, s, t, v are independently integers from 0 to 4, with the proviso that:
   (i) q and r cannot both be 0 at the same time; and
   (ii) s, t, and v cannot all be 0 at the same time;
Z is:

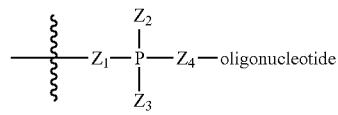

wherein:
Z$_1$, Z$_2$, Z$_3$, and Z$_4$ are independently at each occurrence oxygen or sulfur; and
one of the bonds between P and Z$_2$, and P and Z$_3$, is a single bond and the other bond is a double bond; and

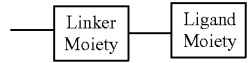

is:

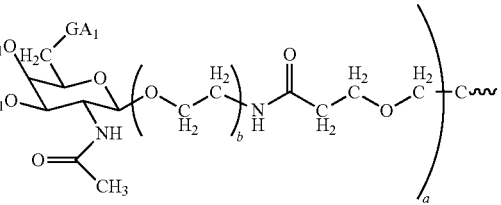

wherein:
A$_1$ is hydrogen;
a is an integer of 2 or 3; and
b is an integer of 2 to 5.

2. The compound according to claim 1, wherein R$_1$ is hydrogen at each occurrence.

3. The compound according to claim 1, wherein m=3.

4. The compound according to claim 1, wherein n=6.

5. The compound according to claim 1, wherein X$_1$ is oxygen and X$_2$ is methylene.

6. The compound according to claim 1, wherein both X$_1$ and X$_2$ are methylene.

7. The compound according to claim 1, wherein the oligonucleotide is an RNA capable of modulating, or inhibiting, expression of a target gene.

8. The compound according to claim 1, wherein the RNA is attached at the 5' end of its second strand to the adjacent phosphate.

9. The compound according to claim 1, wherein the RNA is attached at the 3' end of its second strand to the adjacent phosphate.
10. A compound having the structure of:
(i) Formula (II):
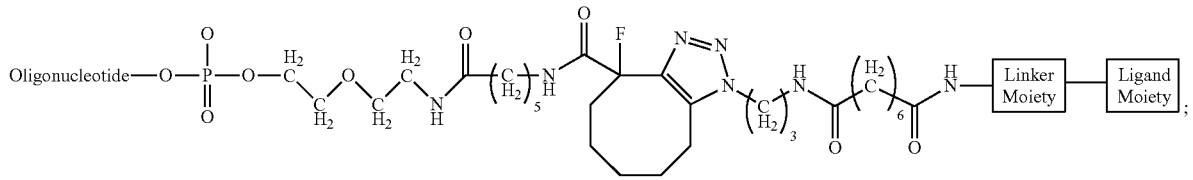
Formula (II)
(ii) Formula (IV):
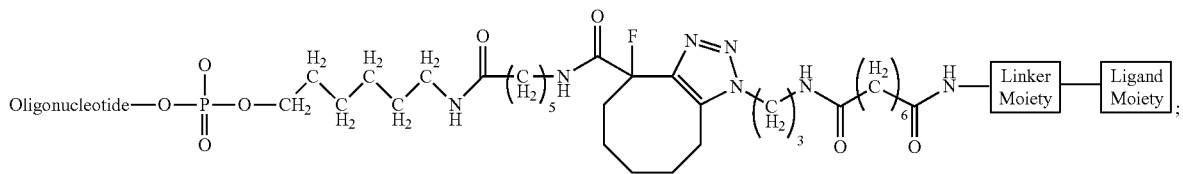
Formula (IV)
(iii) Formula (III):
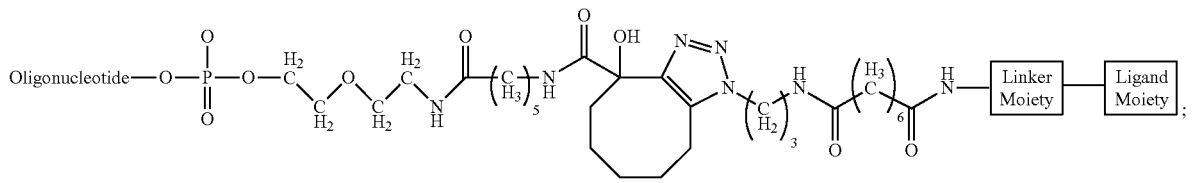
Formula (III)
or
(iv) Formula (V):
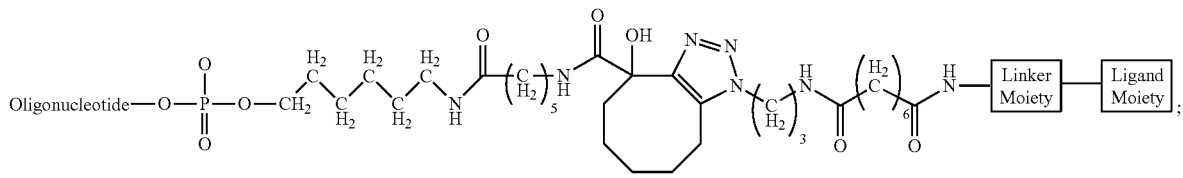
Formula (V)

wherein
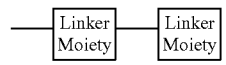
is
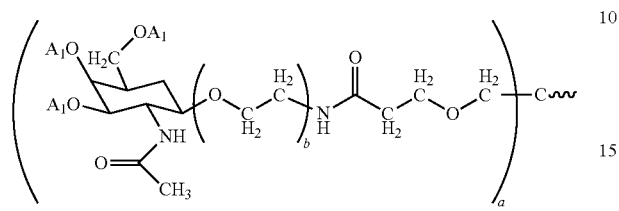
wherein:
A$_1$ is hydrogen;
a is an integer of 2 or 3; and
b is an integer of 2 to 5;
optionally wherein the oligonucleotide comprises one or more degradation protective moieties at one or more ends.
11. A compound having the structure of:
(i) Formula (VIII):
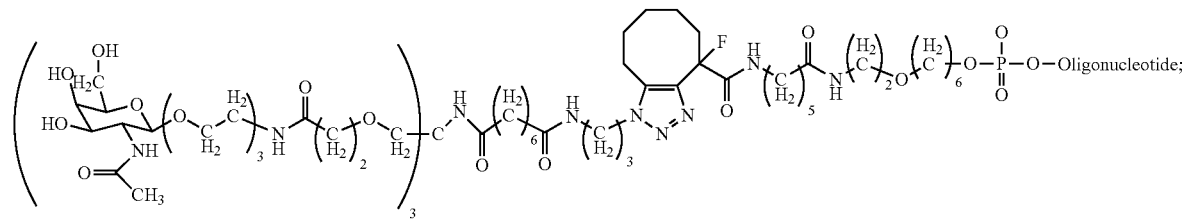
Formula (VIII)
(ii) Formula (X):
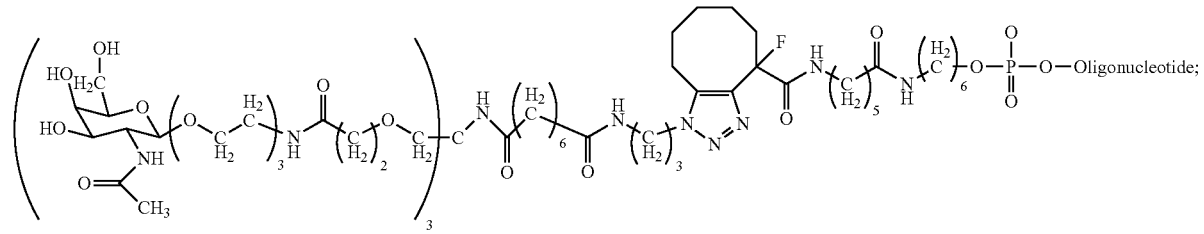
Formula (X)

(iii) Formula (IX):

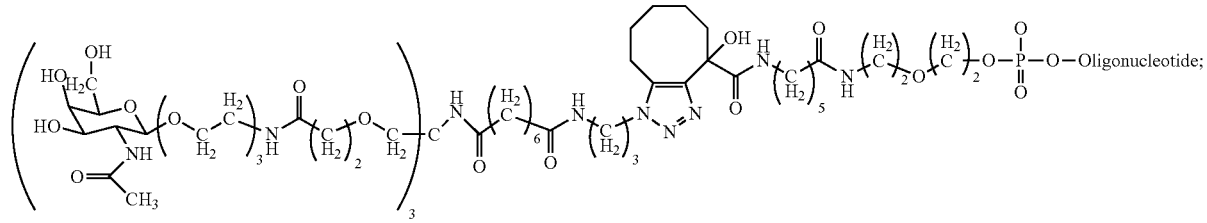

Formula (IX)

or (iv) Formula (XI):

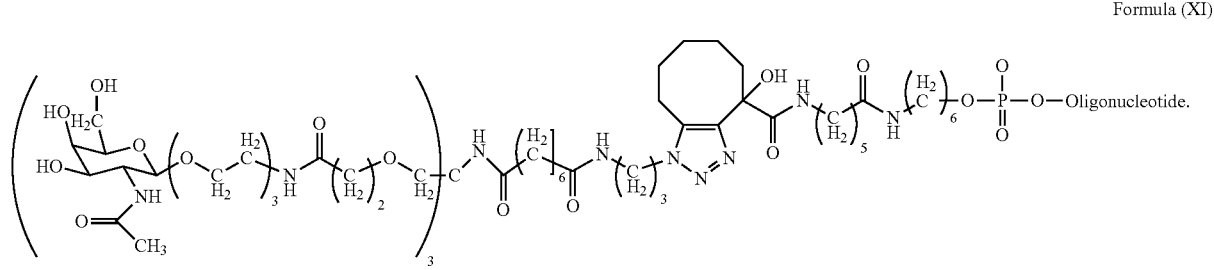

Formula (XI)

12. The compound according to claim 10, wherein the oligonucleotide comprises one or more degradation protective moieties at one or more ends.

13. A pharmaceutical composition comprising of a compound according to claim 1, together with a pharmaceutically acceptable carrier, diluent or excipient.

14. The compound according to claim 5, wherein:
q=1,
r=2,
s=1,
t=1, and
v=1.

15. The compound according to claim 6, wherein:
q=1,
r=3,
s=1,
t=1, and
v=1.

16. The compound according to claim 7, wherein the RNA is an RNA duplex comprising first and second strands, wherein the first strand is at least partially complementary to an RNA sequence of a target gene, and the second strand is at least partially complementary to said first strand, and wherein each of the first and second strands have 5' and 3' ends.

17. The compound according to claim 12, wherein the one or more degradation protective moieties is selected from the group consisting of phosphorothioate internucleotide linkages, phosphorodithioate internucleotide linkages and inverted abasic nucleotides, wherein the inverted abasic nucleotides are present at the distal end of the strand that carries the ligand moieties.

18. The compound according to claim 1, wherein $R_2$ is hydroxy.

19. The compound according to claim 1, wherein $R_2$ is fluoro.

* * * * *

SEQUENCE LISTING

```
Sequence total quantity: 182
SEQ ID NO: 1               moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 1
gactttcatc ctggaaatat a                                                   21

SEQ ID NO: 2               moltype = RNA   length = 23
FEATURE                    Location/Qualifiers
misc_feature               1..23
                           note = modified siRNA
source                     1..23
                           mol_type = other RNA
                           organism = synthetic construct
SEQUENCE: 2
acctgaaagt aggaccttta tat                                                 23

SEQ ID NO: 3               moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 3
aagcaagata tttttataat a                                                   21

SEQ ID NO: 4               moltype = RNA   length = 23
FEATURE                    Location/Qualifiers
misc_feature               1..23
                           note = modified siRNA
source                     1..23
                           mol_type = other RNA
                           organism = synthetic construct
SEQUENCE: 4
ttttcgttct ataaaaatat tat                                                 23

SEQ ID NO: 5               moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 5
tgggatttca tgtaaccaag a                                                   21

SEQ ID NO: 6               moltype = RNA   length = 23
FEATURE                    Location/Qualifiers
misc_feature               1..23
                           note = modified siRNA
source                     1..23
                           mol_type = other RNA
                           organism = synthetic construct
SEQUENCE: 6
ctaccctaaa gtacattggt tct                                                 23

SEQ ID NO: 7               moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 7
gactttcatc ctggaaatat a                                                   21

SEQ ID NO: 8               moltype = RNA   length = 23
FEATURE                    Location/Qualifiers
misc_feature               1..23
                           note = modified siRNA
source                     1..23
                           mol_type = other RNA
                           organism = synthetic construct
```

```
SEQUENCE: 8
acctgaaagt aggaccttta tat                                              23

SEQ ID NO: 9            moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 9
aagcaagata tttttataat a                                                21

SEQ ID NO: 10           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 10
ttttcgttct ataaaatat tat                                               23

SEQ ID NO: 11           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 11
tgggatttca tgtaaccaag a                                                21

SEQ ID NO: 12           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 12
ctaccctaaa gtacattggt tct                                              23

SEQ ID NO: 13           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 13
gactttcatc ctggaaatat a                                                21

SEQ ID NO: 14           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 14
acctgaaagt aggaccttta tat                                              23

SEQ ID NO: 15           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 15
aagcaagata tttttataat a                                                21

SEQ ID NO: 16           moltype = RNA   length = 23
FEATURE                 Location/Qualifiers
misc_feature            1..23
                        note = modified siRNA
```

```
source                   1..23
                         mol_type = other RNA
                         organism = synthetic construct
SEQUENCE: 16
ttttcgttct ataaaatat tat                                            23

SEQ ID NO: 17            moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 17
tgggatttca tgtaaccaag a                                             21

SEQ ID NO: 18            moltype = RNA   length = 23
FEATURE                  Location/Qualifiers
misc_feature             1..23
                         note = modified siRNA
source                   1..23
                         mol_type = other RNA
                         organism = synthetic construct
SEQUENCE: 18
ctaccctaaa gtacattggt tct                                           23

SEQ ID NO: 19            moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 19
gactttcatc ctggaaatat a                                             21

SEQ ID NO: 20            moltype = RNA   length = 23
FEATURE                  Location/Qualifiers
misc_feature             1..23
                         note = modified siRNA
source                   1..23
                         mol_type = other RNA
                         organism = synthetic construct
SEQUENCE: 20
acctgaaagt aggacettta tat                                           23

SEQ ID NO: 21            moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 21
aagcaagata ttttataat a                                              21

SEQ ID NO: 22            moltype = RNA   length = 23
FEATURE                  Location/Qualifiers
misc_feature             1..23
                         note = modified siRNA
source                   1..23
                         mol_type = other RNA
                         organism = synthetic construct
SEQUENCE: 22
ttttcgttct ataaaatat tat                                            23

SEQ ID NO: 23            moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 23
tgggatttca tgtaaccaag a                                             21
```

```
SEQ ID NO: 24          moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 24
ctaccctaaa gtacattggt tct                                              23

SEQ ID NO: 25          moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 25
gactttcatc ctggaaatat a                                                21

SEQ ID NO: 26          moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 26
tatatttcca ggatgaaagt cca                                              23

SEQ ID NO: 27          moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 27
gactttcatc ctggaaatat a                                                21

SEQ ID NO: 28          moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 28
tatatttcca ggatgaaagt cca                                              23

SEQ ID NO: 29          moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 29
aagcaagata tttttataat a                                                21

SEQ ID NO: 30          moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 30
tattataaaa atatcttgct ttt                                              23

SEQ ID NO: 31          moltype = RNA   length = 21
FEATURE                Location/Qualifiers
misc_feature           1..21
                       note = modified siRNA
source                 1..21
                       mol_type = other RNA
                       organism = synthetic construct
```

```
SEQUENCE: 31
aagcaagata tttttataat a                                              21

SEQ ID NO: 32           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 32
tattataaaa atatcttgct ttt                                            23

SEQ ID NO: 33           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 33
tgggatttca tgtaaccaag a                                              21

SEQ ID NO: 34           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 34
tcttggttac atgaaatccc atc                                            23

SEQ ID NO: 35           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 35
tgggatttca tgtaaccaag a                                              21

SEQ ID NO: 36           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 36
tcttggttac atgaaatccc atc                                            23

SEQ ID NO: 37           moltype = RNA  length = 19
FEATURE                 Location/Qualifiers
misc_feature            1..19
                        note = modified siRNA
source                  1..19
                        mol_type = other RNA
                        organism = synthetic construct
SEQUENCE: 37
cttacgctga gtacttcga                                                 19

SEQ ID NO: 38           moltype = RNA  length = 19
FEATURE                 Location/Qualifiers
misc_feature            1..19
                        note = modified siRNA
source                  1..19
                        mol_type = other RNA
                        organism = synthetic construct
SEQUENCE: 38
tcgaagtact cagcgtaag                                                 19

SEQ ID NO: 39           moltype = RNA  length = 19
FEATURE                 Location/Qualifiers
misc_feature            1..19
                        note = modified siRNA
```

```
source                  1..19
                        mol_type = other RNA
                        organism = synthetic construct
SEQUENCE: 39
agatatgcac acacacgga                                                 19

SEQ ID NO: 40           moltype = RNA  length = 19
FEATURE                 Location/Qualifiers
misc_feature            1..19
                        note = modified siRNA
source                  1..19
                        mol_type = other RNA
                        organism = synthetic construct
SEQUENCE: 40
tccgtgtgtg tgcatatct                                                 19

SEQ ID NO: 41           moltype = RNA  length = 19
FEATURE                 Location/Qualifiers
misc_feature            1..19
                        note = modified siRNA
source                  1..19
                        mol_type = other RNA
                        organism = synthetic construct
SEQUENCE: 41
tctcgtggcc ttaatgaaa                                                 19

SEQ ID NO: 42           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 42
tttcattaag gccacgagat t                                              21

SEQ ID NO: 43           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 43
gactttcatc ctggaaatat a                                              21

SEQ ID NO: 44           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 44
aagcaagata ttttttataat a                                             21

SEQ ID NO: 45           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 45
tgggatttca tgtaaccaag a                                              21

SEQ ID NO: 46           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 46
gactttcatc ctggaaatat a                                              21

SEQ ID NO: 47           moltype = RNA  length = 21
FEATURE                 Location/Qualifiers
```

```
misc_feature              1..21
                          note = modified siRNA
source                    1..21
                          mol_type = other RNA
                          organism = synthetic construct
SEQUENCE: 47
aagcaagata tttttataat a                                              21

SEQ ID NO: 48             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 48
tgggatttca tgtaaccaag a                                              21

SEQ ID NO: 49             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 49
gactttcatc ctggaaatat a                                              21

SEQ ID NO: 50             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 50
aagcaagata tttttataat a                                              21

SEQ ID NO: 51             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 51
tgggatttca tgtaaccaag a                                              21

SEQ ID NO: 52             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 52
gactttcatc ctggaaatat a                                              21

SEQ ID NO: 53             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 53
aagcaagata tttttataat a                                              21

SEQ ID NO: 54             moltype = RNA   length = 21
FEATURE                   Location/Qualifiers
misc_feature              1..21
                          note = modified siRNA
source                    1..21
                          mol_type = other RNA
                          organism = synthetic construct
SEQUENCE: 54
tgggatttca tgtaaccaag a                                              21

SEQ ID NO: 55             moltype = RNA   length = 23
```

```
FEATURE                 Location/Qualifiers
misc_feature            1..23
                        note = modified siRNA
source                  1..23
                        mol_type = other RNA
                        organism = synthetic construct
SEQUENCE: 55
tatatttcca ggatgaaagt cca                                               23

SEQ ID NO: 56           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 56
tattataaaa atatcttgct ttt                                               23

SEQ ID NO: 57           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 57
tcttggttac atgaaatccc atc                                               23

SEQ ID NO: 58           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 58
gactttcatc ctggaaatat a                                                 21

SEQ ID NO: 59           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 59
aagcaagata tttttataat a                                                 21

SEQ ID NO: 60           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 60
tgggatttca tgtaaccaag a                                                 21

SEQ ID NO: 61           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 61
gactttcatc ctggaaatat a                                                 21

SEQ ID NO: 62           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 62
aagcaagata tttttataat a                                                 21
```

```
SEQ ID NO: 63           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 63
tgggatttca tgtaaccaag a                                              21

SEQ ID NO: 64           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 64
gactttcatc ctggaaatat a                                              21

SEQ ID NO: 65           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 65
aagcaagata tttttataat a                                              21

SEQ ID NO: 66           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 66
tgggatttca tgtaaccaag a                                              21

SEQ ID NO: 67           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 67
gactttcatc ctggaaatat a                                              21

SEQ ID NO: 68           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 68
aagcaagata tttttataat a                                              21

SEQ ID NO: 69           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 69
tgggatttca tgtaaccaag a                                              21

SEQ ID NO: 70           moltype = RNA    length = 21
FEATURE                 Location/Qualifiers
misc_feature            1..21
                        note = modified siRNA
source                  1..21
                        mol_type = other RNA
                        organism = synthetic construct
SEQUENCE: 70
gactttcatc ctggaaatat a                                              21
```

```
SEQ ID NO: 71           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 71
tatatttcca ggatgaaagt cca                                              23

SEQ ID NO: 72           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 72
gactttcatc ctggaaatat a                                                21

SEQ ID NO: 73           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 73
tatatttcca ggatgaaagt cca                                              23

SEQ ID NO: 74           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 74
aagcaagata tttttataat a                                                21

SEQ ID NO: 75           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 75
tattataaaa atatcttgct ttt                                              23

SEQ ID NO: 76           moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 76
aagcaagata tttttataat a                                                21

SEQ ID NO: 77           moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 77
tattataaaa atatcttgct ttt                                              23

SEQ ID NO: 78           moltype = RNA  length = 21
FEATURE                 Location/Qualifiers
misc_feature            1..21
                        note = modified siRNA
source                  1..21
                        mol_type = other RNA
                        organism = synthetic construct
```

-continued

| | | |
|---|---|---|
| SEQUENCE: 78 | | |
| tgggatttca tgtaaccaag a | | 21 |
| | | |
| SEQ ID NO: 79 | moltype = RNA  length = 23 | |
| FEATURE | Location/Qualifiers | |
| misc_feature | 1..23 | |
| | note = modified siRNA | |
| source | 1..23 | |
| | mol_type = other RNA | |
| | organism = synthetic construct | |
| SEQUENCE: 79 | | |
| tcttggttac atgaaatccc atc | | 23 |
| | | |
| SEQ ID NO: 80 | moltype = RNA  length = 21 | |
| FEATURE | Location/Qualifiers | |
| misc_feature | 1..21 | |
| | note = modified siRNA | |
| source | 1..21 | |
| | mol_type = other RNA | |
| | organism = synthetic construct | |
| SEQUENCE: 80 | | |
| tgggatttca tgtaaccaag a | | 21 |
| | | |
| SEQ ID NO: 81 | moltype = RNA  length = 23 | |
| FEATURE | Location/Qualifiers | |
| misc_feature | 1..23 | |
| | note = modified siRNA | |
| source | 1..23 | |
| | mol_type = other RNA | |
| | organism = synthetic construct | |
| SEQUENCE: 81 | | |
| tcttggttac atgaaatccc atc | | 23 |
| | | |
| SEQ ID NO: 82 | moltype = RNA  length = 21 | |
| FEATURE | Location/Qualifiers | |
| misc_feature | 1..21 | |
| | note = modified siRNA | |
| source | 1..21 | |
| | mol_type = other RNA | |
| | organism = synthetic construct | |
| SEQUENCE: 82 | | |
| gactttcatc ctggaaatat a | | 21 |
| | | |
| SEQ ID NO: 83 | moltype = RNA  length = 23 | |
| FEATURE | Location/Qualifiers | |
| misc_feature | 1..23 | |
| | note = modified siRNA | |
| source | 1..23 | |
| | mol_type = other RNA | |
| | organism = synthetic construct | |
| SEQUENCE: 83 | | |
| tatatttcca ggatgaaagt cca | | 23 |
| | | |
| SEQ ID NO: 84 | moltype = RNA  length = 21 | |
| FEATURE | Location/Qualifiers | |
| misc_feature | 1..21 | |
| | note = modified siRNA | |
| source | 1..21 | |
| | mol_type = other RNA | |
| | organism = synthetic construct | |
| SEQUENCE: 84 | | |
| gactttcatc ctggaaatat a | | 21 |
| | | |
| SEQ ID NO: 85 | moltype = RNA  length = 23 | |
| FEATURE | Location/Qualifiers | |
| misc_feature | 1..23 | |
| | note = modified siRNA | |
| source | 1..23 | |
| | mol_type = other RNA | |
| | organism = synthetic construct | |
| SEQUENCE: 85 | | |
| tatatttcca ggatgaaagt cca | | 23 |
| | | |
| SEQ ID NO: 86 | moltype = RNA  length = 21 | |
| FEATURE | Location/Qualifiers | |
| misc_feature | 1..21 | |
| | note = modified siRNA | |

```
source                  1..21
                        mol_type = other RNA
                        organism = synthetic construct
SEQUENCE: 86
gactttcatc ctggaaatat a                                              21

SEQ ID NO: 87           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 87
tatatttcca ggatgaaagt cca                                            23

SEQ ID NO: 88           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 88
gactttcatc ctggaaatat a                                              21

SEQ ID NO: 89           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 89
tatatttcca ggatgaaagt cca                                            23

SEQ ID NO: 90           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 90
gactttcatc ctggaaatat a                                              21

SEQ ID NO: 91           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 91
tatatttcca ggatgaaagt cca                                            23

SEQ ID NO: 92           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 92
aagcaagata tttttataat a                                              21

SEQ ID NO: 93           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 93
tattataaaa atatcttgct ttt                                            23

SEQ ID NO: 94           moltype = RNA   length = 21
FEATURE                 Location/Qualifiers
```

```
misc_feature            1..21
                        note = modified siRNA
source                  1..21
                        mol_type = other RNA
                        organism = synthetic construct
SEQUENCE: 94
aagcaagata tttttataat a                                              21

SEQ ID NO: 95           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 95
tattataaaa atatcttgct ttt                                            23

SEQ ID NO: 96           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 96
aagcaagata tttttataat a                                              21

SEQ ID NO: 97           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 97
tattataaaa atatcttgct ttt                                            23

SEQ ID NO: 98           moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 98
aagcaagata tttttataat a                                              21

SEQ ID NO: 99           moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 99
tattataaaa atatcttgct ttt                                            23

SEQ ID NO: 100          moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 100
tgggatttca tgtaaccaag a                                              21

SEQ ID NO: 101          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 101
tcttggttac atgaaatccc atc                                            23

SEQ ID NO: 102          moltype = RNA   length = 21
```

```
FEATURE              Location/Qualifiers
misc_feature         1..21
                     note = modified siRNA
source               1..21
                     mol_type = other RNA
                     organism = synthetic construct
SEQUENCE: 102
tgggatttca tgtaaccaag a                                              21

SEQ ID NO: 103       moltype = RNA  length = 23
FEATURE              Location/Qualifiers
misc_feature         1..23
                     note = modified siRNA
source               1..23
                     mol_type = other RNA
                     organism = synthetic construct
SEQUENCE: 103
tcttggttac atgaaatccc atc                                            23

SEQ ID NO: 104       moltype = RNA  length = 21
FEATURE              Location/Qualifiers
misc_feature         1..21
                     note = modified siRNA
source               1..21
                     mol_type = other RNA
                     organism = synthetic construct
SEQUENCE: 104
tgggatttca tgtaaccaag a                                              21

SEQ ID NO: 105       moltype = RNA  length = 23
FEATURE              Location/Qualifiers
misc_feature         1..23
                     note = modified siRNA
source               1..23
                     mol_type = other RNA
                     organism = synthetic construct
SEQUENCE: 105
tcttggttac atgaaatccc atc                                            23

SEQ ID NO: 106       moltype = RNA  length = 21
FEATURE              Location/Qualifiers
misc_feature         1..21
                     note = modified siRNA
source               1..21
                     mol_type = other RNA
                     organism = synthetic construct
SEQUENCE: 106
tgggatttca tgtaaccaag a                                              21

SEQ ID NO: 107       moltype = RNA  length = 23
FEATURE              Location/Qualifiers
misc_feature         1..23
                     note = modified siRNA
source               1..23
                     mol_type = other RNA
                     organism = synthetic construct
SEQUENCE: 107
tcttggttac atgaaatccc atc                                            23

SEQ ID NO: 108       moltype = RNA  length = 19
FEATURE              Location/Qualifiers
misc_feature         1..19
                     note = modified siRNA
source               1..19
                     mol_type = other RNA
                     organism = synthetic construct
SEQUENCE: 108
cttacgctga gtacttcga                                                 19

SEQ ID NO: 109       moltype = RNA  length = 19
FEATURE              Location/Qualifiers
misc_feature         1..19
                     note = modified siRNA
source               1..19
                     mol_type = other RNA
                     organism = synthetic construct
SEQUENCE: 109
tcgaagtact cagcgtaag                                                 19
```

```
SEQ ID NO: 110        moltype = RNA   length = 19
FEATURE               Location/Qualifiers
misc_feature          1..19
                      note = modified siRNA
source                1..19
                      mol_type = other RNA
                      organism = synthetic construct
SEQUENCE: 110
agatatgcac acacacgga                                                   19

SEQ ID NO: 111        moltype = RNA   length = 19
FEATURE               Location/Qualifiers
misc_feature          1..19
                      note = modified siRNA
source                1..19
                      mol_type = other RNA
                      organism = synthetic construct
SEQUENCE: 111
tccgtgtgtg tgcatatct                                                   19

SEQ ID NO: 112        moltype = RNA   length = 19
FEATURE               Location/Qualifiers
misc_feature          1..19
                      note = modified siRNA
source                1..19
                      mol_type = other RNA
                      organism = synthetic construct
SEQUENCE: 112
tctcgtggcc ttaatgaaa                                                   19

SEQ ID NO: 113        moltype = RNA   length = 21
FEATURE               Location/Qualifiers
misc_feature          1..21
                      note = modified siRNA
source                1..21
                      mol_type = other RNA
                      organism = synthetic construct
SEQUENCE: 113
tttcattaag gccacgagat t                                                21

SEQ ID NO: 114        moltype = RNA   length = 21
FEATURE               Location/Qualifiers
misc_feature          1..21
                      note = modified siRNA
source                1..21
                      mol_type = other RNA
                      organism = synthetic construct
SEQUENCE: 114
gactttcatc ctggaaatat a                                                21

SEQ ID NO: 115        moltype = RNA   length = 21
FEATURE               Location/Qualifiers
misc_feature          1..21
                      note = modified siRNA
source                1..21
                      mol_type = other RNA
                      organism = synthetic construct
SEQUENCE: 115
aagcaagata tttttataat a                                                21

SEQ ID NO: 116        moltype = RNA   length = 21
FEATURE               Location/Qualifiers
misc_feature          1..21
                      note = modified siRNA
source                1..21
                      mol_type = other RNA
                      organism = synthetic construct
SEQUENCE: 116
tgggatttca tgtaaccaag a                                                21

SEQ ID NO: 117        moltype = RNA   length = 21
FEATURE               Location/Qualifiers
misc_feature          1..21
                      note = modified siRNA
source                1..21
                      mol_type = other RNA
                      organism = synthetic construct
SEQUENCE: 117
gactttcatc ctggaaatat a                                                21
```

```
SEQ ID NO: 118            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 118
aagcaagata tttttataat a                                              21

SEQ ID NO: 119            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 119
tgggatttca tgtaaccaag a                                              21

SEQ ID NO: 120            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 120
gactttcatc ctggaaatat a                                              21

SEQ ID NO: 121            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 121
aagcaagata tttttataat a                                              21

SEQ ID NO: 122            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 122
tgggatttca tgtaaccaag a                                              21

SEQ ID NO: 123            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 123
gactttcatc ctggaaatat a                                              21

SEQ ID NO: 124            moltype = RNA  length = 21
FEATURE                   Location/Qualifiers
misc_feature              1..21
                          note = modified siRNA
source                    1..21
                          mol_type = other RNA
                          organism = synthetic construct
SEQUENCE: 124
aagcaagata tttttataat a                                              21

SEQ ID NO: 125            moltype = RNA  length = 21
FEATURE                   Location/Qualifiers
misc_feature              1..21
                          note = modified siRNA
source                    1..21
                          mol_type = other RNA
                          organism = synthetic construct
```

```
SEQUENCE: 125
tgggatttca tgtaaccaag a                                              21

SEQ ID NO: 126           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 126
gactttcatc ctggaaatat a                                              21

SEQ ID NO: 127           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 127
aagcaagata tttttataat a                                              21

SEQ ID NO: 128           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 128
tgggatttca tgtaaccaag a                                              21

SEQ ID NO: 129           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 129
gactttcatc ctggaaatat a                                              21

SEQ ID NO: 130           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 130
aagcaagata tttttataat a                                              21

SEQ ID NO: 131           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 131
tgggatttca tgtaaccaag a                                              21

SEQ ID NO: 132           moltype = RNA   length = 21
FEATURE                  Location/Qualifiers
misc_feature             1..21
                         note = modified siRNA
source                   1..21
                         mol_type = other RNA
                         organism = synthetic construct
SEQUENCE: 132
gactttcatc ctggaaatat a                                              21

SEQ ID NO: 133           moltype = RNA   length = 21
FEATURE                  Location/Qualifiers
misc_feature             1..21
                         note = modified siRNA
```

```
source                  1..21
                        mol_type = other RNA
                        organism = synthetic construct
SEQUENCE: 133
aagcaagata tttttataat a                                              21

SEQ ID NO: 134          moltype = RNA   length = 21
FEATURE                 Location/Qualifiers
misc_feature            1..21
                        note = modified siRNA
source                  1..21
                        mol_type = other RNA
                        organism = synthetic construct
SEQUENCE: 134
tgggatttca tgtaaccaag a                                              21

SEQ ID NO: 135          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 135
tatatttcca ggatgaaagt cca                                            23

SEQ ID NO: 136          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 136
tattataaaa atatcttgct ttt                                            23

SEQ ID NO: 137          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 137
tcttggttac atgaaatccc atc                                            23

SEQ ID NO: 138          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 138
tatatttcca ggatgaaagt cca                                            23

SEQ ID NO: 139          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 139
tattataaaa atatcttgct ttt                                            23

SEQ ID NO: 140          moltype = RNA   length = 23
FEATURE                 Location/Qualifiers
misc_feature            1..23
                        note = modified siRNA
source                  1..23
                        mol_type = other RNA
                        organism = synthetic construct
SEQUENCE: 140
tcttggttac atgaaatccc atc                                            23

SEQ ID NO: 141          moltype = RNA   length = 21
FEATURE                 Location/Qualifiers
```

```
misc_feature               1..21
                           note = modified siRNA
source                     1..21
                           mol_type = other RNA
                           organism = synthetic construct
SEQUENCE: 141
gactttcatc ctggaaatat a                                              21

SEQ ID NO: 142             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 142
aagcaagata tttttataat a                                              21

SEQ ID NO: 143             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 143
tgggatttca tgtaaccaag a                                              21

SEQ ID NO: 144             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 144
gactttcatc ctggaaatat a                                              21

SEQ ID NO: 145             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 145
aagcaagata tttttataat a                                              21

SEQ ID NO: 146             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 146
tgggatttca tgtaaccaag a                                              21

SEQ ID NO: 147             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 147
gactttcatc ctggaaatat a                                              21

SEQ ID NO: 148             moltype = RNA   length = 21
FEATURE                    Location/Qualifiers
misc_feature               1..21
                           note = modified siRNA
source                     1..21
                           mol_type = other RNA
                           organism = synthetic construct
SEQUENCE: 148
aagcaagata tttttataat a                                              21

SEQ ID NO: 149             moltype = RNA   length = 21
```

```
FEATURE                 Location/Qualifiers
misc_feature            1..21
                        note = modified siRNA
source                  1..21
                        mol_type = other RNA
                        organism = synthetic construct
SEQUENCE: 149
tgggatttca tgtaaccaag a                                              21

SEQ ID NO: 150          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 150
gactttcatc ctggaaatat a                                              21

SEQ ID NO: 151          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 151
aagcaagata ttttttataat a                                             21

SEQ ID NO: 152          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 152
tgggatttca tgtaaccaag a                                              21

SEQ ID NO: 153          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 153
gactttcatc ctggaaatat a                                              21

SEQ ID NO: 154          moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 154
tatatttcca ggatgaaagt cca                                            23

SEQ ID NO: 155          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 155
gactttcatc ctggaaatat a                                              21

SEQ ID NO: 156          moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 156
tatatttcca ggatgaaagt cca                                            23
```

```
SEQ ID NO: 157           moltype = RNA    length = 21
FEATURE                  Location/Qualifiers
misc_feature             1..21
                         note = modified siRNA
source                   1..21
                         mol_type = other RNA
                         organism = synthetic construct
SEQUENCE: 157
gactttcatc ctggaaatat a                                                    21

SEQ ID NO: 158           moltype = RNA    length = 23
FEATURE                  Location/Qualifiers
misc_feature             1..23
                         note = modified siRNA
source                   1..23
                         mol_type = other RNA
                         organism = synthetic construct
SEQUENCE: 158
tatatttcca ggatgaaagt cca                                                  23

SEQ ID NO: 159           moltype = RNA    length = 21
FEATURE                  Location/Qualifiers
misc_feature             1..21
                         note = modified siRNA
source                   1..21
                         mol_type = other RNA
                         organism = synthetic construct
SEQUENCE: 159
gactttcatc ctggaaatat a                                                    21

SEQ ID NO: 160           moltype = RNA    length = 23
FEATURE                  Location/Qualifiers
misc_feature             1..23
                         note = modified siRNA
source                   1..23
                         mol_type = other RNA
                         organism = synthetic construct
SEQUENCE: 160
tatatttcca ggatgaaagt cca                                                  23

SEQ ID NO: 161           moltype = RNA    length = 21
FEATURE                  Location/Qualifiers
misc_feature             1..21
                         note = modified siRNA
source                   1..21
                         mol_type = other RNA
                         organism = synthetic construct
SEQUENCE: 161
aagcaagata tttttataat a                                                    21

SEQ ID NO: 162           moltype = RNA    length = 23
FEATURE                  Location/Qualifiers
misc_feature             1..23
                         note = modified siRNA
source                   1..23
                         mol_type = other RNA
                         organism = synthetic construct
SEQUENCE: 162
tattataaaa atatcttgct ttt                                                  23

SEQ ID NO: 163           moltype = RNA    length = 21
FEATURE                  Location/Qualifiers
misc_feature             1..21
                         note = modified siRNA
source                   1..21
                         mol_type = other RNA
                         organism = synthetic construct
SEQUENCE: 163
aagcaagata tttttataat a                                                    21

SEQ ID NO: 164           moltype = RNA    length = 23
FEATURE                  Location/Qualifiers
misc_feature             1..23
                         note = modified siRNA
source                   1..23
                         mol_type = other RNA
                         organism = synthetic construct
SEQUENCE: 164
tattataaaa atatcttgct ttt                                                  23
```

```
SEQ ID NO: 165         moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 165
aagcaagata tttttataat a                                                  21

SEQ ID NO: 166         moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 166
tattataaaa atatcttgct ttt                                                23

SEQ ID NO: 167         moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 167
aagcaagata tttttataat a                                                  21

SEQ ID NO: 168         moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 168
tattataaaa atatcttgct ttt                                                23

SEQ ID NO: 169         moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 169
tgggatttca tgtaaccaag a                                                  21

SEQ ID NO: 170         moltype = RNA   length = 23
FEATURE                Location/Qualifiers
misc_feature           1..23
                       note = modified siRNA
source                 1..23
                       mol_type = other RNA
                       organism = synthetic construct
SEQUENCE: 170
tcttggttac atgaaatccc atc                                                23

SEQ ID NO: 171         moltype = RNA   length = 21
FEATURE                Location/Qualifiers
misc_feature           1..21
                       note = modified siRNA
source                 1..21
                       mol_type = other RNA
                       organism = synthetic construct
SEQUENCE: 171
tgggatttca tgtaaccaag a                                                  21

SEQ ID NO: 172         moltype = RNA   length = 23
FEATURE                Location/Qualifiers
misc_feature           1..23
                       note = modified siRNA
source                 1..23
                       mol_type = other RNA
                       organism = synthetic construct
```

```
SEQUENCE: 172
tcttggttac atgaaatccc atc                                          23

SEQ ID NO: 173          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 173
tgggatttca tgtaaccaag a                                            21

SEQ ID NO: 174          moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 174
tcttggttac atgaaatccc atc                                          23

SEQ ID NO: 175          moltype = RNA  length = 21
FEATURE                 Location/Qualifiers
misc_feature            1..21
                        note = modified siRNA
source                  1..21
                        mol_type = other RNA
                        organism = synthetic construct
SEQUENCE: 175
tgggatttca tgtaaccaag a                                            21

SEQ ID NO: 176          moltype = RNA  length = 23
FEATURE                 Location/Qualifiers
misc_feature            1..23
                        note = modified siRNA
source                  1..23
                        mol_type = other RNA
                        organism = synthetic construct
SEQUENCE: 176
tcttggttac atgaaatccc atc                                          23

SEQ ID NO: 177          moltype = RNA  length = 21
FEATURE                 Location/Qualifiers
source                  1..21
                        mol_type = other RNA
                        organism = synthetic construct
misc_feature            1..21
                        note = modified siRNA
SEQUENCE: 177
gactttcatc ctggaaatat a                                            21

SEQ ID NO: 178          moltype = RNA  length = 21
FEATURE                 Location/Qualifiers
source                  1..21
                        mol_type = other RNA
                        organism = synthetic construct
misc_feature            1..21
                        note = modified siRNA
SEQUENCE: 178
aagcaagata ttttttataat a                                           21

SEQ ID NO: 179          moltype = RNA  length = 21
FEATURE                 Location/Qualifiers
source                  1..21
                        mol_type = other RNA
                        organism = synthetic construct
misc_feature            1..21
                        note = modified siRNA
SEQUENCE: 179
tgggatttca tgtaaccaag a                                            21

SEQ ID NO: 180          moltype = RNA  length = 21
FEATURE                 Location/Qualifiers
source                  1..21
                        mol_type = other RNA
                        organism = synthetic construct
```

```
misc_feature         1..21
                     note = modified siRNA
SEQUENCE: 180
gactttcatc ctggaaatat a                                                21

SEQ ID NO: 181       moltype = RNA  length = 21
FEATURE              Location/Qualifiers
source               1..21
                     mol_type = other RNA
                     organism = synthetic construct
misc_feature         1..21
                     note = modified siRNA
SEQUENCE: 181
aagcaagata tttttataat a                                                21

SEQ ID NO: 182       moltype = RNA  length = 21
FEATURE              Location/Qualifiers
source               1..21
                     mol_type = other RNA
                     organism = synthetic construct
misc_feature         1..21
                     note = modified siRNA
SEQUENCE: 182
tgggatttca tgtaaccaag a                                                21
```